(12) United States Patent
Kashyap et al.

(10) Patent No.: US 9,975,956 B2
(45) Date of Patent: May 22, 2018

(54) SURROGATE BINDING PROTEINS WHICH BIND DR4 AND/OR DR5

(71) Applicant: I2 PHARMACEUTICALS, INC., Boulder, CO (US)

(72) Inventors: Arun K. Kashyap, Newark, CA (US); Ramesh R. Bhatt, Belmont, CA (US); Michael Horowitz, Los Altos, CA (US); Lawrence Horowitz, Atherton, CA (US); Sihong Zhou, Foster City, CA (US); Ryann E. O'Neil, San Carlos, CA (US); Charles H. Hannum, Sunnyvale, CA (US); Aaron L. Kurtzman, San Carlos, CA (US); Li Xu, Cupertino, CA (US)

(73) Assignee: i2 PHARMACEUTICALS, INC., Boulder, CO (US)

( * ) Notice: Subject to any disclaimer, the term of this patent is extended or adjusted under 35 U.S.C. 154(b) by 118 days.

(21) Appl. No.: 14/367,862

(22) PCT Filed: Dec. 21, 2012

(86) PCT No.: PCT/US2012/071352
§ 371 (c)(1),
(2) Date: Jun. 20, 2014

(87) PCT Pub. No.: WO2013/096828
PCT Pub. Date: Jun. 27, 2013

(65) Prior Publication Data
US 2015/0004162 A1    Jan. 1, 2015

Related U.S. Application Data

(60) Provisional application No. 61/579,619, filed on Dec. 22, 2011, provisional application No. 61/604,992, filed on Feb. 29, 2012.

(51) Int. Cl.
*C07K 16/28* (2006.01)
*A61K 39/395* (2006.01)
(Continued)

(52) U.S. Cl.
CPC ...... *C07K 16/2878* (2013.01); *A61K 39/3955* (2013.01); *A61K 39/39558* (2013.01);
(Continued)

(58) Field of Classification Search
None
See application file for complete search history.

(56) References Cited

U.S. PATENT DOCUMENTS 4,256,746 A    3/1981  Miyashita et al.
4,307,016 A   12/1981  Asai et al.
(Continued)

FOREIGN PATENT DOCUMENTS

EP    0269127 A2    6/1988
EP    1396500 A1    3/2004
(Continued)

OTHER PUBLICATIONS

Xu et al., Combinantorial surrobody libraries, Proc. Natl. Acad. Sci. USA, 105(31):107556-10761.*
(Continued)

*Primary Examiner* — Claire Kaufman
(74) *Attorney, Agent, or Firm* — Cooley LLP

(57) ABSTRACT

Embodiments concern constructs comprising surrogate light chain sequences. In particular, embodiments concern constructs that can bind to DR4 and/or DR5 and aspects relating to such constructs and their use.

15 Claims, 110 Drawing Sheets

(51) Int. Cl.
*A61K 45/06* (2006.01)
*C07K 16/30* (2006.01)
*A61K 39/00* (2006.01)

(52) U.S. Cl.
CPC .............. *A61K 45/06* (2013.01); *C07K 16/30* (2013.01); *A61K 2039/505* (2013.01); *C07K 2317/33* (2013.01); *C07K 2317/35* (2013.01); *C07K 2317/73* (2013.01); *C07K 2317/75* (2013.01); *C07K 2317/76* (2013.01); *C07K 2319/00* (2013.01)

(56) References Cited

U.S. PATENT DOCUMENTS

| | | | |
|---|---|---|---|
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,439,196 | A | 3/1984 | Higuchi |
| 4,447,224 | A | 5/1984 | De Cant et al. |
| 4,447,233 | A | 5/1984 | Mayfield |
| 4,450,254 | A | 5/1984 | Isley et al. |
| 4,475,196 | A | 10/1984 | La Zor |
| 4,486,194 | A | 12/1984 | Ferrara |
| 4,487,603 | A | 12/1984 | Harris |
| 4,522,811 | A | 6/1985 | Eppstein et al. |
| 4,563,304 | A | 1/1986 | Carlsson et al. |
| 4,596,556 | A | 6/1986 | Morrow et al. |
| 4,683,192 | A | 7/1987 | Nishiyama |
| 4,683,202 | A | 7/1987 | Mullis |
| 4,790,824 | A | 12/1988 | Morrow et al. |
| 4,800,159 | A | 1/1989 | Mullis et al. |
| 4,816,567 | A | 3/1989 | Cabilly et al. |
| 4,941,880 | A | 7/1990 | Burns |
| 4,965,188 | A | 10/1990 | Mullis et al. |
| 5,064,413 | A | 11/1991 | Mc Kinnon et al. |
| 5,182,205 | A | 1/1993 | Bauer et al. |
| 5,208,020 | A | 5/1993 | Chari et al. |
| 5,312,335 | A | 5/1994 | Mc Kinnon, Jr. et al. |
| 5,374,548 | A | 12/1994 | Caras |
| 5,399,163 | A | 3/1995 | Peterson et al. |
| 5,399,331 | A | 3/1995 | Loughrey et al. |
| 5,416,016 | A | 5/1995 | Low et al. |
| 5,416,064 | A | 5/1995 | Chari et al. |
| 5,383,851 | A | 6/1995 | Mc Kinnon, Jr. et al. |
| 5,427,908 | A | 6/1995 | Dower et al. |
| 5,474,765 | A | 12/1995 | Thorpe |
| 5,475,982 | A | 12/1995 | Laude-Bousquet |
| 5,480,968 | A | 1/1996 | Kraus et al. |
| 5,585,499 | A | 12/1996 | Chari et al. |
| 5,622,929 | A | 4/1997 | Willner et al. |
| 5,641,869 | A | 6/1997 | Vandlen et al. |
| 5,762,918 | A | 6/1998 | Thorpe |
| 5,824,805 | A | 10/1998 | King et al. |
| 5,846,545 | A | 12/1998 | Chari et al. |
| 6,333,410 | B1 | 12/2001 | Chari et al. |
| 6,337,070 | B1 | 1/2002 | Yoshinobu et al. |
| 6,441,163 | B1 | 8/2002 | Chari et al. |
| 6,716,821 | B2 | 4/2004 | Zhao et al. |
| 6,720,409 | B2 | 4/2004 | Okuno et al. |
| 7,276,497 | B2 | 10/2007 | Chari et al. |
| 7,473,796 | B2 | 1/2009 | Chari et al. |
| 7,612,181 | B2 | 11/2009 | Wu et al. |
| 8,114,967 | B2* | 2/2012 | Bhatt ............... C07K 16/005 436/512 |
| 8,198,417 | B2 | 6/2012 | Steeves et al. |
| 9,169,318 | B2 | 10/2015 | Howowitz et al. |
| 2002/0054882 | A1 | 5/2002 | Yoshinobu et al. |
| 2003/0198637 | A1 | 10/2003 | Tong et al. |
| 2003/0215453 | A1 | 11/2003 | Dedera et al. |
| 2005/0169933 | A1 | 8/2005 | Steeves et al. |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2006/0147997 | A1 | 7/2006 | Ramakrishnan |
| 2007/0004909 | A1 | 1/2007 | Johnson et al. |
| 2007/0191314 | A1 | 8/2007 | Klucker et al. |
| 2008/0014205 | A1 | 1/2008 | Horowitz et al. |
| 2008/0124345 | A1 | 5/2008 | Rothe |
| 2009/0082213 | A1 | 3/2009 | Horowitz et al. |
| 2009/0098164 | A1 | 4/2009 | Bhatt et al. |
| 2009/0226455 | A1 | 9/2009 | Filvaroff |
| 2009/0274713 | A1 | 11/2009 | Chari et al. |
| 2010/0004139 | A1* | 1/2010 | Ramesh ............... C07K 16/005 506/14 |
| 2010/0040635 | A1 | 2/2010 | Horowitz et al. |
| 2010/0062950 | A1 | 3/2010 | Bhatt et al. |
| 2010/0210034 | A1 | 8/2010 | Bates |
| 2010/0255010 | A1 | 10/2010 | Fuh |
| 2010/0297174 | A1 | 11/2010 | Garcia-Sastre et al. |
| 2011/0256154 | A1 | 10/2011 | Vincent et al. |
| 2012/0123098 | A1 | 5/2012 | Bhatt et al. |
| 2012/0128671 | A1 | 5/2012 | Howowitz et al. |
| 2012/0156217 | A1 | 6/2012 | Setiady et al. |
| 2012/0202713 | A1 | 8/2012 | Bhatt et al. |
| 2012/0294853 | A1 | 11/2012 | McDonagh et al. |
| 2014/0228544 | A1 | 8/2014 | Bhatt et al. |
| 2014/0308287 | A1 | 10/2014 | Bhatt et al. |
| 2015/0011736 | A1 | 1/2015 | Horowitz et al. |
| 2015/0045540 | A1 | 2/2015 | Howowitz et al. |
| 2016/0096882 | A1 | 4/2016 | Howowitz et al. |
| 2016/0354486 | A1 | 12/2016 | Horowitz et al. |

FOREIGN PATENT DOCUMENTS

| | | |
|---|---|---|
| JP | 2011-516423 A | 5/2011 |
| WO | WO 1984/000687 A1 | 3/1984 |
| WO | WO 1997/016208 A1 | 5/1997 |
| WO | WO 2000/073349 A1 | 12/2000 |
| WO | WO 2001/035993 A2 | 5/2001 |
| WO | WO 2001/060402 A2 | 8/2001 |
| WO | WO 2002/030463 A2 | 4/2002 |
| WO | WO 2002/096457 A2 | 12/2002 |
| WO | WO 2004/003019 A2 | 1/2004 |
| WO | WO 2004/010957 A2 | 2/2004 |
| WO | WO 2007/077028 A2 | 7/2007 |
| WO | WO 2007/134327 A2 | 11/2007 |
| WO | WO 2008/028946 A2 | 3/2008 |
| WO | WO 2008/089073 A2 | 7/2008 |
| WO | WO 2008/100624 A2 | 8/2008 |
| WO | WO 2008/118970 A2 | 10/2008 |
| WO | WO 2008/153236 A1 | 12/2008 |
| WO | WO 2009/021754 A2 | 2/2009 |
| WO | WO 2009/079259 A2 | 6/2009 |
| WO | WO 2009/121004 A2 | 10/2009 |
| WO | WO 2009/134976 A1 | 11/2009 |
| WO | WO 2010/006286 A2 | 1/2010 |
| WO | WO 2010/132604 A2 | 11/2010 |
| WO | WO 2010/151808 A1 | 12/2010 |
| WO | WO 2011/071957 A1 | 6/2011 |
| WO | WO 2011/112955 A1 | 9/2011 |
| WO | WO 2011/143307 A1 | 11/2011 |
| WO | WO 2011/153431 A2 | 12/2011 |
| WO | WO 2013/003652 A1 | 1/2013 |
| WO | WO 2013/016714 A1 | 1/2013 |
| WO | WO 2013/096828 A1 | 6/2013 |
| WO | WO 2013/109994 A1 | 7/2013 |

OTHER PUBLICATIONS

MacCallum et al., Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Blol. Chem. 276:36687-94, 2001.*
Xu et al., Surrobodies with functional tails, J.Mol.Biol. 397(1):352-360, 2010.*

(56) References Cited

OTHER PUBLICATIONS

Xu et al., Combinatorial surrobody libraries, Proc. Natl. Acad. Sci. USA, 105(31):10756-61, 2008.*
Ashkenazi, A., Directing cancer cells to self-destruct with pro-apoptotic receptor agonists, Nat. Rev. Drug Discov. 7:1001-1012, Dec. 2008.*
Creative Biolabs, Data sheet for "Recombinant Anti-DR4×Anti-DR5 Bi-specific T-cell engagers (BiTE, 3631-G09(SL231))", [Retrieved online] URL:<http://www.creativebiolabs.net/pdf/BITE-MZ047.pdf>, [Retrieved May 11, 2017) 2017.*
Abbas, Cellular and Molecular Immunology, 4th Ed., Chapter 7, p. 144.
Ada, G.L. and Jones, P.D. "The Immune response to influenza infection", Current topics in Microbiology and Immunology (1986); 128: 1-54.
Adams, Camellia W., et al. "Humanization of a recombinant monoclonal antibody to produce a therapeutic HER dimerization inhibitor, pertuzumab." Cancer Immunology, Immunotherapy (2006); 55.6: 717-727.
Bankovich et al. "Structural insight into pre-B cell receptor function", Science (2007); 316: 291-294.
Bendig, Mary M., "Humanization of Rodent Monoclonal Antibodies by CDR grafting." Methods: Companion to Methods in Enzymology (1995); 8.2: 83-93.
Bowie, James U., et al. "Deciphering the message in protein sequences: tolerance to amino acid substitutions." Science (1990); 247.4948: 1306-1310.
Brummell, David A., et al. "Probing the combining site of an anti-carbohydrate antibody by saturation-mutagenesis: role of the heavy-chain CDR3 residues." Biochemistry (1993); 32.4: 1180-1187.
Burks et al, "In vitro scanning saturation mutagenesis of an antibody binding pocket", PNAS 94: 412-417, (1997).
Carlsson et al., "Protein Thiolation and Reversible Protein-Protein Conjugation", Biochem. J., 173:723-737 (1978).
Casset et al. "A peptide mimetic of an anti-CD4 monoclonal antibody by rational design", Biochemical and Biophysical Research Communications (2003); 307: 198-205.
Chen et al. "Selection and analysis of an optimized anti-VEGF antibody: Crystal structure of an affinity-matured Fabin complex with Antigen", Journal of Molecular Biology (1999); 293: 865-881.
Chumsae, et al: "Comparison of methionine oxidation in thermal stability and chemically stressed samples of a fully human monoclonal antibody", Journal of Chromatography (2007); 850: 285-294.
Colman, "Effects of amino acid sequence changes on antibody-antigen interactions", Research in Immunol. (1994); 145: 33-36.
Collins et al. "A genome annotation-driven approach to cloning the human ORFeome", Genome Biology (2004); 5(10): R84, Epub Sep. 30, 2004.
Colman et al., "Structure of the catalytic and antigenic sites in influenza virus neuraminidase", Nature (1983); 303: 41-44.
Couch and Kasel, "Immunity to influenza in man", Annual Reviews in Microbiology (1983); 37.1: 529-549.
Daniel, Claude, et al. "Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier." Virology (1994); 202.2: 540-549.
Database UniProt (online) Immunoglobulin lambda-like polypeptide 1, XP002498605 (1990), 3 pages.
Davies and Riechmann, "Affinity improvement of single antibody VH domains: residues in all three hyper variable regions affect antigen binding", Immunotechnology (1996); 2.3: 169-179.
De Pascalis et al. "Grafting of "Abbreviated" complementarity-determining regions containing specificity-determining residues essential for ligand contact to engineer a less immunogenic humanized monoclonal antibody", The Journal of Immunology (2002); 169: 3076-3084.

Dubowchik and Walker, "Receptor-mediated and enzyme-dependent targeting of cytotoxic anticancer drugs", Pharm. Therapeutics 83:67-123 (1999).
Extended European Search Report for European Application No. EP 13177665.0, dated Jan. 16, 2014, 14 pages.
Foreman, et al., "ErbB3 Inhibitor Surrobodies inhibit Tumor Cell Proliferation In Vitro and In Vivo", Molecular Cancer Therapeutics (2012); 11.7: 1411-1420.
Francés et al. "A surrogate 15 kDa JC kappa protein is expressed in combination with mu heavy chain by human B cell precursors", EMBO Journal (1994); 13: 5937-5943.
Franklin, Matthew C., et al. "Insights into ErbB signaling from the structure of the ErbB2-pertuzumab complex." Cancer Cell (2004); 5.4: 317-328.
Friedman et al. "Engineering and characterization of a bispecific HER2 × EGFR-binding affibody molecule", Biotechnology and Applied Biochemistry (2009); 54(2): 121-131.
Gauthier et al. "U-surrogate light chain physicochemical interactions of the human preB cell receptor: implications for VH repertoire selection and cell signaling at the preB cell stage", Journal of Immunology (1999); 162: 41-50.
Gocník, et al., "Antibodies specific to the HA2 glycopolypeptide of influenza. A virus haemagglutinin with fusion-inhibition activity contribute to the protection of mice against lethal infection", Journal of General Virology (2007); 88(Part 3): 951-955.
Goudsmit, Japp, "Discovery of a unique set of human monoclonal antibodies active against H5N1." Presentation at 5th International Bird Flu Summit, Sep. 27, 2007, URL link http://investors.crucell.com/C/132631/present 2007 v2.html, 35 pages.
Goudsmit, Japp, "New Directions in Fighting Flu." Presentation at Symposium for 10th Anniversary of Inflexal V, Apr. 26, 2007, 38 pages.
Govorkova, et al., "Immunization with reverse-genetics-produced H5N1 influenza vaccine protects ferrets against homologous and heterologous challenge." Journal of Infectious Diseases (2006); 194.2: 159-167.
Greenspan and Di Cera "Defining epitopes: It's not as easy as it seems." Nature Biotechnology (1999); 17(10): 936-937.
Güssow and Seemann. "[5] Humanization of monoclonal antibodies." Methods in Enzymology (1991); 203: 99-121.
Hagiwara, S. "Transgenic expression of VpreB-3 under the control of the immunoglobulin heavy chain enhancer and SV40 promoter", The Kobe Journal of Medical Sciences (1996); 42(1): 43-49.
Hanson, et al., "Passive immunoprophylaxis and therapy with humanized monoclonal antibody specific for influenza A H5 hemagglutinin in mice", Respiratory Research (2006); 7: 126, pp. 1-10.
Hashida et al., "More Useful Maleimide Compounds for the Conjugation of Fab' to Horseradish Peroxidase through Thiol Groups in the Hinge", J. Applied Biochem. (1984); 6(1-2): 56-63.
Hirabayashi et al. "Kinetic analysis of the interactions of recombinant human VpreBand Ig V domain." Journal of Immunology (1995); 155(3): 1218-1228.
Hollis et al. PIR database, 1996, accession No. A33911, accessed on Sep. 12, 2012, Score Alignment 3 pages.
Hollis, Gregory F., et al. "Immunoglobulin lambda light-chain-related genes 14.1 and 16.1 are expressed in pre-B cells and may encode the human immunoglobulin omega light-chain protein." Proceedings of the National Academy of Sciences (1989); 86.14: 5552-5556.
Holm et al. "Functional mapping and single chain construction of the anti-cytokeratin 8 monoclonal antibody TSI." Molecular Immunology (2007); 44.6: 1075-1084.
Holt, et al., "Domain antibodies: proteins for therapy", Trends in Biotechnology (2003); 21.11: 484-490.
Horváth, et al. "A Hemagglutinin-Based Multipeptide Construct Elicits Enhanced Protective Immune Response in Mice Against Influenza A Virus Infection", Immunology Letters (1998); 60.2: 127-136.
International Search Report and Written Opinion for International Application No. PCT/US2008/058283, dated Oct. 30, 2008, 11 pages.

(56) References Cited

OTHER PUBLICATIONS

International Preliminary Report on Patentability for International Application No. PCT/US2008/058283, dated Sep. 29, 2009, 7 pages.
International Search Report and Written Opinion for International Application No. PCT/US2009/038636, dated Feb. 8, 2010, 21 pages.
International Preliminary Report on Patentability for International Application No. PCT/US2009/038636, dated Sep. 28, 2010, 13 pages.
International Search Report and Written Opinion for International Application No. PCT/US2010/034604, dated Jan. 26, 2011, 21 pages.
International Preliminary Report on Patentability for International Application No. PCT/US2010/034604, dated Nov. 15, 2011, 13 pages.
International Search Report and Written Opinion for International Application No. PCT/US2012/044746, dated Dec. 4, 2012, 10 pages.
International Preliminary Report on Patentability for International Application No. PCT/US2012/044746, dated Jan. 7, 2014, 6 pages.
International Search Report and the Written Opinion for International Application No. PCT/US2012/048730, dated Nov. 6, 2012, 15 pages.
International Preliminary Report on Patentability for International Application No. PCT/US2012/048730, dated Jan. 28, 2014, 7 pages.
International Search Report and the Written Opinion for International Application No. PCT/US2012/071352, dated May 14, 2013, 15 pages.
International Preliminary Report on Patentability for International Application No. PCT/US2012/071352, dated Jun. 24, 2014, 9 pages.
International Search Report and the Written Opinion for International Application No. PCT/US2013/022308, dated Mar. 8, 2013, 9 pages.
International Preliminary Report on Patentability for International Application No. PCT/US2013/022308, dated Jul. 22, 2014, 5 pages.
Jang et al, "The structural basis for DNA binding by an anti-DNA autoantibody", Molecular immunology (1998); 35.18: 1207-1217.
Johnson et al., "Anti-Tumor Activity of CC49-Doxorubicin Immunoconjugates", Anticancer Res. 15:1387-93 (1995).
Kaneko et al., "New Hydrazone Derivatives of Adriamycin and Their Immunoconjugates-a Correlation between Acid Stability and Cytotoxicity", Bioconjugate Chem. 2:133-41 (1991).
Karasuyama et al. "Surrogate light chain in B cell development", Advances in Immunology (1996); 63: 1-41.
Karasuyama et al. "The proteins encoded by the VpreB and _5 pre-B cell-specific genes can associate with each other and with heavy chain", The Journal of Experimental Medicine (1990); 172.3: 969-972.
Kashap, et al. "Combinatorial, antibody libraries from survivors of the Turkish H5NI avian influenza outbreak reveal virus neutralization strategies", Proceedings of the National Academy of Sciences (2008); 105(16): 5986-5991.
Kobayashi et al, "Tryptophan H33 plays an important role in pyrimidine (6-4) pyrimidone photoproduct binding by a high-affinity antibody", Protein Engineering (1999); 12.10: 879-884.
Kong, et al., "Successful treatment of avian influenza with convalescent plasma", Hong Kong Med. Journal (2006); 12(6): 489.
Kudo et al. (PIR database, 1987 accession No. A26166, accessed on Jul. 19, 2010 Score Alignment , 4 pages.
Kumar et al, "Molecular Cloning and Expression of the Fabs of Human Autoantibodies in *Escherichia coli*. Determination of the heavy or light chain contribution to the anti-DNA/-Cardiolipin activity of the Fab", J. Biol. Chem. (2000); 275: 35129-35136.
Lanig et al. "Three dimensional modeling of a pre B-cell receptor", Molecular Immunology (2004); 40(17): 1263-1272.
Lau et al., "Conjugation of Doxorubicin to Monoclonal Anti-carcinoembryonic Antigen Antibody via Novel Thiol-directed Cross-linking Reagents", Bioorg-Med-Chem. 3(10):1299-1304 (1995).
Lau et al., "Novel Doxorubicin-Monoclonal Anti-carcinoembryonic Antigen Antibody Immunoconjugate Activity in vitro", Bioorg-Med-Chem. 3(10): 1305-12 (1995).
Law, et al., "Broadly neutralizing antibodies protect against hepatitis C virus quasispecies challenge", Nature Medicine (2008); 14(1): 25-27.
Lee, et al. "Generation of Bivalent and Bispecific Kringle Single Domains by Loop Grafting as Potent Agonists against Death Receptors 4 and 5." Journal of Molecular Biology (2011); 411(1): 201-219.
Lee, et al., "High-affinity human antibodies from phage-displayed synthetic Fab libraries with a single framework scaffold", J. Mol. Biol., 340: 1073-1093, (2004).
Lerner, et al., "Manufacturing immunity to disease in a test tube: the magic bullet realized", Angewandte Chemie International Edition (2006); 45.48: 8106-8125.
Lerner, et. al., "Rare antibodies from combinatorial libraries suggests an S.O.S. component of the human immunological repertoire", Molecular BioSystems (2011); 7.4: 1004-1012.
Lippincott-Schwartz. "Antibodies as Cell Biological Tools." Current Protocols in Cell Biology (2002); 16.0.1-16.0.2.
Liu et al., "New Procedures for Preparation and Isolation of Conjugates of Proteins and a Synthetic Copolymer of D-Amino Acids and Immunochemical Characterization of Such Conjugatest", Biochem., 18:690-697 (1979).
Lu, et al., "Passive immunotherapy for influenza a H5NI virus infection with equine hyperimmune globulin F(ab')2 in mice", Respiratory Research (2006); 7: 43, pp. 1-7.
Luke, et al., "Meta-analysis: Convalescent blood products for Spanish influenza pneumonia: A future H5N1 treatment", Annals of Internal Medicine (2006); 145.8: 599-609.
Mariuzza, et al. "The structural basis of antigen-antibody recognition." Annual Review of Biophysics and Biophysical Chemistry (1987); 16.1: 139-159.
Mårtensson, Inga-Lill, et al. "The pre-B cell receptor checkpoint." FEBS Letters (2010); 584.12: 2572-2579.
Mateu, et al. "Non-additive effects of multiple amino acid substitutions on antigen-antibody recognition." European Journal of Immunology (1992); 22: 1385-1389.
McKeller, Morgan R., and Martinez-Valdez, Hector. "The K-like pre-B receptor: Surplus biology or a missing link?." Seminars in Immunology (2006); 18(1): 40-43.
Melchers et al. "Fit for life in the immune system? Surrogate L chain tests H chains that test L chains", Proc. Natl. Acad. Sci. USA (1999); 96: 2571-2573.
Melchers et al. "The surrogate light chain in B-cell development", Immunology Today (1993); 14.2: 60-68.
Minegishi et al., "Novel mechanisms control the folding and assembly of 5/14.1 and VpreB to produce an intact surrogate light chain", Proceedings of the National Academy of Sciences (1999); 96.6: 3041-3046.
Morris, Glenn E. "Epitope Mapping of Protein Antigens by Competition ELISA" In: "The Protein Protocols Handbook", Jan. 1, 1996, (Jan. 1, 1996), Humana Press, Totowa, NJ, XP055007939, ISBN: 978-1-60-327259-9, pp. 595-600, DOI: 10.1007/978-1-60327-259-9_96.
Milutinovic, Snezana, et al. "Development of a novel SurrobodyTM that simultaneously activates both death receptors DR4 and DR5 and induces cancer cell death with high potency." Cancer Research (2013); 73.8 Supplement: 4318-4318.
Milutinovic, Snezana, et al. "Dual Agonist Surrobody Simultaneously Activates Death Receptors DR4 and DR5 to Induce Cancer Cell Death." Molecular Cancer Therapeutics (2016); 15.1: 114-124, 11 pages.
Neville, Jr. et al., "Enhancement of Immunotoxin Efficacy by Acid-cleavable Cross-linking Agents Utilizing Diphtheria Toxin and Toxin Mutants", Biol. Chem. 264:14653-14661 (1989).

(56) References Cited

OTHER PUBLICATIONS

Ohnishi and Melchers. "The nonimmunoglobulin portion of λ5 mediates cell-autonomous pre-B cell receptor signaling." Nature Immunology (2003); 4.9: 849-856.

Okuno, et al., "A common neutralizing epitope conserved between the hemagglutinins of influenza A virus H1 and H2 strains." Journal of Virology (1993); 67.5: 2552-2558.

Oner, et al. "Avian influenza A (H5N1) infection in eastern Turkey in 2006." New England Journal of Medicine (2006); 355.21: 2179-2185.

Palese, P. and Shaw, M.L. "Orthomyxoviridae: The viruses and their replication", Fields Virology (2007); 2: 1647-1689.

Pan, et al., "Methionine oxidation in human IgG2 Fc decreases binding affinities to protein A and FcRn", Protein Science (2009); 18.2: 424-433.

Paul, Fundamental Immunology, 3rd Edition, 1993, pp. 292-295.

Portolano, Stefano, et al. "Lack of promiscuity in autoantigen-specific H and L chain combinations as revealed by human H and L chain"roulette"." The Journal of Immunology (1993); 150.3: 880-887.

Rangel et al. "Assembly of the kappa preB receptor requires a V kappa-like protein encoded by a germline transcript", Journal of Biological Chemistry (2005); 280.18: 17807-17814.

Robinson et al., "Targeting ErbB2 and ErbB3 with a bIspecific single-chain Fv enhances targeting 39 selectivity and induces a therapeutic effect In vitro", British Journal of Cancer (2008); 99.9: 1415-1425.

Rudikoff et al. "Single amino acid substitution altering antigen-binding specificity", Proceedings of the National Academy of Sciences (1982); 79.6: 1979-1983.

Simmons, et al., "Prophylactic and therapeutic efficacy of human monoclonal antibodies against H5NI influenza", PLOS Medicine (2007); 4(5): 928-936.

Smirnov, et al., "Prevention and treatment of bronchopneumonia in mice caused by mouse-adapted variant of avian H5N2 influenza A virus using monoclonal antibody against conserved epitope in the HA stem region", Archives of Virology (2000); 145.8: 1733-1741.

Smirnov, et al., "An epitope shared by the hemagglutinins of H1, H2, H5 and H6 subtypes of influenza A virus", Acta Virologica (1999); 43.4: 237-244.

Smith-Gill et al, "Contributions of immunoglobulin heavy and light chains to antibody specificity for lysozyme and two haptens", The Journal of Immunology (1987); 139.12: 4135-4144.

Song et al. "Light chain of natural antibody plays a dominant role in protein antigen binding", Biochemical and Biophysical Research Communications (2000); 268.2: 390-394.

Thompson et al. "A pro-B-cell stage characterized by germline Ig transcription without surrogate light chain expression." Immunogenetics (1998); 48(5): 305-311.

Thorpe et al., "New Coupling Agents for the Synthesis of Immunotoxins Containing a Hindered Disulfide Bond with Improved Stability in Vivo", Cancer Res. 47:5924-5931 (1987).

Throsby, et al., "Heterosubtypic neutralizing monoclonal antibodies cross-protective against H5NI recovered from human IgM memory B cells", PLoS ONE (2008); 3.12:: e3942, pp. 1-15.

Vajdos et al. "Comprehensive functional maps of the antigen-binding site of an Anti-ErbB2 antibody obtained with shotam scanning mutagenesis", Journal of Molecular Biology (2002); 320. 2: 415-428.

Vermot-Desroches, C. et al. "Characterization of monoclonal antibodies directed against trail or trail receptors." Cellular Immunology (2005); 236.1: 86-91.

Ward et al, "Binding activities of a repertoire of single immunoglobulin variable domains secreted from *Escherichia coli*", Nature (1989); 341.6242: 544-546.

Wawrzynczak et al., "In Immunoconjugates: Antibody Conjugates in Radioimagery and Therapy of Cancer," (C.W. Vogel ed., Oxford U. Press (1987).

Wiley and Skehel. "The structure and function of the hemagglutinin membrane glycoprotein of influenza virus." Ann. Rev. Biochem. (1987); 56:365-394.

Wu et al. "Humanization of a Murine monoclonal antibody by simultaneous optimization of framework and CDR residues", Journal of Molecular Biology (1999); 294.1: 151-162.

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., 101:395-399 (1979).

Yuste, L., "Activation of ErbB2 by Overexpression or by Transmembrane Neuregulin Results in Differential Signaling and Sensitivity to Herceptin", Cancer Research (2005); 65.15: 6801-6810.

Zhou, et al., "Treatment with convalescent plasma for influenza a (H5NI) infection", New England Journal of Medicine (2007); 357.14: 1450-1451.

Graduate School of Infection Control Diseases, et al. "Analysis on epitopes of neutralizing antibodies against a highly pathogenic avian influenza H5N1 and preparation of scFv." BMB2007 (30th Meeting of the Molecular Biology Society of Japan/80th Meeting of the Japanese Biochemical Society Joint Meeting) Lecture Abstracts, 2007, p. 851, #4P-1098 (and English translation), 3 pages.

Johnson, George, and Wu, Tai Te. "The Kabat database and a bioinformatics example." Antibody Engineering: Methods and Protocols (2004); 248: 11-25.

Ewert, et al., "Stability improvement of antibodies for extracellular and intracellular applications: CDR grafting to stable frameworks and structure-based framework engineering." Methods (2004); 34(2): 184-199.

* cited by examiner

FIG. 4

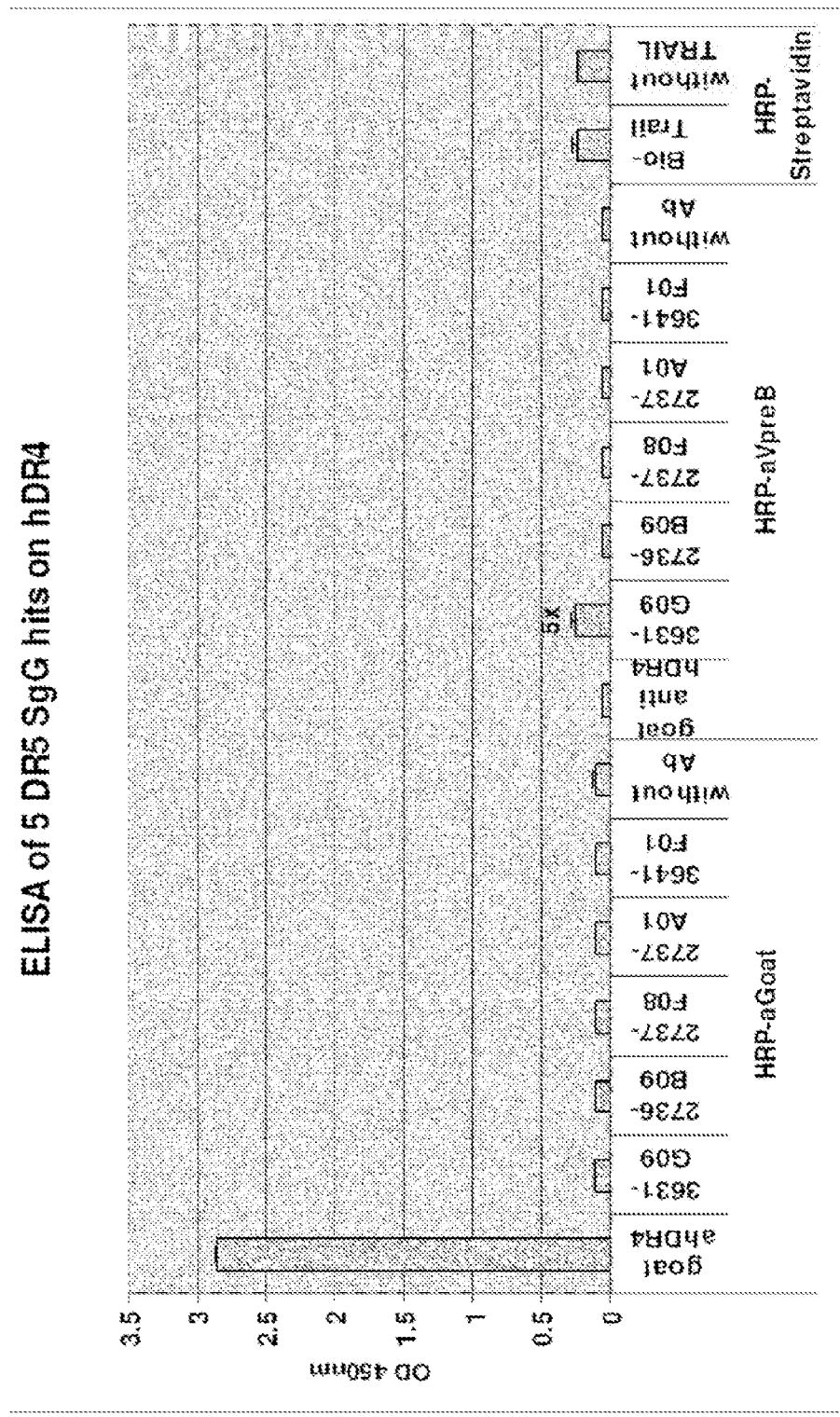

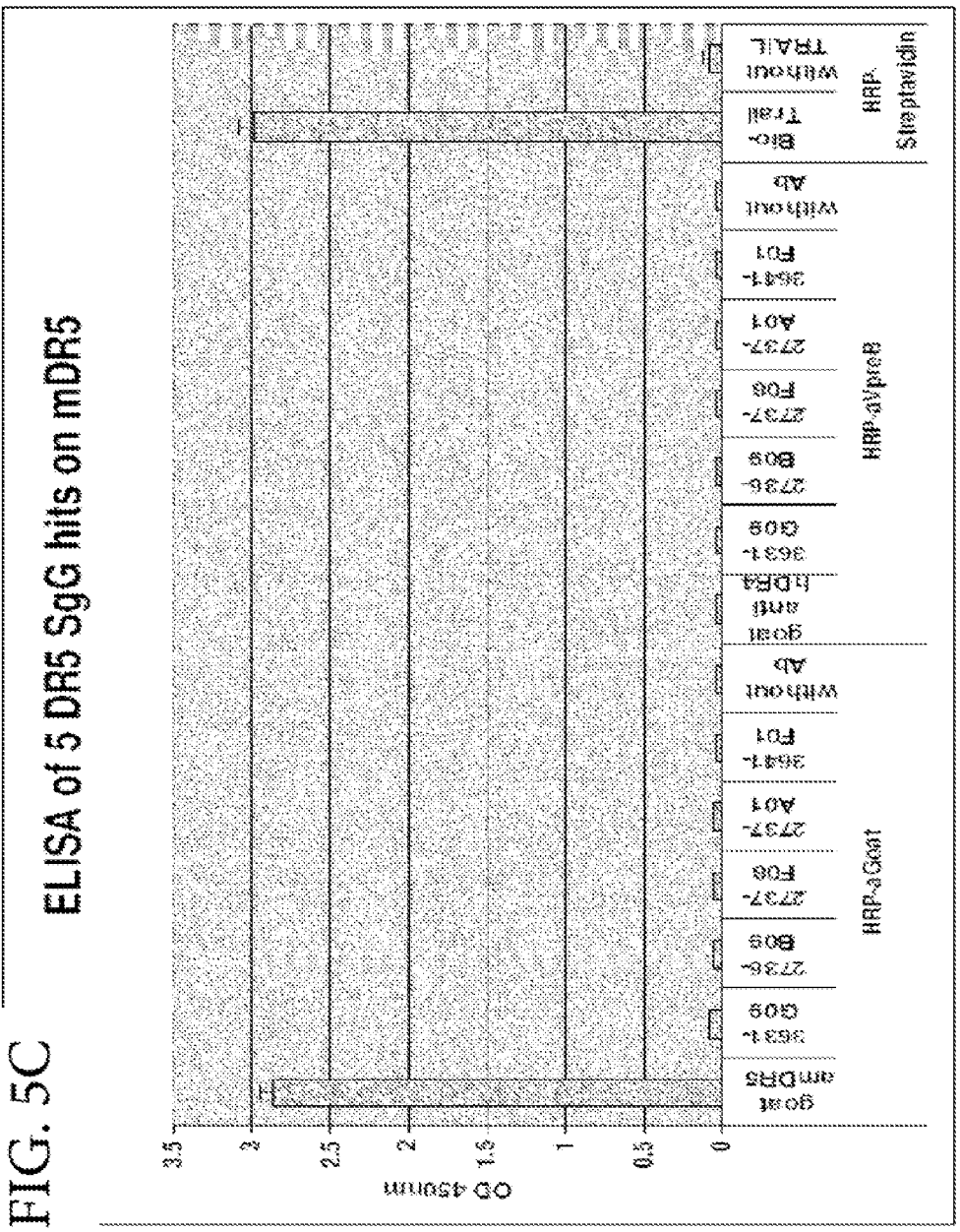

FIG. 6

```
                           1                                                                          75
Human DR4 (SEQ ID NO:25)   ----AATIKLHDQSIGTQQWEHSPLGELCPPGSHRSEHPGACNRCTEGVGYTNASNN-LFACLPCTACKSDEEERS
Human DR5 (SEQ ID NO:26)   ALITQQDLAPQQRVAPQQKRSSPSEGLCPPGHHISEDGRDCISCKYGQDYSTHWND-LLFCLRCTRCDSGEVELS
Mouse DR5 (SEQ ID NO:27)   FVPVTANPAHNRPAGLQRPEESPSRGPCLAGQYLSEG--NCKPCREGIDYTSHSMHSLDSCILCTVCKEDKVVET 76                                                    136
Human DR4 (SEQ ID NO:25)   PCTTTRNTACQCKPGTFRNDWSAEMCRKCSRGCPRGMVKVKDCTPWSDIECVHKESGNGHN
Human DR5 (SEQ ID NO:26)   PCTTTRNTVCQCEEGTFREEDSPEMCRKCRTGCPRGMVKVGDCTPWSDIECVHKESGTEHS
Mouse DR6 (SEQ ID NO:27)   RCNTTNTVCRCKPGTFEDKDSPEICQSCSN--CTDSEEELTSCTPRENRKCVSKTAWASNH
```

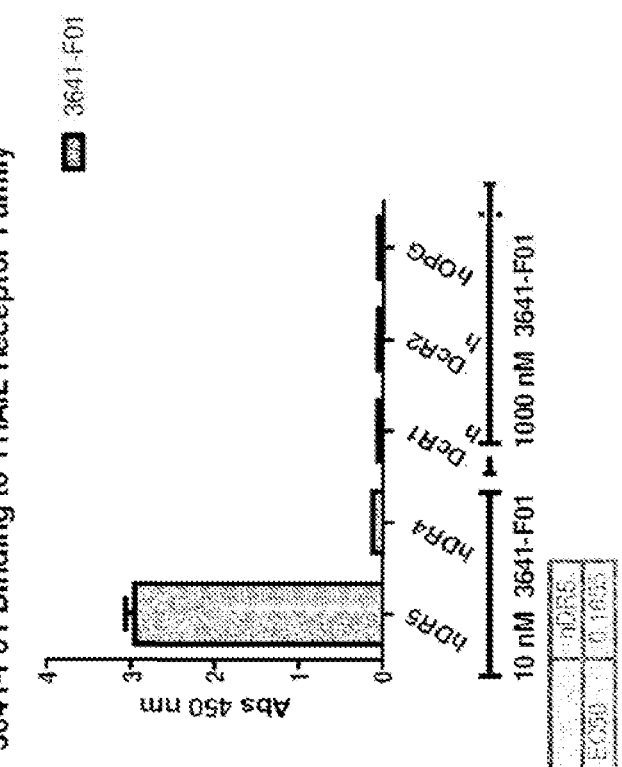
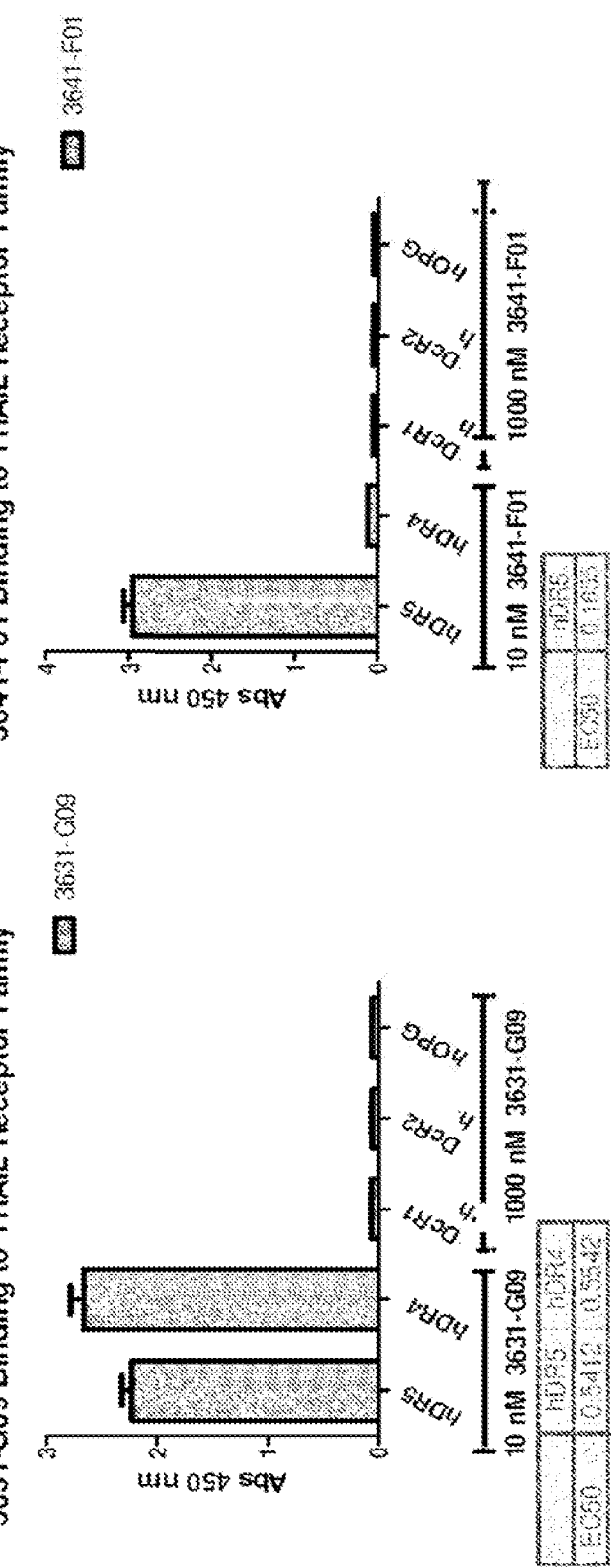

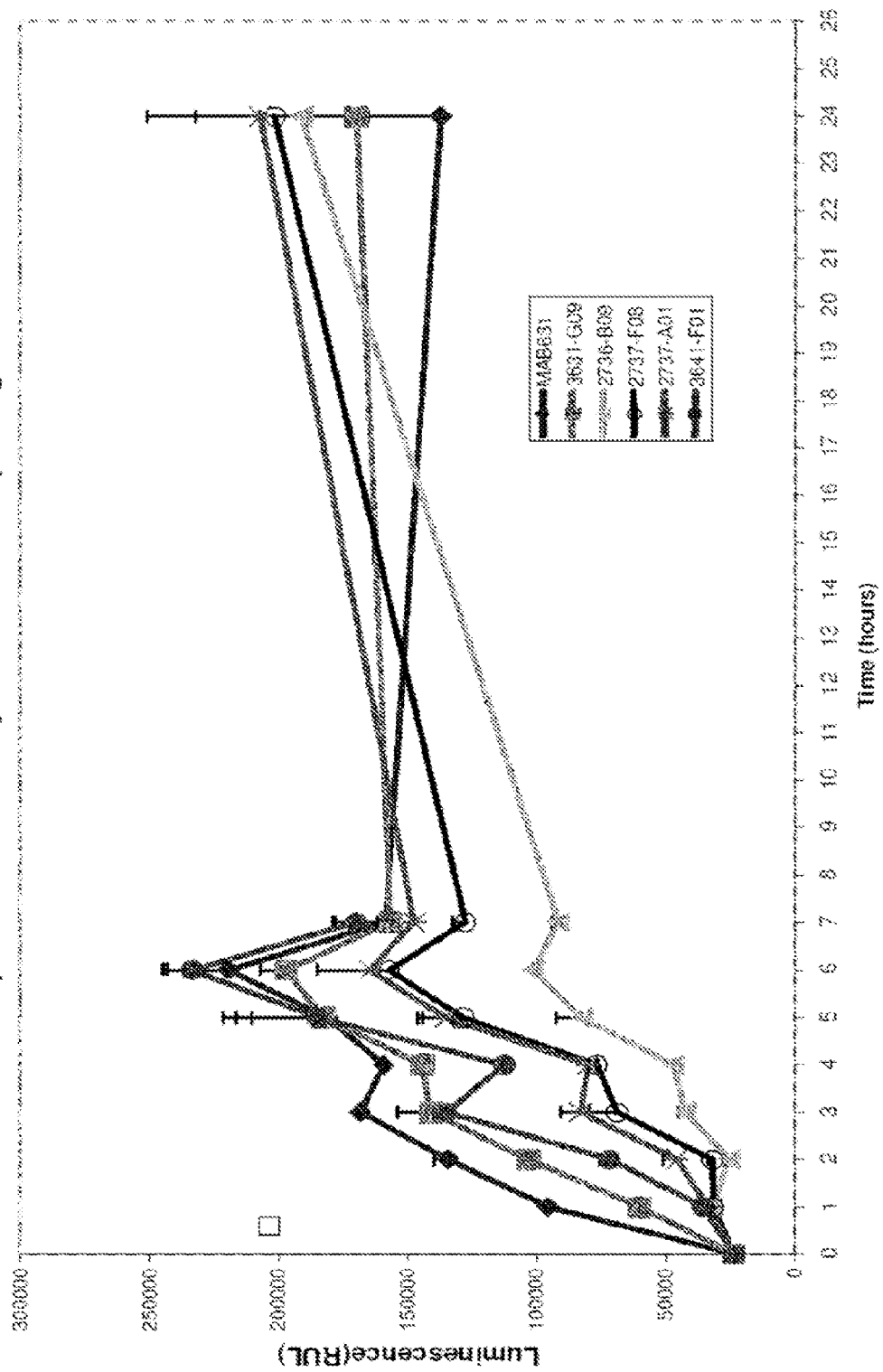

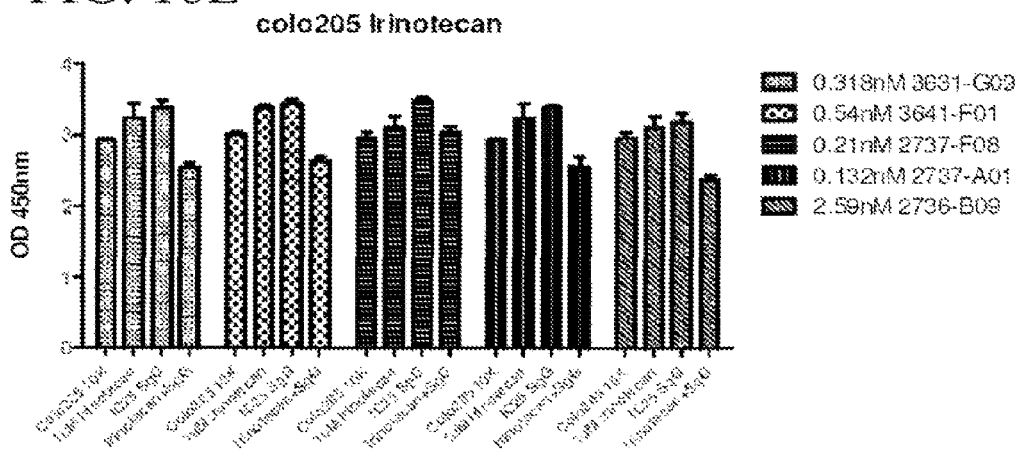
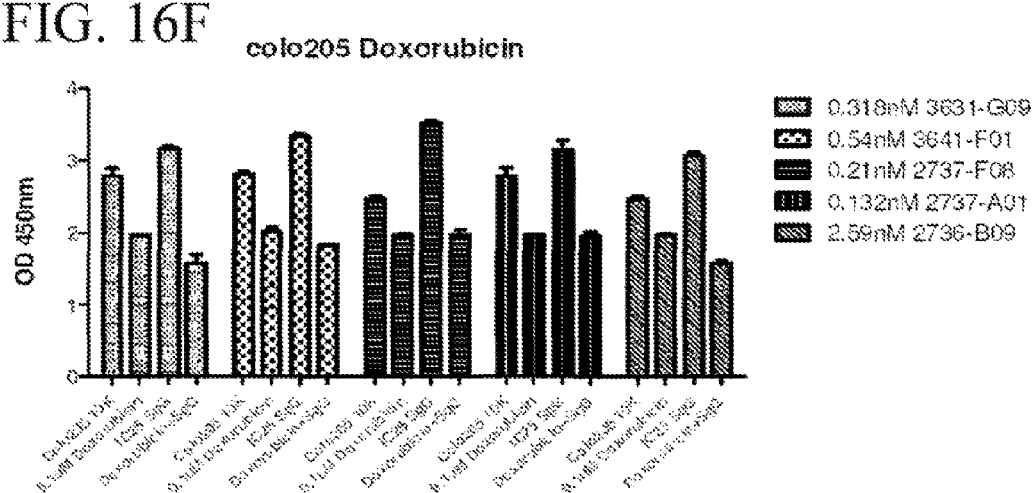

FIG. 26

Surrogate Light Chain Alignment with Variable and Constant Lambda Light Chains

- VPREB1 shares some sequence similarity to classic lambda light chain variable regions
- Lambda 5 shares similarity to Constant lambda regions and Framework region 4
- Surrogate light chain has regions that are analogous to CDR regions

FIG. 30

```
                                      1                                              45
VPREB1_Lambda5_011507 (SEQ ID NO: 13) (1)  AQPVLHQPPAMSSALGTTIRLTCTLRNDHDIGVYSVYWYQQRPGH
                5c    (SEQ ID NO: 14) (1)  -QAVLTQPASLSASPGASASLTCTLRSGINVGTYRIYWYQQKPGS
                5b    (SEQ ID NO: 15) (1)  -QPVLTQPSSHSASSGASVRLTCMLSSGFSVGDFWIRWYQQKPGN
                5e    (SEQ ID NO: 16) (1)  -QPVLTQPPSSASPGESARLTCTLPSDINVGSYNIYWYQQKPGS 46                                             90
VPREB1_Lambda5_011507 (SEQ ID NO: 13) (46) PPRFLLRYFSQSDKSQGPQVPPEFSGSKDVARNRGYLSISELQPE
                5c    (SEQ ID NO: 14) (46) PPQYLLRYKSDSDKQQGSGVPSRFSGSKDASANAGILLISGLQSE
                5b    (SEQ ID NO: 15) (46) PPRYLLYHSDSNKGQGSGVPSRFSGSNDASANAGILRISGLQPE
                5e    (SEQ ID NO: 16) (46) PPRYLIYYSGSDKGQGSGVPSRFSGSKDASANTGILLISGLQSE 91                                             135
VPREB1_Lambda5_011507 (SEQ ID NO: 13) (91) DEAMYYCAMGARSSEKERLPSKPQFWYVFGGGTQLTILGQPKSDP
                5c    (SEQ ID NO: 14) (91) DEADYYCGTWHSNSKT---------------------------
                5b    (SEQ ID NO: 15) (91) DEADYYCGTWHSNSSAS---------------------------
                5e    (SEQ ID NO: 16) (91) DEADYYCMIWPSNAS-----------------------------
```

VpreB1 shares only 56%-62% (amino acids 2-97) to VL lambda5 germlines

FIG. 31

```
                                               1                                                   50
Constant Lambda (SEQ ID NO: 17)     (1)   --------------------------------------------------
Human lambda 5  (SEQ ID NO: 18)     (1)   MRPGTPGQRGLEAPGEPGPMLRQRWPLLLLGLAVTHGLLRPTAASQSRAL 51                                                 100
Constant Lambda (SEQ ID NO: 17)     (1)   --------------------------------------------------
Human lambda 5  (SEQ ID NO: 18)    (51)   GPGAPGCSSRSSLSRWGRPLLQRGSWTGPRCPRGFQSKHMSVTHVFGS 101                                                 150
Constant Lambda (SEQ ID NO: 17)     (1)   GTKLTVLRQPKAAPSVTLFPPSSEELQANKATLVCLISDFYPGAVTVAWK
Human lambda 5  (SEQ ID NO: 18)   (101)   GTQLTVLSQPKAT PSVTLFPPSSEELQANKATLVCLMNDFYPGILTVTWK 151                                                 200
Constant Lambda (SEQ ID NO: 17)    (51)   ADGSPVKAGVETTTPSKQSNNKYAASSYLSLTPEQWKSHKSYSCQVTHEG
Human lambda 5  (SEQ ID NO: 18)   (151)   ADGTFITQGVEMTTPSKQSNNKYAASSYLSLTPEQWRSRSSYSCQVMHEG 201    213
Constant Lambda (SEQ ID NO: 17)   (101)   STVEKTVAPTECS
Human lambda 5  (SEQ ID NO: 18)   (201)   STVEKTVAPAECS
```

Lambda 5 (amino acids 101-213) is 84% identical to Lambda constant region

FIG. 32

```
Human lambda 5  (SEQ ID NO: 19)    (1)    MRPGTVQSGLEAPGEPGPNLEGRWELLLLGLAVVTHGLLRPTAASQSRALGPSAPGGSRSSLRS    65

Constant kappa  (SEQ ID NO: 20)    (1)    ------------------------------------------------KTVAAPSVFIFPPSDEQLKSGT    130
Human lambda 5  (SEQ ID NO: 19)   (66)    RWGRELLQRGSWTGPRCWPRGEQSKHWSVTHVFGSGTQLTVLSQPKATPSVTLFPPSSEELQANK Constant kappa  (SEQ ID NO: 20)   (23)    ASVVCLLNNFYPREAKVQWKVDNALQSGNSQESVTEQDSKDSTYSLSSTLTLSKADYEKHKVYAC    195
Human lambda 5  (SEQ ID NO: 19)  (131)    ATIWCLMVDFYPGILTVTWKAEGTTIT--QGVEMTTPSKQSNNKYAASSYLSLTPEQWKSRRSYSC Constant kappa  (SEQ ID NO: 20)   (88)    EVTHQGLSSPVTKSFNRGEC--                                              213
Human lambda 5  (SEQ ID NO: 19)  (195)    QVMHEGST----VEKTVAPAECS
```

Lambda 5 shares only 35% (amino acids 109-213) to a constant kappa region

MSWAPVLLMLFVYCTGCGPQPVLHQPPAMSSALGTTIRLTCTLRNDHDIGVYSVYWYQQRPGH
PPRFLLRYFSQSDKSQGPQVPPRFSGSKDVARNRGYLSISELQPEDEAMYYCAMGARSSEKEE
REREWEEEMEPTAARTRVP
(Human VpreB1; CAG30495; 145 amino acids; SEQ ID NO:1)

MAWTSVLLMLLAHLTGCGPQPMVHQPPSASSSLGATIRLSCTLSNDHNIGIYSIY
WYQQRPGHPPRFLLRYFSHSDKHQGPDIPPRFSGSKDTARNLGYLSISELQPEDEA
VYYCAVGLRSHEKKRMEREWEGEKSYTDLGS
(Mouse VpreB2; P13373; 142 amino acids; SEQ ID NO:2)

MAWTSVLLMLLAHLTGKGTLGVQGFLAPPVALLCPSDGHASIFSGCGPQPMVH
QPPSASSSLGATIRLSCTLSNDHNIGIYSIYWYQQRPGHPPRFLLRYFSHSDKHQGP
DIPPRFSGSKDTARNLGYLSISELQPEDEAVYYCAVGLRSHEKKRMEREWEGEKS
YTDLGS
(Mouse VpreB2 splice variant; CAA01964; 171 amino acids; SEQ ID NO:3)

MACRCLSFLLMGTFLSVSQTVLAQLDALLVFPGQVAQLSCTLSPQHVTIRDYGV
SWYQQRAGSAPRYLLYYRSEEDHHRPADIPDRFSAAKDEAHNACVLTISPVQPE
DDADYYCSVGYGFSP
(Human VpreB3 splice variant; CAG30496; 123 amino acids; SEQ ID NO:4)

MKLRVGQTLGTIPRQCEVLLLLLLGLVDGVHHILSPSSAERSRAVGPGASVGSNRPSLWALPGR
LLFQIIPRGAGPRQSPHRLPSKPQFWYVFGGGTQLTILGQPKSDPLVTLFLPSLKNLQPTRPHVV
CLVSEFYPGTLVVDWKVDGVPVTQGVETTQPSKQTNNKYMVSSYLTLISDQWMPHSRYSCRVT
HEGNTVEKSVSPAECS
(Mouse lambda 5; CAA01962; 209 amino acids; SEQ ID NO:5)

MRPGTGQGGLEAPGEPGPNLRQRWPLLLLGLAVVTHGLLRPTAASQSRALGPGA
PGGSSRSSLRSRWGRFLLQRGSWTGPRCWPRGFQSKHNSVTHVFGSGTQLTVLS
QPKATPSVTLFPPSSEELQANKATLVCLMNDFYPGILTVTWKADGTPITQGVEMT
TPSKQSNNKYAASSYLSLTPEQWRSRRSYSCQVMHEGSTVEKTVAPAECS
(Human lambda 5; NP_064455; 213 amino acids; SEQ ID NO:6)

MRPGTGQGGLEAPGEPGPNLRQRWPLLLLGLAVVTHGSVTHVFGSGTQLTVLSQPKATPSVTL
FPPSSEELQANKATLVCLMNDFYPGILTVTWKADGTPITQGVEMTTPSKQSNNKYAASSYLSLTP
EQWRSRRSYSCQVMHEGSTVEKTVAPAECS
(Human lambda 5dT; 158 amino acids; SEQ ID NO:7)

MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPED
EAMYYCAMGARSSVTHVFGSGTQLTVLSQPKATPSVTLFPPSSEELQANKATLV
CLMNDFYPGILTVTWKADGTPITQGVEMTTPSKQSNNKYAASSYLSLTPEQWRS
RRSYSCQVMHEGSTVEKTVAPAECS
(VpreB1-Lambda5 (Fusion 1); 242 amino acids; SEQ ID NO:10)

FIG. 33A

METDTLLLWVLLLWVPGSTGQPVLHQPPAMSSALGTTIRLTCTLRNDHDIGVYS
VYWYQQRPGHPPRFLLRYFSQSDKSQGPQVPPRFSGSKDVARNRGYLSISELQPE
DEAMYYCAMGARSSVTHVFGGGTKLTVLSQPKAAPSVTLFPPSSEELQANTATL
VCLISDFYPGAVTVAWKADSSPVKAGVETTTPSKQSNNKYAASSYLSLTPEQWK
SHRSYSCQVTHEGSTVEKTVAPTECS
(VpreB1- CL (Fusion 2); 242 amino acids: SEQ ID NO:11)

VKKLLLFAIPLVVPFYSHSAQPVLHQPPAMSSALGTTIRLTCTLRNDHDIGVYSVY
WYQQRPGHPPRFLLRYFSQSDKSQGPQVPPRFSGSKDVARNRGYLSISELQPEDE
AMYYCAMGARSSVTHVFGSGTQLTVLSQPKATPSVTLFPPSSEELQANKATLVC
LMNDFYPGILTVTWKADGTPITQGVEMTTPSKQSNNKYAASSYLSLTPEQWRSR
RSYSCQVMHEGSTVEKTVAPAECSGAPVPYPDPLEPR
(geneIII VpreB1-Lambda5-E tag Fusion (Fusion 1); 256 amino acids: SEQ ID NO:12)

FIG. 33B

SEQ ID NO:433 "Mature SLC fusion"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPSVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:487 "Mature T18C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPSVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:488 "Mature T21C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPSVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:489 "Mature V107C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVDRVFGSGTQLTVLSQPKATPSVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:490 "Mature K121C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPCATPSVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:491 "Mature S125C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPCVTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:492 "Mature V126C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPSCTLFPPSSEELQANKATLVCLMNDFYPGI
LTVTWKADGTPITQGVEKTTPSKQSNNKYAASSYLSLTPEQWKSRPSYSCQVMHEGSTVEKTVAPAECS

SEQ ID NO:493 "Mature S132C variant"

QPVLHQPPAMSSALGTTIRLPCTLRSDHDIGVYSVYWYQQRPGHPPRFLLRYFSQSDKSQGPQVPPRFSGSKDVARN
RGYLSISELQPEDEAMYYCAMGARSSVTRVFGSGTQLTVLSQPKATPSVTLFPPCSEELQANKATLVCLMNDFYPGI
LTVTWKADGTPITQGVEKTTPSKQSNNKYAASSYLSLTPEQWKSRPSYSCQVMHEGSTVEKTVAPAECS

FIG. 33C

SEQ ID NO:494 "Mature A139C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQGVEMTTPSKQSNKYAASSYLSLTPEQWRSRSYSCQVMHEGSTVEKTVAPAECS

SEQ ID NO:495 "Mature V157C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTCTWKADGTPITQGVEMTTPSKQSNKYAASSYLSLTPEQWRSRSYSCQVMHEGSTVEKTVAPAECS

SEQ ID NO:496 "Mature V170C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQCVEMTTPSKQSNKYAASSYLSLTPEQWRSRSYSCQVMHEGSTVEKTVAPAECS

SEQ ID NO:497 "Mature Q175C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQGVENTPSKCSNKYAASSYLSLTPEQWRSRSYSCQVMHEGSTVEKTVAPAECS

SEQ ID NO:498 "Mature N180C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQGVEMTTPSKQSCNKYAASSYLSLTPEQWRSRSYSCQVMHEGSTVEKTVAPAECS

SEQ ID NO:499 "Mature V213C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQGVEMTTPSKQSNKYAASSYLSLTPEQWRSRCYSCQVMHEGSTCEKTVAPAECS

SEQ ID NO:500 "Mature V217C variant"

QPVLHQPPAMSSALGTTIRLTCTLRNDHDIGVYSVYWYQQRPGHPPRFLLRYFSQSDKSQGPQVPPRFSGSKDVARN
RGYLSISELQPEDEAMYYCAMGARSSVTHVPGSGTQLTVLSQPKATPSVTLFPPSSEELQANKATLVCLMNDFYPGI
LTVTWKADGTPITQGVEMTTPSKQSNKYAASSYLSLTPEQWRSRSYSCQVMHEGSTVEKTCAPAECS

FIG. 33D

3631-G09
EVQLVESGGGLVKPGGSLRLSCAASGFTFSTYGMHWVRQAPGKGLEWVAGINYSGNNKY
YADSVKGRFTISRDNAKNSLYLQMNSLRAEDTAVYYCARDHSTWLSRHLFYWGQGTLVT
VSS (SEQ ID NO: 38)

3631-G09 STYGMH (SEQ ID NO: 39) WVAGINYSGNNKY (SEQ ID
NO: 40) ARDHSTWLSRHLD (SEQ ID NO: 41)

FIG. 35

2736-F10
EVQLVESGGGLVKPGGSLRLSCAASGFTFSSYAMSWVRQAPGKGLEWVSSISSSSSYIYYADSVK
GRFTISRDNAKNSLYLQMNSLRAEDTAVYCARSFGGFYVWGQGTLVTVSS (SEQ ID NO:
42)

2736-F10    SSYAMS (SEQ ID NO: 43)     WVSSISSSSGYIY (SEQ ID NO:
44)         ARSFGGFYV (SEQ ID NO: 45)

3641-F01
EVQLLESGGGLVQPGGSLRLSCAASGFTFRSYAMNWVRQAPGKGLEWVALISYDSSYIYYADSVK
GRFTISRDNSKNTLYLQMNSLRAEDTAVYCARLLRGGFDYWGQGTLVTVSS (SEQ ID NO:
46)

3641-F01    RSYAMN (SEQ ID NO: 47)     WVALISYDSSYIY (SEQ ID NO:
48)         ARLLRGGFD (SEQ ID NO: )49

2741-D11
EVQLLESGGGLVQPGGSLRLSCAASGFTFRSFAMSWVRQAPGKGLEWVATISAGGGYISYADSVK
GRFTISRDNSKNTLYLQMNSLRAEDTAVYCARVQSWVLDYWGQGTLVTVSS (SEQ ID NO:
50)

2741-D11    RSFAMS (SEQ ID NO: 51)     WVATISAGGGYIS (SEQ ID NO:
52)         ARVQSWVLD (SEQ ID NO: 53)

2737-A01
EVQLVESGGGLVKPGGSLRLSCAASGFTFSSYAMSWVRQAPGKGLEWVASIGYDGSYKYYADSVK
GRFTISRDNAKNSLYLQMNSLRAEDTAVYCARGVSRGYVYWGQGTLVTVSS (SEQ ID NO:
54)

2737-A01    SSYAMS (SEQ ID NO: 55)     WVASIGYDGSYKY (SEQ ID NO:
56)         ARGVSRGYV (SEQ ID NO: 57)

2736-B11
QVQLVQSGAEVKKPGASVKVSCKASGYTFSNYAMSWVRQAPGQGLEWMGWITPNSGTAKYAQKFQ
GRVTMTRDTSISTAYMELSRLRSDDTAVYCARGVSGYYDYWGQGTLVTVSS (SEQ ID NO:
58)

2736-B11    SNYAMS (SEQ ID NO: 59)     WMGWITPNSGTAK (SEQ ID NO:
60)         ARGVSGYYD (SEQ ID NO: 61)

2736-F09
QVQLVQSGAEVKKPGSSVKVSCKASGGTFSAYFISWVRQAPGQGLEWMGWISPGSGNTHYAQKFQ
GRVTITADKSTSTAYMELSSLRSEDTAVYCARGVGGYFDYWGQGTLVTVSS (SEQ ID NO:
)62

2736-F09    SAYFIS (SEQ ID NO: 63)     WMGWISPGSGNTH (SEQ ID NO:
64)         ARGVGGYFD (SEQ ID NO: 65)

FIG. 36A

2737-H11
EVQLVESGGGLVKPGGSLRLSCAASGFTFSSYSMNWVRQAPGKGLEWVAAIANDSAYTYYADSVK
GRFTISRDNAKNSLYLQMNSLRAEDTAVYYCARGFSCRLVWGQGTLVTVSS (SEQ ID NO: 66)

2737-H11   SSYSMN (SEQ ID NO: 67)    WVAAIANDSAYTY    (SEQ ID
NO: 68)   ARGFSCRLV (SEQ ID NO: 69)

2736-E10
EVQLVESGGGLVKPGGSLRLSCAASGFTFSSYSMNWVRQAPGKGLEWVAAIANDSAYTYYADSVK
GRFTISRDNAKNSLYLQMNSLRAEDTAVYYCARGFSTRLVWGQGTLVTVSS (SEQ ID NO: 70)

2736-E10   SSYSMN (SEQ ID NO: 71)    WVAAIANDSAYTY    (SEQ ID
NO: 72)   ARGFSTRLV (SEQ ID NO: 73)

2736-H08
EVQLVESGGGLVKPGGSLRLSCAASGFTFRNYAMSWVRQAPGKGLEWVAGINYSGTYTYYADSVK
GRFTISRDNAKNSLYLQMNSLRAEDTAVYYCARGFGRGFVWGQGTLVTVSS (SEQ ID NO: 74)

2736-H08   RNYAMS (SEQ ID NO: 75)    WVAGINYSGTYTY    (SEQ ID
NO: 76)   ARGFGRGFV (SEQ ID NO: 77)

2736-F12
EVQLVESGGGLVKPGGSLRLSCAASGFTFSNYGMSWVRQAPGKGLEWVSISSSSSYTYYADSVK
GRFTISRDNAKNSLYLQMNSLRAEDTAVYYCARGFGRGYVWGQGTLVTVSS (SEQ ID NO: 78)

2736-F12   SNYGMS (SEQ ID NO: 79)    WVSSTSSSSYYY    (SEQ ID
NO: 80)   ARGFGRGYV (SEQ ID NO: 81)

2743-D07
EVQLLESGGGLVQPGGSLRLSCAASGFTFSSYSMSWVRQAPGKGLEWVAGIGWGGTTKYYADSVK
GRFTISRDNSKNTLYLQMNSLRAEDTAVYYCARGGYRAYIDYWGQGTLVTVSS (SEQ ID NO: 82)

2743-D07   SSYSMS (SEQ ID NO: 83)    WVAGIGWGGTTKY (SEQ ID NO: 84)   ARGGYRAYID (SEQ ID NO: 85)

2736-G07
QVQLVQSGAEVKKPGASVKVSCKASGYTFTNYYMHWVRQAPGQGLEWMGWINPNSGNTNYAQKFQ
GRVTMTRDTSISTAYMELSRLRSDDTAVYYCAREVVPYGFDYWGQGTLVTVSS (SEQ ID NO: 86)

2736-G07   TNYYMH (SEQ ID NO: 87)    WMGWINPNSGNTN (SEQ ID NO: 88)   AREVVPYGFD (SEQ ID NO: 89)

FIG. 36B

2737-H03
EVQLVESGGGLVKPGGSLRLSCAASGFTFPNYGMNWVRQAPGKGLEWVAGIKNDGDTKYADSVK
GRFTISRDNAKNSLYLQMNSLRAEDTAVYYCARVRYGHAMDYWGQGTLVTVSS (SEQ ID
NO: 90)

2737-H03  PNYGMN (SEQ ID NO:  91)    WVAGIKNDGDTKY (SEQ ID NO:
92)  AKRVRYGHAMD (SEQ ID NO:  93)

2739-F02
EVQLLESGGGLVQPGGSLRLSCAASGFTFRNFAMNWVRQAPGKGLEWVAGIKYDSNKYADSVK
GRFTISRDNSKNTLYLQMNSLRAEDTAVYYCARRRWAGHGFDYWGQGTLVTVSS (SEQ ID
NO: 94)

2739-F02  RNFAMN (SEQ ID NO:  95)    WVAGIKYDSNKY (SEQ ID NO:
96)  ARRRWAGHGFD (SEQ ID NO:  97)

2738-G07
EVQLLESGGGLVQPGGSLRLSCAASGFTFSNYAMNWVRQAPGKGLEWVSAISGSGGSTYYADSVK
GRFTISRDNSKNTLYLQMNSLRAEDTAVYYCARRRWAGHGFDYWGQGTLVTVSS (SEQ ID
NO: 98)

2738-G07  SNYAMN (SEQ ID NO:  99)    WVSAISGSGGSTY (SEQ ID NO:
100)    ARRRWAGHGFD (SEQ ID NO:  101)

2737-F01
EVQLVESGGGLVKPGGSLRLSCAASGFTFSSYSMNWVRQAPGKGLEWVAAISYNGANKYADSVK
GRFTISRDNAKNSLYLQMNSLRAEDTAVYYCARKVGYPSAFDYWGQGTLVTVSS (SEQ ID
NO: 102)

2737-F01  SSYSMN (SEQ ID NO:  103)    WVAAISYNGANKY (SEQ ID NO:
104)  ARKVGYPSAFD (SEQ ID NO:  105)

2736-G09
EVQLVESGGGLVKPGGSLRLSCAASGFTFSSYAMSWVRQAPGKGLEWVAAISYGSDYINYADSVK
GRFTISRDNAKNSLYLQMNSLRAEDTAVYYCARRYAWGAGMDYWGQGTLVTVSS (SEQ ID
NO: 106)

2736-G09  SSYAMS (SEQ ID NO:  107)    WVAAISYGSDYIN (SEQ ID NO:
108)    ARRYAWGAGMD (SEQ ID NO:  109)

2990-F06
EVQLVESGGGLVKPGGSLRLSCAASGFTFSSYSMSWVRQAPGKGLEWVAGISYGSGYRNYADSVK
GRFTISRDNAKNSLYLQMNSLRAEDTAVYYCARRYAGGYGFDYWGQGTLVTVSS (SEQ ID
NO: 110)

2990-F06  SSYSMS (SEQ ID NO:  111)    WVASISYGSGYRN (SEQ ID NO:
112)    ARRYAGGYGFD (SEQ ID NO:  113)

FIG. 36C

2736-H03
EVQLLESGGGLVQPGGSLRLSCAASGFTFSSYSMSWVRQAPGKGLEWVSAISYNSANIYYADSVK
GRFTISRDNSKNTLYLQMNSLRAEDTAVYYCARRLGWGNGFDYWGQGTLVTVSS (SEQ ID
NO: 114)

2736-H03    SSYSMS (SEQ ID NO: 115)    WVSAISYNSANIY (SEQ ID NO:
116)    ARRLGWGNGFD (SEQ ID NO: 117)

2985-F08
EVQLLESGGGLVQPGGSLRLSCAASGFTFSSYSMSWVRQAPGKGLEWVSAISYNSANIYYADSVK
GRFTISRDNSKNTLYLQMNSLRAEDTAVYYCARRLGWGNGFDYWGQGTLVTVSS (SEQ ID
NO: 118)

2985-F08    SSYSMS (SEQ ID NO: 119)    WVSAISYNSANIY (SEQ ID NO:
120)    ARRLGWGNGFD (SEQ ID NO: 121)

2736-B09
EVQLLESGGGLVQPGGSLRLSCAASGFTFSSYAMSWVRQAPGKGLEWVSVISYSGAYTYYADSVK
GRFTISRDNSKNTLYLQMNSLRAEDTAVYYCARKVGWGHGMDYWGQGTLVTVSS (SEQ ID
NO: 122)

2736-B09    SSYAMS (SEQ ID NO: 123)    WVSVISYSGAYIY (SEQ ID NO:
124)    ARKVGWGHGMD (SEQ ID NO: 125)

2990-G01
EVQLLESGGGLVQPGGSLRLSCAASGFTFSSYAMSWVRQAPGKGLEWVASISNGGTITNYADSVK
GRFTISRDNSKNTLYLQMNSLRAEDTAVYYCARGYASSRGFDYWGQGTLVTVSS (SEQ ID
NO: 126)

2990-G01    SSYAMS (SEQ ID NO: 127)    WVASISNGGTITN (SEQ ID NO:
128)    ARGYASSRGFD (SEQ ID NO: 129)

2737-F08
EVQLVESGGGLVKPGGSLRLSCAASGFTFSDYGMHWVRQAPGKGLEWVARISNDGAIYYADSVK
GRFTISRDNAKNSLYLQMNSLRAEDTAVYYCARGGYGGYYAFDYWGQGTLVTVSS (SEQ ID
NO: 130)

2737-F08    SDYGMH (SEQ ID NO: 131)    WVARISNDGAIY (SEQ ID NO:
132)    ARGGYGGYYAFD (SEQ ID NO: 133)

2737-F09
QVQLVQSGAEVKKPGASVKVSCKASGYTFSNYYMHWVRQAPGQGLEWMGGINPINGTAKYAQKFQ
GRVTMTRDTSISTAYMELSRLRSDDTAVYYCARGYGGYYTFDYWGQGTLVTVSS (SEQ ID
NO: 134)

2737-F09    SNYYMH (SEQ ID NO: 135)    WMGGINPINGTAK (SEQ ID NO:
136)    ARGYGGYYTFD (SEQ ID NO: 137)

FIG. 36D

2736-G08
EVQLLESGGGLVQPGGSLRLSCAASGFTFRNYSMSWVRQAPGKGLEWVAGIGWDSAIKYYADSVK
GRFTISRDNSKNTLYLQMNSLRAEDTAVYYCARGTSGGRDAFDYWGQGTLVTVSS (SEQ ID
NO: 138)

2736-G08   RNYSMS (SEQ ID NO: 139)   WVAGIGWDSAIKY   (SEQ ID
NO: 140)   ARGTSGGRDAFD (SEQ ID NO: 141 )

2736-F09
EVQLVESGGGLVKPGGSLRLSCAASGFTFSDYGMHWVRQAPGKGLEWVARISNNGAIYYADSVK
GRFTISRDNAKNSLYLQMNSLRAEDTAVYYCARGGTSGYYAFDYWGQGTLVTVSS (SEQ ID
NO: 142 )

2736-F09   SDYGMH (SEQ ID NO: 143)   WVARISNNGAIY   (SEQ ID
NO: 144)   ARGGTSGYYAFD (SEQ ID NO: 145)

2737-G08
EVQLLESGGGLVQPGGSLRLSCAASGFTFSSYAMSWVRQAPGKGLEWVSSISYNGGNKYYADSVK
GRFTISRDNSKNTLYLQMNSLRAEDTAVYYCARGQWGYRAFFDYWGQGTLVTVSS (SEQ ID
NO: 146)

2737-G08   SSYAMS (SEQ ID NO: 147)   WVSSISYNGGNKY   (SEQ ID
NO: 148)   ARGQWGYRAFFD (SEQ ID NO: 149)

2998-F08
EVQLLESGGGLVQPGGSLRLSCAASGFTFRNYSMSWVRQAPGKGLEWVASISAGSAYKNYADSVK
GRFTISRDNSKNTLYLQMNSLRAEDTAVYYCARGLWSAGYAFDYGQGTLVTVSS (SEQ ID
NO: 150)

2998-F08   PNYSMS (SEQ ID NO: 151)   WVASISAGSAYKN   (SEQ ID
NO: 152)   ARGLWSAGYAFD (SEQ ID NO: 153)

2737-D11
EVQLLESGGGLVQPGGSLRLSCAASGFTFRSFSMSWVRQAPGKGLEWVAAISYNSANTYYADGVK
GRFTISRDNSKNTLYLQMNSLRAEDTAVYYCARRAAWSRSPFDYWGQGTLVTVSS (SEQ ID
NO: 154)

2737-D11   RSFSMS (SEQ ID NO: 155)   WVAAISYNSANTY   (SEQ ID
NO: 156)   ARRAAWSRSPFD (SEQ ID NO: 157)

2737-H08
QVQLVQSGAEVKKPGASVKVSCKASGYTFTGYYMHWVRQAPGQGLEWMGSINPFNGSTNYAQKFQ
GRVTMTRDTSISTAYMELSRLRSDDTAVYYCARRGWWTSSAFDYWGQGTLVTVSS (SEQ ID
NO: 158)

2737-H08   TGYYMH (SEQ ID NO: 159)   WMGSINPFNGSTN   (SEQ ID
NO: 160)   ARRGWWTSSAFD (SEQ ID NO: 161)

FIG. 36E

2737-H01
EVQLVESGGGLVKPGGSLRLSCAASGFTFRSYAMSWVRQAPGKGLEWVASINSNGAFINYADSVK
GRFTISRDNAKNSLYLQMNSLRAEDTAVYYCARGRGAYDRGFDYWGQGTLVTVSS (SEQ ID
NO: 162)

2737-H01    RSYAMS (SEQ ID NO: 163)    WVASINSNGAYTN    (SEQ ID
NO: 164)    ARGRGAYDRGFD (SEQ ID NO:    165)

2739-E10
EVQLLESGGGLVQPGGSLRLSCAASGFTFSTYAMHWVRQAPGKGLEWVAGISGGGTYKYYADSVK
GRFTISRDNSKNTLYLQMNSLRAEDTAVYYCARPRSVAYANFDYWGQGTLVTVSS (SEQ ID
NO: 166)

2739-E10    STYAMH (SEQ ID NO: 167)    WVAGISGGGTYKY (SEQ ID NO:
168)    ARPRSVAYANFD (SEQ ID NO:    169)

2743-H09
EVQLLESGGGLVQPGGSLRLSCAASGFTFSNYSMHWVRQAPGKGLEWVAGIWGDSGYIYYADSVK
GRFTISRDNSKNTLYLQMNSLRAEDTAVYYCARARVLAADGFDYWGQGTLVTVSS (SEQ ID
NO: 170)

2743-H09    SNYSMH (SEQ ID NO: 171)    WVAGIWGDSGYIY    (SEQ ID
NO: 172)    ARARVLAADGFD (SEQ ID NO:    173)

2737-F10
EVQLVESGGGLVKPGGSLRLSCAASGFTFRNYGMNWVRQAPGKGLEWVAGIKNDGDTKYYADSVK
GRFTISRDNAKNSLYLQMNSLRAEDTAVYYCAKGRYKGYVGPLDYWGQGTLVTVSS (SEQ ID
NO: 174)

2737-F10    RNYGMN (SEQ ID NO: 175)    WVAGIKNDGDTKY (SEQ ID NO:
176)    AKGRYKGYVGPLD (SEQ ID NO:    177)

2739-H03
EVQLVESGGGLVKPGGSLRLSCAASGFTFRNYGMSWVRQAPGKGLEWVAGIWSNSGITNYADSVK
GRFTISRDNAKNSLYLQMNSLRAEDTAVYYCAKSSYASYWSAFDYWGQGTLVTVSS (SEQ ID
NO: 178)

2739-H03    RNYGMS (SEQ ID NO: 179)    WVAGIWSNSGIIN    (SEQ ID
NO: 180)    AKSSYASYWSAFD (SEQ ID NO:    181)

2745-E12
EVQLVESGGGLVKPGGSLRLSCAASGFTFINYAMSWVRQAPGKGLEWVAGIGNDGTNTYYADSVK
GRFTISRDNAKNSLYLQMNSLRAENTAVYYCAKSRYIALSRPLDYWGQGTLVTVSS (SEQ ID
NO: 182)

2745-E12    INYAMS (SEQ ID NO: 183)    WVAGIGNDGTNTY    (SEQ ID
NO: 184)    AKSRYIALSRPLD (SEQ ID NO:    185)

FIG. 36F

2739-D11
EVQLVESGGGLVKPGGSLRLSCAASGFTFSSYSMNWVRQAPGKGLEWVSSISSSSSYIYYADSVK
GRFTISRDNAKNSLYLQMNSLRAEDTAVYYCARGPRPSYYAGNFDYWGQGTLVTVSS (SEQ ID
NO: 186)

2739-D11   SSYSMN (SEQ ID NO: 187)   WVSSISSSSSYIY (SEQ ID NO: 188)   ARGPRPSYYAGNFD (SEQ ID NO: 189)

2741-E10
EVQLVESGGGLVNPGGSLRLSCAASGFTFSNYSMSWVRQAPGKGLEWVSGISGGGAYKYYADSVK
GRFTISRDNAKNSLYLQMNSLRAEDTAVYYCARAGSRSPYYHFDYWGQGTLVTVSS (SEQ ID
NO: 190)

2741-E10   SNYSMS (SEQ ID NO: 191)   WVSGISGGGAYKY  (SEQ ID NO: 192)   ARAGSRSPYYHFD (SEQ ID NO: 193)

2742-D05
QVQLLESGGGDLVHPGGSLRRSCAHRGFTFMSNAWSGVLQAPGKGRLGGVGFSPGPGNITYPNSSK
GFFFFPRDNSNPLNWKMNSLRAENTAFYYCARVARTYEMHYGFDYGGQGTLVTVSS (SEQ ID
NO: 194)

2742-D05   MSNAWS (SEQ ID NO: 195)   GGVGFSRGPGNITRV (SEQ ID NO: 196)   ARTYEMHYGFDY (SEQ ID NO: 197)

2742-F08
EVQLLESGGGLVQPGGSLRLSCAASGFTFSSYAMSWVRQAPGKGLEWVAGISGGSGNTSYADSVK
GRFTISRDNSKNTLYLQMNSLRAEDTAVYYCARVARSYERDYGFDYWGQGTLVTVSS (SEQ ID
NO: 198)

2742-F08   SSYAMS (SEQ ID NO: 199)   WVAGISGGSGNISAPV (SEQ ID NO: 200)   ARSYERDYGFD (SEQ ID NO: 201)

2742-H03
EVQLVESGGGLVKPGGSLRLSCAASGFTFSNYGMHWVRQAPGKGLEWVARISGGSGYTYYADSVK
GRFTISRDNAKNSLYLQMNSLRAEDTAVYYCAREDSLGGGNYYFDYWGQGTLVTVSS (SEQ ID
NO: 202)

2742-H03   SNYGMH (SEQ ID NO: 203)   WVARISGGGGYTY  (SEQ ID NO: 204)   AREDSLGGGNYYFD (SEQ ID NO: 205)

2736-H09
EVQLVESGGGLVKPGGSLRLSCAASGFTFSSYGMSWVRQAPGKGLEWVAGIHSSGRNKYYADSVK
GRFTISRDNAKNSLYLQMNSLRAEDTAVYYCARGFYAVRSDVGAMDYWGQGTLVTVSS (SEQ
ID NO: 206)

2736-H09   SSYGMS (SEQ ID NO: 207)   WVAGINSSGRNKY  (SEQ ID NO: 208)   ARGFYAVRSDVGAMD (SEQ ID NO: 209)

FIG. 36G

2986-F10
EVQLVESGGGLVKPGGSLRLSCAASGFTFSNYGMHWVRQAPGKGLEWVSSISSSGSYIYYADSVK
GRFTISRDNAKNSLYLQMNSLRAEDTAVYYCARAFNAWRGNESNGDYWGQGTLVTVSS (SEQ
ID NO: 210)

2986-F10   SNYGMH (SEQ ID NO: 211)    WVSSISSSSYIY (SEQ ID NO:
212)       ARAFNAWRGNESNGD (SEQ ID NO: 213)

3846-F01
EVQLVESGGGLVKPGGSLRLSCAASGFTFKTYGMHWVRQAPGKGLEWVAGINYSGNNKYYADSVK
GRFTISRDNAKNSLYLQMNSLRAEDTAVYYCARDSSTTRTRALDYWGQGTLVTVSS (SEQ ID
NO 214)
KTYGMH (SEQ ID NO 215)         WVAGINYSGNNKY (SEQ ID NO 216)
ARDSSTTRTRALD (SEQ ID NO 217)

3846-F12
EVQLVESGGGLVKPGGSLRLSCAASGFTFRSYGMHWVRQAPGKGLEWVAGINYSGNNKYYADSVK
GRFTISRDNAKNSLYLQMNSLRAEDTAVYYCARDSSTTRTPALDYWGQGTLVTVSS (SEQ ID
NO 218)
RSYGMH (SEQ ID NO 219)         WVAGINYSGNNKY (SEQ ID NO 220)
ARDSSTTRTPALD (SEQ ID NO 221)

3846-C07
EVQLVESGGGLVKPGGSLRLSCAASGFTFSSFGMHWVRQAPGKGLEWVAGINYSGNNKYYADSVK
GRFTISRDNAKNSLYLQMNSLRAEDTAVYYCARDSSTTRTPALDYWGQGTLVTVSS (SEQ ID
NO 222)
SSFGMH (SEQ ID NO 223)         WVAGINYSGNNKY (SEQ ID NO 224)
ARDSSTTRTRALD (SEQ ID NO 225)

3856-A01
EVQLVESGGGLVKPGGSLRLSCAASGFTFSTYGMHWVRQAPGKGLEWVSGINYSGNNKYYADSVK
GRFTISRDNAKNSLYLQMNSLRAEDTAVYYCARDSSTTRTPALDYWGQGTLVTVSS (SEQ ID
NO 226)
STYGMH (SEQ ID NO 227)         WVSGINYSGNNKY    (SEQ ID NO 228)
ARDSSTTRTRALD (SEQ ID NO 229)

3946-A02
EVQLVESGGGLVKPGGSLRLSCAASGFTFSNYGMHWVRQAPGKGLEWVAGINYSGNNKYYADSVK
GRFTISRDNAKNSLYLQMNSLRAEDTAVYYCARDSSTTRTRALDYWGQGTLVTVSS (SEQ ID
NO 230)
SNYGMH (SEQ ID NO 231)         WVAGINYSGNNKY (SEQ ID NO 232)
ARDSSTTRTRALD(SEQ ID NO 233)

FIG. 36H

3846-A01
EVQLVESGGGLVKPGGSLRLSCAASGFTFSSYGMHWVRQAPGKGLEWVAGINYSGNNKYYADSVKGRFTISR
DNAKNSLYLQMNSLRAEDTAVYYCARDSSTTRTRALDYWGQGTLVTVSS (SEQ ID NO 234)
SSYGMH (SEQ ID NO 235)        WVAGINYSGNNKY (SEQ ID NO 236)
ARDSSTTRTRALD (SEQ ID NO 237)

3766-A06
EVQLVESGGGLVKPGGSLRLSCAASGFTFRSFGMHWVRQAPGKGLEWVAGINYSGNNKYYADSVKGRFTISR
DNAKNSLYLQMNSLRAEDTAVYYCARDSSTTRTRALDYWGQGTLVTVSS (SEQ ID NO 238)
RSFGMH (SEQ ID NO 239)        WVAGINYSGNNKY (SEQ ID NO 240)
ARDSSTTRTRALD (SEQ ID NO 241)

3846-C05
EVQLVESGGGLVKPGGSLRLSCAASGFTFSSYGMHWVRQAPGKGLEWVAGINFSGNNKYYADSVKGRFTISR
DNAKNSLYLQMNSLRAEDTAVYYCARDSSTTRTRALDYWGQGTLVTVSS (SEQ ID NO 242)
SSYGMH (SEQ ID NO 243)        WVAGINFSGNNKY (SEQ ID NO 244)
APDSSTTRTRALD (SEQ ID NO 245)

3846-E08
EVQLVESGGGLVKPGGSLRLSCAASGFTFSSYGMHWVRQAPGKGLEWVTGINYSGNNRYYADSVKGRFTISR
DNAKNSLYLQMNSLRAEDTAVYYCARDSSTTRTRALDYWGQGTLVTVSS (SEQ ID NO 246)
SSYGMH (SEQ ID NO 247)        WVTGINYSGNNRY (SEQ ID NO 248)
ARDSSTTRTRALD (SEQ ID NO 249)

3846-B10
EVQLVESGGGLVKPGGSLRLSCAASGFTFSDYGMHWVRQAPGKGLEWVAGNNYSGNNKYYADSVKGRFTISR
DNAKNSLYLQMNSLRAEDTAVYYCARDSSTTRTRALDYWGQGTLVTVSS (SEQ ID NO 250)
SDYGMH (SEQ ID NO 251)        WVAGNNYSGNNKY (SEQ ID NO 252)
APDSSTTRTRALD (SEQ ID NO 253)

3846-A05
EVQLVESGGGLVKPGGSLRLSCAASGFTFSDYGMHWVRQAPGKGLEWVAGINYSGNNKYYADSVKGRFTISR
DNAKNSLYLQMNSLRAEDTAVYYCARDSSTTRTRALDYWGQGTLVTVSS (SEQ ID NO 254)
SDYGMH (SEQ ID NO 255)        WVAGINYSGNNKY (SEQ ID NO 256)
ARDSSTTRTRALD (SEQ ID NO 257)

3766-B02
EVQLVESGGGLVKPGGSLRLSCAASGFTFRSFGMHWVRQAPGKGLEWVAGINYSGNNRYYADSVKGRFTISR
DNAKNSLYLQMNSLRAEDTAVYYCARDSSTVRTRALDYWGQGTLVTVSS (SEQ ID NO 258)
RSFGMH (SEQ ID NO 259)        WVAGINYSGNNKY (SEQ ID NO 260)
APDSSTVRTRALD (SEQ ID NO 261)

FIG. 36I

3766-F05
EVQLVESGGGLVKPGGSLRLSCAASGFTFRSFGMHWVRQAPGKGLEWVAGINYSGNNRYYADSVK
GRFTISRDNAKNSLYLQMNSLRAEDTAVYYCARDSSTTPTRSLDYWGQGTLVTVSS (SEQ ID
NO 262)
RSFGMH (SEQ ID NO 263)            WVAGINYSGNNRY (SEQ ID NO 264)
ARDSSTTPTRSLD (SEQ ID NO 265)

3767-H08
EVQLVESGGGLVKPGGSLRLSCAASGFTFRSFGMHWVRQAPGKGLEWVAGINYSGNNRYYADSVK
GRFTISRDNAKNSLYLQMNSLRAEDTAVYYCARDSSTTRTRSLDYWGQGTLVTVSS (SEQ ID
NO 266)
RSFGMH (SEQ ID NO 267)            WVAGINYSGNNRY (SEQ ID NO 268)
ARDSSTTRTRSLD (SEQ ID NO 269)

3856-B12
EVQLVESGGGLVKPGGSLRLSCAASGFTFSTYGMHWVRQAPGKGLEWVSGINYSGNNIYYADSVK
GRFTISRDNAKNSLYLQMNSLRAEDTAVYYCARDSSTTRTRSLDYWGQGTLVTVSS (SEQ ID
NO 270)
STYGMH (SEQ ID NO 271)            WVSGINYSGNNIY (SEQ ID NO 272)
ARDSSTTRTRSLD (SEQ ID NO 273)

3856-A03
EVQLVESGGGLVKPGGSLRLSCAASGFTFSTYGMHWVRQAPGKGLEWVAGINYSGNNIYYADSVK
GRFTISRDNAKNSLYLQMNSLRAEDTAVYYCARDSSTTRTRSLDYWGQGTLVTVSS (SEQ ID
NO 274)
STYGMH (SEQ ID NO 275)            WVAGINYSGNNIY (SEQ ID NO 276)
ARDSSTTRTRSLD (SEQ ID NO 277)

3846-H07
EVQLVESGGGLVKPGGSLRLSCAASGFTFSDYGMHWVRQAPGKGLEWVAGVNYSGNNIYYADSVK
GRFTISRDNAKNSLYLQMNSLRAEDTAVYYCARDSSTTRTRSLDYWGQGTLVTVSS (SEQ ID
NO 278)
SDYGMH (SEQ ID NO 279)            WVAGVNYSGNNIY (SEQ ID NO 280)
ARDSSTTRTRSLD (SEQ ID NO 281)

3766-A07
EVQLVESGGGLVKPGGSLRLSCAASGFTFRSFGMHWVRQAPGKGLEWVAGVNYSGNNIYYADSVK
GRFTISRDNAKNSLYLQMNSLRAEDTAVYYCARDSSTNRGRSLDYWGQGTLVTVSS (SEQ ID
NO 282)
RSFGMH (SEQ ID NO 283)            WVAGVNYSGNNIY (SEQ ID NO 284)
ARDSSTNRGRSLD (SEQ ID NO 285)

3766-D03
EVQLVESGGGLVKPGGSLRLSCAASGFTFRSFGMHWVRQAPGKGLEWVAGVNYSGNNIYYADSVK
GRFTISRDNAKNSLYLQMNSLRAEDTAVYYCARDSSIRGRPLDYWGQGTLVTVSS (SEQ ID
NO 286)
RSFGMH (SEQ ID NO 287)            WVAGVNYSGNNIY (SEQ ID NO 288)
ARDSSIRGRPLD(SEQ ID NO 289)

FIG. 36J

3767-A01
EVQLVESGGGLVKPGGSLRLSCAASGFTFSNFGMHWVRQAPGKGLEWVAAISYSGSYTYYADSVK
GRFTISRDNAKNSLYLQMNSLRAEDTAVYYCARDSSAVRGPPLDYWGQGTLVTVSS (SEQ ID
NO 290)
SNFGMH (SEQ ID NO 291)    WVAAISYSGSYTY (SEQ ID NO 292)
ARDSSAVRGPPLD (SEQ ID NO 293)

3706-A01
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRTRALDYWGQGTLVTVSS (SEQ ID
NO 294)

3706-A01   STYGMH (SEQ ID NO 295)     WVAGINYSGNNKY (SEQ ID NO
296)  ARDSSTNRTRALD (SEQ ID NO 297)

3706-A03
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNLTRSLDYWGQGTLVTVSS (SEQ ID
NO 298)

3706-A03   STYGMH (SEQ ID NO 299)     WVAGINYSGNNKY (SEQ ID NO
300)  ARDSSTNLTRSLD (SEQ ID NO 301)

3736-C08
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNLTRTLDYWGQGTLVTVSS (SEQ ID
NO 302)
3736-C08   STYGMH (SEQ ID NO 303)     WVAGINYSGNNKY (SEQ ID NO
304)  ARDSSTNLTRTLD (SEQ ID NO 305)

3706-A05
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNLTRALDYWGQGTLVTVSS (SEQ ID
NO 306)

3706-A05   STYGMH (SEQ ID NO 307)     WVAGINYSGNNKY (SEQ ID NO
308)  ARDSSTNLTRALD (SEQ ID NO 309)

3736-B01
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRTRALDYWGQGTLVTVSS (SEQ ID
NO 310)

3736-B01   STYGMH (SEQ ID NO 311)     WVAGINYSGNNKY (SEQ ID NO
312)  ARDSSTNRTRALD (SEQ ID NO 313)

FIG. 36K

```
3726-C06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNWTRALDYWGQGTLVTVSS (SEQ ID
NO 314)

3726-C06   STYGMH (SEQ ID NO 315)      WVAGINYSGNNKY (SEQ ID NO
316)  ARDSSTNWTRALD (SEQ ID NO 317)

3736-A05
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNYTRALDYWGQGTLVTVSS (SEQ ID
NO 318)

3736-A05   STYGMH (SEQ ID NO 319)      WVAGINYSGNNKY (SEQ ID NO
320)  ARDSSTNYTRALD (SEQ ID NO 321)

3706-A06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSNRSRSLDYWGQGTLVTVSS (SEQ ID
NO 322)

3706-A06   STYGMH (SEQ ID NO 323)      WVAGINYSGNNKY (SEQ ID NO
324)  ARDHSSNRSRSLD (SEQ ID NO 325)

3706-F06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSNVSRSLDYWGQGTLVTVSS (SEQ ID
NO 326)

3706-F06   STYGMH (SEQ ID NO 327)      WVAGINYSGNNKY (SEQ ID NO
328)  ARDHSSNVSRSLD (SEQ ID NO 329)

3706-D08
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSNRSRDLDYWGQGTLVTVSS (SEQ ID
NO 330)

3706-D08   STYGMH (SEQ ID NO 331)      WVAGINYSGNNKY (SEQ ID NO
332)  ARDHSSNRSRDLD (SEQ ID NO 333)

3736-D04
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSNFSRHLDYWGQGTLVTVSS (SEQ ID
NO 334)

3736-D04   STYGMH (SEQ ID NO 335)      WVAGINYSGNNKY (SEQ ID NO
336)  ARDHSSNFSRHLD (SEQ ID NO 337)
```

FIG. 36L

3706-C09
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSTRGRSLDYWGQGTLVTVSS (SEQ ID
NO 338)

3706-C09   STYGMH (SEQ ID NO 339)      WVAGINYSGNNKY (SEQ ID NO
340)  ARDHSSTRGRSLD (SEQ ID NO 341)

3706-D10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSTRSRSLDYWGQGTLVTVSS (SEQ ID
NO 342)

3706-D10   STYGMH (SEQ ID NO 343)      WVAGINYSGNNKY (SEQ ID NO
344)  ARDHSSTRSRSLD (SEQ ID NO 345)

3736-A10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSTWSRSLDYWGQGTLVTVSS (SEQ ID
NO 346)

3736-A10   STYGMH (SEQ ID NO 347)      WVAGINYSGNNKY (SEQ ID NO
348)  ARDHSSTWSRSLD (SEQ ID NO 349)

3736-B10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSNRGRSLDYWGQGTLVTVSS (SEQ ID
NO 350)

3736-B10   STYGMH (SEQ ID NO 351)      WVAGINYSGNNKY (SEQ ID NO
352)  ARDHSSNRGRSLD (SEQ ID NO 353)

3706-B06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTLYRALDYWGQGTLVTVSS (SEQ ID
NO 354)

3706-B06   STYGMH (SEQ ID NO 355)      WVAGINYSGNNKY (SEQ ID NO
356)  ARDHSSTLYRALD (SEQ ID NO 357)

3756-E09
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSTLHRALDYWGQGTLVTVSS (SEQ ID
NO 358)

3756-E09   STYGMH (SEQ ID NO 359)      WVAGINYSGNNKY (SEQ ID NO
360)  ARDHSSTLHRALD (SEQ ID NO 361)

FIG. 36M

3736-B03
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSSNLYRALDYWGQGTLVTVSS (SEQ ID
NO 362)

3736-B03   STYGMH (SEQ ID NO 363)      WVAGINYSGNNKY (SEQ ID NO
364)  ARDHSSNLYRALD (SEQ ID NO 365)

3746-F11
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSGYWTRSLDYWGQGTLVTVSS (SEQ ID
NO 366)

3746-F11   STYGMH (SEQ ID NO 367)      WVAGINYSGNNKY (SEQ ID NO
368)  ARDHSGYWTRSLD (SEQ ID NO 369)

3746-C09
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDRSHIVGRPLDYWGQGTLVTVSS (SEQ ID
NO 370)

3746-C09   STYGMH (SEQ ID NO 371)      WVAGINYSGNNKY (SEQ ID NO
372)  ARDRSHIVGRPLD (SEQ ID NO 373)

3746-E08
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDRSSIPGRPLDYWGQGTLVTVSS (SEQ ID
NO 374)

3746-E08   STYGMH (SEQ ID NO 375)      WVAGINYSGNNKY (SEQ ID NO
376)  ARDRSSIPGRPLD (SEQ ID NO 377)

3756-A10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDRSTTYSRALDYWGQGTLVTVSS (SEQ ID
NO 378)

3756-A10   STYGMH (SEQ ID NO 379)      WVAGINYSGNNKY (SEQ ID NO
380)  ARDRSTTYSRALD (SEQ ID NO 381)

FIG. 36N

3756-H10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDRSTTLHRALDYWGQGTLVTVSS (SEQ ID
NO 382)

3756-H10    STYGMH (SEQ ID NO 383)     WVAGINYSGNNKY (SEQ ID NO
384) ARDRSTTLHRALD (SEQ ID NO 385)

3736-A06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSTNRGRSLDYWGQGTLVTVSS (SEQ ID
NO 386)

3736-A06    STYGMH (SEQ ID NO 387)     WVAGINYSGNNKY (SEQ ID NO
388) ARDHSTNRGRSLD (SEQ ID NO 389)

3736-A12
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDHSTHLGRSLDYWGQGTLVTVSS (SEQ ID
NO 390)

3736-A12    STYGMH (SEQ ID NO 391)     WVAGINYSGNNKY (SEQ ID NO
392) ARDHSTHLGRSLD (SEQ ID NO 393)

3736-D12
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCAKDHSTNRRRXLDYWGQGTLVTVSS (SEQ ID
NO 394)

3736-D12    STYGMH (SEQ ID NO 395)     WVAGINYSGNNKY (SEQ ID NO
396) ARDHSTNRRRXLD (SEQ ID NO 397)

3706-B04
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCAKDSSTNRSRSLDYWGQGTLVTVSS (SEQ ID
NO 398)

3706-B04    STYGMH (SEQ ID NO 399)     WVAGINYSGNNKY (SEQ ID NO
400) ARDSSTNRSRSLD (SEQ ID NO 401)

3726-C12
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTTRSRTLDYWGQGTLVTVSS (SEQ ID
NO 402)

3726-C12    STYGMH (SEQ ID NO 403)     WVAGINYSGNNKY (SEQ ID NO
404) ARDSSTTRSRTLD (SEQ ID NO 405)

FIG. 36O

3736-E03
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTTRSPSLDYWGQGTLVTVSS (SEQ ID
NO 406)

3736-E03    STYGMH (SEQ ID NO 407)    WVAGINYSGNNKY (SEQ ID NO
408)   ARDSSTTRSPSLD (SEQ ID NO 409)

3706-C05
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRSPALDYWGQGTLVTVSS (SEQ ID
NO 410)

3706-C05    STYGMH (SEQ ID NO 411)    WVAGINYSGNNKY (SEQ ID NO
412)   ARDSSTNRSPALD (SEQ ID NO 413)

3706-C01
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNPGRALDYWGQGTLVTVSS (SEQ ID
NO 414)

3706-C01    STYGMH (SEQ ID NO 415)    WVAGINYSGNNKY (SEQ ID NO
416)   ARDSSTNPGRALD (SEQ ID NO 417)

3726-C08
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTVRGRALDYWGQGTLVTVSS (SEQ ID
NO 418)

3726-C08    STYGMH (SEQ ID NO 419)    WVAGINYSGNNKY (SEQ ID NO
420)   ARDSSTVRGRALD (SEQ ID NO 421)

3706-A10
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNPTRSLDYWGQGTLVTVSS (SEQ ID
NO 422)

3706-A10    STYGMH (SEQ ID NO 423)    WVAGINYSGNNKY (SEQ ID NO
424)   ARDSSTNPTRSLD (SEQ ID NO 425)

3746-B11
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRTRSLDYWGQGTLVTVSS (SEQ ID
NO 426)

3746-B11    STYGMH (SEQ ID NO 427)    WVAGINYSGNNKY (SEQ ID NO
428)   ARDSSTNRTRSLD (SEQ ID NO 429)

FIG. 36P

3706-F12
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTVRTRSLDYWGQGTLVTVSS (SEQ ID
NO 430)

3706-F12    STYGMH (SEQ ID NO 431)       WVAGINYSGNNKY (SEQ ID NO
432)  ARDSSTVRTRSLD (SEQ ID NO 433)

3726-C02
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTTRTRSLDYWGQGTLVTVSS (SEQ ID
NO 434)

3726-C02    STYGMH (SEQ ID NO 435)       WVAGINYSGNNKY (SEQ ID NO
436)  ARDSSTTRTRSLD (SEQ ID NO 437)

3706-G02
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDTSTNRTRGLDYWGQGTLVTVSS (SEQ ID
NO 438)

3706-G02    STYGMH (SEQ ID NO 439)       WVAGINYSGNNKY (SEQ ID NO
440)  ARDTSTNRTRGLD (SEQ ID NO 441)

3726-B07
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRTRGLDYWGQGTLVTVSS (SEQ ID
NO 442)

3726-B07    STYGMH (SEQ ID NO 443)       WVAGINYSGNNKY (SEQ ID NO
444)  ARDSSTNRTRGLD (SEQ ID NO 445)

3706-G07
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTIRTRGLDYWGQGTLVTVSS (SEQ ID
NO 446)

3706-G07    STYGMH (SEQ ID NO 447)       WVAGINYSGNNKY (SEQ ID NO
448)  ARDSSTIRTRGLD (SEQ ID NO 449)

3726-F09
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTTRTRGLDYWGQGTLVTVSS (SEQ ID
NO 450)

3726-F09    STYGMH (SEQ ID NO 451)       WVAGINYSGNNKY (SEQ ID NO
452)  ARDSSTTRTRGLD (SEQ ID NO 453)

FIG. 36Q

3726-F06
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTNRTRTLDYWGQGTLVTVSS (SEQ ID
NO 454)

3726-F06    STYGMH (SEQ ID NO 455)      WVAGINYSGNNKY (SEQ ID NO
456)  ARDSSTNRTRTLD (SEQ ID NO 457)

3706-A02
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTTRTRALDYWGQGTLVTVSS (SEQ ID
NO 458)

3706-A02    STYGMH (SEQ ID NO 459)      WVAGINYSGNNKY (SEQ ID NO
460)  ARDSSTTRTRALD (SEQ ID NO 461)

3726-A01
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTVRTPALDYWGQGTLVTVSS (SEQ ID
NO 462)

3726-A01    STYGMH (SEQ ID NO 463)      WVAGINYSGNNKY (SEQ ID NO
464)  ARDSSTVRTPALD (SEQ ID NO 465)

3726-D07
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTISTPALDYWGQGTLVTVSS (SEQ ID
NO 466)

3726-D07    STYGMH (SEQ ID NO 467)      WVAGINYSGNNKY (SEQ ID NO
468)  ARDSSTISTPALD (SEQ ID NO 469)

3756-A01
EVQLVESGGGLVKPGGSLRLSCAASGFTFSTYGMHWVRQAPGKGLEWVAGINYSGNNKYYADSVK
GRFTISRDNAKNSLYLQMNSLRAEDTAVYYCARDSSTIRTPALDYWGQGTLVTVSS (SEQ ID
NO 470)

3756-A01    STYGMH (SEQ ID NO 471)      WVAGINYSGNNKY (SEQ ID NO
472)  ARDSSTIRTPALD (SEQ ID NO 473)

FIG. 36R

DR4 Sequences

APPPARVHLGAFLAVTPNPGSAASGTEAAAATPSKVWGSSAGRIEPRGGGRGALPTSMGQHGPSARARAGPA
PGPRPAREASPRLRVHKTPKFVVVGVLLQVVPSSAATIKLHDQSIGTQQWEHSPLGELCPPGSHRSEHPGAC
NRCTEGVGYTNASNNLFACLPCTACKSDEEERSPCTTTRNTACQCKPGTFPNDNSAEMCRKCSPGCPRGMVK
VKDCTPWSDIECVHKESGNGHNIWVILVVTLVVPLLLVAVLIVCCCIGSGCGGDPKCMDRVCFWRLGLLRGP
GAEDNAHNEILSNADSLSTFVSEQQMESQEPADLTGVTVQSPGEAQCLLGPAEAEGSQRRRLLVPANGADPT
ETLMLFFDKFANIVPFDSWDQLMRQLDLTKNEIDVVRAGTAGPGDALYAMLMKWVNKTGRNASIHTLLDALE
RMEERHAKEKIQDLLVDSGKFIYLEDGTGSAVSLE    (SEQ ID NO 474)

MAPPPARVHLGAFLAVTPNPGSAASGTEAAAATPSKVWGSSAGRIEPRGGGRGALPTSMGQHGPSARARAGR
APGPRPAREASPRLRVHKTPKFVVVGVLLQVVPSSAATIKLHDQSIGTQQWEHSPLGELCPPGSHRSEHPGA
CNRCTEGVGYTNASNNLFACLPCTACKSDEEERSPCTTTRNTACQCKPGTFPNDNSAEMCRKCSTGCPRGMV
KVKDCTPWSDIECVHKESGNGHNIWVILVVTLVVPLLLVAVLIVCCCIGSGCGGDPKCMDRVCFWRLGLLRG
PGAEDNAHNEILSNADSLSTFVSEQQMESQEPADLTGVTVQSPGEAQCLLGPAEAEGSQRRRLLVPANGADP
TETLMLFFDKFANIVPFDSWDQLMRQLDLTKNEIDVVRAGTAGPGDALYAMLMKWVNKTGRNASIHTLLDAL
ERMEERHAKEKIQDLLVDSGKFIYLEDGTGSAVSLE    (SEQ ID NO 475)

MAPPPARVHLGAFLAVTPNPGSAASGTEAAAATPSKVWGSSAGRIEPRGGGRGALPTSMGQHGPSARARAGR
APGPRPAREASPRLRVHKTPKFVVVGVLLQVVPSSAATIKLHDQSIGTQQWEHSPLGELCPPGSHRSERPGA
CNRCTEGVGYTNASNNLFACLPCTACKSDEEERSPCTTTRNTACQCKPGTFPNDNSAEMCRKCSTGCPRGMV
KVKDCTPWSDIECVHKESGNGHNIWVILVVTLVVPLLLVAVLIVCCCIGSGCGGDPKCMDRVCFWRLGLLRG
PGAEDNAHNEILSNADSLSTFVSEQQMESQEPADLTGVTVQSPGEAQCLLGPAEAEGSQRRRLLVPANGADP
TETLMLFFDKFANIVPFDSWDQLMRQLDLTKNEIDVVRAGTAGPGDALYAMLMKWVNKTGRNASIHTLLDAL
ERMEERHAKEKIQDLLVDSGKFIYLEDGTGSAVSLE    (SEQ ID NO 476)

MAPPPARVHLGAFLAVTPNPGSAASGTEAAAATPSKVWGSSAGRIEPRGGGRGALPTSMGQHGPSARARAGR
APGPRPAREASPRLRVHKTPKFVVVGVLLQVVPSSAATIKLHDQSIGTQQWEHSPLGELCPPGSHPSERPGA
CNRCTEGVGYTNASNNLFACLPCTACKSDEEERSPCTTTRNTACQCKPGTFPNDNSAEMCRKCSTGCPPGMV
KVKDCTPWSDIECVHKESGNGHNIWVILVVTLVVPLLLVAVLIVCCCIGSGCGGDPKCMDRVCFWRLGLLRG
PGAEDNAHNEILSNADSLSTFVSEQQMESQEPADLTGVTVQSPGEAQCLLGPAEAEGSQRRRLLVPANGADP
TETLMLFFDKFANIVPFDSWDQLMPQLDLTKNEIDVVRAGTAGPGDALYAMLMKWVNKTGRNASTHTLLDAL
ERMEERHAKEKIQDLLVDSGKFIYLEDGTGSAVSLE    (SEQ ID NO 477)

FIG. 37

DR5 Sequences

MEQRGQNAPAASGARKRHGPGPREARGARPGFRVPKTLVLVVAAVLLLVSAESALITQQDLAPQQ
RAAPQQKPSSPSEGLCPPGHHISEDGRDCISCKYGQDYSTHWNDLLFCLRCTRCDSGEVELSPCT
TTRNTVCQCEEGTFREEDSPEMCRKCRTGCPRGMVKVGDCTPWSDIECVHKESGTKHSGEAPAVE
ETVTSSPGTPASPCSLSGIIIGVTVAAVVLIVAVFVCKSLLWKKVLPYLKGICBIVALENTSBPG
GDPERVDRSSQRFGAEDNVLNEIVSILQPTQVPEQEMEVQEPAEPTGVNMLSPGESEHLLEPAEA
ERSQRRLLVPANEGDPTETLRQCFDDFADLVPFDSWEPLMRKLGLMDNETKVAKAEAAGHRDTL
YTMLIKWVNKTGRDASVHTLLDALETLGERLAKQKIEDHLLSSGKFMYLEGNADSAMS (SEQ
ID NO 478)

MEQRGQNAPAASGARKRHGPGPREARGARPGFRVPKTLVLVVAAVLLLVSAESALITQQDLAPQQ
RAAPQQKPSSPSEGLCPPGHHISEDGRDCISCKYGQDYSTHWNDLLFCLRCTRCDSGEVELSPCT
TTRNTVCQCEEGTFREEDSPEMCRKCRTGCPRGMVKVGDCTPWSDIECVHKESGTKHSGEVPAVE
ETVTSSPGTPASPCSLSGIIIGVTVAAVVLIVAVFVCKSLLWKKVLPYLKGICBIVALENTSBPG
GDPERVDRSSQRFGAEDNVLNEIVSILQPTQVPEQEMEVQEPAEPTGVNMLSPGESEHLLEPAEA
ERSQRRLLVPANEGDPTETLRQCFDDFADLVPFDSWEPLMRKLGLMDNETKVAKAEAAGHRDTL
YTMLIKWVNKTGRDASVHTLLDALETLGERLAKQKIEDHLLSSGKFMYLEGNADSAMS (SEQ
ID NO 479)

MEQRGQNAPAASGARKRHGPGPREARGARPGLRVPKTLVLVVAAVLLLVSAESALITQQDLAPQQ
RAAPQQKRSSPSEGLCPPGHHISEDGRDCISCKYGQDYSTHWNDLLFCLRCTRCDSGEVELSPCT
TTRNTVCQCEEGTFREEDSPEMCRKCRTGCPRGMVKVGDCTPWSDIECVHKESGTKHSGEAPAVE
ETVTSSPGTPASPCSLSGIIIGVTVAAVVLIVAVFVCKSLLWKKVLPYLKGICBIVALENTSBPG
GDPERVDRSSQRPGAEDNVLNEIVSILQPTQVPEQEMEVQEPAEPTGVNMLSPGESEHLLEPAEA
ERSQRRPLLVPANEGDPTETLRQCFDDFADLVPFDSWEPLMRKLGLMDNETKVAKAEAAGHPDTL
YTMLIKWVNKTGRDASVHTLLDALETLGERLAKQKIEDHLLSSGKFMYLEGNADSAMS (SEQ
ID NO 480)

MEQRGQNAPAASGARKRHGPGPREARGARPGLRVPKTLVLVVAAVLLLVSAESALITQQDLAPQQ
RVAPQQHRSSPSEGLCPPGHHISEDGRDCISCKYGQDYSTHWNDLLFCLRCTRCDSGEVELSPCT
TTRNTVCQCEEGTFREEDSPEMCRKCRTGCPRGMVKVGDCTPWSDIECVHKESGTKHSGEAPAVE
ETVTSSPGTPASPCSLSGIIIGVTVAAVVLIVAVFVCKSLLWKKVLPYLKGICBIVALENTSBPG
GDPERVDRSSQRPGAEDNVLNEIVSILQPTQVPEQEMEVQEPAEPTGVNMLSPGESEHLLEPAEA
ERSQRRPLLVPANEGDPTETLRQCFDDFADLVPFDSWEPLMRKLGLMDNETKVAKAEAAGHRDTL
YTMLIKWVNKTGRDASVHTLLDALETLGERLAKQKIEDHLLSSGKFMYLEGNADSAMS (SEQ
ID NO 481)

MEQRGQNAPAASGARKRHGPGPREAWGARPGLRVPKTLVLVVAAVLLLVSAESALITQQDLAPQQ
RVAPQQKRSSPSEGLCPPGHHISEDGRDCISCKYGQDYSTHWNDLLFCLRCTRCDSGEVELSPCT
TTRNTVCQCEEGTFREEDSPEMCRKCRTGCPRGMVKVGDCTPWSDIECVHKESGTKHSGEAPAVE
ETVTSSPGTPASPCSLSGIIIGVTVAAVVLIVAVFVCKSLLWKKVLPYLKGICBIVALENTSBPG
GDPERVDRSSQRPGAEDNVLNEIVSILQPTQVPEQEMEVQEPAEPTGVNMLSPGESEHLLEPAEA
ERSQRRPLLVPANEGDPTETLPQCFDDFADLVPFDSWEPLMRKLGLMDNETKVAKAEAAGHRDTL
YTMLIKWVNKTGRDASVHTLLDALETLGERLAKQKIEDHLLSSGKFMYLEGNADSAMS (SEQ
ID NO 482)

FIG. 38

FIG. 44A
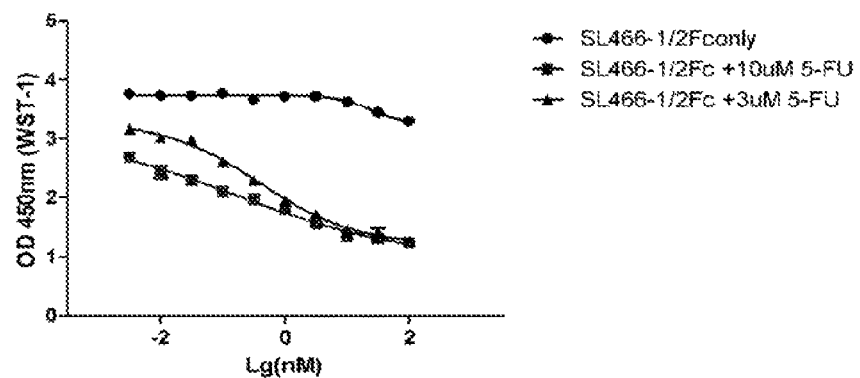
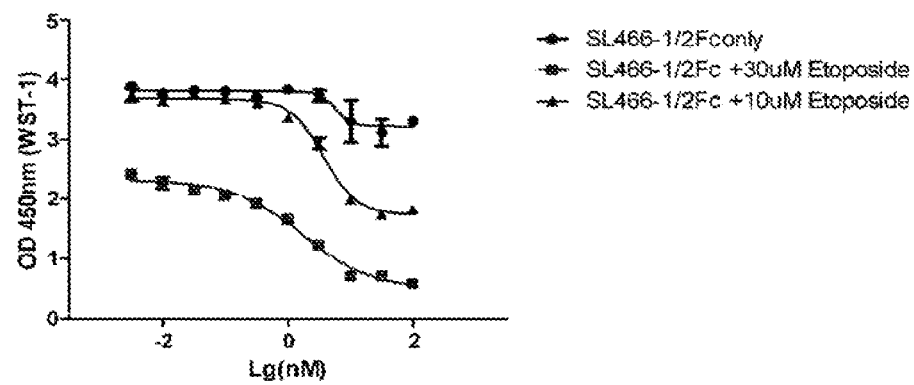
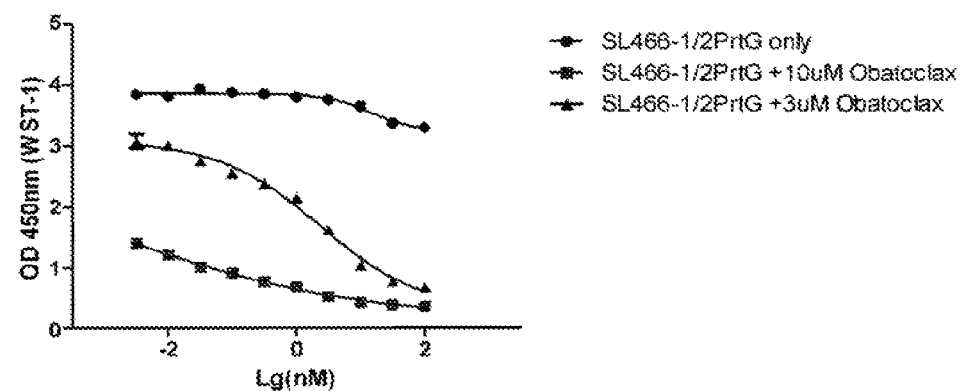

FIG. 44B
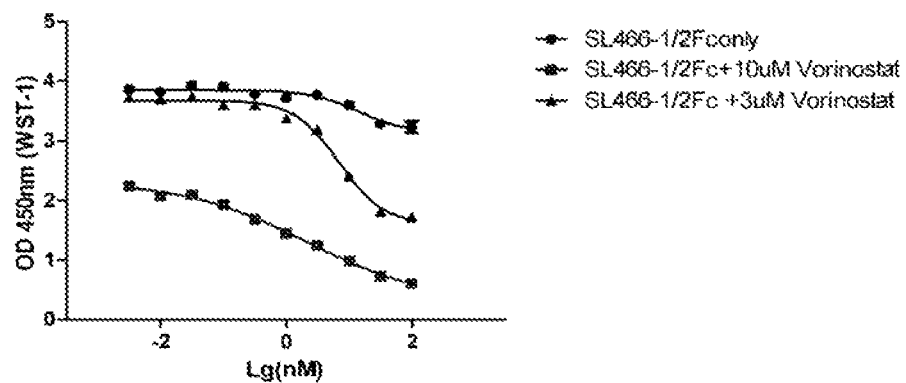
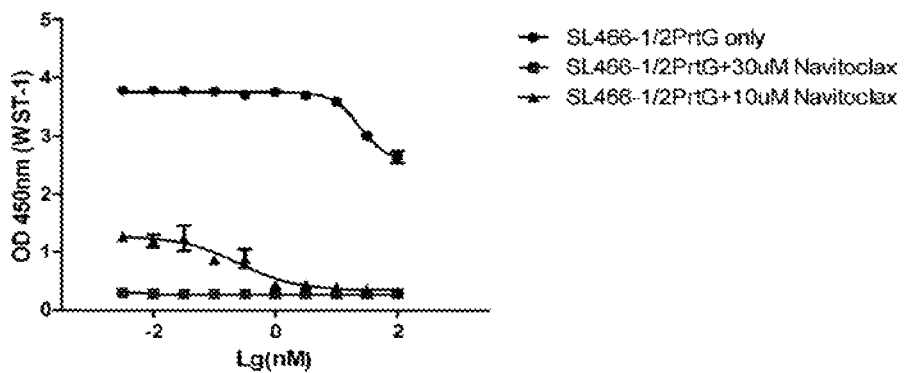

FIG. 45A
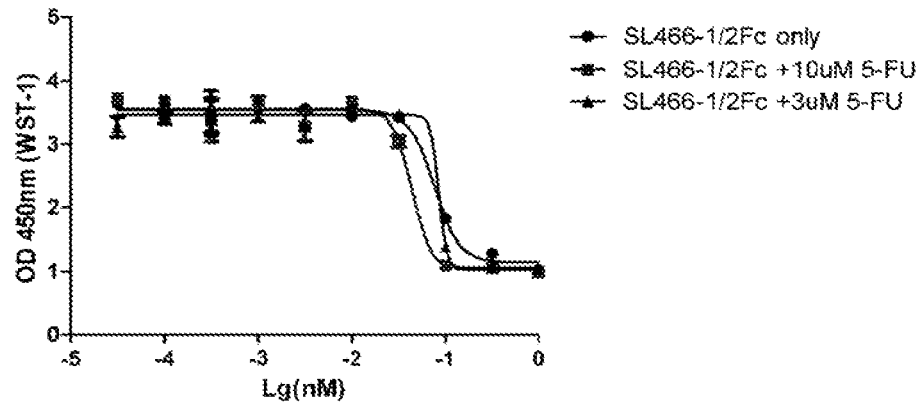
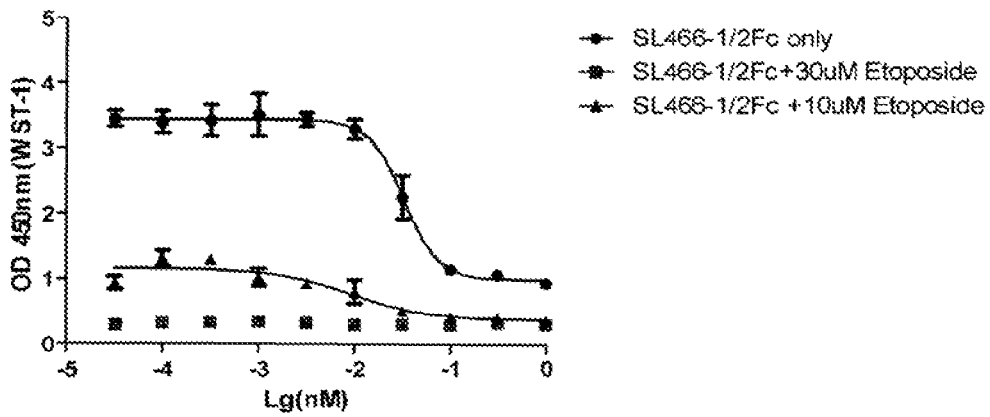
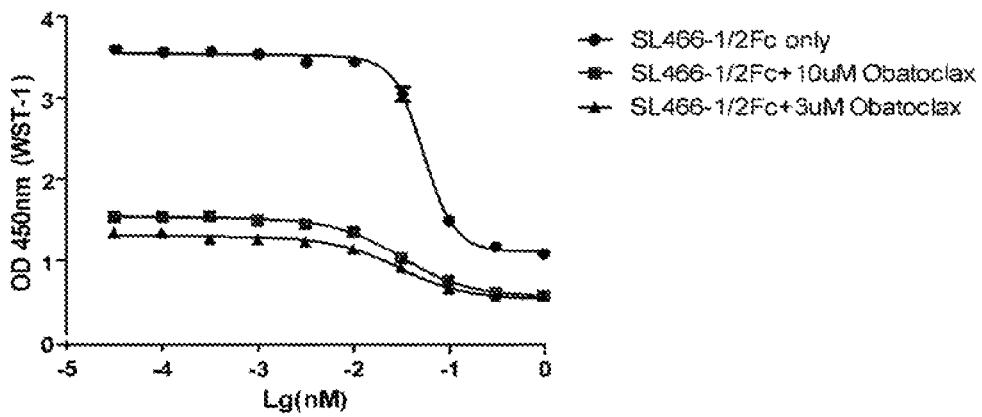

FIG. 45B
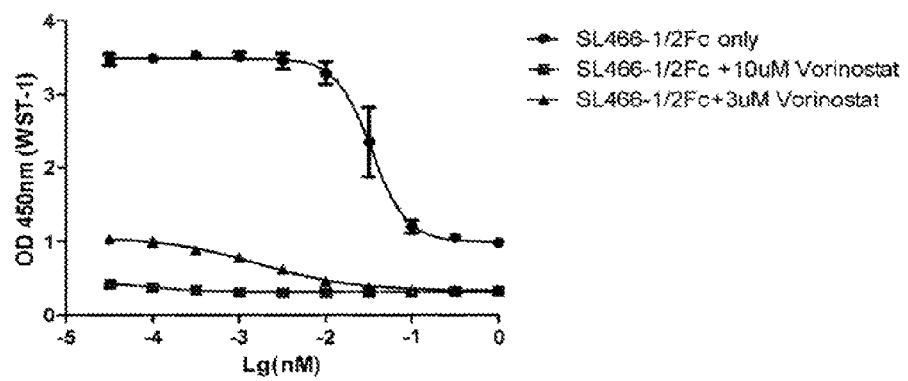
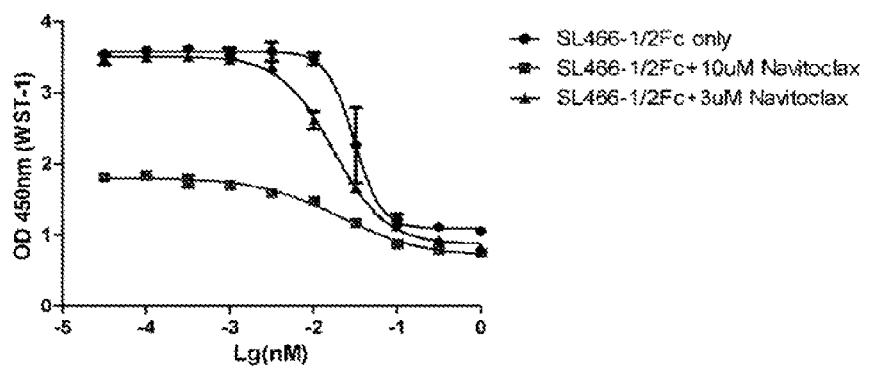

SURROGATE BINDING PROTEINS WHICH BIND DR4 AND/OR DR5

CROSS-REFERENCE TO RELATED APPLICATION

The present application is the U.S. National Phase of International Application No. PCT/US2012/071352, filed Dec. 21, 2012, which claims priority under 35 U.S.C. § 119(e) to U.S. provisional patent application No. 61/579,619, filed Dec. 22, 2011 and 61/604,992, filed Feb. 29, 2012. The aforementioned priority applications are incorporated herein by reference in their entireties.

SEQUENCE LISTING

The present application is amended to include a Sequence Listing in electronic format. The Sequence Listing is provided as a file entitled SLBIO002WOSEQLIST.TXT, created Dec. 19, 2012, which is 269,443 bytes in size. The information in the electronic format of the Sequence Listing is incorporated herein by reference in its entirety.

FIELD OF THE INVENTION

The present invention generally relates to surrogate light chain constructs and other binding proteins.

BACKGROUND

Apoptosis plays a variety of roles, including the elimination of abnormal cells such as tumor cells. Apoptosis can be activated by two pathways: an intrinsic pathway involving mitochondrial dysfunction and an extrinsic pathway via death receptor stimulation. Death receptors are cell surface receptors in the tumor necrosis factor receptor (TNFR) superfamily and include TNF-R1, CD95 (APO-1, Fas), TNF-related apoptosis-inducing ligand receptor 1 (TRAIL-R1; DR4) and TRAIL-R2 (DR5). Death receptors comprise a cytoplasmic death domain and binding of their respective ligands leads to activation. TNF-related apopotosis-inducing ligand (TRAIL) is a ligand for DR4 and DR5. Ligand binding leads to association with the Fas-Associated Death Domain (FADD). This adaptor recruits caspase-8 and caspase-10 to form a Death-Inducing Signaling Complex (DISC), leading to effector caspase activation and cell death.

TNF-R1 and CD95 activation has been shown to efficiently kill tumor cells. Thus, cancer therapies have been implemented that attempt to induce apoptosis of tumor cells by activating these death receptors using ligands and agonist antibodies. However, such efforts have been limited by the severe side effects that have been observed. On the other hand, activation of DR4 and DR5 has been shown to selectively eliminate cancer cells without life-threatening toxicity, and the ligand has been shown to have synergistic effects with other chemotherapeutics in killing tumor cells without additional side effects.

SUMMARY

In some embodiments, a sur-binding protein ("SBP") is provided. The SBP can comprise a VpreB sequence, a λ5 sequence, or a VpreB sequence and a λ5 sequence; and a heavy chain variable region amino acid sequence that is paired with the VpreB sequence, the λ5 sequence, or the VpreB sequence and the λ5 sequence to form a sur-binding protein. The sur-binding protein binds to a DR4 receptor, a DR5 receptor or both DR4 and DR5 receptors. In some embodiments the SBP binds to DR4 but not DR5. In some embodiments the SBP binds to DR5 but not DR4. In some embodiments the SBP binds to both DR4 and DR5 but does not bind to decoy receptors. The SBP may act as an agonist to DR4, DR5 or DR4 and DR5.

In some embodiments, a bispecific sur-binding protein is provided. The bispecific sur-binding protein can comprise a first VpreB sequence, a first λ5 sequence, or a first VpreB sequence and a first λ5 sequence and a first heavy chain variable region amino acid sequence that is paired with the first VpreB sequence, the first λ5 sequence, or the first VpreB sequence and the first λ5 sequence to form a first sur-binding protein binding site. The sur-binding protein binding site binds to and/or activates a DR4 receptor or a DR5 receptor. The bispecific SBP can further comprise a second VpreB sequence, a second λ5 sequence, or a second VpreB sequence and a second λ5 sequence; and a second heavy chain variable region amino acid sequence that is paired with the second VpreB sequence, the second λ5 sequence, or the second VpreB sequence and the second λ5 sequence to form a second sur-binding protein site. In some embodiments the second sur-binding protein site binds to and/or activates a second target, for example the other of the DR4 receptor or a DR5 receptor targeted by the first SBP binding site. In some embodiments the second sur-binding protein site binds to and/or inhibits a target involved in cancer pathogenesis that is not a DR4 or DR5 receptor.

In some embodiments, a bispecific sur-binding protein is provided. The SBP can comprise a VpreB sequence, a λ5 sequence, or a VpreB sequence and a λ5 sequence, a first heavy chain variable region amino acid sequence that is paired with the VpreB sequence, the λ5 sequence, or the VpreB sequence and first λ5 sequence to form a first binding site. The first sur-binding protein binding site binds to and/or activates a DR4 or DR5 receptor. The SBP can further comprise a light chain variable region. The SBP can further comprise a second heavy chain variable region amino acid sequence that is paired with the light chain variable region to form a second binding site, wherein said second binding site binds to and/or activates a second target, for example the other of the DR4 receptor or DR5 receptor targeted by the first binding site. In some embodiments the second binding site binds to and/or inhibits a target involved in cancer pathogenesis that is not DR4 or DR5.

In some embodiments a dual DR4 and DR5 agonist SBP is provided. In some embodiments the dual agonist SBP may bind to human DR4 and human DR5 as well as nonhuman primate DR4 and DR5, such as cyno DR4 and DR5. In some embodiments the dual agonist SBP does not bind to decoy receptors. In some embodiments the dual DR4 and DR5 agonist SBP comprises one or more binding domains from SL466 (also referred to herein as 3706-A02) or SL231 (also referred to herein as 3631-G09).

In some embodiments, a sur-binding protein is provided that can reduce cancer cell proliferation, cancer cell growth, or cancer cell proliferation and growth, where the cancer cells express DR4 and/or DR5.

In some embodiments, provided herein are antibodies that bind DR4 and/or DR5 and that can reduce cancer cell proliferation, cancer cell growth, or cancer cell proliferation and growth, wherein the cancer cell is driven by overexpression of ErbB2.

In some embodiments, provided herein are antibodies and/or SBPs that bind to a same or an overlapping epitope of any of the sur-binding proteins provided herein.

In some embodiments, an antibody that displaces any one of the sur-binding proteins provided herein is provided, when the antibody binds to an epitope on DR4, DR5 or DR4 and DR5.

In some embodiments, methods for stimulating apoptosis in cells that express DR4, DR5 or DR4 and DR5 are provided. The methods can comprise providing a DR4 and/or DR5 agonist sur-binding protein to cells that express DR4 and/or DR5. The cells may be, for example, tumor cells. In some embodiments the SBP is a dual DR4 and DR5 receptor agonist, such as SL466 (3706-A02) or SL231 (3631-G09) or an SBP comprising one or more CDRs from SL466 or SL231. In some embodiments the cells differentially express DR4 and DR5.

In some embodiments, methods for suppressing proliferation of cells that express DR4, DR5 or DR4 and DR5 are provided. The methods can comprise providing a DR4 and/or DR5 agonist sur-binding protein to cells that express DR4 and/or DR5. The cells may be, for example, tumor cells. In some embodiments the SBP is a dual DR4 and DR5 receptor agonist, such as SL466 (3706-A02) or SL231 (3631-G09) or an SBP comprising one or more CDRs from SL466 or SL231. In some embodiments the cells differentially express DR4 and DR5.

In some embodiments, a method for killing cancerous cells in a subject are provided. The methods comprise identifying a subject having a cancerous cell, wherein said cancerous cell expresses DR4, DR5 or DR4 and DR5, and administering to the subject a DR4, DR5 or DR4 and DR5 agonist sur-binding protein in an amount sufficient to bind to and activate DR4, DR5 or DR4 and DR5 on the cancerous cell, thereby activating a death receptor pathway. Activation of the death receptor pathway can result in apoptosis of the cancerous cell, thereby killing the cell. In some embodiments the SBP is a dual DR4 and DR5 receptor agonist, such as SL466 (3706-A02) or SL231 (3631-G09) or an SBP comprising one or more CDRs from SL466 or SL231. In some embodiments the cancerous cell differentially expresses DR4 and DR5.

In some embodiments, a method of treating cancer is provided. The method comprises identifying a subject to receive a treatment for cancer, wherein cells associated with said cancer express DR4, DR5 or DR4 and DR5; and administering to the subject a DR4, DR5 or DR4 and DR5 sur-binding protein or antigen binding portions thereof. In some embodiments the SBP is a dual DR4 and DR5 receptor agonist, such as SL466 (3706-A02) or SL231 (3631-G09) or an SBP comprising one or more CDRs from SL466 or SL231. In some embodiments the SBP may be conjugated to a therapeutic agent, such as a toxin In some embodiments, a method of treating cancer is provided. The method comprises administering a chemotherapeutic or a biologic to a subject and administering a DR4, DR5 or DR4 and DR5 agonist SBP to a subject. In some embodiments the SBP is a dual DR4 and DR5 receptor agonist, such as SL466 (3706-A02) or SL231 (3631-G09) or an SBP comprising one or more CDRs from SL466 or SL231. In some embodiments the SBP may be conjugated to a therapeutic agent, such as a toxin.

BRIEF DESCRIPTION OF THE DRAWINGS

FIG. 4 is a sequence alignment of human DR4, DR5, DcR1 and DcR2 extracellular domains.

FIGS. 5A-5C illustrate the results of tests of SBP binding to human DR4, human DR5 and mouse DR5.

FIG. 6 is an alignment of human DR4, human DR5 and mouse DR5 TRAIL-binding domain amino acid sequences.

FIGS. 7C and 7D illustrate the results of bivalent SBP binding to human DR4 and DR5, human decoy receptors DcR1 and DcR2, and Osteoprotegrin.

FIGS. 11A-11C illustrate activation of apoptosis inducing caspases by cross-linked, bivalent anti-death receptor SBPs.

FIGS. 16A-16F illustrate the antiproliferative effects of cross-linked, bivalent SBPs in combination with chemotherapeutic agents in the colo205 colon cancer cell line.

FIG. 26 shows the alignment of human VpreB1 (SEQ ID NO: 1) and human λ5 (SEQ ID NO: 6) with antibody λ chain variable (SEQ ID NO: 501) and constant regions (SEQ ID NO: 17). VpreB1 shares some sequence similarity to antibody λ chain variable regions, while λ5 shares some similarly to antibody λ chain constant regions and framework region 4. The boxed regions identify VpreB1 and λ5 loop regions 1 (LR1), 2 (LR2) and 3 (LR3).

FIG. 30 is the alignment of human VpreB1 sequences with antibody λ5 light chain variable region germline sequences. Regions with the highest degree of sequence similarity are boxed. As shown in the figure, VpreB1 shows only 56%-62% (amino acids 2 to 97) sequence identity to the λ5 light chain variable region germline sequences.

FIG. 31 is the alignment of a λ5 sequence with an antibody λ light chain constant region sequence. As shown in the figure, the aligned λ5 sequence shows only 62% (amino acids 97 to 209) sequence identity to the corresponding antibody λ light chain constant region sequence.

FIG. 32 is the alignment of a λ5 sequence with an antibody κ light chain constant region sequence. As shown in the figure, the aligned λ5 sequence shows only 35% (amino acids 105 to 209) sequence identity to the corresponding antibody κ light chain constant region sequence.

FIGS. 33A-33D show the human VpreB1 sequence of SEQ ID NO: 1. the mouse VpreB2 sequences of SEQ ID NOS: 2 and 3; the human VpreB3 sequence of SEQ ID NO: 4, the human λ5 sequence of SEQ ID NO: 5 and the human λ5-like protein sequence of SEQ ID NO: 6, and sequences of various constructs used in the Examples.

FIG. 35 provides the amino acid sequence of the heavy chain variable region and heavy chain CDR1, CDR2 and CDR3 regions of an SBP (3631) that binds DR4 and DR5.

FIGS. 36A-36R provide the amino acid sequences of the heavy chain variable region and heavy chain CDR1, CDR2 and CDR3 regions of a number of SBPs that bind DR4, DR5 or DR4 and DR5.

FIG. 37 provides the amino acid sequences of DR4.

FIG. 38 provides the amino acid sequences of DR5.

FIGS. 44A-44B illustrate the anti-proliferative effects of cross-linked dual DR4 and DR5 agonist SBPs in combination with chemotherapeutic treatment in the PANC-1 pancreatic cancer cell line.

FIGS. 45A-45B illustrate the anti-proliferative effects of cross-linked dual DR4 and DR5 agonist SBPs in combination with chemotherapeutic treatment in the MiaPaCa pancreatic cancer cell line.

DETAILED DESCRIPTION OF THE PREFERRED EMBODIMENT

Figure 1A:
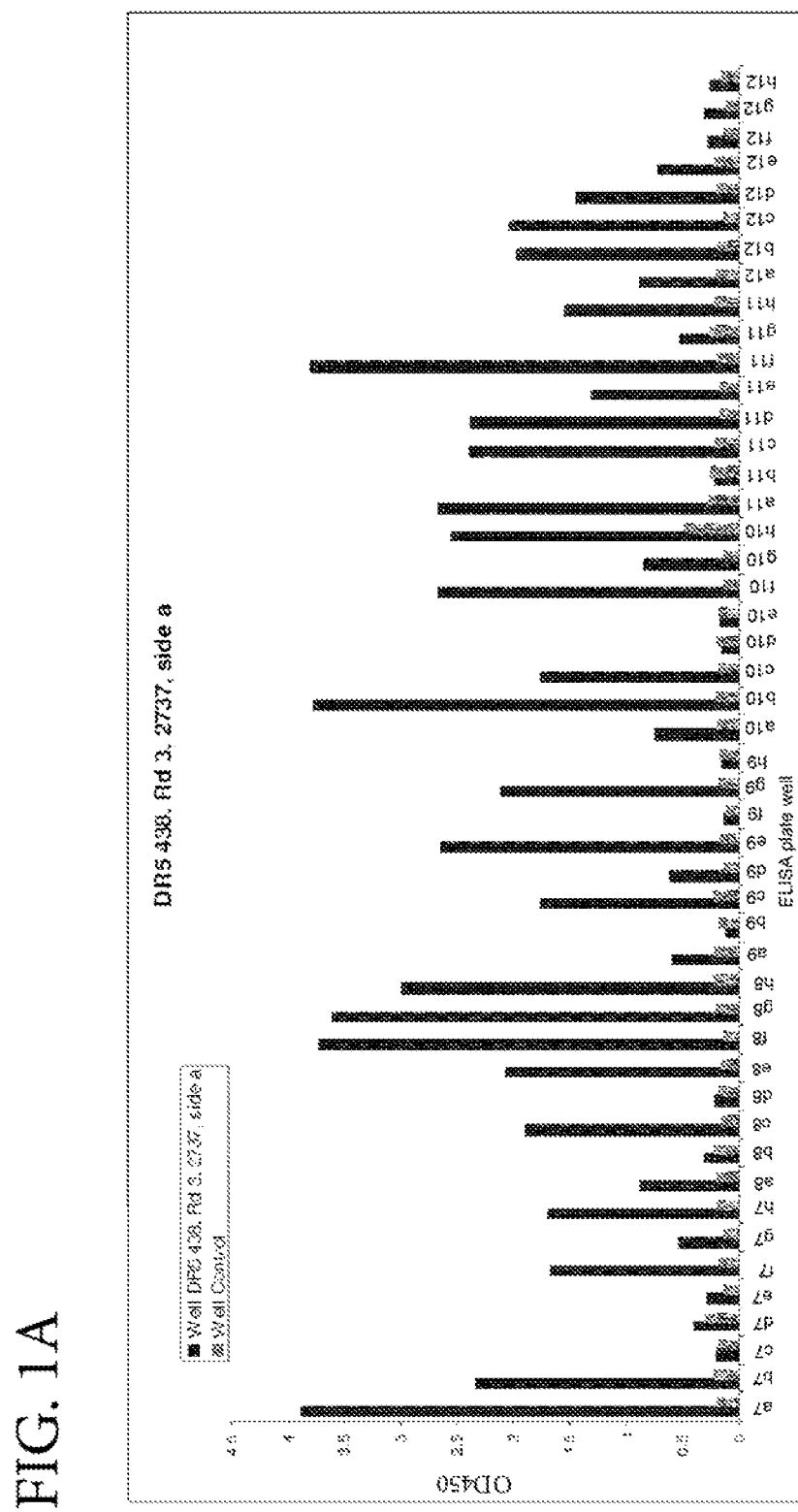
FIGS. 1A and 1B illustrate binding of clones from phage-display screening to DR5.

Death receptor 4 (DR4) and death receptor 5 (DR5) activation can lead to apoptosis and, in some instances, to selective apoptosis in cancer cells relative to healthy cells. In some embodiments surrogate binding proteins (SBPs) are provided that can bind to DR4 and/or DR5. In some embodiments SBPs are provided that bind to DR5 but not DR4. In some embodiments the SBPs can be DR4 and/or DR5 agonists and thus able to activate DR4 and/or DR5. Such activation can stimulate apoptosis in cells comprising the activated receptor(s). In some embodiments, antibodies or antibody-like molecules that bind DR4 and/or DR5 are provided, rather than SBPs. Such antibodies can, however, include the SBP's heavy chain variable region, or one or more of the heavy chain CDRs of the SBP, as described herein. The SBPs, antibodies or antibody-like molecules that bind to and activate DR4 and/or DR5 can be used therapeutically in instances where cell death and/or reduction of cellular proliferation is desirable, for example in the treatment of cancer. In some embodiments, the SBPs, antibodies or antibody-like molecules are combined with one or more additional therapeutic agents.

The present specification first provides a list of definitions and/or embodiments. The specification then goes on to discuss various embodiments of the SBPs and/or antibodies. That section is then followed by a description of various aspects regarding SBPs generically (setting forth additional embodiments for the specific SBPs, exemplary VpreB and lambda 5 sequences, etc.). That section is then followed by a set of examples for DR4/DR5 embodiments, which is then followed by a set of examples regarding SBPs generally (which, of course, are contemplated in combination with the specific SBP embodiments disclosed herein). The headings and sections provided herein are provided for convenience only and are not to be read as limiting in any way on the embodiments or combinations provided by this disclosure to those of skill in the art.

A. Definitions

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which can be used in the practice of the present invention. Indeed, the present invention is in no way limited to the methods and materials described. For purposes of the present invention, the following terms are defined below.

The term "surrogate light chain," as used herein, refers to either a VpreB, λ5 or a VpreB and a λ5 protein.

The term "VpreB" is used herein in the broadest sense and refers to any native sequence or variant VpreB polypeptide, specifically including, without limitation, human VpreB1 of SEQ ID NO: 1, mouse VpreB2 of SEQ ID NOS: 2 and 3, human VpreB3 of SEQ ID NO: 4 and isoforms, including splice variants and variants formed by posttranslational modifications, other mammalian homologues thereof, as well as variants of such native sequence polypeptides.

The term "λ5" is used herein in the broadest sense and refers to any native sequence or variant λ5 polypeptide, specifically including, without limitation, mouse λ5 of SEQ ID NO: 5, human λ5 of SEQ ID NO: 6, and their isoforms, including splice variants and variants formed by posttranslational modifications, other mammalian homologous thereof, as well a variant of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody A or K light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another embodiment the "variant VpreB polypeptide" can contain up to 80%, or up to 90%, or up to 100% antibody light chain variable framework regions. In another preferred embodiment, the "variant VpreB polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another embodiment the "variant λ5 polypeptide" can contain up to 80%, or up to 90%, or up to 100% antibody light chain variable J regions. In another embodiment the "variant λ5 polypeptide" can contain up to 80%, or up to 90%, or up to 100% antibody light chain constant regions. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

Percent amino acid sequence identity can be determined using the sequence comparison program NCBI-BLAST2 (Altschul et al., *Nucleic Acids Res.* 25:3389-3402 (1997)). The NCBI-BLAST2 sequence comparison program can be downloaded from http://followed by www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "surrogate light chain sequence," as defined herein, means any polypeptide sequence that comprises a "VpreB sequence" and/or a "λ5 sequence," as hereinabove defined. The "surrogate light chain sequence," as defined herein, specifically includes, without limitation, the human VpreB1 sequence of SEQ ID NO 1, the mouse VpreB2 sequences of SEQ ID NOS: 2 and 3, and the human VpreB3 sequence of SEQ ID NO: 4, and their various isoforms, including splice variants and variants formed by posttranslational modifications, homologues thereof in other mammalian species, as well as fragments and variants thereof. The term "surrogate light chain sequence" additionally includes, without limitation, the human λ5 sequence of SEQ ID NO: 6, the mouse sequence of SEQ ID NO: 5, and their isoforms, including splice variants and variants formed by posttranslational modifications, homologues thereof in other mammalian species, as well as fragments and variants thereof The term "surrogate light chain sequence" additionally includes a sequence comprising both VpreB and λ5 sequences as hereinabove defined.

For the three-dimensional structure of the pre-B-cell receptor (pre-BCR), including the structure of the surrogate light chain (SLC) and its components see, e.g. Lanig et al., *Mol. Immunol.* 40(17): 1263-72 (2004).

The surrogate light chain sequence can be optionally conjugated to a heterogeneous amino acid sequence, or any other heterogeneous component, to form a "surrogate light chain construct" herein. Thus, the term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the SBPs herein. Thus, a "heterogenous amino acid sequence" relative to a VpreB is any amino acid sequence not associated with native VpreB in its native environment, including, without limitation, λ5 sequences that are different from those λ5 sequences that, together with VpreB, form the surrogate light chain on developing B cells, such as amino acid sequence variants, e.g. truncated and/or derivatized λ5 sequences. A "heterogeneous amino acid sequence" relative to a VpreB also includes λ5 sequences covalently associated with, e.g. fused to, VpreB, including native sequence λ5, since in their native environment, the VpreB and λ5 sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the term "target" is a substance that interacts with a polypeptide herein. Targets, as defined herein, specifically include antigens with which the lambda-5-containing constructs, VpreB-containing constructs, or both the lambda-5-containing constructs and the VpreB-containing constructs of the present invention interact. In some embodiments, as defined herein, "targets" specifically include antigens with which the heavy chain interacts, e.g., CDRH1, CDRH2, CDRH3, and any combination. Preferably, interaction takes place by direct binding.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids can be used as desired. Thus, modified and unusual amino acids listed in 37 CFR 1.822 (b)(4) are specifically included within this definition and expressly incorporated herein by reference. Amino acids can be subdivided into various sub-groups. Thus, amino acids can be grouped as having a nonpolar side chain (e.g., Ala, Cys, Gly, Ile, Leu, Met, Phe, Pro, Trp, Val); a negatively charged side chain (e.g., Asp, Glu); a positively charged side chain (e.g., Arg, His, Lys); or an uncharged polar side chain (e.g., Asn, Gln, Gly, Ser, Thr, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp,), amides (Asn, Gln), acidic (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides can be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" to a specified residue is meant insertion within one to two residues thereof. The insertion can be N-terminal or C-terminal to the specified residue.

An "amino acid substitution" refers to the replacement of at least one existing amino acid residue in a predetermined amino acid sequence with another different "replacement" amino acid residue. The replacement residue or residues can be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244: 182 (1989) and Ellman et al., supra, can be used. Briefly, these procedures involve chemically activating a suppressor tRNA with a non-naturally occurring amino acid residue followed by in vitro transcription and translation of the RNA An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) can be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

In the context of the present invention, the term "antibody" (Ab) is used in its broadest sense. This includes, for example, a native antibody composed of both a recombined heavy chain, a product typically derived from V(D)J gene recombination, and a recombined light chain, also a product typically derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J Mol. Biol.* 186:651 (1985); Novotny and Haber, *Proc. Natl. Acad. Sci. U.S.A.* 82:4592 (1985).

The term "monoclonal antibody" as used herein refers to an antibody obtained from or prepared as a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is typically directed against a single determinant on the antigen. Monoclonal antibodies can be prepared using any art recognized technique and those described herein such as, for example, a hybridoma method, as described by Kohler et al. (1975) Nature, 256:495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clackson et al., Nature, 352:624-628 (1991) and Marks et al., J. Mol. Biol., 222:581-597 (1991). Monoclonal antibodies include chimeric antibodies, human antibodies and humanized antibodies and can occur naturally or are recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies can have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, cannot naturally exist within the human antibody germline repertoire in vivo.

The term "chimeric immunoglobulin" or "chimeric antibody" refers to an immunoglobulin or antibody or SBP with at least one variable region derived from a first species and at least one constant region derived from a second species. Chimeric immunoglobulins or antibodies or SBPs can be constructed, for example by genetic engineering.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. The human antibody can have twenty or more positions replaced with amino acid residues which are not part of the human germline immunoglobulin sequence. In some embodiments, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A "bispecific" or "bifunctional" Surrobody™ binding protein and/or antibody is an artificial hybrid SBP and/or antibody having two different heavy/light chain pairs and two or more different binding sites. Bispecific SBPs and/or antibodies can be produced by a variety of methods including fusion of hybridomas or linking of Fab' fragments. See, e.g., Songsivilai & Lachmann, (1990) Clin. Exp. Immunol. 79, 315-321; Kostelny et al. (1992) J. Immunol. 148, 1547-1553. In some embodiments, a bispecific SBP or antibody includes binding sites for both DR4 and DR5. In some embodiments the bispecific SBP or antibody binds to and/or activates DR4 and DR5. In some embodiments the bispecific antibody and/or SBP induces apoptosis in cells comprising DR4 and/or DR5.

As used herein, a "heterologous" antibody is defined in relation to the transgenic non-human organism or plant producing such an antibody.

An "isolated" antibody, as used herein, is intended to refer to an antibody which is substantially free of other antibodies having different antigenic specificities (e.g., an isolated antibody that specifically binds to DR5 is substantially free of antibodies that specifically bind antigens other than DR5). In addition, an isolated antibody is typically substantially free of other cellular material and/or proteins. In some embodiments, a combination of "isolated" antibodies having different DR4 and/or DR5 binding specificities are combined in a well defined composition.

As used herein, "isotype" refers to the antibody class (e.g., IgM or IgG1) or SBP that is encoded by heavy chain constant region genes. In some embodiments, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, an antibody is of the IgG 1 isotype. In some embodiments, an antibody is of the IgG2 isotype.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence regions in a gene encoding an antibody. Non-classical isotype switching can occur by, for example, homologous recombination between human sigma$_{mu}$ and human .SIGMA$_{mu}$ (.delta.-associated deletion). Alternative non-classical switching mechanisms, such as intertransgene and/or interchromosomal recombination, among others, can occur and effectuate isotype switching.

The term "variable" with reference to SBP or antibody chains (for heavy and antibody light chains, but not for the surrogate light chain) is used to refer to portions of the SBP and/or antibody chains which differ extensively in sequence among SBP or antibody heavy chains and participate in the binding and specificity of each particular SBP and/or antibody for its particular antigen. Such variability is concentrated in three segments called hypervariable regions both in the light chain and the heavy chain variable domains for antibodies (and just the heavy chain variable domains for the SBPs (but in both the light chain and the heavy chain variable domains for antibodies). The more highly conserved portions of variable domains are called the framework region (FR). The variable domains of native heavy and antibody light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669). The constant domains are not involved directly in binding an antibody and/or SBP to an antigen, but exhibit various effector functions, such as participation of the antibody and/or the SBP in antibody-dependent or SEP-dependent cellular toxicity, respectively.

The term "hypervariable region" when used herein refers to the amino acid residues of an antibody and/or SBP which are primarily responsible for antigen-binding. The hypervariable region comprises amino acid residues from a "complementarity determining region" or "CDR" that has a great propensity for target contact (i.e., residues 30-35 (H1), 47-58 (H2) and 93-101 (H3) in the heavy chain variable domain; MacCallum et al., *J Mol Biol*. 262(5):732-45 (1996)). Alternatively they are defined by others to similar regions see Chothia and/or Kabat.

The term "loop region" ("LR"), "LR1 region" and "LR2" denotes a region in the VpreB that forms a looped structure adjacent, or proximal, to heavy chain CDRs. "Loop region" or "LR3 region" can also denote the small predicted loop structure (approximately 10 amino acids long) created through recombinant fusion of 1) VpreB and λ5, or 2) VpreB and constant light chain that may contain a J-region, or 3) Variable light region, with or without a J-region and λ5.

The term "framework region" refers to the art recognized portions of an antibody and/or SBP variable region that exist between the more divergent regions. Such framework regions are typically referred to as frameworks 1 through 4

(FR1, FR2, FR3, and FR4) and provide a scaffold for holding, in three-dimensional space, the three CDRs found in a heavy or light chain antibody and/or SBP variable region, such that the CDRs can form an antigen-binding surface. As will be appreciated by those of skill in the art, minor variations are possible and contemplated for various embodiments involving framework regions. The term "FR analogous region", "FR1 analogous region", "FR2 analogous region", "FR3 analogous region," or "FR4 analogous region" denotes a region in the VpreB or λ5 that would otherwise correspond to a FR region (or FR1, FR2, FR3, or FR4 region respectively) in an antibody's light chain, or otherwise lies adjacent to the "loop regions".

Depending on the amino acid sequence of the constant domain of their heavy chains, antibodies can be assigned to different classes. There are five major classes of antibodies IgA, IgD, IgE, IgG, and IgM, and several of these can be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof Examples of antibody fragments include, but are not limited to, Fab, Fab', F(ab')$_2$, Dab, scFv, and (scFv)$_2$ fragments. "SBP fragments" comprise a corresponding portion of a full length SBP, generally the antigen binding or a variable domain thereof. Examples of SBP fragments include, but are not limited to, monovalent SBP, monovalent SBP', Sab, Sab', S(ab')$_2$, scSv, and (scSv)$_2$ fragments. The term "Sur-binding protein" or "SBP" encompasses both full length surroglobulins (bivalent SBP) and binding fragments thereof, including, but not limited to monovalent SBP, bivalent SBP, (2-piece or 3 piece), single chain SBP (scSv), and/or SLC domain As used herein the term "antibody binding region" refers to one or more portions of an immunoglobulin or antibody variable region capable of binding a target. Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody. Examples of antibody binding regions encompassed within the term include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242, 423-426; and Huston et al. (1988) Proc. Natl. Acad. Sci. USA 85, 5879-5883). Such single chain antibodies are also intended to be encompassed within the term "antibody binding region" of an antibody. These antibody fragments are obtained using conventional techniques known to those with skill in the art, and the fragments are screened for utility in the same manner as are intact antibodies. Antibody binding regions can be produced by recombinant DNA techniques, or by enzymatic or chemical cleavage of intact immunoglobulins.

As used herein the term "Sur-binding protein" or "SBP" refers to one or more portions of a Surroglobulin or SBP variable region capable of binding an antigen or antigens. In some embodiments, the SBP binding region is or includes, for example, an antibody heavy chain (VH) (or variable region thereof), a heavy chain Fd region, a VpreB and/or lambda 5 and an antibody heavy chain (or variable region thereof) such as a monovalent SBP, a S(ab')2 (a F(ab')2 type structure) or single chain SBP (scSv), or a full length surroglobulin (bivalent SBP). Examples of SBP binding regions encompassed within the term include (i) a Surroglobulin which refers to a bivalent binding protein including the VpreB1 and/or lambda 5 or CL or, VL and lambda 5, $V_H$, CH1 domain, and an Fc (CH2 and CH3 domains); (ii) a monovalent SBP fragment, a monovalent fragment including the VpreB1 and/or lambda 5 or CL, $V_H$ and CH1 domains; (iii) a S(ab')$_2$ fragment, a bivalent fragment comprising two monovalent SBP fragments linked by a disulfide bridge at the hinge region; (iv) a Fd fragment consisting of the $V_H$ and CH1 domains; (v) a Sv fragment including the VpreB and/or lambda 5 and $V_H$ domains of a single arm of an antibody, (vi) a dAb including $V_H$ and VpreB and/or lambda 5 domains; (vii) a dAb fragment (Ward et al. (1989) Nature 341, 544-546), which includes of a $V_H$ domain; (viii) a dAb which includes a VH or a VpreB and/or lambda 5 domain; and (ix) an isolated complementarity determining region (CDR) or (x) a combination of two or more isolated CDRs which may optionally be joined by a synthetic linker. Furthermore, although the two domains of the Sv fragment, VpreB and/or lambda 5 and $V_H$, are coded for by separate genes, they can be joined, using recombinant methods, by a synthetic linker that enables them to be made as a single protein chain in which the VpreB and/or lambda 5 and $V_H$ regions pair to form monovalent molecules (referred here as single chain Sv (scSv); for corresponding antibody correlates see e.g., Bird et al. (1988) Science 242, 423-426; and Huston et al. (1988) Proc. Natl. Acad. Sci. USA 85, 5879-5883). Such single chain SBPs are also intended to be encompassed within the term "SBP binding region" of an SBP. These SBP fragments are obtained using conventional techniques known to those with skill in the art, and the fragments are screened for utility in the same manner as are intact antibodies or SBPs. SBP binding regions can be produced by recombinant DNA techniques, or by enzymatic or chemical cleavage of intact Surroglobulins.

In some embodiments, the heavy chain CDR is CDR1, CDR2, or CDR3. In some embodiments, two heavy chain CDRs are included, and can be selected from CDR1 and CDR2, CDR2 and CDR3, or CDR1 and CDR3. In some embodiments, the SBP comprises a surrogate light chain sequence and a heavy chain CDR1 (HCDR1), a heavy chain CDR2 (HCDR2), and a heavy chain CDR3 (HCDR3). In some embodiments, the SBP comprises a surrogate light chain sequence and a heavy chain variable region. In some embodiments, the SBP comprises a surrogate light chain sequence and a heavy chain sequence. The term SBP also encompasses monovalent SBPs, bivalent SBP, and other forms of variations on antibody type structures (including those outlined herein, for example, Fab, Fab', F(ab')$_2$, scFv, and (scFv)$_2$, except, for example, with at least one VpreB and/or lambda 5 sequence instead of the corresponding light chain section).

As used herein the term "binding region" refers to one or more portions of a binding protein, such as a SBP, capable of binding a target. Typically, the binding region is, for example, an antibody light chain (VL) (or variable region thereof and/or surrogate light chain), an antibody heavy chain (VH) (or variable region thereof), a heavy chain Fd region, a combined antibody light (and/or surrogate light chain) and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody. In some embodiments, the lambda 5 sequence and/or the VpreB sequence is employed in place of an antibody light chain or fragment thereof.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, is bound by a SBP and/or an antibody. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors." The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogenous polypeptide on its surface, and includes, without limitation, fl, fd, Pfl, and M13. The filamentous phage can contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

The term "activation" as used herein, refers to any statistically significant increase in biological activity. For example, "activation" can refer to an increase of about 10%, 20%, 30%, 40%, 50%, 60%, 70%, 80%, 90%, or 100% in biological activity. In some embodiments the biological activity may be apoptosis.

The term "inhibition" as used herein refers to any statistically significant decrease in biological activity. For example, "inhibition" can refer to a decrease of about 10%, 20%, 30%, 40%, 50%, 60%, 70%, 80%, 90%, or 100% of a biological activity. In some embodiments the biological activity may be cell proliferation.

The terms "treat" or "prevent" do not require complete treatment or complete prevention under all conditions. A slowing of the onset of a disorder or its symptoms or a decrease in the symptoms can be adequate "prevention" in some embodiments. Similarly, a decrease in the severity of the symptoms of the disorder can also be an effective treatment for a disorder.

The term "consensus sequence", as used herein with respect to complementarity determining regions (CDRs), refers to a composite or genericized sequence for a CDR that has been defined based on information as to which amino acid residues within the CDR are amenable to modification without detriment to antigen binding. Thus, in a "consensus sequence" for a CDR, certain amino acid positions are occupied by one of multiple possible amino acid residues at that position. For example, within a CDR, if antigen binding has been found to be unaffected by the presence of either a tyrosine or a phenylalanine at a particular position, then that particular position within the consensus sequence can be either tyrosine or phenylalanine (Y/F). Consensus sequences for CDRs can be defined, for example, by scanning mutagenesis (e.g., alanine scanning mutagenesis) of amino acid residues within the antibody and/or SBP CDRs, followed by evaluation of the binding of the mutants to the antigen to determine whether the mutated amino acid position affects antigen binding.

As used herein, the terms "specific binding," "specifically binds," "selective binding," and "selectively binds," mean that a SBP, antigen-binding portion thereof, or antibody exhibits appreciable affinity for a particular antigen or epitope and, generally, does not exhibit significant non-specific binding with other antigens and epitopes. "Appreciable" or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{11}$ $M^{-1}$, more preferably $10^8$ to $10^{12}$ $M^{-1}$. An antibody and/or SBP that "does not exhibit significant non-specific binding" is one that will not appreciably bind to an undesirable entity (e.g., an undesirable proteinaceous entity). For example, in some embodiments, an antibody and/or SBP or antigen-binding portion thereof that specifically binds to DR5 will appreciably bind that DR5 molecule but will not significantly react with other death receptor molecules and non-death receptor proteins or peptides. In some embodiments an antibody, antigen-binding portion thereof, or SBP can be considered to "specifically bind" two or more antigens or epitopes, for example if it exhibits appreciable affinity for the two or more particular antigens or epitopes but does not exhibit significant cross-reactivity with other antigens or other epitopes. For example, in some embodiments, an antibody and/or SBP or antigen-binding portion thereof that specifically binds to DR4 and DR5 will appreciably bind both DR4 and DR5 molecules but will not significantly react with other death receptor molecules and non-death receptor proteins or peptides. Specific or selective binding can be determined and analyzed according to any art-recognized means for determining such binding, including, for example, according to Scatchard analysis and/or competitive binding assays.

The term "$K_D$," as used herein, is intended to refer to the dissociation equilibrium constant of a particular SBP and/or antibody-antigen interaction or the affinity of an antibody and/or SBP for an antigen, preferably as measured using a surface plasmon resonance assay (e.g., as determined in a BIACORE 3000 instrument (GE Healthcare) using recombinant DR4 or DR5 as the analyte(s) and the antibody and/or SBP as the ligand) or a cell binding assay. In some embodiments, the SBP, antigen binding portion, and/or antibody binds an antigen (e.g., DR5 and/or DR4) with an affinity ($K_D$) of 50 nM or better (i.e., or less) (e.g., 40 nM or 30 nM or 20 nM or 10 nM or less). In some particular embodiments, an SBP, antigen binding portion, and/or antibody binds DR5 and/or DR4 with an affinity ($K_D$) of 8 nM or better (e.g., 7 nM, 6 nM, 5 nM, 4 nM, 2 nM, 1.5 nM, 1.4 nM, 1.3 nM, 1 nM, 0.5 nM, 0.1 nM, 0.05 nM or less. In some embodiments, an SBP, antigen binding portion, and/or antibody binds an antigen (e.g., DR5 and/or DR4) with an affinity ($K_D$) of approximately less than $10^{-7}$ M, such as approximately less than $10^{-8}$ M, $10^{-9}$ M or $10^{-10}$ M or even lower, and binds to the predetermined antigen with an affinity that is at least two-fold greater than its affinity for binding to a non-specific antigen (e.g., BSA, casein) other than the predetermined antigen or a closely-related antigen. The term "$K_{off}$" as used herein, is intended to refer to the off rate constant for the dissociation of an SBP and/or antibody from the antibody and/or SBP/antigen complex.

The term "EC50," as used herein, refers to the concentration of an SBP or an antigen-binding portion thereof and/or antibody, which induces a response, either in an in vitro or an in vivo assay, which is 50% of the maximal response, i.e, halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

In some embodiments, antibodies and/or SBPs are provided that bind the same or an overlapping epitope as the antibodies and/or SBPs for which amino acid sequences are disclosed herein, e.g., antibodies and/or SBPs that compete for binding to DR5 and/or DR4, or bind epitopes which overlap with epitopes bound by the antibodies or SBPs described herein. SBPs and/or antibodies that recognize the same epitope can be identified using routine techniques such as an immunoassay, for example, by showing the ability of one antibody and/or SBP to block the binding of another antibody and/or SBP to a target antigen, i.e., a competitive binding assay. Competitive binding is determined in an assay in which the immunoglobulin under test inhibits specific binding of a reference antibody and/or SBP to a common antigen, such as DR5 and/or DR4. Numerous types of competitive binding assays are known, for example: solid phase direct or indirect radioimmunoassay (MA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label MA using 1-125 label (see Morel et al., (1988) Mol. Immunol. 25(1):7); solid phase direct biotin-avidin EIA (Cheung et al., (1990) Virology 176:546); and direct labeled MA (Moldenhauer et al., (1990) Scand. J. Immunol. 32:77). Typically, such an assay involves the use of purified antigen (e.g., DR5 and/or DR4) bound to a solid surface or cells bearing either of these, an unlabeled test surroglobulin and a labeled reference immunoglobulin and/or SBP. Competitive inhibition is measured by determining the amount of label bound to the solid surface or cells in the presence of the test surroglobulin. Usually the test surroglobulin is present in excess. Usually, when a competing antibody and/or SBP is present in excess, it will inhibit specific binding of a reference antibody and/or SBP to a common antigen by at least 50-55%, 55-60%, 60-65%, 65-70% 70-75% or more.

The term "sample" refers to tissue, body fluid, or a cell from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained and appropriately prepared. Other patient samples, including urine, tear drops, serum, cerebrospinal fluid, feces, sputum, cell extracts etc. can also be useful for particular tumors.

The term "patient" includes human and other mammalian subjects that receive either prophylactic or therapeutic treatment.

As used herein, the term "subject" includes any human or non-human animal. For example, the methods and compositions disclosed herein can be used to treat a subject having cancer. In a preferred embodiment, the subject is a human. The term "non-human animal" includes all vertebrates, e.g., mammals and non-mammals, such as non-human primates, sheep, dog, cow, etc.

The terms "anti-cancer agent" and "antineoplastic agent" refer to drugs used to treat malignancies, such as cancerous growths. Drug therapy can be used alone, or in combination with other treatments such as surgery or radiation therapy. Several classes of drugs can be used in cancer treatment, depending on the nature of the organ involved. Anti-cancer agents for use in certain methods of the present invention include, among others, the agents in Table 0.1

TABLE 0.1

| Anti-Cancer Agent | Comments | Examples |
|---|---|---|
| Antibodies | Antibodies which bind IGF-1R (insulin-like growth factor type 1 receptor), which is expressed on the cell surface of must human cancers | A12 (fully humanized mAb) 19D12 (fully humanized mAb) CP751-871 (fully humanized mAb) H7CIO (humanized mAb) alphaIRS (mouse) scFV/FC (mouse/human chimera) EM/I64 (mouse) AMG 479 (fully humanized mAb; Amgen) IMCA 12 (fully humanized mAb; Imclone) NSC-742460 (Dyax) MR-0646, F50035 (Pierre Fabre Medicament, Merck) |
| | Antibodies which bind EGFR; Mutations affecting EGFR expression or activity can result in cancer | matuzumab (EMD72000) Erbitux ®/cetuximab (Imclone) Vectibix ®/panitumumab (Amgen) mAb 806 nimotuzumab (TheraCIM) INCB7839 (Incyte) |
| | Antibodies which bind cMET (mesenchymal epithelial transition factor); a member of the MET family of receptor tyrosine kinases) | AVEO (AV299) (AVEO) AMGI02 (Amgen) 5D5 (OA-5D5) (Genentech) |
| | Anti-ErbB3 antibodies | 1B4C3; 2DID12 (U3 PharmaAG) U3-1287/AMG888 (U3 PharmaIAmgen) MM6 (Merrimack) |
| | Anti-ErbB2 (HER2) antibodies | Herceptin ® (trastuzumab; Genentech/Roche) binds ectodomain Domain II of ErbB2; Omnitarg ® (pertuzumab; 2C4, RI273; Genentech/Roche) binds Domain N of ErbB2 |
| Small Molecules Targeting IGF1R | IGF-1R (insulin-like growth factor type 1 receptor), which is expressed on the cell surface 0 f must human cancers | NVP-AEW541-A BMS-536,924 (IH-benzoimidazol-2-yl)-IH pyridin-2-one) BMS-554,417 Cycloligan TAE226 PQ401 |
| Small Molecules Targeting EGFR | EGFR; Mutations affecting EGFR expression or activity can result in cancer | Iressa ®/gefitinib (AstraZeneca) CI-1033 (PD 183805) (Pfizer) TYVERB/lapatinib (GlaxoSmithKline) Tykerb ®/lapatinib ditosylate (SmithKline Beecham) Tarceva ®/Erlotinib HCL (OSI Pharma) PKI-166 (Novartis) PD-158780 EKB-569 Tyrphostin AG 1478(4-(3-Chloroanillino)-6,7-dimetboxyquinazoline) |
| Small Molecules Targeting ErbB2 | ErbB2, also known as HER2, a member of the ErbB family of receptors, which is expressed on certain cancer cells | HKI-272 (neratinib; Wyeth) KOS-953 (tanespimycin; Kosan Biosciences) |
| Small Molecules Targeting cMET | cMET (Mesenchymal epithelial transition factor); a member of the MET family of receptor tyrosine kinases) | PHA665752 ARQ 197 (ArQule) ARQ-650RP (ArQule) |
| Antimetabolites | An antimetabolite is a chemical with a similar structure to a substance (a | flourouracil (5-FU) capecitabine/XELODA ® (HLR Roche) 5-trifluoromethyl-2'-deoxyuridine |

TABLE 0.1-continued

| Anti-Cancer Agent | Comments | Examples |
|---|---|---|
| | metabolite) required for normal biochemical reactions, yet different enough to interfere with the normal functions of cells, including cell division. | metbotrexate sodium (Trexall) (Barr) raltitrexed/Tomudex ® (AstraZaneca) pemetrexed/Alimta ® (Lilly) tegafur cytosine arabinoside (Cytarabine, Ara-C)/ tioguanine/Lanvis ® (GlaxoSmithKline) 5-azacytidine 6-mercaptopurine (Mercaptopurine, 6-MP) azatbioprine/Azasan ® (AAIPHARMA LLC) 6-thioguanine (6-TG)/Purinethol ® (TEVA) pentostatin/Nipent ® (Hospira Inc.) fludarabine phosphate/Fludara ® (Bayer Health Care) cladribine/Leustatin ® (2-CdA, 2-chlorodeoxyadenosine) (Ortho Biotech) floxuridine (5-fluoro-2'-deoxyuridine)/ FUDR ® (Hospira, Inc,) |
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | Ribonucleotide Reductase Inhibitor (RNR) cyclophosphamide/Cytoxan ® (BMS)/ Neosar ® (TEVA) ifosfamide/Mitoxana ® (ASTA Medica) ThioTEPA (Bedford, Abraxis, Teva) BCNU → 1,3-bis(2-chloroethyl)-1-nitosourea CCNU → 1,-(2-chloroethyl)-3-cyclohexyl-l nitrosourea (methyl CCNU) hexamethylmelamine (altretamine, HMM)/ Hexalen ® (MGI Pharma Inc.) busulfan/Myleran ® (GlaxoSmithKline) procarbazine HCL/Matulane ® (Sigma Tau) Dacarbazine (DTIC ®) chlorambucil/Leukaran ® (SmithKline Beecham) Melphalan/Alkeran ® (GlaxoSmithKline) cisplatin (Cisplatinum, CDDP)/Platinol (Bristol Myers) carboplatin/Paraplatin (BMS) oxaliplatin/Eloxitan ® (Sanofi-Aventis US) Bendamustine carboquone carmustine chloromethine dacarbazine (DTIC) fotemustine lomustine mannosulfan nedaplatin nimustine prednimustine ranimustine satraplatin semustine streptozocin temozolomide treosulfan triaziquone triethylene melamine triplatin tetranitrate trofosfamide uramustine |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | doxorubicin HCL/Doxil ® (Alza) daunorubicin citrate/Daunoxome ® (Gilead) mitoxantrone HCL/Novantrone (EMD Serono) actinomycin D etoposide/Vepesid ® (BMS)/Etopophos ® (Hospira, Bedford, Teva Parenteral, Etc.) topotecan HCL/Hycamtin ® (GlaxoSmithKline) teniposide (VM-26)Vumon ® (BMS) irinotecan HCL(CPT-II)/ camptosar ® (Pharmacia & Upjohn) camptothecin (CPT) belotecan rubitecan |

TABLE 0.1-continued

| Anti-Cancer Agent | Comments | Examples |
| --- | --- | --- |
| Microtubule targeting agents | Microtubules are one of the components of the cytoskeleton. They have diameter of-24 nm and length varying from several micrometers to possibly millimeters in axons of nerve cells. Microtubules serve as structural components within cells and are involved in many cellular processes including mitosis, cytokinesis, and vesicular transport. | vincristine/Oncovin ® (Lilly)<br>vinblastine sulfate/Velban ®(discontinued) (Lilly)<br>vinorelbine tartrate/Navelbine ® (PierreFabre)<br>vindesine sulphate/Eldisine ® (Lilly)<br>paclitaxel/Taxol ® (BMS)<br>docetaxel/Taxotere ® (Sanofi Aventis US)<br>Nanoparticle paclitaxel (ABI-007)!<br>Abraxane ® (Abraxis BioScience, Inc.)<br>ixabepilone/IXEMPRA ™ (BMS)<br>larotaxel<br>ortataxel<br>tesetaxel<br>vinflunine |
| Kinase inhibitors | Tyrosine kinases are enzymes within the cell that function to attach phosphate groups to the amino acid tyrosine. By blocking the ability of protein tyrosine kinases to function, these compounds provide a tool for controlling cancerous cell growth. | imatinib mesylate/Gleevec (Novartis)<br>sunitinib malate/Sutent ® (Pfizer)<br>sorafenib tosylate/Nexavar ® (Bayer)<br>nilotinib hydrochloride monohydrate/ Tasigna ® (Novartis)<br>AMG 386 (Amgen)<br>axitinib (AG-013736; Pfizer, Inc.)<br>bosutinib (SKI-606; Wyeth)<br>brivanib alalinate (BMS-582664; BMS)<br>cediranib (AZD2171; Recentin, AstraZeneca)<br>dasatinib (BMS-354825: Sprycel ®; BMS)<br>lestaurtinib (CEP-701; Cephalon)<br>motesanib diphosphage (AMG-706; Amgen/Takeda)<br>pazopanib HCL (GW786034; Armala, GSK)<br>semaxanib (SU5416; Pharmacia)<br>vandetanib (AZD647; Zactima; AstraZeneca)<br>vatalanib (PTK-787; Novartis, Bayer Schering Pharma)<br>XL184 (NSC718781; Exelixis, GSK) |
| Protein synthesis inhibitors | Induces cell apoptosis | L-asparaginase/Elspar ® (Merck & Co.) |
| Immunotherapeutic agents | Induces cancer patients to exhibit immune responsiveness | Alpha interferon<br>Angiogenesis Inhibitor/Avastin ® (Genentech)<br>IL-2 → Interleukin 2 (Aldesleukin)/ Proleukin ® (Chiron)<br>IL-12 → Interleukin 12 |
| Hormonal therapies | Hormonal therapies associated with menopause and aging seek to increase the amount of certain hormones in the body to compensate for age-or disease-related hormonal declines. Hormonal therapy as a cancer treatment generally either reduces the level of one or more specific hormones, blocks a hormone from interacting with its cellular receptor or otherwise alters the cancer's ability to be stimulated by hormones to grow and spread. Such hormonal therapies thus include hormone antagonists and hormone synthesis inhibitors. In some instances hormone agonists can also be used as anticancer hormonal therapies. | Ttoremifene citrate/Fareston ® (GTX, Inc.)<br>fulvestrant/Faslodex ® (AstraZeneca)<br>raloxifene HCL/Evista ® (Lilly)<br>anastrazole/Arimidex ® (AstraZeneca)<br>letrozole/Femara ® (Novartis)<br>fadrozole (CGS 16949A)<br>exemestane/Aromasin ® (Pharmacia & Upjohn)<br>leuprolide acetate/Eligard ® (QTL USA)<br>Lupron ® (TAP Pharm.)<br>goserelin acetate/Zoladex ® (AstraZeneca)<br>triptorelin pamoate/Trelstar ® (Watson Labs)<br>buserelin/Suprefact ® (Sanofi Aventis)<br>nafarelin<br>cetrorelix/Cetrotide ® (EMD Serono)<br>bicalutamide/Casodex ® (AstraZeneca)<br>nilutamide/Nilandron ® (Aventis Pharm.)<br>megestrol acetate/Megace ® (BMS)<br>somatostatin Analogs (e.g., Octreotide acetate/ Sandostatin ® (Novartis))<br>abarelix (Plenaxis TM; Amgen)<br>abiraterone acetate (CB7630; BTG plc)<br>afunoxifene (TamoGel; Ascend Therapeutics, Inc.)<br>aromatase inhibitor (Atamestane plus toremifene; Intarcia Therapeutics, Inc.)<br>arzoxifene (Eli Lilly & Co)<br>Asentar ™; DN-101 (Novacea; Oregon Health Sciences U)<br>flutamide (Eulexin ®, Schering; Prostacur, Laboratorios Almirall, S.A)<br>letrozole (CGS20267) (Femara ®, Chugai; Estrochek ®, (Jagsonpal Pharmaceuticals Ltd;) |

TABLE 0.1-continued

| Anti-Cancer Agent | Comments | Examples |
|---|---|---|
| | | Delestrogen ®, estradiol valerate (Jagsonpal) magestrol acetate/Megace ® medroxyprogesteone acetate (Veraplex ®; Combiphar) MT206 (Medisyn Technologies, Inc.) nandrolone decanoate (Zestabolin ®; Mankind Pharma Ltd) tamoxifen (Taxifen ®, Yung Shin Pharmaceutical; Tomifen ®, Alkem Laboratories Ltd.) tamoxifen citrate (Nolvadex, AstraZeneca; soltamox, EUSA Pharma Inc; tamoxifen citrate SOPHARMA, Sopharma JSCo.) |
| Glucocorticoids | Anti-inflammatory drugs used to reduce swelling that causes cancer pain. | predinsolone dexamethasone/Decadron ® (Wyeth) prednisone (Deltasone, Orasone, Liquid Pred, Sterapred ®) |
| Aromatase inhibitors | Includes imidazoles The | ketoconazole |
| mTOR inhibitors | mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase (PI-3K) to cell growth, proliferation, and angiogenesis. | sirolimus (Rapamycin)/Rapamune ® (Wyeth) Temsirolimus (CCI-779)/Torisel ® (Wyeth) Deforolimus (AP23573) (Ariad Pharm.) Everolimus (RAD001)/Certican ® (Novartis) |
| Chemotherapeutic agents | | adriamycin, 5-fluorouracil, cytoxin, bleomycin, mitomycin C, daunomycin, carminomycin, aminopterin, dactinomycin, mitomycins, esperamicins, clofarabine, mercaptopurine, pentostatin, thioguanine, cytarabine, decitabine, floxuridine, gemcitabine (Gemzar), enocitabine, sapacitabine |
| Protein Kinase B (PKB) Inhibitors | | AKT Inhibitor Astex ® (Astex Therapeutics) AKT Inhibitors NERVIANO (Nerviano Medical Sciences) AKT Kinase Inhibitor TELIK (Telik Inc) AKT DECIPHERA (Deciphera Pharmaceuticals, LLC) perifosine (KRX0401, D-21266; Keryx Biopharmaceuticals Inc, AEterna Zentaris Inc) perifosine with Docetaxel (Keryx Biopharmaceuticals Inc, AEterna Zentaris Inc) perifosine with Gemcitabine (AEterna Zentaris Inc) perifosine with paclitaxel (AEterna Zentaris Inc) protein kinase-B inhibitor DEVELOGEN (DeveloGen AG) PX316 (Oncothyreon, Inc.) RX0183 (Rexahn Pharmaceuticals Inc) RX0201 (Rexahn Pharmaceuticals Inc) VQD002 (VioQuest Pharmaceuticals Inc) XL418 (Exelixis Inc) ZEN027 (AEterna Zentaris Inc) |
| Phosphatidylinositol 3-Kinase (PI3K) Inhibitors | | BEZ235 (Novartis AG) BGT226 (Novartis AG) CAL101 (Calistoga Pharmaceuticals, Inc.) CHR4432 (Chroma Therapeutics Ltd) Erk/PI3K Inhibitors ETERNA (AEtema Zentaris Inc) GDC0941 (Genentech Inc/Piramed |

TABLE 0.1-continued

| Anti-Cancer Agent | Comments | Examples |
|---|---|---|
| | | Limited/Roche Holdings Ltd) |
| | | enzastaurin HCL (LY317615; Enzastaurin; Eli Lilly) |
| | | LY294002/Wortmannin |
| | | P13K Inhibitors SEMAFORE (Semafore Pharmaceuticals) |
| | | PX866 (Oncothyreon, Inc.) |
| | | SF1126 (Semafore Pharmaceuticals) |
| | | VMD-8000 (VM Discovery, Inc.) |
| | | XL147 (Exelixis Inc) |
| | | XL147 with XL647 (Exelixis Inc) |
| | | XL765 (Exelixis Inc) PI-103 (Roche/Piramed) |
| Cyclin Dependent Kinase Inhibitors | | CYC200, R-roscovitine (Seliciclib; Cyclacel Pharma) NSC-649890, L86-8275, HMR-I275 (alvocidib; NCI) |
| TLr9, CD289 | | IMOxine (Merck KGaA) |
| | | HYB2055 (Idera) IMO-2055 (Isis Pharma) |
| | | 1018 ISS (DynavaxTechnologies/UCSF) |
| | | PF-3512676 (Pfizer) |
| Enzyme Inhibitor | | Ionafarnib(SCH66336; Sarasar; SuperGen, U Arizona) |
| Anti-TRAIL | | AMG-655 (Amgen, Aeterna Zentaris, Keryx Biopharma) |
| | | Apo2L/TRAIL, AMG951 (Genentech, Amgen) |
| | | PRO95780 or drozitumab (fully human mAb; Genentech) |
| | | CS-1008 ortigatuzumab (humanized mAb; Daiichi Sankyo) |
| MEK Inhibitors | [Mitogen-Activated Protein Kinase Kinase 1 (MAP2K1); Mitogen Activated Protein Kinase Kinase 2 (MAP2K2)] | ARRY162 (Array BioPharma Inc) |
| | | ARRY704 (Array BioPharma Inc) |
| | | ARRY886 (Array BioPharma Inc) |
| | | AS703026 (Merck Serono S.A) |
| | | AZD6244 (AstraZeneca Plc) |
| | | AZD8330 (AstraZeneca Plc) |
| | | RDEA119 (Ardea Biosciences, Inc.) |
| | | RDEA436 (Ardea Biosciences, Inc.) |
| | | XL518 (Exelixis Inc; Genentech Inc) |
| Miscellaneous Inhibitors | | Imprime PGG (Biothera) |
| | | CHR-2797 (AminopeptidaseM1 inhibitor; Chroma Therapeutics) |
| | | E7820, NSC 719239 (Integrin-alpha2 inhibitor, Eisai) |
| | | INCB007839 (ADAM 17, TACE Inhibitor; Incyte) |
| | | CNF2024, BIIB021 (Hsp90 Inhibitor; Biogen Idec) |
| | | MP470, HPK-56 (Kit/Mel/Ret Inhibitor; Schering-Plough) |
| | | SNDX-275/MS-275 (HDAC Inhibitor; Syndax) |
| | | Zarnestra TM, Tipifarnib, R115777 (Ras Inhibitor; Janssen Pharma) |
| | | volociximab; Eos 200-4, M200 (alpha581 integrin inhibitor; Biogen Idec; Eli Lilly/UCSF/PDL BioPharma) |
| | | apricoxib (TP2001; COX-2 Inhibitor, Daiichi Sankyo; Tragara Pharma) |

Other anti-cancer agents that may be used in some embodiments include Bortezomib (Velcade), a proteosome inhibitor (Takeda/Millenium); Obatoclax (Cepheid/Teva), a Bcl-2 family inhibitor; Navitoclax (Abbott/Genentech) a Bcl-2 and Bcl-xL inhibitor; and HGS 1029 (HGS/Aegera), a XIAP inhibitor.

Unless indicated otherwise, the term "DR4" refers to human DR4, for example as described in Pan, et al, Science 276, 111 (1997). DR4 protein sequences are provided in FIG. 4 (SEQ ID NO: 22), and in FIG. 37 (SEQ ID NOs: 474, 475, 476 and 477).

Unless indicated otherwise, the term "DR5" refers to human DR5, for example as described in Walczak, et al, EMBO J, v16, no 17 (1997). DR5 protein sequences are provided in FIG. 4 (SEQ ID NO: 24) and in FIG. 38 (SEQ ID NOs: 478, 479, 480, 481, 482).

An "antigen" is an entity (e.g., a proteinaceous entity or peptide) to which a SBP, antigen-binding portion thereof, and/or antibody binds. In various embodiments disclosed herein, an antigen is DR4. In some embodiments it is human DR4. In some embodiments an antigen is DR5 and can be, for example, human DR5.

The term "disease associated with DR4 and/or DR5 dependent signaling," or "disorder associated with DR4 and/or DR5 dependent signaling," as used herein, includes disease states and/or symptoms associated with a disease state, where increased levels of DR4 and/or DR5 and/or activation of cellular cascades involving DR4 and/or DR5 are found. In general, the term "disease associated with DR5 and/or DR5 dependent signaling" refers to any disorder, the onset, progression or the persistence of the symptoms of which requires the participation of DR4 and/or DR5. However, in some embodiments, diseases associated with DR4 and/or DR5 dependent signaling include disease states where an increased sensitivity to DR4, DR5 and/or agonists of DR4 and/or DR5 is seen. The term "disease associated with DR4 and/or DR5 dependent signaling" also includes disease states and/or symptoms associated with disease states where increased or decreased levels of DR4 and/or DR5 activity are found. Exemplary DR4 and/or DR5-mediated disorders include, but are not limited to, cancer and inflammation.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods disclosed herein is selected from melanoma, breast cancer, ovarian cancer, renal carcinoma, gastrointestinal/colon cancer (including gastric cancer), lung cancer, leukemia, non-Hodgkin's lymphoma and prostate cancer.

The term "effective amount," as used herein, refers to that amount of an antibody, an antigen binding portion thereof, and/or SBP that binds DR5 and/or DR4, which is sufficient to effect treatment of a disease or disorder by activation of DR5 and/or DR4.

A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 .mu.g to about 3,500 mg, about 5 .mu.g to about 3,000 mg, about 10 .mu.g to about 2,600 mg, about 20 .mu.g to about 2,575 mg, about 30 .mu.g to about 2,550 mg, about 40 .mu.g to about 2,500 mg, about 50 .mu.g to about 2,475 mg, about 100 .mu.g to about 2,450 mg, about 200 .mu.g to about 2,425 mg, about 300 .mu.g to about 2,000, about 400 .mu.g to about 1,175 mg, about 500 .mu.g to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody, antigen binding portion thereof, or and/or SBP according to the invention. Dosage regimens may be adjusted to provide the optimum therapeutic response. An effective amount is also one in which any toxic or detrimental effects (i.e., side effects) of an antibody, antigen binding portion thereof, and/or SBP are minimized and/or outweighed by the beneficial effects. Additional preferred dosages regimens are described further below in the section pertaining to pharmaceutical compositions.

Prognosis or diagnosis of a disease associated with DR4 and/or DR5 dependent signaling, can be carried out in some embodiments. Prior to therapeutic use of a Death Receptor agonist bivalent SBP or Sur-binding protein, an assessment may be made to the suitability of the approach, for example to ensure the target_cell population expresses DR5 and/or DR4. Radiolabeled or fluorescently labeled Sur-binding proteins can be used to demonstrate receptor expression on the target cells. Additionally, Death Receptor Sur-binding proteins may be used to assess the prognosis of a patient in some embodiments. For example, in colorectal cancer patients, detection of activated c-Met and DR5 has been correlated with improved survival compared to patients lacking the expression of either of the proteins.

In some embodiments, SBPs and antibodies disclosed herein are DR5 and/or DR4 agonists and stimulate apoptosis in cells comprising DR5 and/or DR4. Accordingly, the phrase "stimulation of apoptosis" as used herein, refers to the ability of an SBP, antigen binding portion, and/or antibody to statistically significantly increase apoptosis in a population of cells expressing DR5 and/or DR4, relative to an untreated (control) cell population. The cell population which expresses DR5 and/or DR4 can comprise naturally occurring cells or be a naturally occurring cell line, or can be recombinantly produced by introducing nucleic acids encoding DR5 and/or DR4 into one or more host cells. In some embodiments, the SBP, antigen binding portion thereof, and/or antibody increases apoptosis by at least 10%, or at least 20%, or at least 30%, or at least 40%, or at least 50%, or at least 60%, or at least 70%, or at least 80%, or at least 90%, or at least 91, 92, 93, 94, 95, 96, 97, 98, 99% or 100%, as determined, for example, by using art recognized techniques which measure cell death and/or other hallmarks of apoptosis. Cellular apoptosis can be assayed, for example, using art recognized techniques which measure cellular viability, metabolic activity, annexin V binding, apoptotic caspase activation, and/or rate of cell loss from a cell population due to terminal differentiation or cell death (e.g., using a CellTiter-Glo™. assay or thymidine incorporation). Exemplary assays for measuring apoptosis are described below. In some embodiments, any of the SBPs, antigen-binding portion thereof, and/or antibodies disclosed herein can be used to increase apoptosis in a population of cells. In some embodiments, a method for increasing apoptosis can comprise contacting a population of cells with one or more DR4 and/or DR5 agonist SBPs, antigen-binding portion thereof or antibodies disclosed herein.

In some embodiments, SBPs, antigen-binding fragments thereof and/or antibodies disclosed herein are DR5 and/or DR4 agonists and inhibit proliferation of cells comprising DR5 and/or DR4. The phrase "inhibition of proliferation" of a cell expressing DR4 and/or DR5, as used herein, refers to the ability of an SBP, an antigen-binding portion thereof, and/or antibody to statistically significantly decrease proliferation of a cell expressing DR5 and/or DR4 relative to the proliferation in the absence of the SBP, antigen-binding fragment and/or antibody. In some embodiments, the proliferation of a cell expressing DR5 and/or DR4 (e.g., a cancer cell) may be decreased by at least 10%, or at least 20%, or at least 30%, or at least 40%, or at least 50%, or at least 60%, or at least 70%, or at least 80%, or at least 90%, or at least 91, 92, 93, 94, 95, 96, 97, 98, 99%, or 100% when the cells are contacted with an SBP, antigen binding portion thereof, and/or antibody, relative to the proliferation measured in the absence of the SBP, antigen binding portion thereof, and/or antibody (control). Cellular proliferation can be assayed using art recognized techniques which measure rate of cell division, the fraction of cells within a cell population undergoing cell division, and/or rate of cell loss from a cell population due to terminal differentiation or cell death (e.g., using a CellTiter-Glo™. assay or thymidine incorporation). Exemplary assays for measuring proliferation are described below.

The term "human SBP," as used herein, is intended to include SBPs having variable regions in which both the framework and other regions are derived from human heavy chain immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the SBP contains a constant region, the constant region also is derived from human heavy chain immunoglobulin sequences. The human SBPs can include amino acid residues not encoded by human germline immunoglobulin sequences (e.g., mutations introduced by random or site-specific mutagenesis in vitro or by somatic mutation in vivo). However, the term "human SBP", as used herein, is not intended to include SBPs in which CDR sequences derived from the germline of another mammalian species, such as a mouse, have been grafted onto human framework sequences.

The term "humanized SBP" refers to a SBP that includes at least one humanized immunoglobulin chain (e.g., a humanized heavy chain). The term "humanized SBP" refers to a SBP chain having a variable region that includes a variable framework region substantially from a human SBP and complementarity determining regions (CDRs) (e.g., at least one CDR, preferably two CDRs, more preferably three CDRs) substantially from a non-human heavy chain.

B. Detailed Description

Techniques for performing some of the basic methods of noted herein are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Analytical Chemistry of Bacillus Thuringiensis*, Hickle and Fitch, eds., *Am. Chem. Soc.*, 1990; *Bacillus thuringiensis: biology, ecology and safety*, T. R. Glare and M. O'Callaghan, eds, John Wiley, 2000; *Antibody Phage Display Methods and Protocols*, Humana Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and *PCR Protocols: A Guide to Methods and Applications*, Innis et al., eds, Academic Press, San Diego, Calif. (1990).

In some embodiments, the present disclosure provides polypeptides comprising VpreB and/or λ5 sequences and having the ability to bind a target. Targets specifically include all types of targets generally referred to as "antigens" in the context of antibody binding. In some embodiments, the target is a DR4 receptor, a DR5 receptor, or both DR4 and DR5 receptors. In some embodiments SBPs to DR4, DR5 or both DR4 and DR5 are provided. In some embodiments the SBPs bind to DR4, DR5 or both DR4 and DR5. In some embodiments the SBPs are agonists that bind to and activate DR4, DR5 or both DR4 and DR5.

Figure 1B:
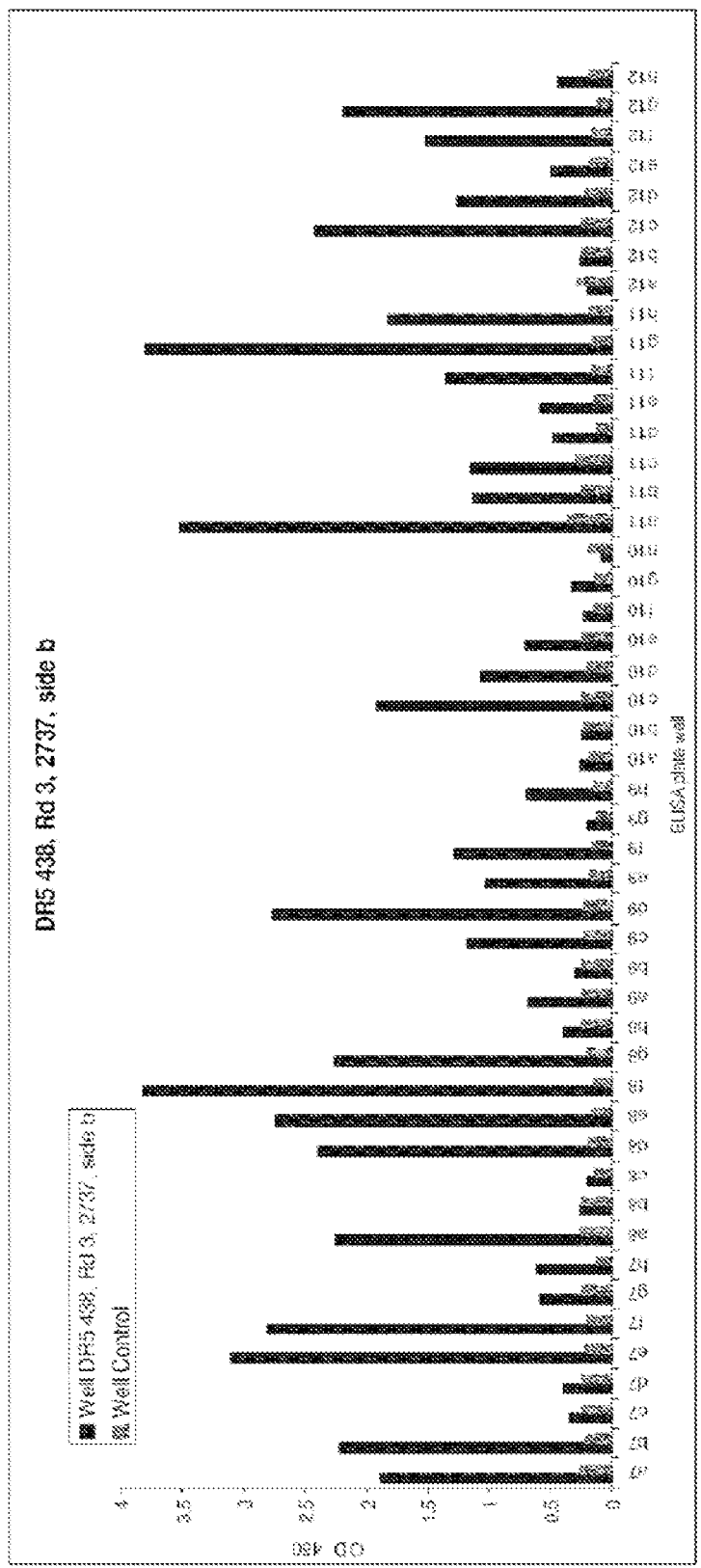
Figure 2B:
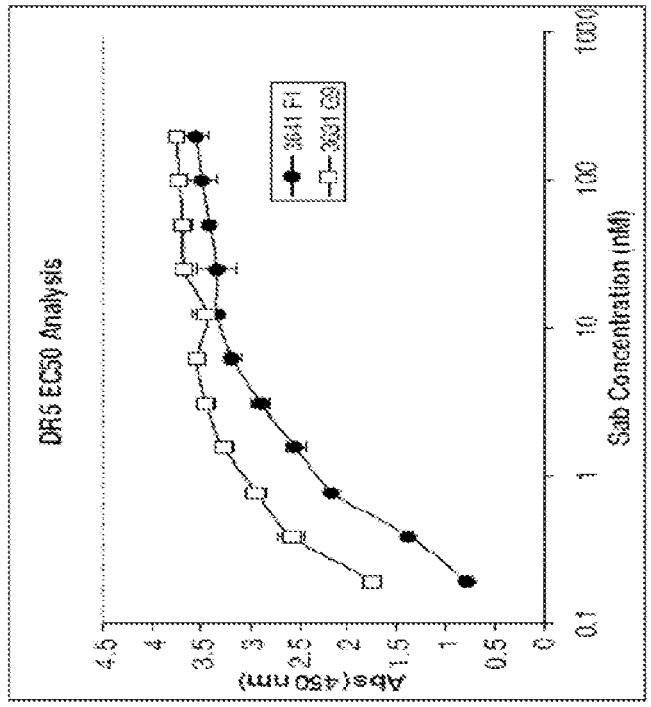
FIGS. 2A and 2B illustrate DR4 and DR5 binding analysis of two monovalent SBPs.
Figure 2A:
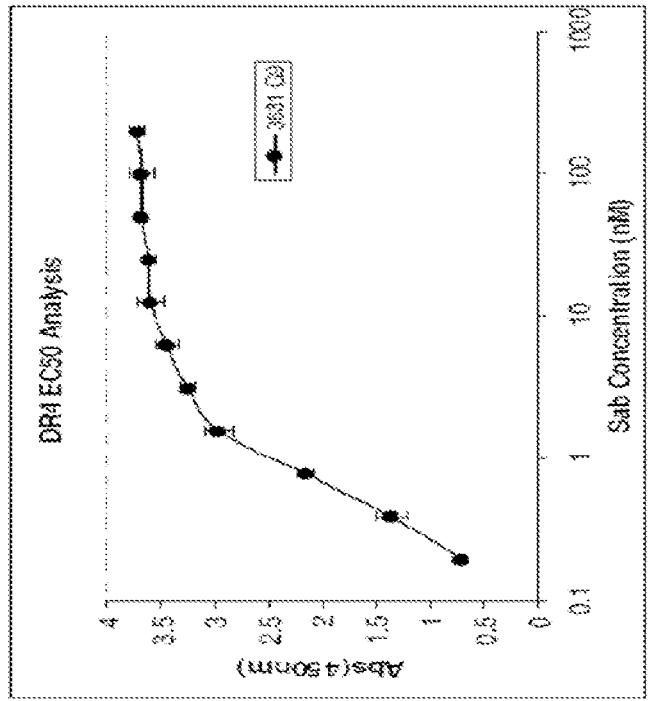
Figure 3A:
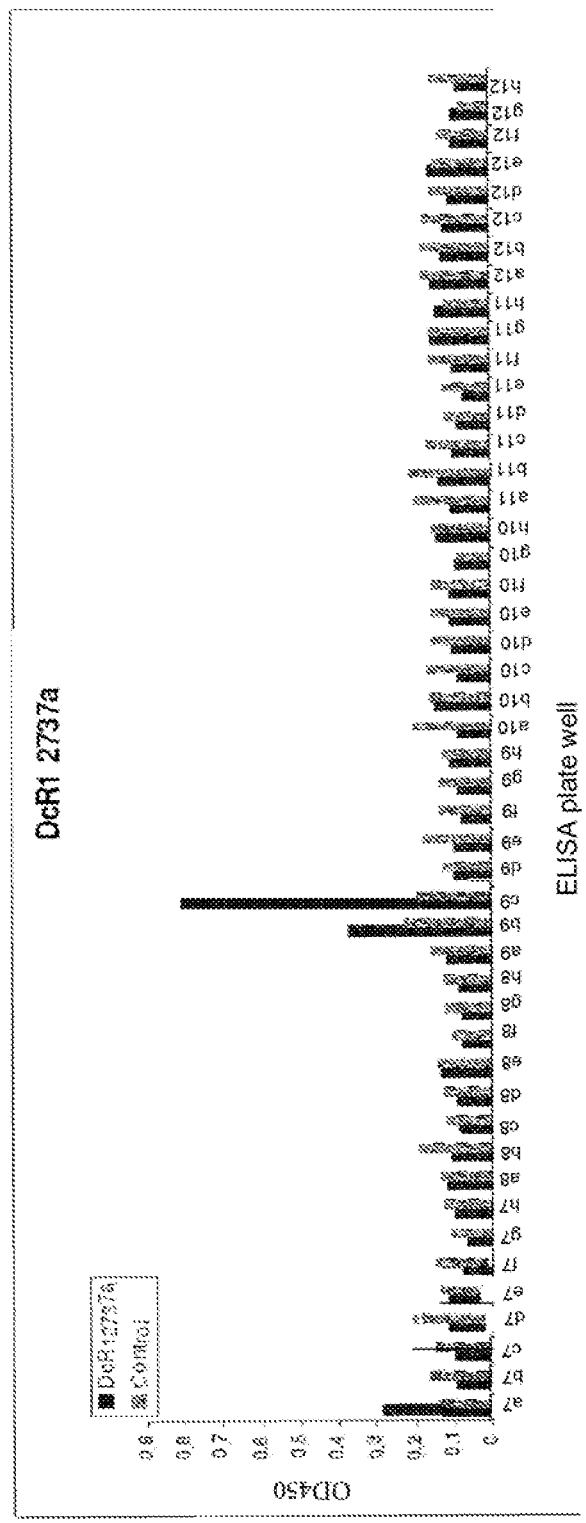
FIGS. 3A-3D show the results of ELISA binding analysis of the same clones shown in FIG. 1 on decoy receptors DcR1 and DcR2.
Figure 3B:
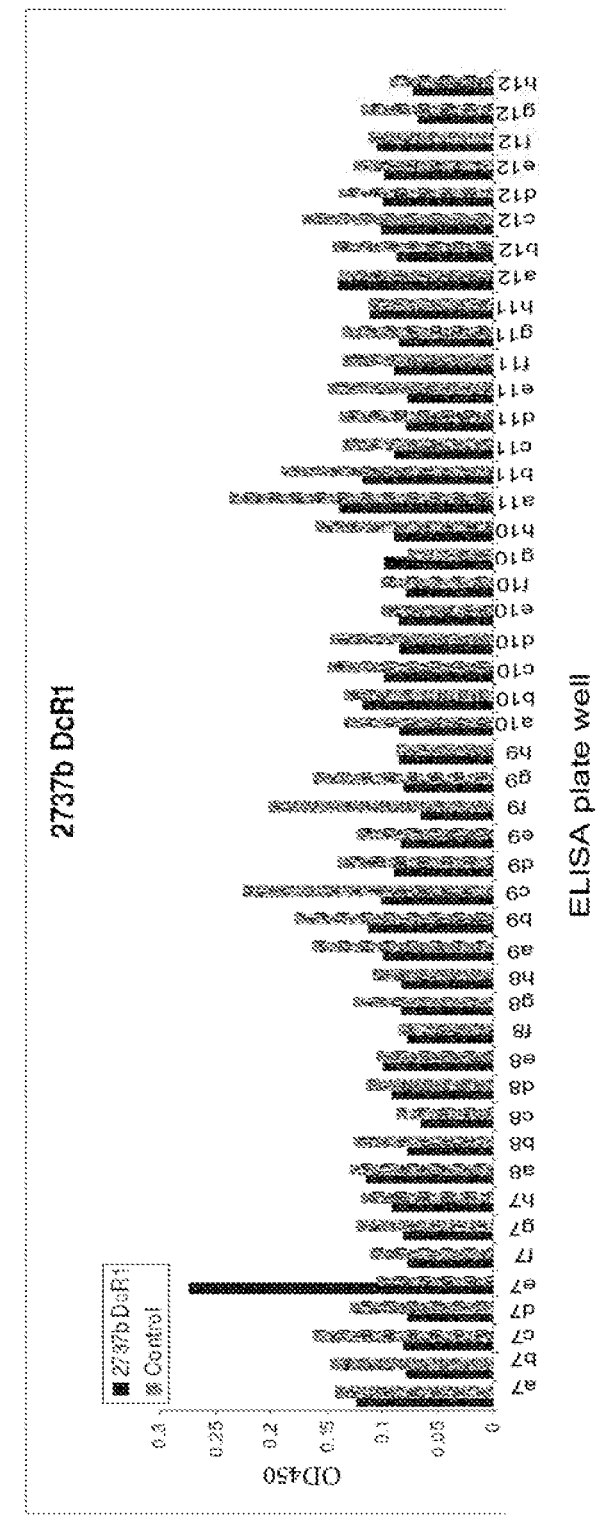
Figure 3C:
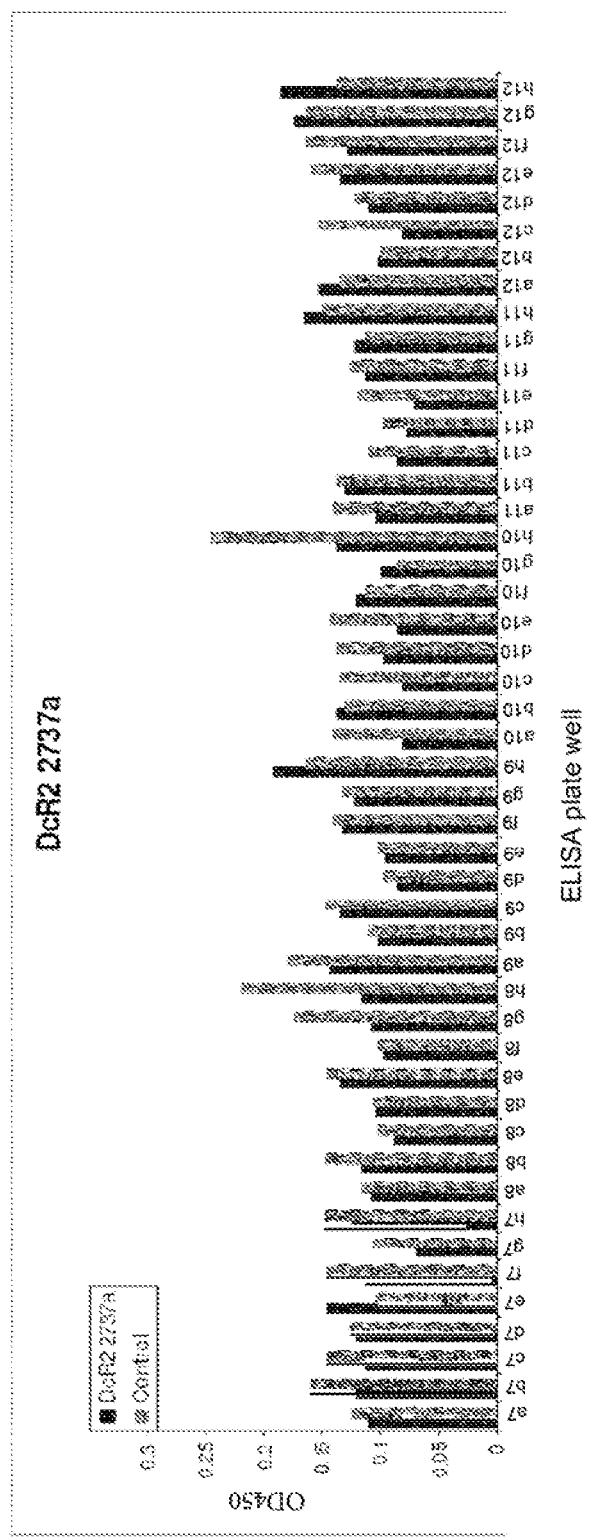
Figure 3D:
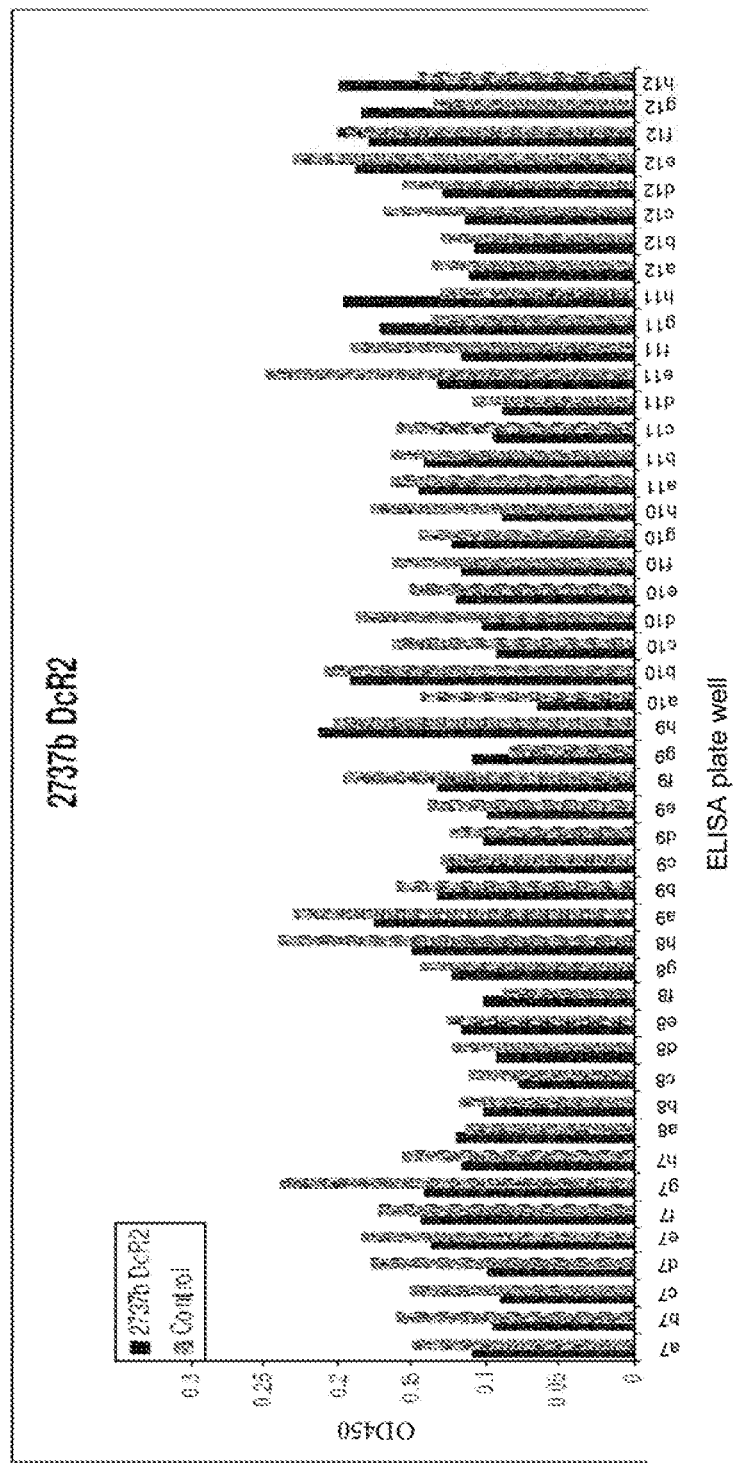

As shown in Example 1 a number of SBPs that bind to DR4 and/or DR5 were identified by phage display screening (FIGS. 1 and 2). The sequences of a number of SBPs are outlined in FIGS. 35 and 36.

The SBPs exhibit a range of abilities to bind to DR4 and DR5 (FIG. 7). In some embodiments, SBPs do not bind appreciably to the decoy receptors DcR1 and DcR2.

In some embodiments the SBPs are DR4 and/or DR5 agonists. As described in the Examples below and shown, for example, in FIGS. 8-12, a number of SBP's stimulate caspase activity and induce apoptosis.

In some embodiments, variants of SBPs are provided. In some embodiments, the SBPs will include a heavy chain variable region that is at least 85% identical to one of the sequences in FIG. 35 or FIG. 36. In some embodiments, the variant heavy chain for the SBPs will be 85, 86, 87, 88, 89, 90, 91, 92, 93, 94, 95, 96, 97, 98, 99%, or nearly identical to any one or more of the sequences in FIG. 35 or FIG. 36. In some embodiments, the variant heavy chain for the SBPs will be 85, 86, 87, 88, 89, 90, 91, 92, 93, 94, 95, 96, 97, 98, 99%, or nearly identical to the variable heavy chain region of 3706-A02 (also referred to herein as SL-466), 3631-G09 bivalent SBP (also referred to herein as SL-231), 3641-F01 bivalent SBP, 2737-F08 bivalent SBP, 2737-A01 bivalent SBP, 3706-B03 (also referred to herein as SL46S), 3706-001 (also referred to herein as SL467), 3726-A01 (also referred to herein as SL-468) or SL-144.

In some embodiments, variants of nucleic acids encoding SBPs are provided. In some embodiments, the nucleic acids encoding the SBPs will include a sequence that encodes a heavy chain variable region that is at least 85% identical to one of the sequences in FIG. 35 or FIG. 36. In some embodiments, the nucleic acids that encode the SBPs will include a nucleic acid sequence that encodes a heavy chain variable region that is at least 85, 86, 87, 88, 89, 90, 91, 92, 93, 94, 95, 96, 97, 98, 99, or nearly identical to one of the sequences in FIG. 35 or FIG. 36.

In some embodiments, the SBPs are binding fragment forms, such as monovalent SBPs. In some embodiments, the SBPs are full Surroglobulin forms, such as bivalent SBP. Example 6 outlines a method by which various initial monovalent SBPs were converted to bivalent SBP. Table 0.2 below shows the nomenclature of several monovalent SBPs that were converted to bivalent SBP.

TABLE 0.2 monovalent SBP Clone 3631-G09 = 3631-G09 bivalent SBP (bivalent SBP format)
monovalent SBP Clone 3641-F01 = 3641-F01 bivalent SBP (bivalent SBP format)
monovalent SBP Clone 2737-F08 = 2737-F08 bivalent SBP (bivalent SBP format)

TABLE 0.2-continued monovalent SBP Clone 2736-B09 = SL-144 (bivalent SBP format)
monovalent SBP Clone 2737-A01 = 2737-A01 bivalent SBP (bivalent SBP format)

In some embodiments an SBP binds to both human DR4 and human DR5. In some embodiments, an SBP binds to one or both of human DR4 and DR5 but does not bind to the mouse DR5. In some embodiments an SBP prevents binding of DR5 to TRAIL, as described in Example 3. In some embodiments an SBP does not bind appreciably to decoy receptors DcR1 and/or DcR2. See Example 4. In some embodiments an SBP binds human DR5 but not mouse DR5, for example as described in Example 7.

In some embodiments, an SBP can bind DR5 that is expressed in cells. In some embodiments, the EC50 of the SBP for such an interaction with human DR5 expressed in a cell is less than 0.5 nM, for example 0.3, 0.2, 0.15, 0.1 0.09, 0.08, 0.07, 0.06, 0.05, 0.04, 0.03, 0.02 nM or less, include any range lower than any of the preceding values and any range defined between any two of the preceding values.

In some embodiments, a surroglobulin can bind DR4 that is expressed in cells. In some embodiments, the EC50 of the surroglobulin for such an interaction with human DR4 expressed in a cell is less than 20 nM, for example 15, 10, 5, 2, 1, 0.5, 0.3, 0.2, 0.15, 0.1 0.09, 0.08, 0.07, 0.06, 0.05, 0.04, 0.03 nM or less, include any range lower than any of the preceding values and any range defined between any two of the preceding values.

In some embodiments, a SBP can bind DR5 and DR4 that is expressed in cells. In some embodiments, the EC50 of the SBP can be as described above for DR5 and DR4 respectively.

In some embodiments, the SBP can bind DR4 and/or DR5 and inhibit proliferation of cells in vitro or in vivo. In some embodiments, the SBP can bind to DR5 and/or DR4 and inhibit cell proliferation in vivo. In some embodiments, a surroglobulin can bind to DR5 and/or DR4 and activate apoptotic activity in cells, either in vitro or in vivo. In some embodiments a SBP can bind to DR5 and/or DR4 and activate caspase pathways, including caspase 3/7, caspase 8 and caspase 9, either in vitro or in vivo.

In some embodiments an SBP can bind DR4 and DR5. In some embodiments the SBP is a DR4 and DR5 dual agonist. In some embodiments a dual DR4 and DR5 agonist SBP can increase apoptotic activity in cells expressing DR4 and DR5. In some embodiments a dual DR4 and DR5 agonist SBP can increase caspase activity in cells expressing DR4 and DR5. The increased caspase activity may be increased caspase 3/, caspase 8 and or caspase 9 activity. In some embodiments a dual DR4 and DR5 agonist SBP can inhibit cell proliferation in cells expressing DR4 and DR5. The DR4 and DR5 dual agonist SBP may, in some embodiments, be more potent than TRAIL in increasing apoptotic activity, increasing caspase activity and/or inhibiting cell proliferation in cells expressing DR4 and DR5. In some embodiments the dual DR4 and DR5 agonist SBP does not bind decoy receptors.

In some embodiments, SBPs can be cross-linked prior to administration. For example, SBPs can be cross-linked with anti-Fc antibody or protein G. In some embodiments cross-linking can be carried out as described below.

In some embodiments, an SBP comprises a VpreB sequence, a λ5 sequence, or a VpreB sequence and a λ5 sequence and a heavy chain variable region amino acid sequence that is paired with the VpreB sequence, the λ5 sequence, or the VpreB sequence and the λ5 is sequence to form the SBP that can bind to a DR5 and/or DR4 protein. In some embodiments a VpreB sequence is fused to a constant light chain sequence.

Figure 4:
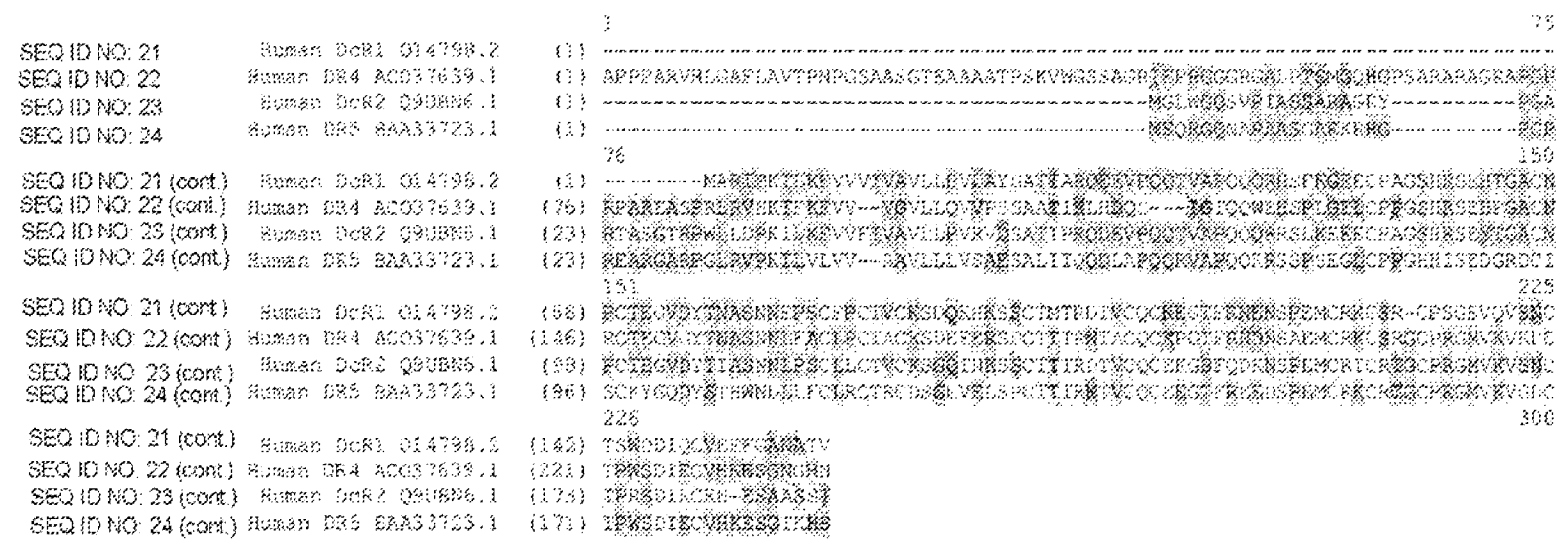

In some embodiments the human DR5 protein to which the SBP binds is one depicted in FIG. 4 or provided in FIG. 38. In some embodiments the DR5 comprises one or more of SEQ ID NO: 24, SEQ ID NO: 26, SEQ ID NO: 478, SEQ ID NO 479, SEQ ID NO 480, SEQ ID NO 481, and SEQ ID NO 482. In some embodiments a SBP binds to a human DR4 protein depicted in FIG. 4 or provided in FIG. 37. In some embodiments the DR4 comprises one or more of the amino acid sequences of SEQ ID NO: 22, SEQ ID NO: 25, SEQ ID NO 474, SEQ ID NO 475, SEQ ID NO 476, and SEQ ID NO 477.

In some embodiments, the SBP (or Ab) comprises a heavy chain variable region. In some embodiments, the heavy chain variable region comprises a sequence as shown in FIG. 35 or FIG. 36. In some embodiments, for example, variants that are 80, 85, 90, 95, 96, 97, 98, 99% identical to the sequences in FIG. 35 and/or FIG. 36 can be employed for the SBP. In some embodiments, the SBP comprises a heavy chain variable region, or variant thereof, from FIG. 35 or FIG. 36 in combination with a VpreB sequence and/or a λ5 sequence. In some embodiments, the VpreB sequence and/or λ5 sequence comprises part or all of one or more of the sequences shown in FIG. 26, 30, 31, 32 or 33.

In some embodiments, the SBP (or Ab) comprises one or more heavy chain CDR regions (e.g., 1, 2, or 3), such as the heavy chain CDR regions provided in FIG. 35 or FIG. 36. In some embodiments, the heavy chain CDR region comprises a sequence as shown in FIG. 35 or FIG. 36. In some embodiments, for example, variants that are 80, 85, 90, 95, 96, 97, 98, 99% identical to 1, 2, or 3 of the CDR sequences in FIG. 35 and/or FIG. 36 can be employed for the SBP. In some embodiments an SBP comprises CDR1, 2 and 3 from an SBP in FIG. 35 or FIG. 36. In some embodiments an SBP comprises CDR1 and 3, CDR2 and 3 or CDR1 and 2 from an SBP in FIG. 35 or FIG. 36. In some embodiments an SBP comprises one or more CDR sequences from FIG. 35 or FIG. 36. In some embodiments, the SBP comprises 1, 2, or 3 CDRs or variants thereof, from FIG. 35 or FIG. 36 in combination with a VpreB sequence and/or a λ5 sequence. In some embodiments, the VpreB sequence and/or λ5 sequence comprises part or all of one or more of the sequences shown in FIG. 26, 30, 31, 32 or 33. In some embodiments, the CDRs are selected from the following group: CDR1, CDR2, CDR3, CDR1 and CDR2, CDR2 and CDR3, CDR1 and CDR3, and CDR1 CDR2 and CDR3. In some embodiments, the CDR is defined as a Kabat sequence. In some embodiments, the CDR is defined as a Chothia sequence In some embodiments, the SBP comprises a SBP combination as put forth in Table 0.3 below:

TABLE 0.3

| Heavy Chain Variable Region and/or CDR | VpreB and/or lambda 5 |
| --- | --- |
| Any heavy chain variable region from SEQ IDs 38-473 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 38 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 42 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 46 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 50 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 54 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 58 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 62 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 66 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 70 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 74 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 78 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 82 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 86 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 90 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |

TABLE 0.3-continued

| Heavy Chain Variable Region and/or CDR | VpreB and/or lambda 5 |
|---|---|
| 94 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 98 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 102 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 106 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 110 | SEQ ID NO: 1, 2, 3, 4, 5, 6, 7, 10, 11, 12, and/or sequences within FIGS.: 26, 30, 31, 32, and 33 (and variants thereof, such as outlined in SEQ ID NO: 190, 191, and 192) |
| 114 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 118 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 122 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 126 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 130 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 134 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 138 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 142 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 146 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 150 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |

TABLE 0.3-continued

| Heavy Chain Variable Region and/or CDR | VpreB and/or lambda 5 |
|---|---|
| 154 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 158 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 162 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 166 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 170 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 174 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 178 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 182 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 186 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 190 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 194 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 198 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 202 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 206 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 210 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| Any one or more CDRs from SEQ IDs 38-473 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 39, 40, and/or 41 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 43, 44, and/or 45 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 47, 48, and/or 49 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 51, 52, and/or 53 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 55, 56, and/or 57 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 59, 60, and/or 61 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63, 64, and/or 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 67, 68, and/or 69 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 71, 72 and/or 73 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 75, 76 and/or 77 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 79, 80 and/or 81 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 83, 84 and/or 85 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 87, 88 and/or 89 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 91, 92 and/or 93 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| 95, 96 and/or 97 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 99, 100 and/or 101 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 103, 104 and/or 105 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 107, 108 and/or 109 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 111, 112 and/or 113 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 115, 116 and/or 117 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 119, 120 and/or 121 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 123, 124 and/or 125 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 127, 128 and/or 129 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 131, 132 and/or 133 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 135, 136 and/or 137 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 139, 140 and/or 141 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 143, 144 and/or 145 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 147, 148 and/or 149 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 151, 152 and/or 153 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
|  | 500 and/or sequences within FIGS.: 26, 30, 31, 32, and 33 (and variants thereof, such as outlined in SEQ ID NO: 484, 485, and 486) |
| 155, 156 and/or 157 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 159, 160 and/or 161 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 163, 164 and/or 165 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 167, 168 and/or 169 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 171, 172 and/or 173 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 175, 176 and/or 177 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 179, 180 and/or 181 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 183, 184 and/or 185 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 187, 188 and/or 189 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 191, 192 and/or 193 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 195, 196 and/or 197 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 199, 200 and/or 201 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 203, 204 and/or 205 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 207, 208 and/or 209 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 211, 212 and/or 213 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| Any combination of two CDRs from SEQ IDs 38-473 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 39 and 40; 40 and 41; 39 and 41 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 43 and 44; 44 and 45; 43 and 45 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 47 and 48, 49 and 49; 47 and 49 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 51 and 52; 52 and 53; 51 and 53 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 55 and 56; 56 and 57; 55 and 57 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 59 and 60; 60 and 61; 59 and 61 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 63 and 64; 64 and 65; 63 and 65 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 67 and 68; 68 and 69; 67 and 69 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 71 and 72; 72 and 73; 71 and 73 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 75 and 76; 76 and 77; 75 and 77 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 79 and 80; 80 and 81; 79 and 81 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 83 and 84; 84 and 85; 83 and 85 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 87 and 88; 88 and 89; 87 and 89 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 91 and 92; 92 and 93; 91 and 93 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 95 and 96; 96 and 97; 95 and 97 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| 99 and 100; 100 and 101; 99 and 101 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 103 and 104; 104 and 105; 103 and 105 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 107 and 108; 108 and 109; 107 and 109 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 111 and 112; 112 and 113; 111 and 113 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 115 and 116; 116 and 117; 115 and 117 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 119 and 120; 120 and 121; 119 and 121 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 123 and 124; 124 and 125; 123 and 125 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 127 and 128; 128 and 129; 127 and 129 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 131 and 132; 132 and 133; 131 and 133 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 135 and 136; 136 and 137; 135 and 137 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 139 and 140; 140 and 141; 139 and 141 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 143 and 144; 144 and 145; 143 and 145 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 147 and 148; 148 and 149; 147 and 149 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 151 and 152; 152 and 153; 151 and 153 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 155 and 156; 156 and 157; 155 and 157 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |
| 159 and 160; 160 and 161; 159 and 161 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 163 and 164; 164 and 165; 163 and 165 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 167 and 168; 168 and 169; 167 and 169 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 171 and 172; 172 and 173; 171 and 173 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 175 and 176; 176 and 177; 175 and 177 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 179 and 180; 180 and 181; 179 and 181 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 183 and 184; 184 and 185; 183 and 185 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 187 and 188; 188 and 189; 187 and 189 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 191 and 192; 192 and 193; 191 and 193 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 195 and 196; 196 and 197; 195 and 197 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 199 and 200; 200 and 201; 199 and 201 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 203 and 204; 204 and 205; 203 and 205 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 207 and 208; 208 and 209; 207 and 209 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| 211 and 212; 212 and 213; 211 and 213 | SEQ ID NO: 1, 2, 3, 4, 5, 6, 7, 10, 11, 12, 483, 487, 488, 489, 490, 491, 492, 493, 494, 495, 496, 497, 498, 499 500 and/or sequences within FIGS.: 26, 30, 31, 32, and 33 (and variants thereof, such as outlined in SEQ ID NO: 484, 485, and 486) |
| Any combination of three CDRs from SEQ IDs 38-473 | SEQ ID NO: 1, 2, 3, 4, 5, 6, 7, 10, 11, 12, 483, 487, 488, 489, 490, 491, 492, 493, 494, 495, 496, 497, 498, 499 |

TABLE 0.3-continued

| Heavy Chain Variable Region and/or CDR | VpreB and/or lambda 5 |
|---|---|
| | 500 and/or sequences within FIGS.: 26, 30, 31, 32, and 33 (and variants thereof, such as outlined in SEQ ID NO: 484, 485, and 486) |

In some embodiments, any of the heavy chain variable regions and/or heavy chains CDR options outlined in Table 0.3 or provided in FIG. 35 or FIG. 36 can be combined with an antibody light chain variable region to DR5 or DR4 or one or more light chain CDRs to DR5 or DR4. In some embodiments, any light chain, germline or rearranged, can be employed. In some embodiments, lambda is employed. In some embodiments, kappa is employed.

The selectivity and strength of SBP binding can be attributed to the combination of variable heavy chain frameworks and specific CDR composition. It is predicted that these binding attributes can be altered by judicious substitutions of specific surrogate light chain residues. For example it is predicted that loops in VpreB, lambda 5, or a loop formed by the chimeric fusion of both VpreB and lambda 5, can be substituted with other residues to allow these changes. The nature of these substitutions can be conservative, nonconservative, or a combination of either, or both.

Substitution of any of the residues of the surrogate light chain proximal to, or distant from, the heavy chain CDRs can be made for purposes of affinity optimization. The benefit of these conservative changes can derive from improving access between the target and the heavy chain. By maintaining the side chain chemistry termini and altering the lengths to the peptide backbone, the requisite complementary structure and its steric accessibility can be improved. Decreasing the side chain or repositioning the side chain termini can provide more free room that can result in better binding. Alternatively, opposing changes that reduce the distance from side chain chemistries to peptide bond could bring interactive chemistries into better and closer position for binding. Tables 0.3B-0.3D provide a list of some options for areas of the surrogate light chain that can be changed and some examples of how they can be changed.

TABLE 0.3B

| Position | 29 | 30 | 31 | 32 | 33 | 34 | 35 | 36 | 37 | 38 |
|---|---|---|---|---|---|---|---|---|---|---|
| Existing residue | D | I | G | V | Y | S | V | Y | W | Y |
| Possible residues | E | V | A | I | F | T | I | F | | F |
| | | | L | | L | | L | | | |
| SEQ ID NO: 484 | $X_{301}$ | $X_{302}$ | $X_{303}$ | $X_{304}$ | $X_{305}$ | $X_{306}$ | $X_{307}$ | $X_{308}$ | W | $X_{309}$ |

TABLE 0.3C

| Position | 49 | 50 | 51 | 52 | 53 | 54 | 55 | 56 | 57 | 58 | 59 | 60 | 61 |
|---|---|---|---|---|---|---|---|---|---|---|---|---|---|
| Existing residue | L | L | R | Y | F | S | Q | S | D | K | S | Q | G |
| Possible residues | I | I | K | F | Y | T | N | T | E | R | T | N | A |
| | V | V | | | | | | | | | | | |
| SEQ ID NO: 485 | $X_{310}$ | $X_{311}$ | $X_{312}$ | $X_{313}$ | $X_{314}$ | $X_{315}$ | $X_{316}$ | $X_{317}$ | $X_{318}$ | $X_{319}$ | $X_{320}$ | $X_{321}$ | $X_{322}$ |

TABLE 0.3D

| Position | 97 | 98 | 99 | 100 | 101 | 102 | 103 | 104 | 105 | 106 |
|---|---|---|---|---|---|---|---|---|---|---|
| Existing residue | A | M | G | A | R | S | S | V | T | H |
| Possible residues | G | L | A | G | K | T | T | I | S | |
| | | | | | | | | | L | |
| SEQ ID NO: 486 | $X_{323}$ | $X_{324}$ | $X_{325}$ | $X_{326}$ | $X_{327}$ | $X_{328}$ | $X_{329}$ | $X_{330}$ | $X_{331}$ | H |

The numbering of the residues noted above is in regard to SEQ ID NO: 483 (FIG. 33). Thus, any of the residues noted above can be altered within SEQ ID NO: 276 and still be predicted to be acceptable. In some embodiments, other residues within the surrogate light chain can be altered (for example 80%, 85%, 90%, 95%, 98%, and 99% identical sequences to the surrogate light chain sequences provided herein (for example, FIG. 33)).

It is possible to incorporate chemically diverse amino acids that create new opportunistic interactions with either the target or the complementary heavy chain structure in a structurally similarly manner as that described above, except that the improved "fitness" to target is derived from previously nonexisting side chain interactions. Possible substitutions within predicted target adjacent loops (SEQ ID 484-486) as shown by their respective positions within Tables 0.3B, 0.3C, and/or 0.3D). In some embodiments, any of the surrogate light chains provided herein can be paired with any of the heavy chain sequences provided herein.

The above description highlights changes to affinity, but can be extended to other beneficial functions, such as thermal stability, pharmacokinetic properties, immunogenicity, solubility, expression, and aggregation.

In some embodiments, any of the heavy chain variable regions and/or heavy chain CDR options outlined in Table 0.3 or provided in FIG. 35 or FIG. 36 can be combined with 1, 2, and/or 3 light chain CDR analogous regions from any of the sequences listed in Table 0.3. In some embodiments, LR2 and LR3 are employed. In some embodiments, LR1 and LR3 regions are employed. Exemplary Loop Regions can be found in FIG. 26.

In some embodiments, the SBP and/or antibody binds to a DR4 or DR5 epitope that is important for TRAIL binding or transmitting a signal. In some embodiments, the SBP and/or antibody binds both DR4 and DR5, disrupts TRAIL binding to both receptors, and binds to and activates non-human primate DR4 and DR5. In some embodiments, the SBP and/or antibody binds human DR4 and DR5 and non-human primate DR4 and DR5. In some embodiments a dual DR4 and DR5 agonist is provided that binds to human DR4 and DR5 as well as non-human DR4 and DR5. The dual DR4 and DR5 agonist may, in some embodiments, comprise one or more binding domains of SL466 (3706-A02) or SL231 (3631-G09).

In some embodiments, the SBP has a $K_D$ that is less than 100 nM, preferably between 0.01 nM and 10 nM.

In some embodiments, the VpreB sequence is selected from the group consisting of a native VpreB1 sequence, a native VpreB2 sequence, a native VpreB3 sequence, fragments of any of the preceding, and variants of any of the preceding. In some embodiments, the native VpreB sequence is selected from the group consisting of human VpreB1 of SEQ ID NO: 1, mouse VpreB2 of SEQ ID NOS: 2 and 3, human VpreB3 of SEQ ID NO: 4, fragments of any of the preceding, and variants of any of the preceding.

In some embodiments, the SBP includes the λ5 sequence. In some embodiments, the λ5 sequence comprises all or part of a human λ5 of SEQ ID NO: 6 or a mouse polypeptide of SEQ ID NO: 5. In some embodiments, the λ5 sequence is fused to said VpreB sequence. In some embodiments, the SBP comprises a VpreB sequence fused to a λ5 sequence. In some embodiments, the VpreB sequence is selected from the group consisting of human VpreB1 of SEQ ID NO: 1, mouse VpreB2 of SEQ ID NOS: 2 and 3, human VpreB3 of SEQ ID NO: 4, fragments of any of the preceding, variants of any of the preceding, and any combination thereof. In some embodiments, the λ5 sequence is selected from the group consisting of a human λ5 of SEQ ID NO: 6, mouse of SEQ D NO:6, fragments of any of the preceding, variants, and any combination thereof. In some embodiments, the VpreB sequence is fused to the λ5 sequence at or around a LR3 of said VpreB sequence and λ5, respectively. In some embodiments, the λ5 is covalently linked to the VpreB sequences. In some embodiments, the λ5 is covalently linked to the VpreB sequences by a connecting peptide or polypeptide sequence. In some embodiments, the surrogate binding protein comprises the VpreB and the λ5 sequence and the VpreB sequence is conjugated to the λ5 sequence by a non-covalent association, and wherein at least one of said VpreB and λ5 sequences is other than a full-length native VpreB and λ5 sequence, respectively. In some embodiments, at least one of said VpreB and λ5 sequences is a fragment or variant of a native VpreB and λ5 sequence, respectively. In some embodiments, the VpreB sequence is fused to the λ5 sequence, and the VpreB sequence fused to the λ5 sequence is paired with the heavy chain variable region amino acid sequence. In some embodiments, the VpreB, λ5, or VpreB and λ5 sequence is fused to a variable heavy chain construct as disclosed herein. In some embodiments, the antibody heavy chain variable region amino acid sequence is covalently paired via a peptide linker.

In some embodiments, the SBP comprises a VpreB sequence fused to a λ5 sequence, wherein the antibody heavy chain variable region amino acid sequence is conjugated to the VpreB sequence fused to the λ5 sequence by non-covalent association, to form a dimeric complex. In some embodiments the SBP comprises a VpreB fused to a constant light sequence. In some embodiments, the SBP comprises a Lambda-5 fused to a variable light sequence.

In some embodiments, the heavy chain variable region amino acid sequence binds to DR4 and/or DR5 and the VpreB sequence, the λ5 sequence, or the VpreB sequence and the λ5 sequence also bind to DR4 and/or DR5.

In some embodiments, the heavy chain variable region amino acid sequence binds to a target different from the target to which the VpreB sequence, the λ5 sequence, or the VpreB sequence and the λ5 sequence binds.

In some embodiments, the VpreB sequence, the λ5 sequence, or the VpreB sequence and the λ5 sequence binds to DR4 and/or DR5 and the heavy chain variable region amino acid sequence binds to a different target and/or epitope. In some embodiments the heavy chain variable region amino acid sequence binds to a target and/or epitope that is not DR4 or DR5 or a portion thereof.

In some embodiments, the heavy chain variable region amino acid sequence binds to DR4 and the VpreB sequence, the λ5 sequence, or the VpreB sequence and the λ5 sequence binds to DR5. In some embodiments, the heavy chain variable region amino acid sequence binds to DR5 and the VpreB sequence, the λ5 sequence, or the VpreB sequence and the λ5 sequence binds to DR4. In some embodiments, the heavy chain variable region amino acid sequence binds to DR4 and/or DR5 and the VpreB sequence, the λ5 sequence, or the VpreB sequence and the λ5 sequence binds to a different target and/or epitope.

In some embodiments, the heavy chain variable region amino acid sequence is non-covalently associated with the VpreB sequence and λ5 sequence, which are also non-covalently associated with each other, to form a trimeric complex. In some embodiments, the heavy chain variable region amino acid sequence (in an Ab or an SBP) binds to DR4 and/or DR5.

In some embodiments, a bispecific SBP or antigen binding portions thereof comprises a first VpreB sequence, a first λ5 sequence, or a first VpreB sequence and a first λ5 sequence. It can further include a first heavy chain variable region amino acid sequence that is paired with the first VpreB sequence, the first λ5 sequence, or the first VpreB sequence and the first λ5 sequence to form a first SBP binding site, wherein said SBP or antigen binding portion thereof binds to and/or activates DR4 and/or DR5. In some embodiments, it can further include a second VpreB sequence, a second λ5 sequence, or a second VpreB sequence and a second λ5 sequence. In some embodiments, it can further include a second heavy chain variable region amino acid sequence that is paired with the second VpreB sequence, the second λ5 sequence, or the second VpreB sequence and the second λ5 sequence to form a second SBP site. The second SBP site can bind to and/or activate DR4 and/or DR5 or another target. For example, the first SBP binding site may bind to and/or activate DR5 and the second SBP site may bind to and/or activate DR5, or vice versa. In some embodiments the second SBP site binds to a target that is not DR4 or DR5, such as a target involved in cancer pathogenesis. In some embodiments the second SBP site binds to and inhibits a target while in other embodiments the second SBP site binds to and activates a target.

In some embodiments, a bispecific sur-binding protein is provided that comprises a VpreB sequence, a λ5 sequence, or a VpreB sequence and a λ5 sequence, a first heavy chain variable region amino acid sequence that is paired with the VpreB sequence, the λ5 sequence, or the VpreB sequence and first λ5 sequence to form a first binding site. The first sur-binding protein binding site binds to and/or activates a DR4 or DR5 receptor. The SBP can further comprise a light chain variable region. The SBP can further comprise a second heavy chain variable region amino acid sequence that is paired with the light chain variable region to form a second binding site, wherein said second binding site binds to a second target, for example the other of the DR4 receptor or DR5 receptor targeted by the first binding site. In some embodiments the second binding site binds to a target involved in cancer pathogenesis that is not DR4 or DR5. In some embodiments the second SBP site binds to and inhibits a target while in other embodiments the second SBP site binds to and activates a target.

In some embodiments, the SBP comprises a CDR analogous region of a VpreB sequence and/or a λ5 sequence which is engineered by grafting corresponding CDR sequences from a therapeutic antibody.

The SBP may increase apoptotic activity, increase caspase activity and/or inhibit cell proliferation in cells expressing DR4 and/or DR5. In some embodiments a dual agonist SBP selectively binds to and activates DR4 and DR5. The dual agonist SBP may increase apoptotic activity, increase caspase activity and/or inhibit cell proliferation in cells expressing DR4 and DR5. In some embodiments the dual agonist SBP is more effective than an SBP that targets DR4 alone, an SBP that targets DR5 alone, or a combination of SBPs that individually target DR4 and DR5. In some embodiments the dual agonist SBP that binds to and activates DR4 and DR5 provides at least 10% greater inhibition of cell proliferation over SBPs targeting DR4 or DR5 individually, and/or a combination of two different SBPs targeting DR4 and DR5, for example at least 10, 50, 100, 200, 300, 400, 500, 600, 700, 800, 900, 1000% or greater inhibition (for example, concentration required to achieve a particular percent inhibition). In some embodiments the dual agonist SBP that binds to and activates DR4 and DR5 provides at least 10% greater increase of apoptotic activity relative to SBPs targeting DR4 or DR5 individually, and/or a combination of two different SBPs targeting DR4 and DR5, for example at least 10, 50, 100, 200, 300, 400, 500, 600, 700, 800, 900, 1000% or greater increase of apoptotic activity. In some embodiments the dual agonist SBP that binds to and activates DR4 and DR5 provides at least 10% greater increase in caspase activity over SBPs targeting DR4 or DR5 individually, and/or a combination of two different SBPs targeting DR4 and DR5, for example at least 10, 50, 100, 200, 300, 400, 500, 600, 700, 800, 900, 1000% or greater increase in caspase activity (for example, activation of caspase 3/7).

In some embodiments, two or more of the disclosed SBPs bind to a similar, same, or overlapping epitope. In some embodiments they bind to non-overlapping epitopes.

In some embodiments, the SBPs can bind to any of the epitopes that the SBPs in Table 0.3 can bind to. In some embodiments the SBPs can bind to any of the epitopes that the SBPs in FIG. 35 or 36 bind to, or to similar or overlapping epitopes.

In some embodiments, an antibody is provided that binds to a same or an overlapping epitope that any of the SBPs disclosed herein binds to. In some embodiments, the Ab has the same or similar heavy chain CDR, CDRs, or heavy chain variable regions of any of the SBPs herein (including those noted in Table 0.3). In some embodiments, the antibody displaces the SBP when the antibody binds to an epitope on DR4 and/or DR5. In some embodiments, the antibody will not displace an SBP if the SBP is already bound to DR4 or DR5.

In some embodiments, a bispecific SBP will include at least one of the heavy chain CDRs from SL-466 (3706-A02) (SEQ ID NOs: 459, 460, 461; FIG. 35) and/or SL-231 (3631-G09) (SEQ ID NOs: 39, 40, 41; FIG. 36). In some embodiments, the bispecific SBP can include any of the surrogate light chains provided herein. In some embodiments, the bispecific SBP will include at least one heavy chain CDR from SL-466 (3706-A02) and/or SL-231 (3631-G09). In some embodiments, the bispecific SBP will include at least two heavy chain CDRs from SL-466 (3706-A02) and/or SL-231 (3631-G09). In some embodiments, the bispecific SBP will include at least three heavy chain CDRs from SL-466 (3706-A02) and/or SL-231 (3631-G09). In some embodiments, the bispecific SBP will include at least the heavy chain variable region of at least one of SL-466 (3706-A02) (SEQ ID NO: 458) and/or SL-231 (3631-G09) (SEQ ID NO: 38). In some embodiments, the bispecific SBP will include at least a heavy chain variable region that is at least 85% identical to the sequence of the heavy chain variable region of SL-466 (3706-A02) and/or SL-231 (3631-G09). In some embodiments, the bispecific SBP will include at least a heavy chain variable region that is at least 90% identical to the sequence of the heavy chain variable region of SL-466 (3706-A02) and/or SL-231 (3631-G09). In some embodiments, the bispecific SBP will include at least a heavy chain variable region that is at least 95% identical to the sequence of the heavy chain variable region of SL-466 (3706-A02) and/or SL-231 (3631-G09). In some embodiments, the bispecific SBP will include at least a heavy chain variable region that is at least 98% identical to the sequence of the heavy chain variable region of SL-466 (3706-A02) and/or SL-231 (3631-G09). In some embodiments, the bispecific SBP will include at least a heavy chain variable region that is at least 99% identical to the sequence of the heavy chain variable region of SL-466 (3706-A02) and/or SL-231 (3631-G09).

Surrogate Light Chain Constructs

Precursors of B cells (pre-B cells) have been identified in the bone marrow as lymphocytes at a developmental stage that produce μ heavy chains but have not yet begun to produce light chains but instead express a set of B lineage-specific genes called VpreB(1-3) and λ5 respectively.

One isoform of human VpreB1 (GenBank ID No: CAG30495) is a 145 aa-long polypeptide (SEQ ID NO: 1). It has an Ig V domain-like structure, but lacks the last (β-strand (β7) of a typical V domain, and instead has a carboxyl terminal end that shows no sequence homologies to any other proteins VpreB2 has several isoforms, including a 142-amino acid mouse VpreB2 polypeptide (GenBank ID No: P13373; SEQ ID NO: 2), and a 171-amino acid long splice variant of the mouse VpreB2 sequence (GenBank ID No:_CAA019641 SEQ ID NO: 3). VpreB1 and VpreB2 sequences have been disclosed in EP 0 269 127 and U.S. Pat. No. 5,182,205; Collins et al., *Genome Biol.* 5(10):R84 (2004); and Hollins et al., *Proc. Natl. Acad. Sci. USA* 86(14):5552-5556 (1989). One isoform of human VpreB3 (SEQ ID NO: 4) is a 123 amino acid long protein (GenBank ID No: CAG30496), disclosed in Collins et al., *Genome Biol.* 5(10):R84 (2004).

In some situations, VpreB(1-3) can be non-covalently associated with another protein, λ5. The human λ5 is a 209-amino acid polypeptide (GenBank ID No: CAA01962; SEQ ID NO: 6) that carries an Ig C domain-like structure with strong homologies to antibody light chains and, towards its amino terminal end, two functionally distinct regions, one of which shows strong homology to the β7 strand of the Vλ domains. A mouse λ5-like protein has 209 amino acids (GenBank ID No: CAA01962; SEQ ID NO: 5) and shows about 62% sequence identity to the antibody λ light chain constant region.

For further details, see the following review papers: Karasuyama et al., *Adv. Immunol.* 63: 1-41 (1996); Melchers et al., *Immunology Today* 14:60-68 (1993); and Melchers, *Proc. Natl. Acad Sci. USA* 96:2571-2573 (1999).

Traditionally, the VpreB and λ5 polypeptides together form a non-covalently associated structure, called a surrogate light chain. On the surface of early preB cells, the surrogate light chain is complexed to membrane-bound Ig μ heavy chain in association with a signal transducer CD79a/CD79b heterodimer to form a B cell receptor-like structure, the so-called preB cell receptor (preBCR).

As discussed above, pre-B cells have been identified in the bone marrow as lymphocytes that produce μ heavy chains but instead of the fully developed light chains express a set of B lineage-specific genes called VpreB(1-3) and λ5, respectively. The VpreB and λ5 polypeptides together form a non-covalently associated structure, called the surrogate light chain. The surrogate light chain, although not an antibody chain, naturally associates with all recombined antibody heavy chains.

In some embodiments, SBPs include, without limitation, conjugates of VpreB sequences to heterogeneous amino acid sequences, provided that they retain the ability to bind a desired target. The binding of the VpreB sequence to the heterogeneous amino acid sequence can be either covalent or non-covalent, and can occur directly, or through a linker, including peptide linkers.

Specific examples of the polypeptide constructs herein include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are illustrated in FIGS. 27 and 34.

In a direct fusion, typically the C-terminus of a VpreB sequence (e.g. a VpreB1, VpreB2 or VpreB3 sequence) is fused to the N-terminus of a λ5 sequence. While it is possible to fuse the entire length of a native VpreB sequence to a full-length λ5 sequence (see, e.g. the first diagram in FIG. 27), typically the fusion takes place at or around a non-immunoglobulin like peptide site in each of the two polypeptides. Such similar sites for VpreB1 and λ5 are illustrated in FIG. 26, and a representative fusion construct is illustrated in FIG. 27. In this embodiment, the fusion can take place within, or at a location within about 10 amino acid residues at either side of this region. In a preferred embodiment, the fusion takes place between about amino acid residues 116-126 of the native human VpreB1 sequence (SEQ ID NO: 1) and between about amino acid residues 87 and 97 of the native human λ5 sequence (SEQ ID NO: 6).

Figure 27:
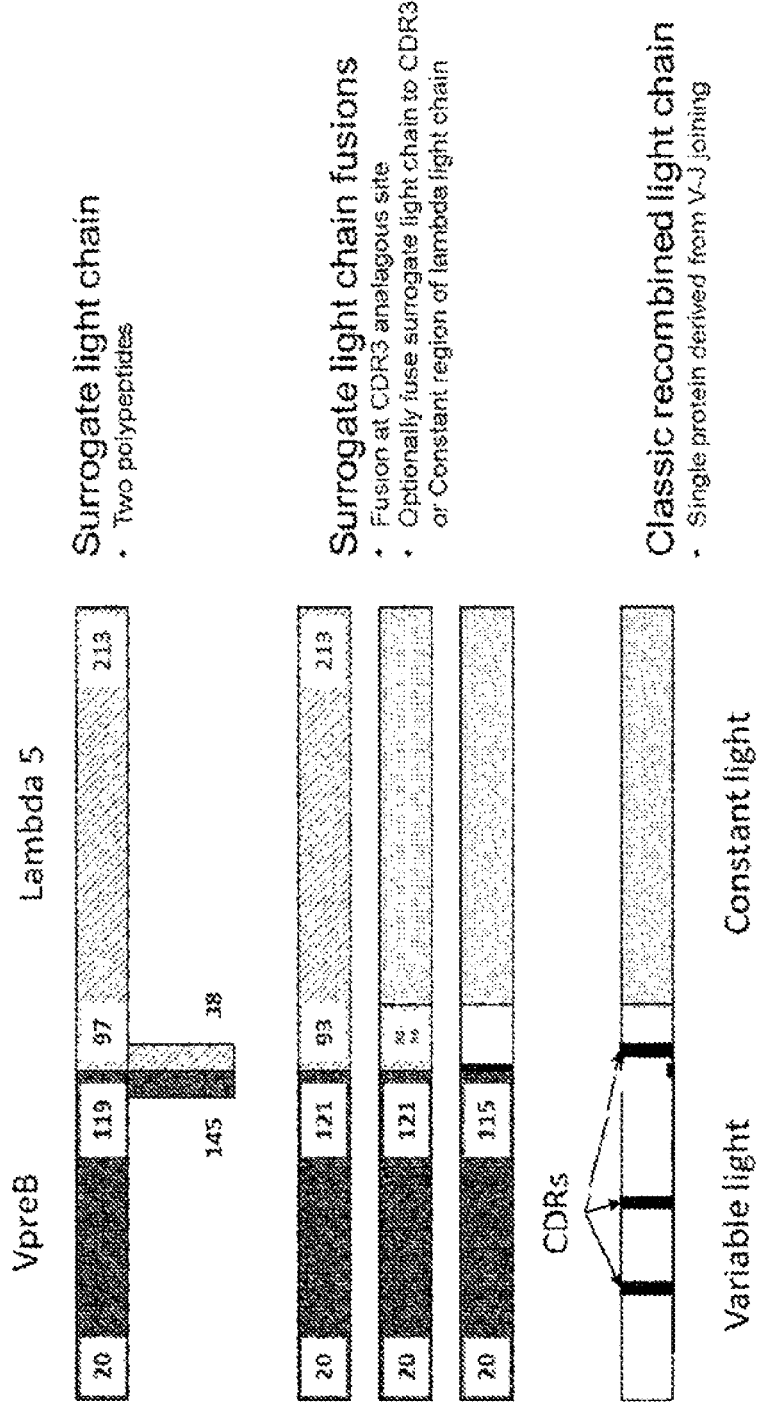
FIG. 27 is a schematic illustration of a surrogate light chain formed by VpreB and λ5 sequences, illustrative fusion polypeptides comprising surrogate light chain sequences, and an antibody light chain structure derived from V-J joining.
Figure 28:
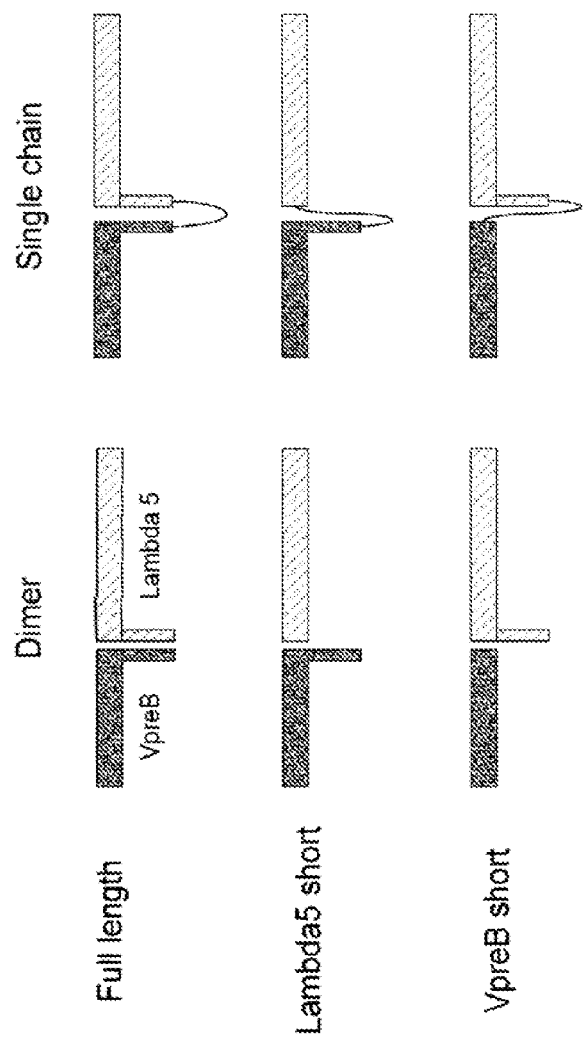
FIG. 28 is a schematic illustration of various surrogate light chain deletion and single chain constructs.

It is also possible to fuse the VpreB sequence to the CDR3 region of an antibody λ light chain, as shown in FIG. 27. It is also possible to fuse the carboxy terminus of a VpreB and λ5 construct to the amino terminus of the constant light chain region of antibody λ light chain, also as shown in FIG. 27. Further constructs, in which only one of VpreB and λ5 is truncated are shown in FIG. 28. Similar constructs can be prepared using antibody κ light chain sequences.

Figure 34:
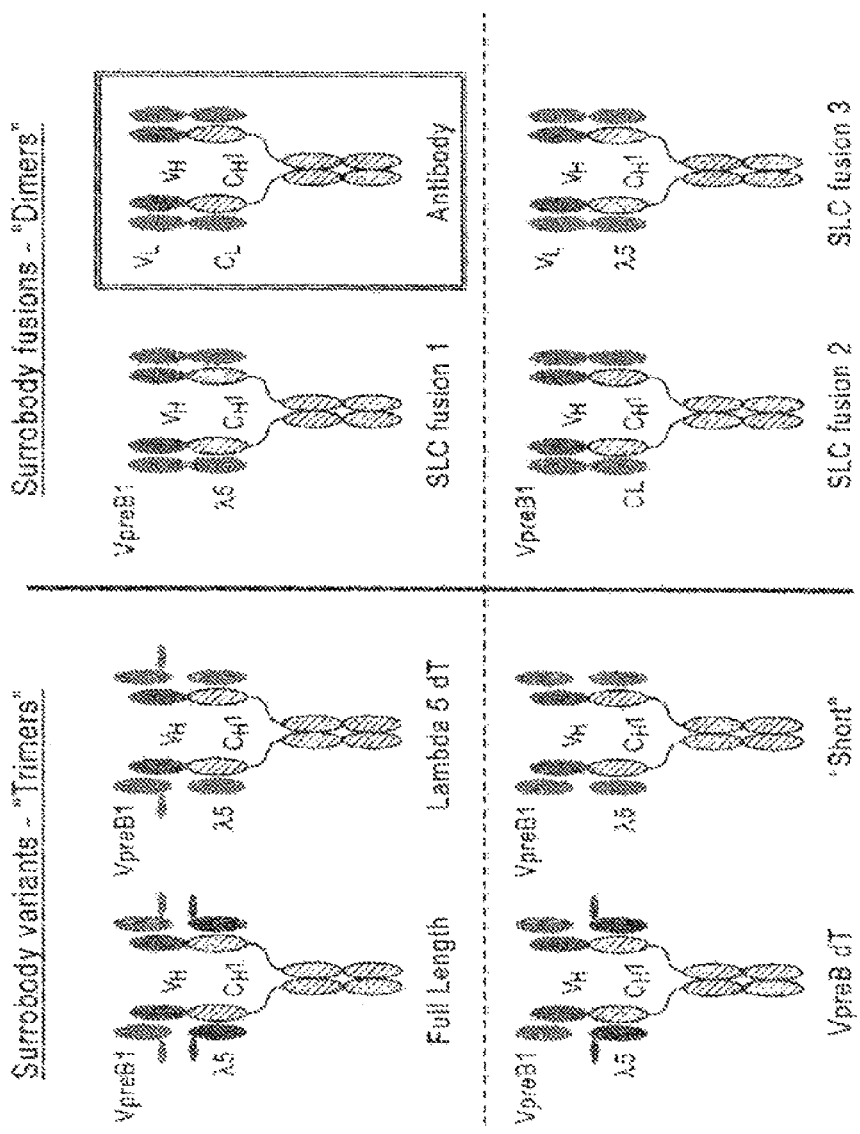
FIG. 34 illustrates various embodiments of trimeric and dimeric SBPs.

Further direct fusion structures are illustrated on the right side of FIG. 34. The structure designated "SLC fusion 1" is a tetramer, composed of two dimers, in which the fusion of a truncated V-preB1 sequence (lacking the characteristic "tail" at the C-terminus of native VpreB1) to a similarly truncated λ5 sequence is non-covalently associated with an antibody heavy chain. The structure designated "SLC fusion 2" is a tetramer, composed of two dimers, in which the fusion of a truncated VpreB1 sequence (lacking the characteristic "tail" at the C-terminus of native VpreB1) to an antibody light chain constant region is non-covalently associated with an antibody heavy chain. The structure designated "SLC fusion 3" is a tetramer, composed of two dimers, in which the fusion of an antibody light chain variable region to a truncated λ5 sequence (lacking the characteristic "tail" at the N-terminus of native is) is non-covalently associated with an antibody heavy chain.

As noted above, in addition to direct fusions, the polypeptide constructs include non-covalent associations of a VpreB sequence (including fragments and variants of a native sequence) with a heterogeneous sequence, such as a λ5 sequence (including fragments and variants of the native sequence), and/or an antibody sequence. Thus, for example, a full-length VpreB sequence can be non-covalently associated with a truncated λ5 sequence. Alternatively, a truncated VpreB sequence can be non-covalently associated with a full-length λ5 sequence.

Surrogate light chain constructs comprising non-covalently associated VpreB1 and λ5 sequences, in non-covalent association with an antibody heavy chain, are shown on the left side of FIG. 34. As the various illustrations show, the structures may include, for example, full-length VpreB1 and λ5 sequences, a full-length VpreB1 sequence associated with a truncated λ5 sequence ("Lambda 5dT"), a truncated V-reB1 sequence associated with a full-length λ5 sequence (VpreB dT") and a truncated VpreB1 sequence associated with a truncated λ5 sequence ("Short").

Although FIG. 34 illustrates certain specific constructs, one of ordinary skill will appreciate that a variety of other constructs can be made and used in a similar fashion. For example, the structures can be asymmetrical, comprising different surrogate light chain sequences in each arm, and/or having trimeric or pentameric structures, as opposed to the structures illustrated in FIG. 34. It is also possible to include different functionalities in various portions of the surrogate light chain constructs, thereby producing multi-specific and/or multivalent constructs.

If desired, the constructs can be engineered, for example, by incorporating or appending known sequences or sequence motifs from the CDR1, CDR2 and/or CDR3 regions of antibodies, including known therapeutic antibodies into similar regions of the surrogate light chain constructs. This allows the creation of molecules that are not antibodies, but will exhibit binding specificities and affinities very similar to those of a known therapeutic antibody.

Figure 29:
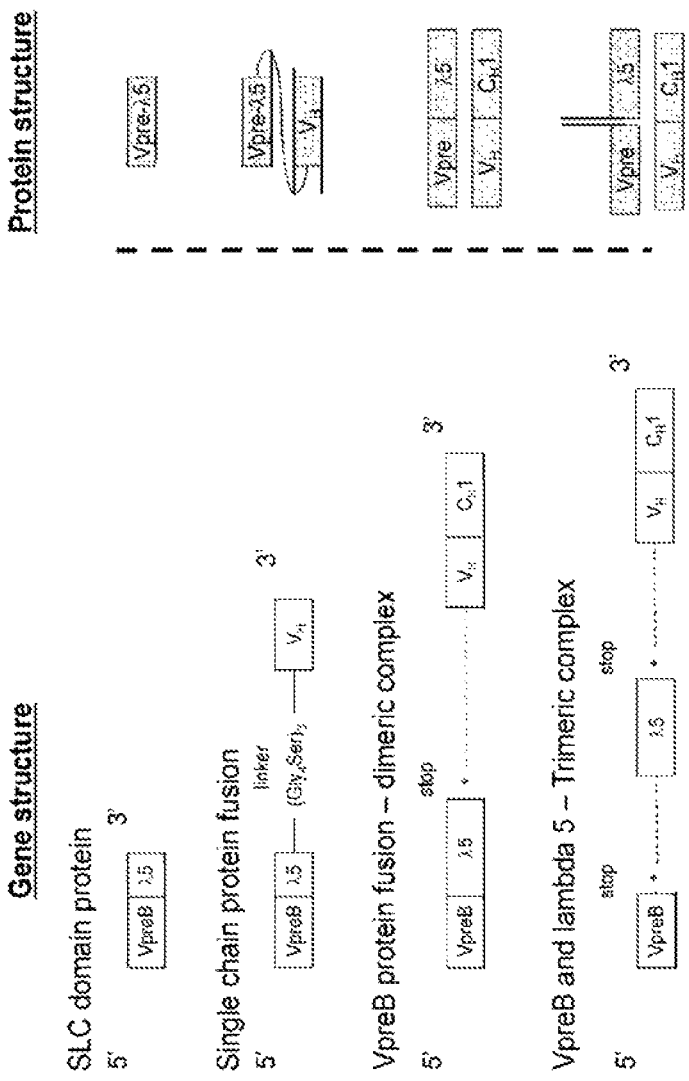
FIG. 29 shows the gene and protein structures of various illustrative sur-binding proteins.

All surrogate light chain constructs herein may be associated with antibody heavy chain sequences. For example, as shown in FIG. 29, a VpreB-λ5 fusion can be linked to an antibody heavy chain variable region sequence by a peptide linker. In some embodiments, a VpreB-λ5 fusion is associated with an antibody heavy chain, or a fragment thereof including a variable region sequence to form a dimeric complex. In yet another embodiment, the VpreB and λ5 sequences are associated with each other and an antibody heavy chain, or a fragment thereof including a variable region sequence, thereby forming a trimeric complex. Exemplary constructs comprising an antibody heavy chain are illustrated in FIG. 34.

While the constructs are illustrated by reference to certain embodiments, one of ordinary skill will understand that numerous further embodiments obtained by various permutations of surrogate light chain and antibody sequences are possible, and are within the scope of the present invention. The present invention includes all constructs that comprise surrogate light chain sequences and have the ability to bind a desired target. In certain embodiment, the constructs also have the ability to associate with antibody heavy chain variable region sequences.

The constructs may be used to build libraries of surrogate light chain sequences, which can be used for various purposes, similarly to antibody libraries, including selection of constructs with the desired binding specificities and affinities.

When the VpreB and λ5 surrogate light chain sequences are non-covalently associated with each other, the free ends of one or both components (i.e. the C-terminal end of the VpreB sequence and/or the N-terminal end of the λ5 sequence) are available for incorporating an additional diversity into the library of such sequences. For instance, a random peptide library can be appended or substituted to one of these free ends and panned for specific binding to a particular target. By combining the surrogate light chain identified to have the desired binding specificity with a heavy chain or heavy chain fragment from an antibody to the same target, a molecule can be created that has the ability to bind to the cognate target on two distinct places. This tandem binding, or "chelating" effect, strongly reinforces the binding to a single target, similarly to the avidity effects seen in dimeric immunoglobulins. It is also possible to use components binding to different targets. Thus, for example, the surrogate light chain component with the desired binding specificity can be combined with an antibody heavy chain or heavy fragment binding to a different target. For instance, the surrogate light chain component can bind a tumor antigen while the antibody heavy chain or heavy chain fragment can bind to effector cells. This way, a single entity with targeting and anti-tumor activity can be created. In a particular embodiment, the appendage or the polypeptide that connects the VpreB and λ5 sequences can be an antibody or antibody fragment, such as a Fab or a scFv fragment. The incorporation of an antibody sequence will not only create a "chelating" effect but can also generate bispecificity in a single molecule, without the need of a second independent arm, such as that found in bispecific antibodies. The two specificities can be to different parts of the same target, to disparate targets, or to a target antibody complex. Similarly, multi-specific constructs can be made with any type of molecule, other than antibodies or antibody fragments, including peptides, proteins, enzymes, and the like. For example, the surrogate light chain component with the desired specificity can be combined with any therapeutic peptide or protein.

In some embodiments, the VpreB and λ5 components of the SBP can be modified in numerous ways to improve the structure, performance, and/or stability of resulting SBPs. An approach to improving the qualities of the SBPs can be accomplished by incorporating elements of antibody light chains into the surrogate light chain. One example would be the substitution of one or more framework regions of antibody light chain variable domains into the structurally similar regions of the surrogate light chain. Specifically one could substitute Contact defined variable light chain framework-related Kabat numbered residues 1-29, 37-45, or 56-88, for VpreB residues 21-47, 58-67, or 82-117, respectively. Alternatively, one could substitute Chothia defined variable light chain framework-related Kabat numbered residues 1-23, 35-49, 57-88, for VpreB residues 21-41, 56-71, or 83-117, respectively. These regional substitutions can be done in whole, or as a continuous or discontinuous portion to achieve the desired surrogate light chain. Additionally, substitution of one or more regions of the antibody light chain variable and constant domains into the structurally similar regions of the surrogate light chain can be performed. In this instance one could substitute light chain domain Kabat residues 97-215 for λ5 residues 94-211 respectively. This regional substitution can also be done in whole or as a continuous or discontinuous portion to achieve the desired surrogate light chain. Also combinations of such substitutions for both VpreB and λ5 can be incorporated to achieve the desired light chain. In any event any or all of the modified surrogate light chains and their respective resulting SBPs can be produced in protein expression systems and tested, or used for their potential improved qualities.

Preparation of Surrogate Light Chain Constructs

The surrogate light chain constructs can be prepared by methods known in the art, including well known techniques of recombinant DNA technology.

Nucleic acid encoding surrogate light chain, e.g. VpreB and λ5 polypeptides, can be isolated from natural sources, e.g. developing B cells and/or obtained by synthetic or semi-synthetic methods. Once this DNA has been identified and isolated or otherwise produced, it can be ligated into a replicable vector for further cloning or for expression.

Cloning and expression vectors that can be used for expressing the coding sequences of the polypeptides herein are well known in the art and are commercially available. The vector components generally include, but are not limited to, one or more of the following: a signal sequence, an origin of replication, one or more marker genes, an enhancer element, a promoter, and a transcription termination sequence. Suitable host cells for cloning or expressing the DNA encoding the surrogate light chain constructs in the vectors herein are prokaryote, yeast, or higher eukaryote (mammalian) cells, mammalian cells are being preferred.

Examples of suitable mammalian host cell lines include, without limitation, monkey kidney CV1 line transformed by SV40 (COS-7, ATCC CRL 1651); human embryonic kidney line 293 (293 cells) subcloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, Biol. Reprod. 23:243-251 (1980)); monkey kidney cells (CV1 ATCC CCL 70); African green monkey kidney cells (VER0-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

For use in mammalian cells, the control functions on the expression vectors are often provided by viral material. Thus, commonly used promoters can be derived from the genomes of polyoma, Adenovirus2, retroviruses, cytomegalovirus, and Simian Virus 40 (SV40). Other promoters, such as the β-actin protomer, originate from heterologous sources. Examples of suitable promoters include, without limitation, the early and late promoters of SV40 virus (Fiers et al., *Nature,* 273: 113 (1978)), the immediate early promoter of the human cytomegalovirus (Greenaway et al., *Gene,* 18: 355-360 (1982)), and promoter and/or control sequences normally associated with the desired gene sequence, provided such control sequences are compatible with the host cell system.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity Enhancers are relatively orientation and position independent, but preferably are located upstream of the promoter sequence present in the expression vector. The enhancer can originate from the same source as the promoter, such as, for example, from a eukaryotic cell virus, e.g. the SV40 enhancer on the late side of the replication origin (bp 100-270), the cytomegalovirus early promoter enhancer, the polyoma enhancer on the late side of the replication origin, and adenovirus enhancers.

Expression vectors used m mammalian host cells also contain polyadenylation sites, such as those derived from viruses such as, e.g., the SV40 (early and late) or HBV.

An origin of replication can be provided either by construction of the vector to include an exogenous origin, such as can be derived from SV40 or other viral (e.g., Polyoma, Adeno, VSV, BPV) source, or can be provided by the host cell.

The expression vectors usually contain a selectable marker that encodes a protein necessary for the survival or growth of a host cell transformed with the vector. Examples of suitable selectable markers for mammalian cells include dihydrofolate reductase (DHFR), thymidine kinase (TK), and neomycin.

Suitable mammalian expression vectors are well known in the art and commercially available. Thus, for example, the surrogate light chain constructs can be produced in mammalian host cells using a pCI expression vector (Promega), carrying the human cytomegalovirus (CMV) immediate-early enhancer/promoter region to promote constitutive expression of a DNA insert. The vector can contain a neomycin phosphotransferase gene as a selectable marker.

The surrogate light chain constructs can also be produced in bacterial host cells. Control elements for use in bacterial systems include promoters, optionally containing operator sequences, and ribosome binding sites. Suitable promoters include, without limitation, galactose (gal), lactose (lac), maltose, tryptophan (trp), β-lactamase promoters, bacteriophage λ and T7 promoters. In addition, synthetic promoters can be used, such as the tac promoter. Promoters for use in bacterial systems also generally contain a Shine-Dalgarno (SD) sequence operably linked to the DNA encoding the Fab molecule. The origin of replication from the plasmid pBR322 is suitable for most Gram-negative bacteria.

The coding sequences of the individual chains within a multi-chain construct comprising antibody surrogate light chain sequences can be present in the same expression vector, under control of separate regulatory sequences, or in separate expression vectors, used to cotransfect a desired host cells, including eukaryotic and prokaryotic hosts. Thus, multiple genes can be coexpressed using the Duet™ vectors commercially available from Novagen.

The transformed host cells can be cultured in a variety of media. Commercially available media for culturing mammalian host cells include Ham's F10 (Sigma), Minimal Essential Medium (MEM), (Sigma), RPMI-1640 (Sigma), and Dulbecco's Modified Eagle's Medium ((DMEM), Sigma). In addition, any of the media described in Ham et al., *Meth. Enz.* 58:44 (1979) and Barnes et al., *Anal. Biochem.* 102:255 (1980) can be used as culture media for the host cells. The culture conditions, such as temperature, pH, and the like, are those previously used with the host cell selected for expression, and are included in the manufacturer's instructions or will otherwise be apparent to the ordinarily skilled artisan.

Further suitable media for culturing mammalian, bacterial (e.g. *E. coli*) or other host cells are also described in standard textbooks, such as, for example, Sambrook et al., supra, or Ausubel et al., supra.

Purification can be performed by methods known in the art. In a preferred embodiment, the surrogate antibody molecules are purified in a 6×His-tagged form, using the Ni-NTA purification system (Invitrogen).

Uses of Surrogate Light Chain Sequences, Constructs and Libraries Containing Same The libraries can be used to identify surrogate light chain sequences and surrogate light chain constructs, such as fusions comprising surrogate light chain sequences, with desired properties. For example, in vitro or in vivo screening of the libraries herein can yield polypeptides comprising surrogate light chain sequences binding to desired targets with high binding specificity and affinity. Thus, the libraries herein can be used to identify molecules for therapeutic and diagnostic purposes, such as polypeptides comprising surrogate light chain sequences that bind to tumor markers or other molecular targets of therapeutic intervention. In addition, by the techniques described above, highly diverse libraries of surrogate light chain polypeptides can be engineered, including libraries comprising a collection of polypeptides binding to the same target, libraries of polypeptides binding to different targets, libraries of polypeptides with multiple specificities, and the like.

As a result of their ability to bind to any desired target, the antibody surrogate light chain constructs can be used in analytical and diagnostic assays, to detect the presence of a desired target molecule, such as a tumor antigen or any polypeptide associated with a disease state or condition. In some embodiments the presence of cells expressing DR4 and/or DR5 can be detected. In addition, the surrogate light chain constructs can be used as therapeutic agents, such as, for example, in cancer therapy, to target cells that associated with a disease or disorder and in which apoptosis or reduced proliferation would be desirable, such as in the treatment of cancer. In some embodiments a DR4 and or DR5 expressing cells are determined to be associated with the development and/or spread of cancer and are targeted.

Coupling SBPs to Therapeutic Agents or Labels

While, for some embodiments, the binding of the SBPs to their ligands can modulate the biological activity of the target cell by, for example, activating DR4 and/or DR5, the effect of the SBPs on biological activity can be increased by coupling a therapeutic agent to the SBPs. In some embodiments, therefore, the SBPs are derivatized to introduce functional groups permitting the attachment of a therapeutic agent. The SBP can be derivatized to introduce, for example, side chains terminating in hydrazide, hydrazine, primary amine, or secondary amine groups. Therapeutic agents can be conjugated through, for example, a Schiffs base linkage, a hydrazone or acyl hydrazone bond or a hydrazide linker (see, e.g, U.S. Pat. Nos. 5,474,765 and 5,762,918, each of which is specifically incorporated herein by reference). A number of other chemistries suitable for conjugating therapeutic agents to SBP are well known in the art, as exemplified by Hermanson, G., Bioconjugate Techniques, Academic Press, San Diego, Calif. (1996).

In some embodiments, a cysteine residue can be substituted into a surrogate light chain in order to accommodate drug conjugation. For example, the surrogate light chain illustrated in SEQ ID NO: 483 can be modified to substitute a cysteine at various positions, including positions 16 (SEQ ID NO: 487), 21 (SEQ ID NO: 488), 107 (SEQ ID NO: 489), 121 (SEQ ID NO: 490), 125 (SEQ ID NO: 491), 126 (SEQ ID NO: 492), 132 (SEQ ID NO: 493), 138 (SEQ ID NO: 494), 157 (SEQ ID NO: 495), 170 (SEQ ID NO: 496), 178 (SEQ ID NO: 497), 180 (SEQ ID NO: 498), 213 (SEQ ID NO: 499), or 217 (SEQ ID NO: 480). For example, cysteine can be substituted for a threonine at position 21 (SEQ ID NO: 488), or for a valine at position 213 (SEQ ID NO: 499). In some embodiments an SBP comprises one of these light chain sequences. A therapeutic label or agent can be bound to the SBP through the substituted cysteine. For example, maleimide chemistry can be used to attach a toxin such as monomethyl auristatin.

Therapeutic agents can be selected from, for example, anti-neoplastic agents, anti-metabolic agents, radioactive agents, cytotoxic agents, and chemotherapeutic agents.

Anticancer agents include cytotoxic agents, such as the following: auristatins and derivatives, calicheamicins and derivatives, maytansinoids and derivatives, *Pseudomonas* exotoxin, ricin, diphtheria toxin, gemcitabine; methotrexate; 5-FU; FUDR; FdUMP; hydroxyurea; docetaxel; discodermolide; epothilones; vincristine; vinblastine; vinorelbine; meta-pac; irinotecan; SN-3 8; 10-OH campto; topotecan; etoposide; adriamycin; flavopiridol; cisplatin; carboplatin; bleomycin; mitomycin C; mithraniycin; capecitabine; cytarabine; 2-C1-2' deoxyadenosine; mitoxantrone; mitozolomide; pentostatin; and raltitrexed.

The SBPs can further be modified or labeled to facilitate diagnostic or therapeutic uses. For example, detectable labels such as a radioactive, fluorescent, heavy metal, or other label, can be conjugated to the SBPs. Single, dual, or multiple labeling of the SBPs can be advantageous. For example, a SBP can be dual labeled, with both radioactive iodination of one or more residues and the coupling of, for example, $^{90}$Y via a chelating group to amine-containing side or reactive groups. This combination labeling can be useful for specialized diagnostic needs such as identification of widely dispersed small neoplastic cell masses.

Radioisotopes for radiolabeling the SBPs can include any radioisotope that can be conjugated or coupled to a residue of the SBPs. The radioisotopes can be selected from radioisotopes that emit either beta or gamma radiation, or alternatively, the peptide agents can be modified to contain chelating groups that, for example, can be covalently bonded to lysine residue(s) of the analog. The chelating groups can then be modified to contain any of a variety of radioisotopes, such as iodine, gallium, indium, technetium, ytterbium, rhenium, or thallium (e.g., $^{125}$I, $^{67}$Ga, $^{111}$In, $^{99}$mTc, $^{169}$Yb, $^{186}$Re, $^{201}$Tl).

Chelating groups can be used to indirectly couple detectable labels or other molecules to the SBP. For example, a bifunctional stable chelator may be linked to one or more terminal or internal amino acid reactive groups via an isothiocyanate beta-Ala or an appropriate non alpha-amino acid linker which prevents Edman degradation. Examples of chelators known m the art include, for example, the ininocarboxylic and polyaminopolycarboxylic reactive groups, DTPA (N,N-Bis[2-[bis(carboxymethyl)amino]ethyl]glycine), and DOTA (1,4,7,10-tetraazacyclododecane-1,4,7,10-tetraacetic acid).

In terms of diagnosis and treatment of diseases or disorders such as cancer, the SBP can be used to prepare diagnostic and imaging compositions, and kits utilizing the SBPs in diagnostic and imaging methods (e.g., in vivo and in vitro diagnostic methods). For example, a vascularized tumor can be imaged using a diagnostically effective amount of a SBP that includes at least a first binding molecule that binds to an accessible component of a tumor cell, tumor vasculature, or tumor stroma, attached to an in vivo diagnostic imaging agent.

In some embodiments in which the disease or disorder is cancer, pre-imaging before cancer treatment may be carried out by: (a) administering to the animal or patient a diagnostically effective amount of a pharmaceutical composition comprising a detectably-labeled SBP that has a first binding molecule that binds with high affinity to a highly expressed receptor characteristic of a tumor cell, or to the tumor vasculature or tumor stroma, and a second binding molecule that binds with at least an order of magnitude lower affinity to a second ubiquitously-expressed receptor; and (b) subsequently detecting the detectably-labeled SBP bound to the tumor cells, tumor blood vessels, or tumor stroma; thereby obtaining an image of the tumor, tumor vasculature, and/or tumor stroma.

Therapeutic Uses

In some embodiments, SBPs can be used for/in therapies which involve administering SBPs to an animal, preferably a mammal, and most preferably a human patient, for treating one or more diseases or disorders. In some embodiments the SBPs or binding portions thereof are used to treat a disease or disorder associated with DR4 and/or DR5 dependent signaling, or a disease or disorder involving cells that express DR4 and/or DR5. Therapeutic compounds include, but are not limited to, SBPs or antigen binding portions thereof The SBPs or antigen binding portions thereof can be used to treat, inhibit, or prevent diseases in which reduction of cell proliferation or apoptosis of cells that naturally express or are engineered to express DR4 and/or DR5 would be beneficial, including the diseases and disorders disclosed herein. In some embodiments, diseases or disorders to be treated are associated with aberrant cell proliferation. The treatment and/or prevention of diseases and disorders can include, but is not limited to, alleviating symptoms associated with the diseases and disorders. SBPs or antigen binding portions thereof may be provided in pharmaceutically acceptable compositions as known in the art or as described herein. Armed with the teachings provided herein, one of ordinary skill in the art will know how to use the SBPs or antigen binding portions thereof for diagnostic, monitoring and therapeutic purposes without undue experimentation.

In some embodiments, the SBPs may be administered alone or in combination with other types of treatments (e.g., radiation therapy, chemotherapy, hormonal therapy, immunotherapy and anti-tumor agents). As discussed above, in some embodiments the SBPs may be coupled to a therapeutic agent and/or diagnostic agent. For example, an SBP may be coupled to a toxin.

Methods of using SBPs, antigen-binding portions thereof, and antibodies that bind DR4 and/or DR5 in a variety of ex vivo and in vivo diagnostic and therapeutic applications are also provided. For example, SBPs and/or antibodies disclosed herein can be used for treating a disease in which cells that are to be targeted express DR4 and/or DR5, including a variety of cancers. In some embodiments cells associated with a disease or disorder can be assayed for the expression of DR4 and or DR5 prior to treatment. In some embodiments cells associated with a disease or disorder can be engineered to express DR4 and/or DR5 prior to treatment with an SBP or antigen binding portion thereof In some embodiments, methods for treating a disease are provided in which cells expressing DR4 and/or DR5 are to be killed or their proliferation inhibited by administering to a subject a therapeutically effective amount of an SBP, antigen binding portion thereof, and/or antibodies in an amount effective to treat the disease. In some embodiments the SBP is a dual agonist SBP, such as SL-466 or SL-231. In some embodiments the SBP is coupled to a different therapeutic agent, such as a toxin. Suitable diseases include, for example, a variety of cancers including, but not limited to, melanoma, breast cancer, ovarian cancer, renal carcinoma, lymphoid cancers, gastrointestinal cancer, colon cancer, epidermal cancers, lung cancer (e.g., non-small cell lung cancer), pancreatic cancer and prostate cancer; infectious viral diseases such as influenza, HIV, CMV, RSV, and HTLV; and autoimmune inflammatory disease such as systemic lupus erythmatosis and rheumatoid arthritis.

In some embodiments, the SBP, antigen binding portion thereof and/or antibodies can be administered alone or with another therapeutic agent which acts in conjunction with or synergistically with the SBP, antigen-binding portion thereof and/or antibodies to treat the disease or disorder. Such therapeutic agents can include, for example, the anticancer agents described infra (e.g., cytotoxins, chemotherapeutic agents, small molecules and radiation). In some embodiments, the therapeutic agents for combination therapy include erlotinib (Tarceva®), paclitaxel (Taxol™) and cisplatin (CDDP). In some embodiments the agents include aromatase inhibitors, estrogen receptor inhibitors, lapatinib, gefitinib, PI3kinase inhibitors, and/or AKT inhibitors.

In certain aspects, SBPs, antigen binding portions thereof, and/or antibodies disclosed herein are administered to patients.

In some embodiments, methods are provided for diagnosing a disease (e.g., a cancer) associated with Death Receptor expression in a subject, by contacting antibodies, antigen binding portions, and/or SBPs disclosed herein (e.g., ex vivo or in vivo) with cells from the subject, and measuring the level of binding to DR4, DR5 or both DR4 and DR5 on the cells. Abnormally high levels of binding to Death Receptors indicate that the subject has a disease for which Death Receptor agonist sur-binding proteins are or may be a treatment option.

In some embodiments, methods of suppressing tumor growth are provided. The methods can include providing a DR4 and/or DR5 SBP or antigen binding portions thereof, such as described herein, to a tumor that comprises cells expressing DR4 and/or DR5. The SBP may reduce proliferation of the tumor cells, for example by stimulating the death receptor pathway. In some embodiments methods of suppressing tumor growth comprise providing a dual DR4 and DR5 agonist SBP to a tumor that comprises cells expressing DR4 and DR5. The dual agonist SBP may be, for example, SL-466 or SL-231 or comprise one or more antigen binding portions thereof. The SBP may be conjugated to a therapeutic agent such as a toxin. In some embodiments the dual DR4 and DR5 agonist SBP may be more effective in suppressing tumor growth than single receptor agonists.

In some embodiments methods of killing tumor cells are provided. The methods can comprise contacting tumor cells that express DR4 and/or DR5 with a SBP or antigen binding portions thereof as described herein. The SBP may trigger apoptosis in the tumor cells. In some embodiments the tumor cells are contacted in vivo. In some embodiments the SBPs are administered in combination with another composition that reduces tumor cell proliferation and/or kills tumor cells. In some embodiments methods of killing tumor cells comprise providing a dual DR4 and DR5 agonist SBP to a tumor that comprises cells expressing DR4 and DR5. The dual agonist SBP may be, for example, SL-466 or SL-231, or comprise one or more antigen binding portions thereof. The SBP may be conjugated to a therapeutic agent such as a toxin. In some embodiments a dual agonist SBP is able to activate apoptosis in tumors that are weakly or not responsive to single receptor agonists.

In some embodiments the SBPs disclosed herein, or antigen binding portions thereof, can be used to inhibit, block or reduce the proliferation of cells in vitro, in vivo or ex vivo. In some embodiments the cells comprising DR4 and/or DR5 are contacted with an SBP or antigen binding portions thereof. The SBP can induce apoptosis in the cells. In some embodiments the methods comprise contacting the cells with a dual agonist SBP to a tumor that comprises cells expressing DR4 and DR5. The dual agonist SBP may be, for example, SL-466 or SL-231, or comprise one or more antigen binding portions thereof.

In some embodiments methods of stimulating apoptosis in cells expressing DR4 and/or DR5 are provided. The methods may be carried out in vitro, in vivo or ex vivo. The methods can comprise contacting cells that express DR4 and/or DR5 with a SBP or antigen binding portions thereof as described herein. The SBP may stimulate apoptosis in the cells. In some embodiments the cells are contacted in vivo. In some embodiments the SBPs are administered in combination with another composition that reduces cell proliferation and/or kills cells. In some embodiments the SBP is conjugated to a composition that reduces cell proliferation and/or kills cells. In some embodiments methods of stimulating apoptosis in cells comprise providing a dual DR4 and DR5 agonist SBP to cells expressing DR4 and DR5. The dual agonist SBP may be, for example, SL-466 or SL-231, or comprise one or more antigen binding portions thereof The SBP may be conjugated to an agent such as a toxin. In some embodiments a dual agonist SBP is able to stimulate apoptosis in cells that are weakly or not responsive to single receptor agonists.

In some embodiments, the amount of any of the sur-binding proteins provided herein (for example, SL466 and/or SL231) can be used at an amount of at least 0.001 mg/kg of subject weight, e.g., 0.001, 0.01, 0.1, 1, 10, 20, 30, 40, 50, 60, 70, 80, 90, or 100 mg/kg of subject weight, including any range defined between any two of the preceding values. In some embodiments, the amount of the sur-binding protein used is from 0.1 to 100 mg/kg.

In some embodiments a dual agonist DR4 and DR5 SBP is used therapeutically to treat a disease or disorder that is weakly responsive or not responsive to agents that target DR4 or DR5 individually. In some embodiments a dual agonist DR4 and DR5 SBP is used to treat a disease or disorder characterized by cells that have heterogeneous death receptor profiles, such as cells that have differential expression of DR4 and DR5. In some embodiments differential expression may include, but is not limited to, no or low DR4 expression and high DR5 expression. In some embodiments the disease or disorder may be pancreatic cancer, lymphoma, such as Burkitt's lymphoma or T-cell lymphoma, or breast cancer. In some embodiments, a dual agonist DR4 and DR5 SBP is used therapeutically and is more effective than either a DR4 SBP or antibody, a DR5 SBP or antibody or a combination of a DR4 SBP or antibody and a DR5 SBP or antibody. In some of the above-mentioned embodiments the dual agonist DR4 and DR5 SBP may be SL466 (3706-A02) or SL231 (3631-G09), or an SBP comprising one or more CDRs or binding domains from SL466 or SL231. In some embodiments the dual agonist SBP may be conjugated to a therapeutic agent, such as a toxin or chemotherapeutic agent. In some embodiments the dual agonist SBP may be administered along with a chemotherapeutic agent, for example obatoclax or doxorubicin.

Sur-Binding Protein-Based Therapeutic/Prophylactic Compositions and Administration Thereof Some embodiments provide methods of treatment, inhibition, and prophylaxis by administration to a subject of an effective amount of a SBP or antigen binding portion thereof. In some embodiments, the SBP or antigen binding portion thereof is substantially purified (e.g., substantially free from substances that limit its effect or produce undesired side effects). The subject can be an animal, including but not limited to animals such as cows, pigs, horses, chickens, cats, and dogs, and is preferably a mammal, and in some embodiments a human.

Various delivery systems are known and can be used to administer a SBP, e.g., encapsulation in liposomes, microparticles, microcapsules, recombinant cells capable of expressing the SBP or antigen binding portions thereof, receptor-mediated endocytosis (see, e.g., Wu and Wu, J. Biol. Chem. 262:4429-4432, 1987), construction of a nucleic acid as part of a retroviral or other vector, etc. Methods of introduction include but are not limited to intradermal, intramuscular, intraperitoneal, intravenous, subcutaneous, intranasal, epidural, and oral routes. The SBPs or antigen binding portions thereof can be administered by any convenient route, for example by infusion or bolus injection, by absorption through epithelial or mucocutaneous linings (e.g., oral mucosa, rectal and intestinal mucosa, etc.), and can be administered together with other biologically active agents. Administration can be systemic or local. In addition, it can be desirable to introduce the SBP or antigen binding portions thereof into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it may be desirable to administer the SBPs or antigen binding portions thereof locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, when administering a SBP or antigen binding portions thereof, care can be taken to use materials to which the SBP or antigen binding portion thereof does not absorb.

In some embodiments, the SBPs, antigen binding portions thereof and/or antibodies can be delivered in a vesicle, in particular a liposome (see Langer, Science 249:1527-1533, 1990; and Treat et al., in Liposomes in the Therapy of Infectious Disease and Cancer, Lopez-Berestein and Fidler (eds.), Liss, New York, pp. 353-365, 1989).

In some embodiments, the SBP, antigen binding portions thereof and/or antibodies can be delivered in a controlled release system. In some embodiments, a pump can be used (see Langer, supra; Sefton, CRC Crit. Ref Biomed. Eng. 14:201, 1987; Buchwald et al., Surgery 88:507, 1980; Saudek et al., N. Engl. J. Med. 321:574, 1989). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In some embodiments, a controlled release system can be placed in proximity of the therapeutic target, e.g., an affected organ of the body, such as the brain, lungs, kidney, liver, ovary, testes, colon, pancreas, breast, and skin, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249: 1527-1533).

SBPs, antigen binding portions thereof and/or antibodies can also be provided m a pharmaceutical composition. Such compositions comprise a therapeutically effective amount of a SBP, antigen binding portions thereof and/or antibodies and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington: The Science and Practice of Pharmacy," A. R. Gennaro, ed. Lippincott Williams & Wilkins, Philadelphia, Pa. (20th Ed., 2003). Such compositions will contain a therapeutically effective amount of the compound, preferably in purified form, together with a suitable amount of carrier so as to provide the form for proper administration to the patient. The formulation should suit the mode of administration.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The SBPs, antigen binding portions thereof and/or antibodies, when formulated in pharmaceutical compositions, can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, or procaine.

The amount of the SBP, antigen binding portions thereof and/or antibodies that will be effective in the treatment, inhibition and prevention of a disease or disorder, such as one associated with aberrant cellular activity, can be determined by standard clinical techniques, in light of the disclosure presented herein. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

For SBPs or antigen binding portions thereof, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. The dosage and frequency of administration of SBPs or antigen binding portions thereof can be reduced by enhancing uptake and tissue penetration of the SBPs or antigen binding portions thereof by modifications such as, for example, lipidation.

In some embodiments, any of the disclosed SBPs can be used for the preparation of a medicament for the treatment of any of the above disorders.

In another aspect, the present invention provides a composition, e.g., a pharmaceutical composition, containing one or a combination of SBPs, antigen-binding portion(s) thereof, and/or antibodies disclosed herein, formulated together with a pharmaceutically acceptable carrier. In some embodiments, the compositions include a combination of multiple (e.g., two or more) isolated agents which bind different epitopes on DR4 and/or DR5. In some embodiments the compositions include dual DR4 and DR5 agonist SBPs or binding portions thereof. In some embodiments the compositions comprise one or both of SL-466 and SL-231.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active agent, i.e., SBP or binding portion thereof, antibody or antibody fragment, bispecific and multispecific molecule, can be coated in a material to protect the agent from the action of acids and other natural conditions that can inactivate it.

A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can comprise other agents. For example, the composition can include at least one or more additional therapeutic agents, such as the anti-cancer agents described infra. The pharmaceutical compositions can also be administered in conjunction with radiation therapy and/or surgery. Alternately a composition can be separately co-administered with at least one or more additional therapeutic agents, such as the anti-cancer agents described infra.

For the therapeutic compositions, formulations include those suitable for oral, nasal, topical (including buccal and sublingual), transdermal, subcutaneous, intrathecal, intraspinal, rectal, vaginal and/or parenteral administration. The formulations can conveniently be presented in unit dosage form and can be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations which are suitable for vaginal administration also include pessaries, tampons, creams, gels, pastes, foams or spray formulations containing such carriers as are known in the art to be appropriate. Dosage forms for the topical or transdermal administration of compositions include powders, sprays, ointments, pastes, creams, lotions, gels, solutions, patches and inhalants. The active agent may be mixed under sterile conditions with a pharmaceutically acceptable carrier, and with any preservatives, buffers, or propellants.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous earners which can be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes which contain a membrane-bound hemagglutinin and neuraminidase derived from the influenza virus).

Prevention of presence of microorganisms can be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In addition, prolonged absorption of the injectable pharmaceutical form can be brought about by the inclusion of agents which delay absorption such as aluminum monostearate and gelatin.

When the SBPs of the present disclosure are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the SBPs, which may be used in a suitable hydrated form, and/or the pharmaceutical compositions, are formulated into pharmaceutically acceptable dosage forms by conventional methods known to those of skill in the art.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage levels will depend upon a variety of pharmacokinetic factors including the activity of the particular compositions employed, or, for compounds co-administered with antibodies or fragments thereof provided herein, the ester, salt or amide thereof, the route of administration, the time of administration, the rate of excretion of the particular agent being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the SBPs, antigen binding portions thereof and/or antibodies employed in the pharmaceutical composition at levels lower than that required in order to achieve the desired therapeutic effect and gradually increase the dosage until the desired effect is achieved. In general, a suitable daily dose of a composition will be that amount which provides the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition can be administered as two, three, four, five, six or more sub-doses administered separately at appropriate intervals throughout the day, optionally, in unit dosage forms. While it is possible for an SBP, antigen binding portion and/or antibody of the present disclosure to be administered alone, it is preferable to administer the SBP, antigen binding portion and/or antibody as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art. In some embodiments, an SBP, antigen binding portion thereof and/or antibody can be administered intravenously, transdermally, subcutaneously, intraperitoneally, intrathecally, epidurally, and/or spinal.

In certain embodiments, compositions disclosed herein can be formulated to ensure proper distribution in vivo. For example, the blood-brain barrier (BBB) excludes many highly hydrophilic compounds. To ensure that therapeutic compounds cross the BBB (if desired), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39: 180); surfactant protein A receptor (Briscoe et al. (1995) Am. J. Physiol. 1233:134), different species of which can comprise the formulations, as well as components of the invented molecules; p 120 (Schreier et al. (1994) J. Biol. Chem. 269:9090); see also K Keinanen; M. L Laukkanen (1994) FEBS Lett. 346:123; J. J. Killion; I. J. Fidler (1994) Immunomethods 4:273.

In some embodiments, an SBP compound or composition includes more than one SBP, antigen binding portion thereof and/or antibody. In some embodiments, the composition comprises at least one SBP or antigen binding portion thereof that binds DR4 and/or DR5. In some embodiments, the composition comprises at least one SBP or antigen binding portion thereof that binds both DR4 and DR5. In some embodiments, the composition comprises at least one SBP or antigen binding portion thereof that binds DR4 and/or DR5 and a second SBP or antigen binding portion thereof that binds DR4 and/or DR5. In some embodiments, the two or more SBPs or antigen binding portions thereof bind to different epitopes or do not compete with one another for binding to DR4 and/or DR5. In some embodiments, the two or more SBPs or antigen binding portions thereof bind to similar or overlapping epitopes.

In some embodiments, a composition comprises at least one SBP or antigen binding portion thereof that binds DR5 and a second SBP or antigen binding portion thereof that binds DR4. In some embodiments, a composition comprises at least one SBP or antigen binding portion thereof that binds DR5 and DR4 and a second SBP or antigen binding portion thereof that binds one or both of DR5 and DR4. In some embodiments, the composition comprises at least one SBP or antigen binding portion thereof that binds DR5 and/or DR4 and an antibody that binds that DR5 and/or DR4. In some embodiments, the composition comprises at least one SBP or antigen binding portion thereof that binds DR5 and an antibody that binds DR4, or vice versa. In some embodiments, the composition comprises at least one SBP or antigen binding portion thereof that binds DR5 and DR4 and an antibody that binds DR5 or DR4. For the relevant embodiments above, the SBPs can either be a single bispecific construct or a pair of constructs.

In some embodiments, one can combine a SBP, antigen binding portion thereof or antibody with one or more growth factor inhibitors or other compositions to increase tumor cell killing.

In some embodiments, one or more SBPs, antigen binding portions thereof, or antibodies can be combined with one or more traditional chemotherapeutic agents, growth factor tyrosine kinase inhibitors, protein kinase inhibitors, caspase or apoptotic activators, microtubule inhibitors (e.g. taxanes), estrogen receptor inhibitors (tamoxifen), aromatase inhibitors and/or HSP90 inhibitors.

In some embodiments, any of the methods provided herein can employ any of the compositions, compounds, kits, SBPs, SBP combinations, etc. disclosed herein.

Kits

Some embodiments also encompass kits for use in therapy or in detecting cells expressing or overexpressing target molecules in vivo, or in biological samples. In some embodiments, the kits contain SBPs, antigen binding portions thereof and/or antibodies targeted to DR4 and/or DR5. In some embodiments the kits contain SBPs, antigen binding portions thereof, or antibodies, targeting DR4 and DR5. Depending on use, the SBPs, antigen binding portions thereof and/or antibodies can be functionalized with linkers or chelators, or both, for coupling to an effector (e.g. a radioactive moiety, a liposome, a cytotoxin, an antibody, a SBP or antigen binding portion thereof, etc.) as described herein. The kits optionally further comprise buffers and compositions to be used for detection of the SBP or antigen binding portion thereof.

The kits can also include instructional materials teaching the use of the SBPs or antigen binding portions thereof, for therapy or for detecting, e.g. cancer cells, and/or teaching the combination of the SBPs or antigen binding portions thereof with functionalizing reagents or teaching the use of functionalized SBPs or antigen binding portions thereof for imaging and/or therapeutic applications. In some embodiments, the SBP or antigen binding portion thereof is provided functionalized with a linker and/or a chelator (in one container) along with one or more effectors, e.g. cytotoxins, radioactive labels (in a second container) such that the two components can be separately administered (e.g. in pre-targeting approaches) or such that the two components can be combined shortly before use.

Certain instructional materials can provide recommended dosage regimen, counter indications, and the like. While the instructional materials typically comprise written or printed materials, any medium capable of storing such instructions and communicating them to an end user is contemplated by this invention. Such media include, but are not limited to electronic storage media (e.g., magnetic discs, tapes, cartridges, chips), optical media (e.g., CD ROM), and the like, or internet locations that provide the instructions. In some embodiments, a pharmaceutical pack or kit comprising one or more containers filled with one or more of the ingredients of the pharmaceutical compositions of the SBP is also provided. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, any of the disclosed SBPs can be part of a kit for the treatment of one of the above disorders. In some embodiments, the kit will include a unit dose to be administered to a subject 1, 2, 3, 4, 5, 6, 7, 8, 9, 10, 11, 12, 13, 14, 15, 16, 17, 18, 19, 20, 21, 22, 23, or 24 times a day. In some embodiments, the composition is configured for subcutaneous, or IV administration.

Further details of the invention are provided in the following non-limiting Examples.

Example 1

Identification of DR5-Binding Monovalent SBPs from Phage Display Screening

This example outlines the construction of a surroglobulin (monovalent SBPs in particular) library and the identification of surroglobulins (monovalent SBPs in particular) that bind DR5.

Phage displayed libraries were composed of diversified monovalent SBPs displayed as PIII fusions on the surface of M13 bacteriophage. Monovalent SBPs comprise heavy chain frameworks (in particular VH1 or VH3), including the CH1 region, diversified in CDRs 1, 2, and 3 and complexed with the surrogate light chain fusion 1. (Xu, Yee et al. 2008). The design and construction of diversified heavy chains for use in phage display is described in U.S. Pat. App. No. 20090082213 CONSTRUCTION OF DIVERSE SYNTHETIC PEPTIDE AND POLYPEPTIDE LIBRARIES.

Phagemid expression of monovalent SBP libraries was accomplished by standard methods. TG-1 cells transformed with expression plasmids were grown to mid log (O.D. 600 ~0.3) in 2-YT media supplemented with 100 mcg/ml ampicillin and 2% glucose repression and then infected with m13K07 helper phage and grown overnight in 2-YT media supplemented with 100 mcg ampicillin, 70 mcg/ml kanamycin, and 200 micromolar IPTG. Phage containing supernatants were precipitated using polyethylene glycol and PBS resuspended phage were used to pan on immobilized DR5.

Panning of the libraries was performed by using either sDR5 (Peprotech) immobilized on the wells of a microtiter dish or biotinylated sDR5 immobilized on streptavidin derivatized magnetic beads (Dynal).

In the plate-based format, Immulon 4HBX ELISA plates were coated with sDR5. Plates were then blocked in PBS, 0.05% Tween 20, 4% non-fat dried milk for 1 hour. Approximately $10^{12}$-$10^{13}$ phage were blocked as above and applied to the target coated wells. Following a two hour incubation, the wells were washed using PBS, 0.05% Tween 20. Phage were then eluted 0.2M Glycine-HCl, pH 2.2, 1 mg/ml BSA. Eluted phage were neutralized using 2M Tris base. The eluted phage were subjected to additional rounds of amplification and panning until the titer of the phage eluted from the DR5 coated wells exceeded the titer eluted from uncoated, blocked wells.

In bead based panning, sDR5 was biotinylated using a NHS-PEO$_4$-biotinylation kit (Pierce). The biotinlyated protein was then immobilized on magnetic streptavidin beads (Dynal). Panning was carried out essentially as described above for plate based panning except that PBS, 0.05% Tween 20, 1% BSA was used as the blocking agent. Beads were collected magnetically following the initial phage binding and after each wash step.

To identify phage clones that encoded DR5-binding monovalent SBPs, a portion of the eluted phage were used to infect *E. coli* HB2151 allowing expression of periplasmic phage-encoded monovalent SBPs. Individual clones were picked into deep-well plates and grown overnight in 2YT containing ampicillin and 0.2 mM IPTG. Bacteria were lysed in BPERII and the lysates were applied to sDR5 coated plates. Following washing, binding of surroglobulins was detected using an HRP-conjugated anti-E tag antibody (Abcam).

Analysis of the third round of panning resulted in over 72% of tested clones binding to DR5. See FIGS. 1A and B.

Example 2

DR4 and DR5 Binding Analysis of Monovalent SBPs Identified from Screening on DR4 or DR5

Monovalent SBP's 3631-G09 and 3641-F01 were tested for binding of DR4 and DR5. Binding of monovalent SBPs in a dilution series was performed on microtiter wells coated with 100 ul of either 1 microgram/ml DR4 or DR5. The presence of bound monovalent SBPs was detected using an anti-E-tag antibody conjugated to HRP. Monovalent SBP 3631-G09 recognizes both DR4 and DR5, while 3641-F01 is specific for DR5. See FIGS. 2A and B.

Example 3

DR5-Binding Monovalent SBPs Exhibit a Range of Ability to Inhibit DR5 Binding to Trail Monovalent SBPs confirmed to bind DR5 were tested for their ability to block the interaction of TRAIL with DR5. Briefly, 8 nM DR5 in 1×PBST+4% (final concentration) Non-Fat Dry Milk (NFDM) was mixed with HB2151 lysate of DR5 binding monovalent SBPs and incubated for 1 hour at room temperature. The mixture was then added to a microtiter plate previously coated with 20 nM TRAIL and blocked with NFDM. The complexes were incubated with TRAIL for 1 hour at room temperature and then the unbound proteins washed out 3× with 1×PBST. The presence of bound DR5 was detected with a polyclonal goat anti-DR5 antibody and an HRP conjugated polyclonal anti-goat antibody.

As shown in Table 0.4, below, DR5-binding monovalent SBPs demonstrated different capacities to block DR5 binding to TRAIL. Those showing >40% inhibition were selected for additional analysis.

TABLE 0.4

| Well ID | OD450 nM | % inhibition | |
|---|---|---|---|
| Trail in Lysate | 0.1 | 100.0 | Background |
| DR5 in Lysate | 0.7 | 0.0 | Total Signal |
| 2737-F08 | 0.2 | 81.7 | Positive Control monovalent SBP |
| 2986-B04 | 0.1 | 93.8 | |
| 2989-B03 | 0.1 | 93.2 | |
| 2742-H03 | 0.1 | 91.0 | |
| 2744-B01 | 0.2 | 76.3 | |
| 2987-D02 | 0.3 | 63.9 | |
| 2986-F10 | 0.4 | 55.3 | |
| 2744-E10 | 0.4 | 53.9 | |
| 2743-H09 | 0.4 | 51.5 | |
| 2987-C12 | 0.4 | 51.4 | |
| 2743-D07 | 0.4 | 46.5 | |
| 2990-F06 | 0.4 | 45.3 | |
| 2742-F08 | 0.4 | 44.6 | |
| 2988-F08 | 0.5 | 43.1 | |
| 2985-E08 | 0.5 | 41.4 | |
| 2989-C12 | 0.5 | 29.6 | |
| 2743-F02 | 0.6 | 28.0 | |
| 2745-D02 | 0.6 | 25.9 | |
| 2985-B01 | 0.6 | 25.9 | |
| 2745-A12 | 0.6 | 25.8 | |
| 2742-G12 | 0.6 | 20.7 | |
| 2745-E08 | 0.6 | 20.0 | |
| 2743-G12 | 0.6 | 18.1 | |
| 2744-A12 | 0.6 | 15.9 | |
| 2744-F02 | 0.6 | 14.8 | |

TABLE 0.4-continued

| Well ID | OD450 nM | % inhibition |
|---|---|---|
| 2987-F09 | 0.6 | 14.8 |
| 2744-H12 | 0.6 | 14.5 |
| 2985-D12 | 0.6 | 13.9 |
| 2985-A12 | 0.7 | 13.4 |
| 2742-G11 | 0.7 | 12.2 |
| 2744-G01 | 0.7 | 11.3 |
| 2745-B01 | 0.7 | 11.0 |
| 2985-E09 | 0.7 | 10.8 |
| 2743-E01 | 0.7 | 10.0 |
| 2744-C01 | 0.7 | 9.8 |
| 2744-H01 | 0.7 | 9.7 |
| 2745-A11 | 0.7 | 9.1 |
| 2745-G11 | 0.7 | 8.8 |
| 2744-G12 | 0.7 | 7.4 |
| 2743-E04 | 0.7 | 4.8 |
| 2985-G08 | 0.7 | 3.4 |
| 2985-A11 | 0.7 | 2.7 |
| 2987-G11 | 0.7 | 2.4 |
| 2742-A12 | 0.7 | 1.7 |
| 2744-D01 | 0.7 | 0.9 |
| 2985-E10 | 0.7 | 0.8 |
| 2985-G11 | 0.7 | −0.8 |
| 2985-G12 | 0.8 | −2.9 |
| 2744-G02 | 0.8 | −6.0 |
| 2742-H12 | 0.8 | −10.2 |
| 2745-G12 | 0.8 | −12.7 |

Example 4

DR5 Screen Hits do not Bind Decoy Receptors DCRt and DcR2

Monovalent SBPs were tested for their ability to bind decoy receptors DcR1 and DcR2. ELISA binding analysis was performed similarly to the method described in Example 1, with the exception that DcR1 and DcR2 were used to coat the microtiter wells, each at 1 microgram/ml concentration and 100 ul used per well. The results are shown in FIGS. 3A-D.

Hits identified binding to DR5 or DR4 and DR5 are specific and do not bind to either DcR1 or DcR2.

Example 5

Trail Binding Domains

Human DR4 (SEQ ID NO: 22), DR5 (SEQ ID NO: 24), DcR1 (SEQ ID NO: 21) and DcR2 (SEQ ID NO: 23) show limited similarity in the proteins' extracellular TRAIL binding domains (FIG. 4). Significant divergence occurs within the Cysteine Rich Domain (CRD) containing 6 conserved cysteine pairs that participate in disulfide bonding to form the TRAIL binding domain. Homology between the proteins is shown in Table 0.5, below, with the highest homology between DcR1 and DcR2. Because of such sequence divergence, it is possible to identify surrogate binding proteins that bind to one family member or a subset of family members and not the others.

TABLE 0.5

| Protein Comparison | % Similarity | % Identity |
|---|---|---|
| DcR1 DcR2 | 74.8 | 71.1 |
| DcR1 DR4 | 65.2 | 58.5 |
| DcR1 DR5 | 50.4 | 48.1 |
| DcR2 DR4 | 60 | 52.6 |
| DcR2 DR5 | 59.3 | 54.8 |
| DR4 DR5 | 59.3 | 56.3 |

Example 6

Modification of SABS to Human Surroglobulins

This example outlines reformatting of monovalent SBPs to bivalent SBP. In this example, bivalent SBP are comprised of a full length heavy chain framework complexed with the surrogate light chain fusion 1. (Xu, Yee et al. 2008 Proc Natl Acad Sci USA 105(31): 10756-61). The heavy chain in this example contains a human Fc gamma I. The sequences of the heavy chains were optimized for expression in mammalian cells by DNA 2.0 (Menlo Park, Calif.). Following synthesis, they were subcloned into a mammalian expression vector such that variable regions were fused to a full length IgG1 Fc. These constructs were co-transfected along with a surrogate light chain expression vector that was similarly optimized for expression in mammalian cells. Bivalent SBP were transiently produced in HEK293-based systems essentially as described (Xu, Yee et al. (2008) "Combinatorial surrobody libraries." Proc Natl Acad Sci USA 105(31): 10756-61). The resulting bivalent SBP described in the examples were FPLC purified via Protein A chromatography.

Example 7

Death Receptor Binding Surroglobulins Bind Human and not Mouse Death Receptors

Figure 5B:
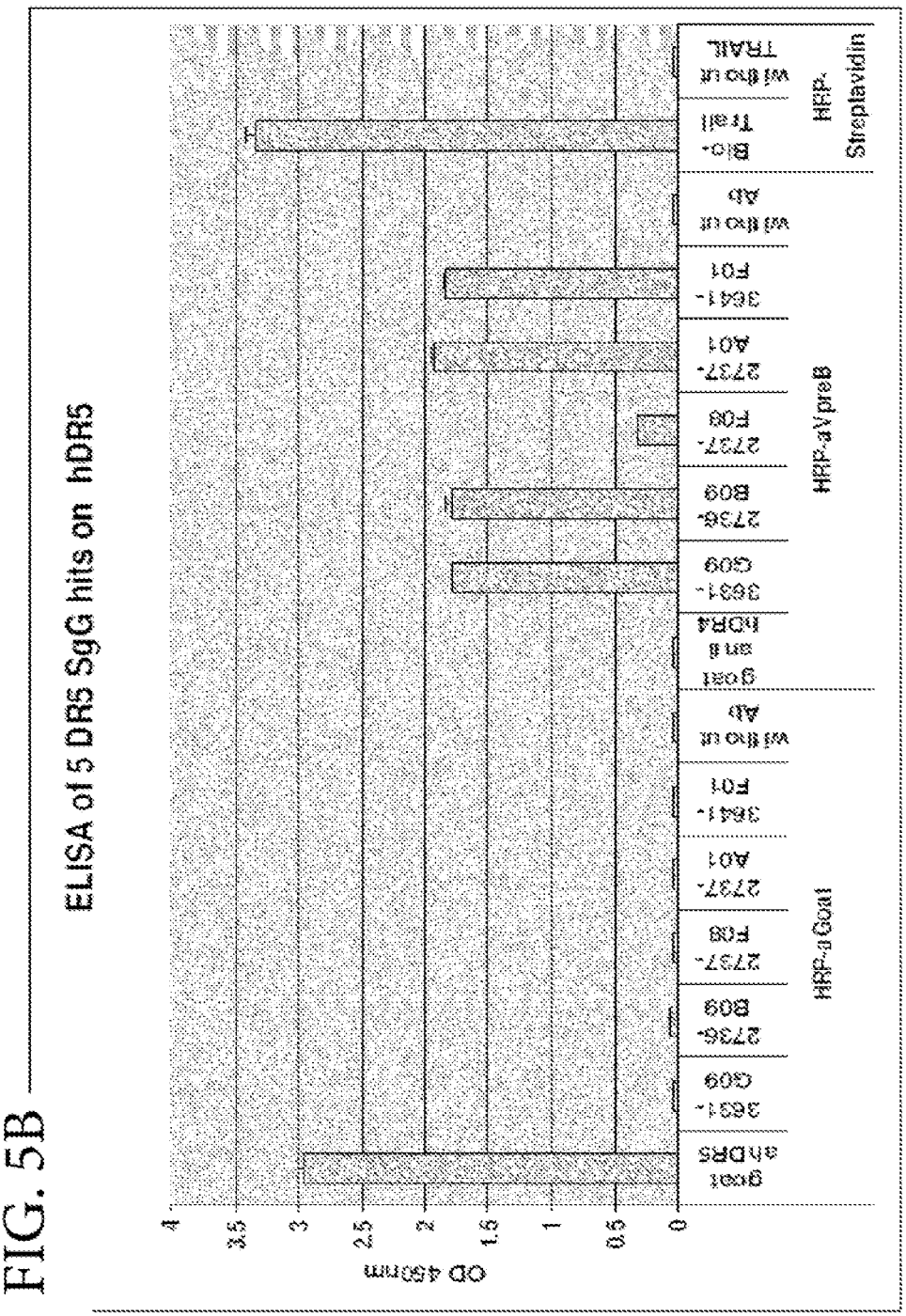

Bivalent SBP derived from phage display panning on human DR4 or DR5 are specific for the human proteins and do not bind the mouse death receptor. 5 Death Receptor binding surrogate binding proteins were tested for their ability to bind human DR4, human DR5 and mouse DR5. 100 nanograms/well of human DR4-Fc, human DR5-Fc or mounse DR5-Fc were coated in microtiter wells and 10 nM bivalent SBP, control anti-target polyclonal antibodies or biotinylated TRAIL used for detection and confirmation of binding activity. As shown in FIGS. 5A-C, one bivalent SBP, 3631-G09 binds to both human DR4 and human DR5, but not to mouse DR5. The other bivalent SBP all bind human DR5 and not mouse DR5.

Example 8

Mouse Death Receptor DR5 has Poor Homology with Human Death Receptors

The TRAIL binding domain of human DR4, human DR5, and mouse DR5 were aligned for comparison. FIG. 6. The CRD with the 6 pairs of cysteines, a hallmark feature of the death receptor family, is conserved, but overall similarity is poor in this region. Mouse DR5 shares 44.9% (34.6%) and 42.6% (36.8%) similarity (identity) with human DR4 and DR5, respectively. Despite limited sequence similarity with the human proteins, the mouse death receptor is able to bind human TRAIL.

Example 9

Death Receptor Bivalent SBP Demonstrate High Affinity by Antigen ELISA

Figure 7A:
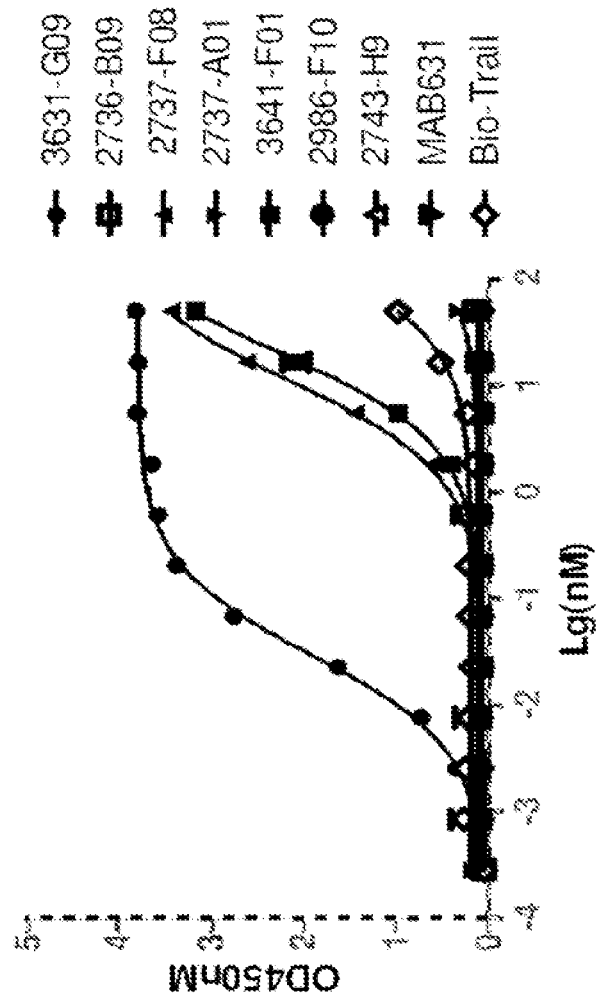
FIGS. 7A and 7B illustrate the results of bivalent SBP binding to human DR4 and human DR5 in an ELISA assay.
Figure 7B:
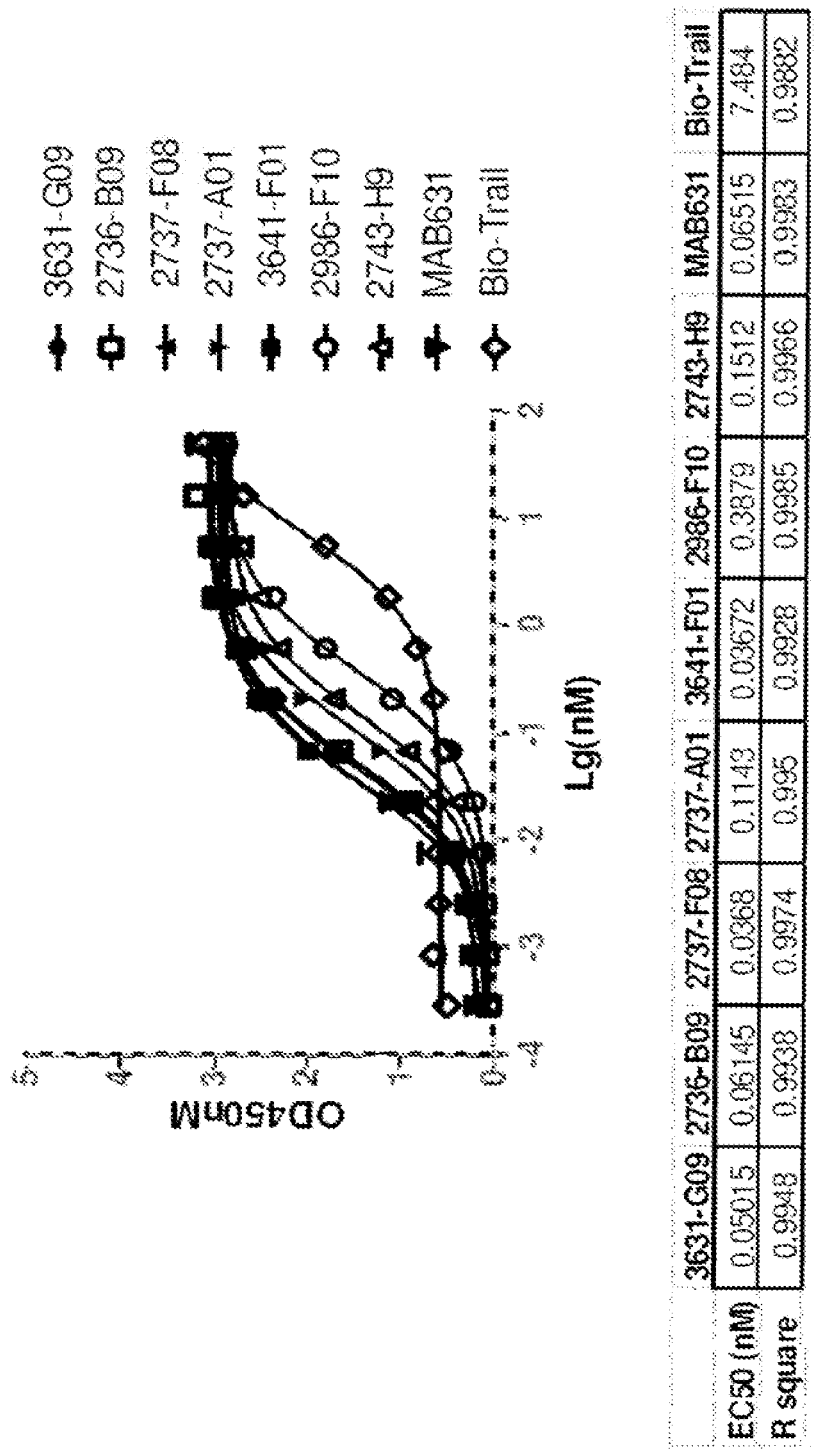

Death Receptor bivalent SBP have strong binding to DR5 or DR4 and DR5 and demonstrate specificity for the antigens in ELISA. Bivalent SBP 3631-G09 demonstrates strong binding to both DR4 and DR5. FIGS. 7A and 7B.

Wells coated with 100 ul of 1 microgram/ml human DR4 or human DR5 were blocked and then exposed to a half-log dilution series of various anti-death receptor SBPs in 1×PBST, 4% NFDM. The bivalent SBP were detected using an anti-human Fc antibody conjugated to HRP. Control IgG Mab631 (R&D Systems, Minneapolis Minn.) was detected with an anti-mouse polyclonal antibody-HRP conjugate and biotinylated TRAIL was detected with Streptavidin HRP. 3631-G09 (SL231) has high affinity for DR4 and DR5, with a half maximal binding concentrations of ~30 pM and 50 pM, respectively. Despite showing no binding as monovalent monovalent SBPs, 2737-F08 and 3641-F01 show weak binding to DR4 as bivalent SBP with 11.7 nM and 21 nM half maximal ELISA signal concentrations. All of the bivalent SBP tested here have <1 nM half-maximal ELISA signal concentrations on their respective targets.

In addition to analysis on DR4 and DR5, 3631-G09 (SL231) and 3641-F01 bivalent SBPs were analyzed for binding to DcR1, DcR2, and Osteoprotegrin (FIGS. 7C and 7D). The lowest concentration demonstrating maximal binding is plotted with EC50 determination provided in the table inset (FIGS. 7C and 7D). No binding was observed to the decoy receptors at 1000 nM, while maximal binding to the Death Receptors was seen at 10 nM

Example 10

Death Receptor Monovalent SBP Inhibits Cell Proliferation in Colo205 Cells

Figure 8:
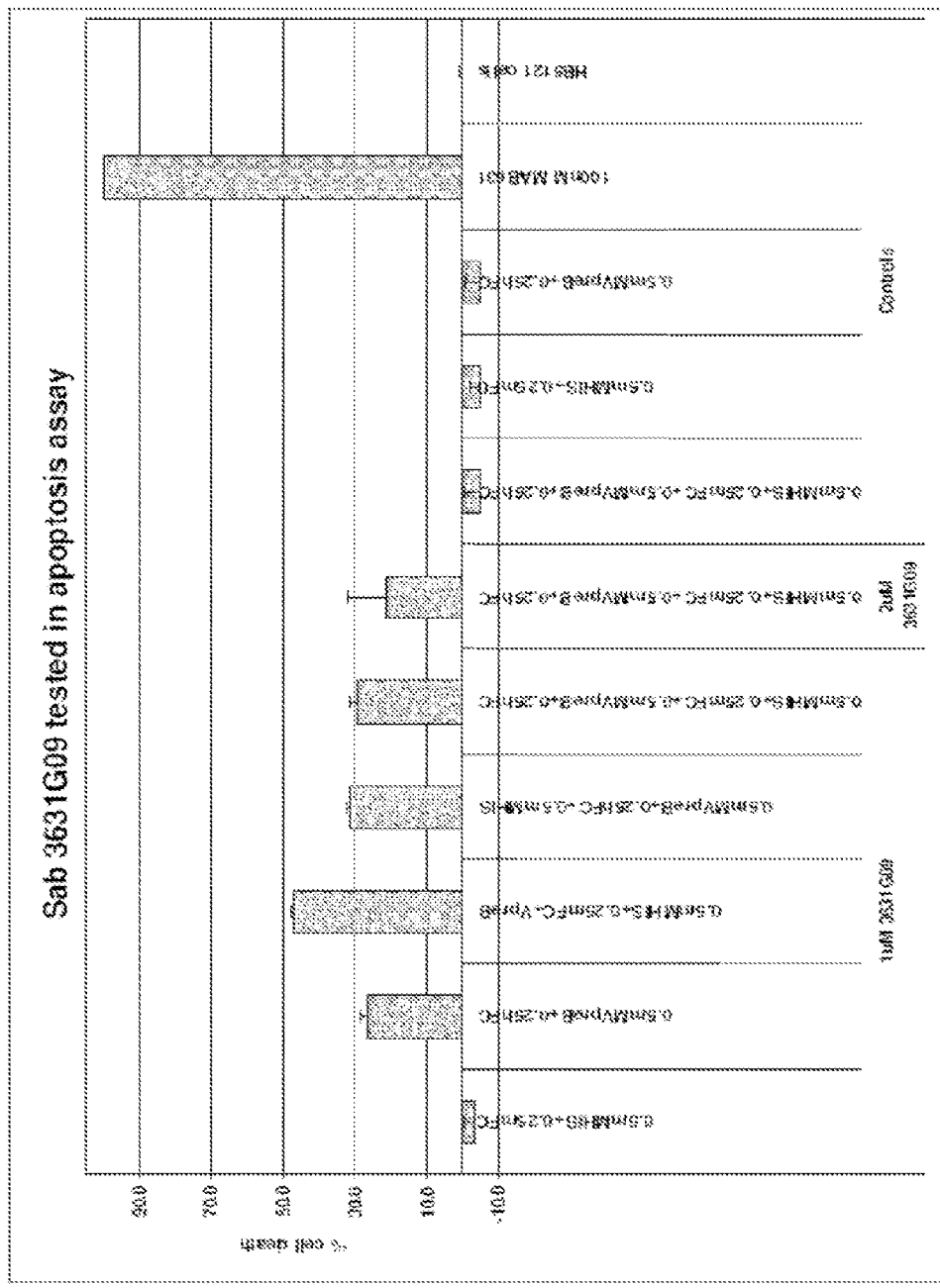
FIG. 8 illustrates inhibition of cell proliferation by a monovalent SBP when cross-linked by multiple antibodies.

Anti-Death Receptor monovalent SBP inhibits cell proliferation when cross-linked by multiple antibodies and enables functional testing of bacterially expressed monovalent SBPs. FIG. 8.

Colo205 cells were grown in 96-well microtiter plates seeded at a density of 10,000 cells/well. 3631-G09 (SL231) monovalent SBP was prepared by mixing 1 uM monovalent SBP with 500 nM of an anti-His tag monoclonal antibody, 250 nM of an anti-mouse polyclonal antibody and 500 nM anti-VpreB antibody for 1 hour to promote monovalent SBP cross-linking. Cross linked monovalent SBP/antibody mixture was then serially diluted in half-log increments, added to the cells, and incubated at 37 C for 48 hours. Wells containing the antibodies used to cross-link without monovalent SBP were used as controls, in addition to Mab631 and HB2151 cell lysate only. To develop the assay, 10 uL WST reagent (Roche) was added and the cells incubated for an additional 4 hours. The plates were read with a Molecular Devices microplate reader with a 450 nm filter. The data was analyzed and plotted using Microsoft Excel.

Figure 9:
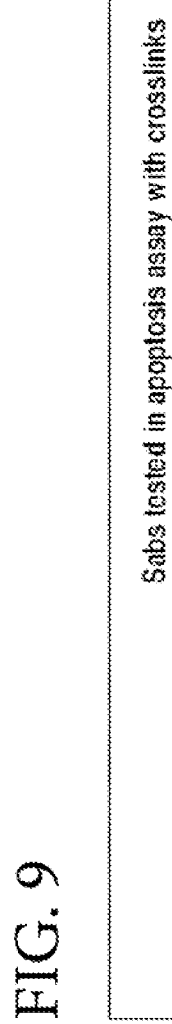
FIG. 9 illustrates the results of testing of multiple monovalent SBPs when cross-linked by multiple antibodies

Agonist DR5 monovalent SBPs were rapidly identified by functional testing m a cell based-assay developed using the fluorescent substrate Cell-TiterGlo (Promega). Monovalent SBPs identified using the TRAIL interference assay were tested (FIG. 9).

Example 11

Figure 10A:
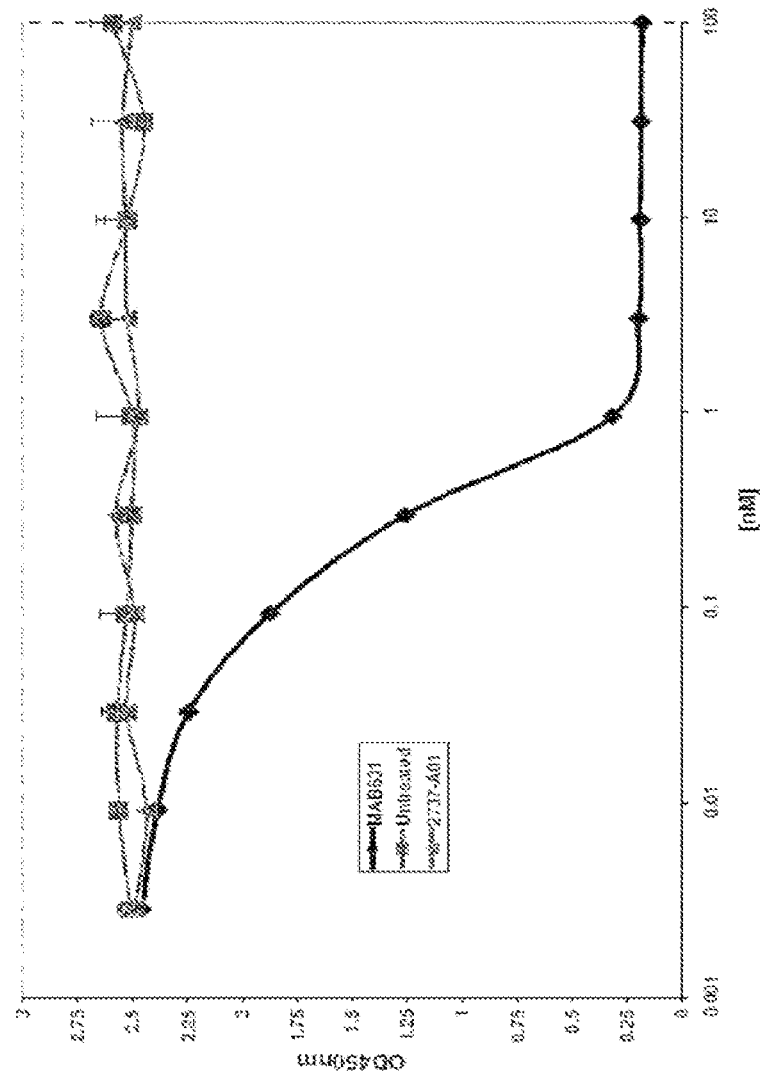
FIGS. 10A and 10B illustrate the inhibition of cell proliferation by bivalent agonist death receptor SBPs.
Figure 10B:
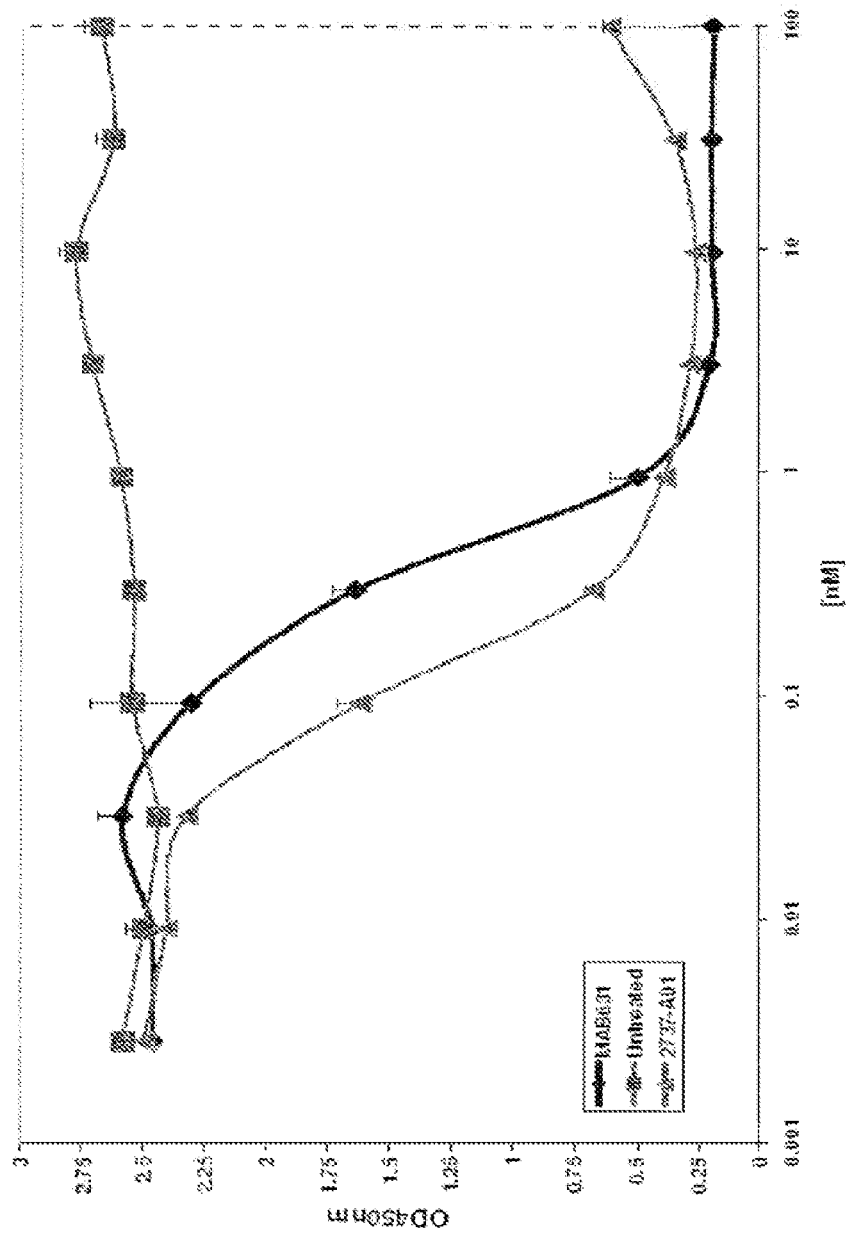

Agonist Death Receptor Bivalent SBP Inhibit Cell Proliferation in a Cell-Based Assay Cross-linking of an anti-DR5 bivalent SBP, shown to disrupt DR5 binding to TRAIL as a monovalent SBP, potently inhibits cell proliferation. FIGS. 10A and B. Colo205 cells were seeded at 10,000 cells/well in a 96-well tissue culture plate. Serial dilutions of the bivalent SBP were added to the cells (FIG. 10A) and incubated for 48 hours prior to development with WST-1 reagent. Alternatively, serial half-log dilutions of bivalent SBP were mixed with an anti-human-Fc antibody at 50% of the concentration of the bivalent SBP and this mixture was added to the cells (FIG. 10B) and similarly developed. Untreated cells and Mab631 (R&D Systems) were used as controls.

Example 12

Figure 11B:
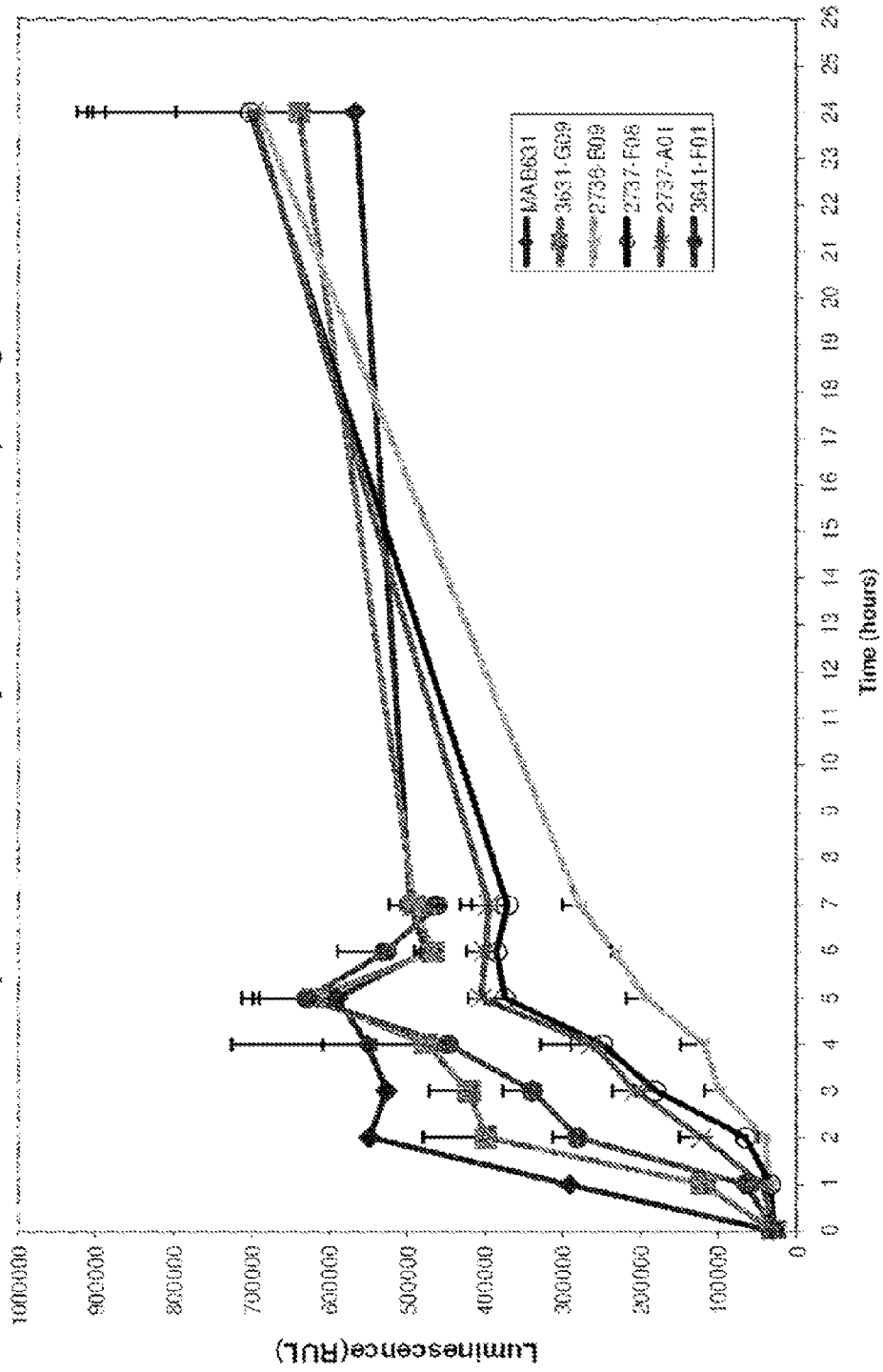
Figure 11C:
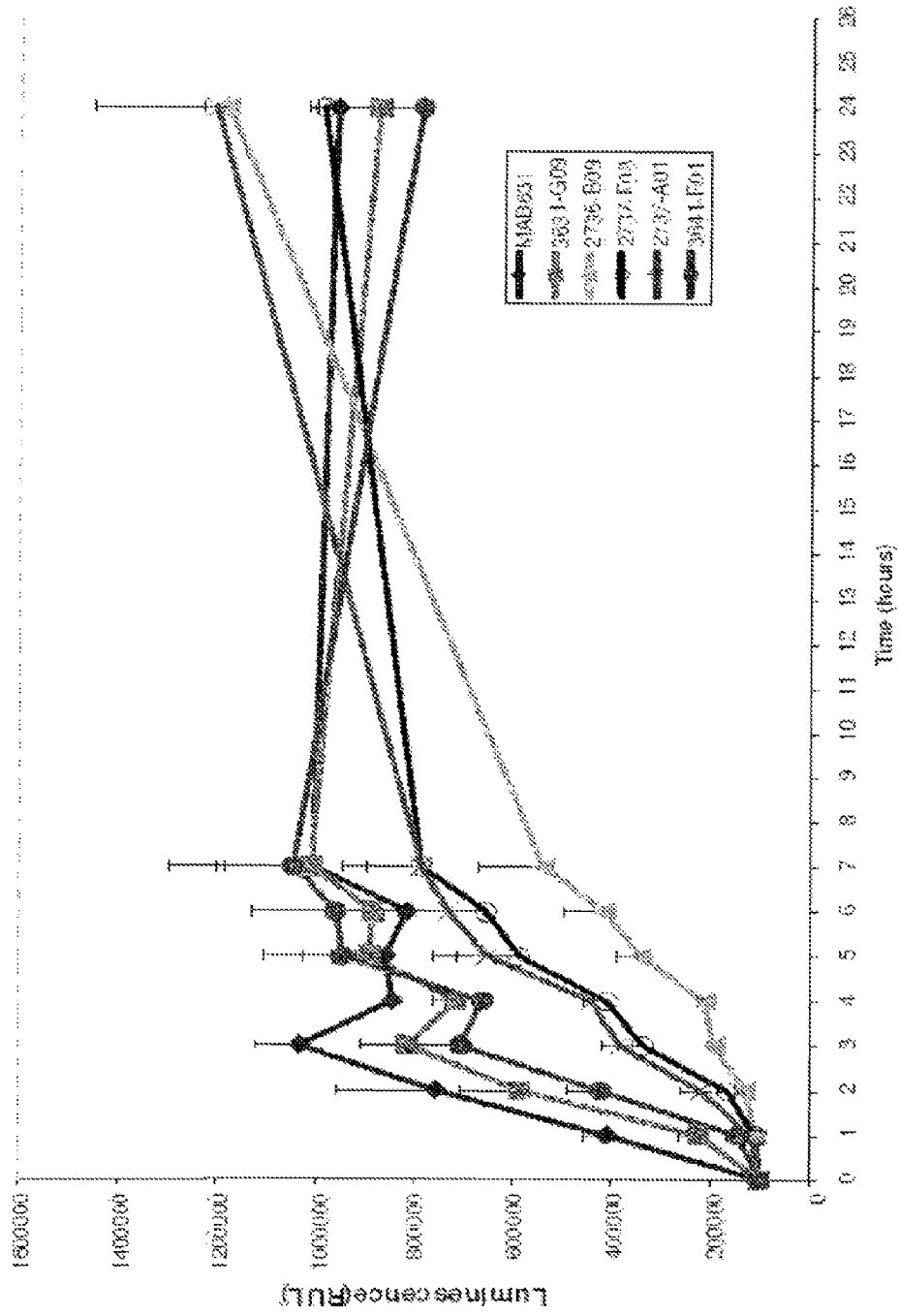

Activation of the Apoptosis-Inducing Caspase Pathways by Cross-Linked Anti-Death Receptor Surroglobulins Inhibition of cell proliferation caused by bivalent SBP cross-linking of anti-death receptor surroglobulins is due to the activation of the pro-apoptotic caspase pathway. FIGS. 11A, B and C. Colo205 cells were plated at 10,000 cells/well in a 96-well tissue culture plate and incubated overnight. The following day, 20 nM bivalent SBP+10 nM anti-Fc antibody or Mab631 (R&D Systems) was added to the wells. Caspase activation was monitored at time 0 and then hourly for seven hours and at 24 hours. Caspase-specific peptide substrates that become luminescent upon cleavage were added (Caspase 8 Glo, Caspase 3/7 Glo, and Caspase 9 Glo, Promega) at the appropriate time interval and the luminescence measured.

Example 13

Figure 12:
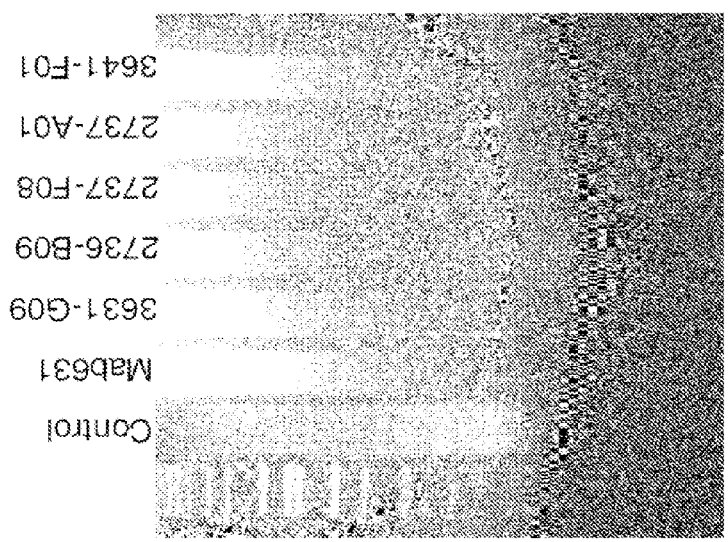
FIG. 12 is a gel showing that cross-linked, bivalent anti-death receptor SBPs induce apoptoctic DNA laddering in the Colo205 colon cancer cell line.

Cross-Linked Anti-Death Receptor Bivalent SBP Activate Apoptosis as Shown by DNA Cleavage Death receptor-induced inhibition of cell proliferation is mediated by the activation of pro-apoptotic pathways that culminate in the irreversible phase of DNA cleavage. FIG. 12. Colo205 cells (2 million per treatment) were incubated with 100 nM bivalent SBP+50 nM anti-Fc antibody or 100 nM Mab631 alone for 5 hours. The DNA was purified from the cells and analyzed by gel electrophoresis and ethidium bromide staining for visualization. The lane marked control contains U87 cell apoptotic DNA provided by the kit manufacturer (Roche)

Example 14

Activation of Bivalent SBP Apoptotic Activity in Colo205 Cells by Anti-Fc or Protein G Cross-Linking A comparison of different cross-linking agents and ratios of cross-linker: bivalent SBP was performed with the read-out being Colo205 cell proliferation. An anti-Fc antibody or protein G was incubated at 50% molar equivalence or as a fixed concentration (protein G only) across a half-log dilution range of the test articles. Cells (10,000/well) were incubated for 48 hours in the presence of test agent prior to addition of WST-1 for development.

Anti-Fc cross-linked bivalent SBP had the highest activity and half-concentration protein G was more consistent (smaller range). The 50% molar equivalence condition had lower variation and the values generated are likely to represent the EC50s for bivalent SBP dimers and not higher order complexes. See Table 0.6, below.

TABLE 0.6

| | Cross-linking Treatment | | | | |
|---|---|---|---|---|---|
| No crosslink | anti-Fc | | Fixed Protein G | Halt-concentration Protein G | |
| Rep1 (nm) | Rep1 (nM) | Rep2 (nM) | 1 ug/ml Protein G | Rep1 (nM) | Rep2 (nM) |
| Trail | 1 | ND | ND | ND | ND | ND |
| MAB631 | 0.3 | 0.03 | ND | 0.3 | 0.3 | 0.3 |
| 3631-G09 | IA | 0.08 | 0.07 | 0.22 | 1 | 1.3 |
| 3641-F01 | IA | 0.1 | 0.1 | 1 | 1.3 | 1.8 |
| 2736-B09 | IA | 1.9 | 5 | 4 | 4 | 5 |
| 2737-F08 | IA | 0.4 | 0.63 | 1.4 | 2 | 1.9 |
| 2737-A01 | IA | 0.17 | 0.13 | 0.66 | 0.8 | 1 |

Example 15

Activity of Death Receptor Agonist Bivalent SBP Against A Panel of Cell Lines Representing Several Cancer Types Similar to the cell-based assays using the Colo205 line, SgGs were tested on cell lines of lymphoid, hepatic, epidermal, and pancreatic origin. Assays were performed essentially as described for the Colo205 cell line, above.

Figure 13A:
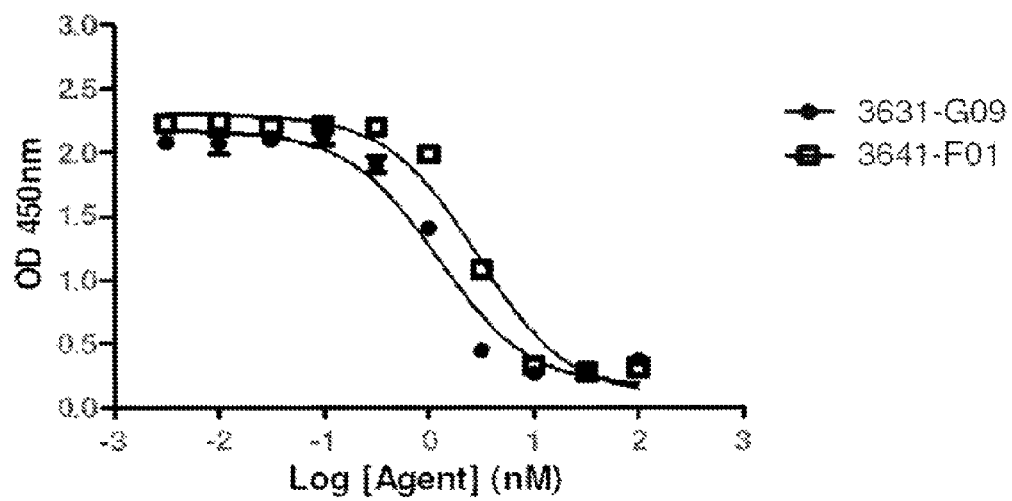
FIGS. 13A-13G illustrate the activity of Death Receptor agonist SBPs against a panel of cell lines representing several cancer types.
Figure 13B:
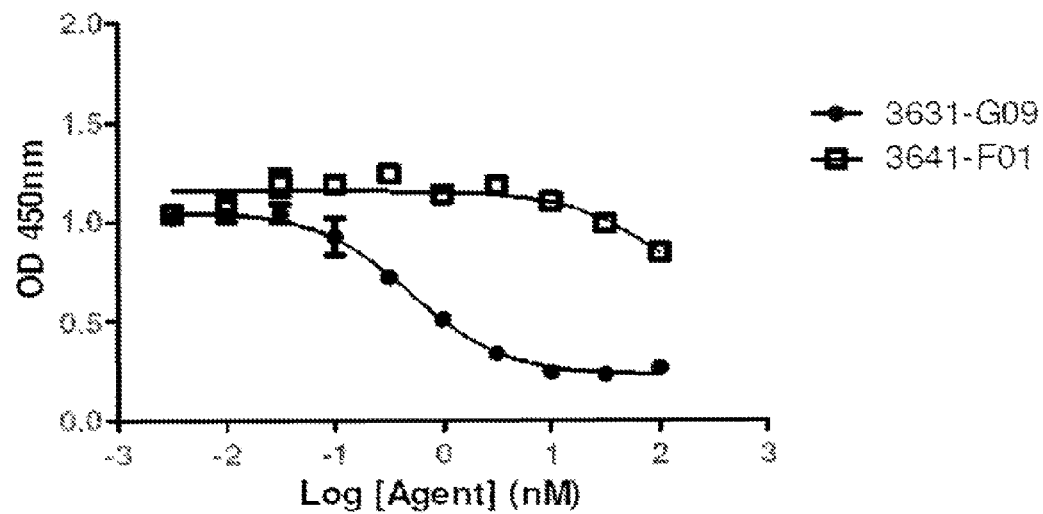
Figure 13C:
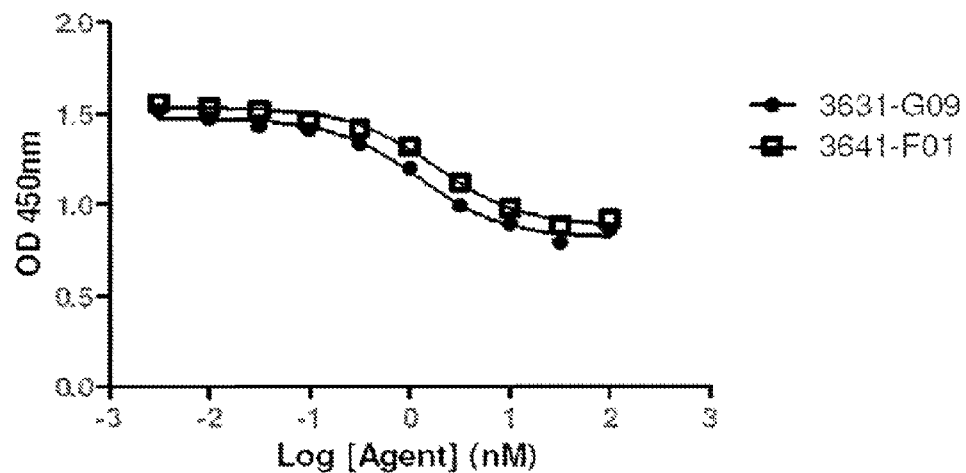
Figure 13D:
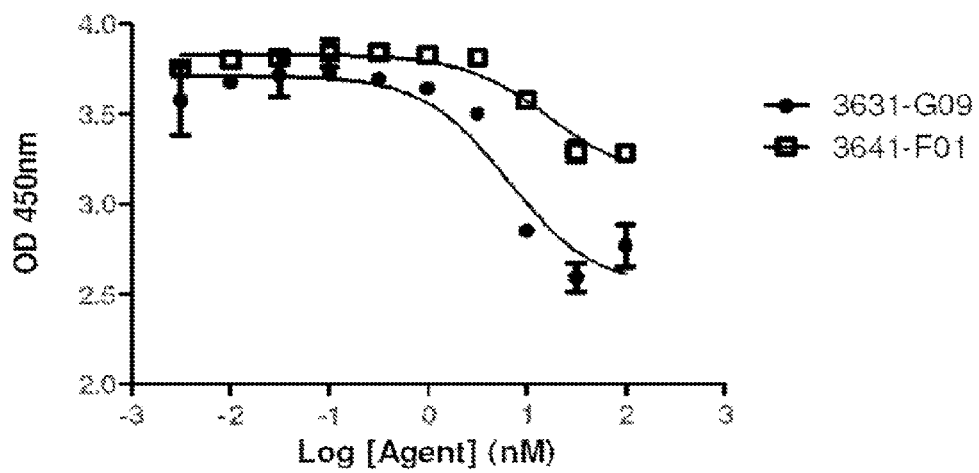
Figure 13E:
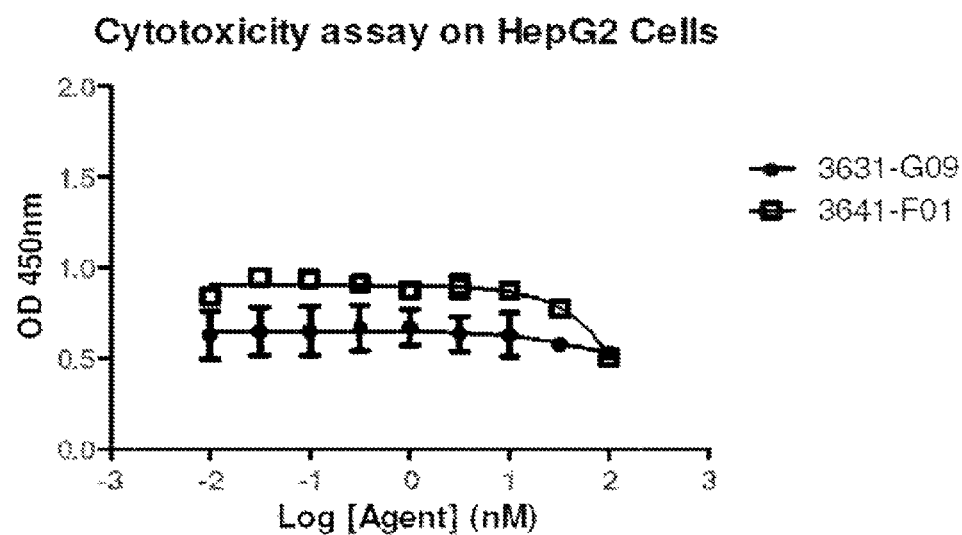
Figure 13F:
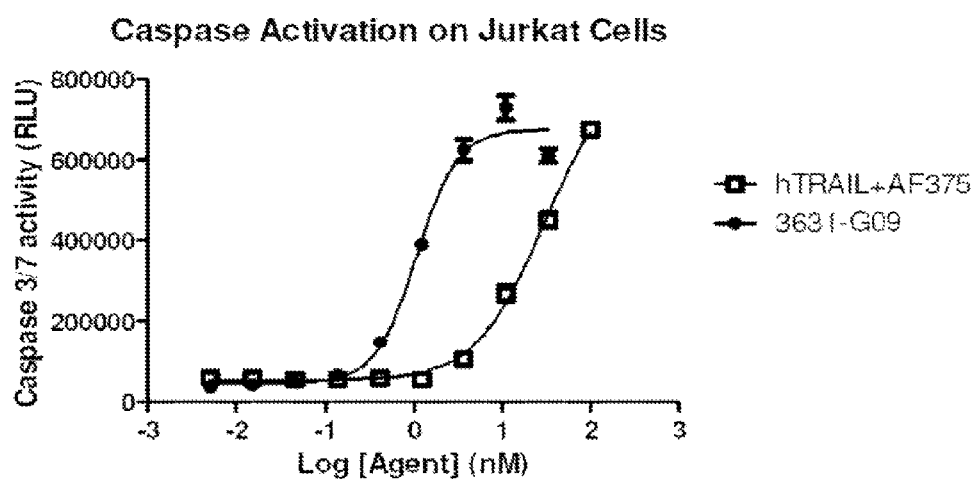
Figure 13G:
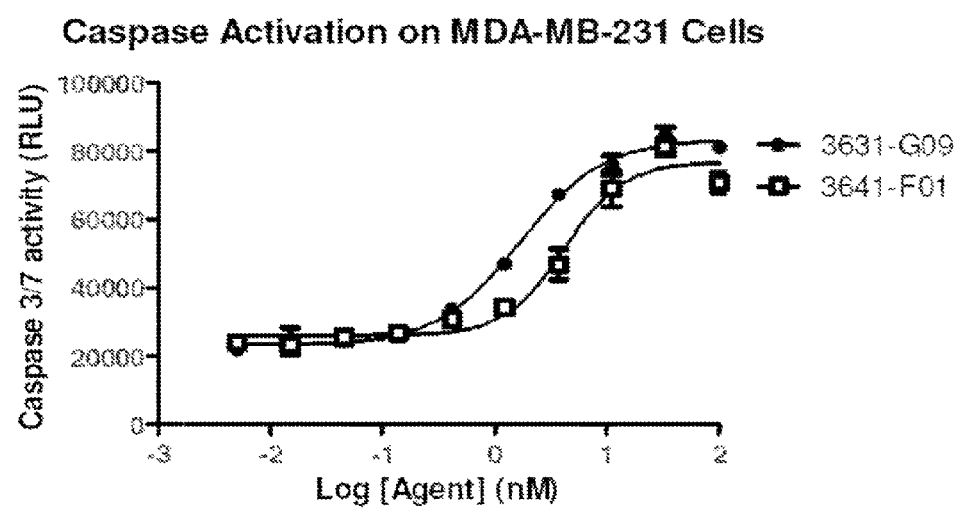

Cell lines from different tissues of origin (colon—Colo205, lymphoid-Ramos-RA1 Jurkat, epidermal (lung)—A549, liver—HepG2, breast—MDA-MB-231 and pancreatic—BxPC3) show sensitivity to death receptor agonism (FIG. 13A-G). 3631-G09, cross-reactive with DR4 and DR5 in biochemical assays, shows activity in the Ramos cell line which predominantly expresses DR4, confirming dual-reactivity and death receptor activation in cells. 3641-F01, a DR5-specific agonist molecule, had very little effect on these cells, demonstrating that DR4 agonism is responsible for the effect on cell proliferation (FIG. 13B). EC50s are provided in Table 0.7. In these assays, all cell lines were used at 10,000 cells/well except Ramos cells, which were used at 50,000 per well. The following growth medium was used for the indicated cell lines: RPMI 1640+10% FBS-Colo205, Ramos, Jurkat, BxPC3; F12K+10% FBS-A549; EMEM+ 10% FBS-HepG2; Leibowitz's L-15+10% FBS-MDA-MB-231. All cell lines were obtained from ATCC and maintained according the recommended specifications. Serial half log dilutions of SgG were mixed with an anti-human-Fc antibody or Protein G at 50% of the concentration of the SgG. This was followed by incubation at 37 C+5% CO2 for 48 hours prior to development with WST-1 reagent. In assays with Jurkat and MDA-MB-231 cells, the assays were incubated for 18 hours followed by development with Caspase 3/7 GLO. The data was analyzed with Prism GraphPad software and results are shown in FIG. 13 and Table 0.7.

TABLE 0.7

| | EC50 (nM) | | | | | | |
|---|---|---|---|---|---|---|---|
| | Colo205 | Ramos | BxPC3 | HepG2 | A549 | Jurkat | MDA-MB-231 |
| 3631-G09 | 1.22 | 0.498 | 1.24 | >100 | 6.55 | 1.1 | 1.7 |
| 3641-F01 | 2.89 | >100 | 1.8 | >100 | 17 | ND | 4.2 |
| TRAIL | 0.466 | 2.15 | 1.17 | >100 | IA | 30.1 | 3.8 |

Example 16

Figure 14A:
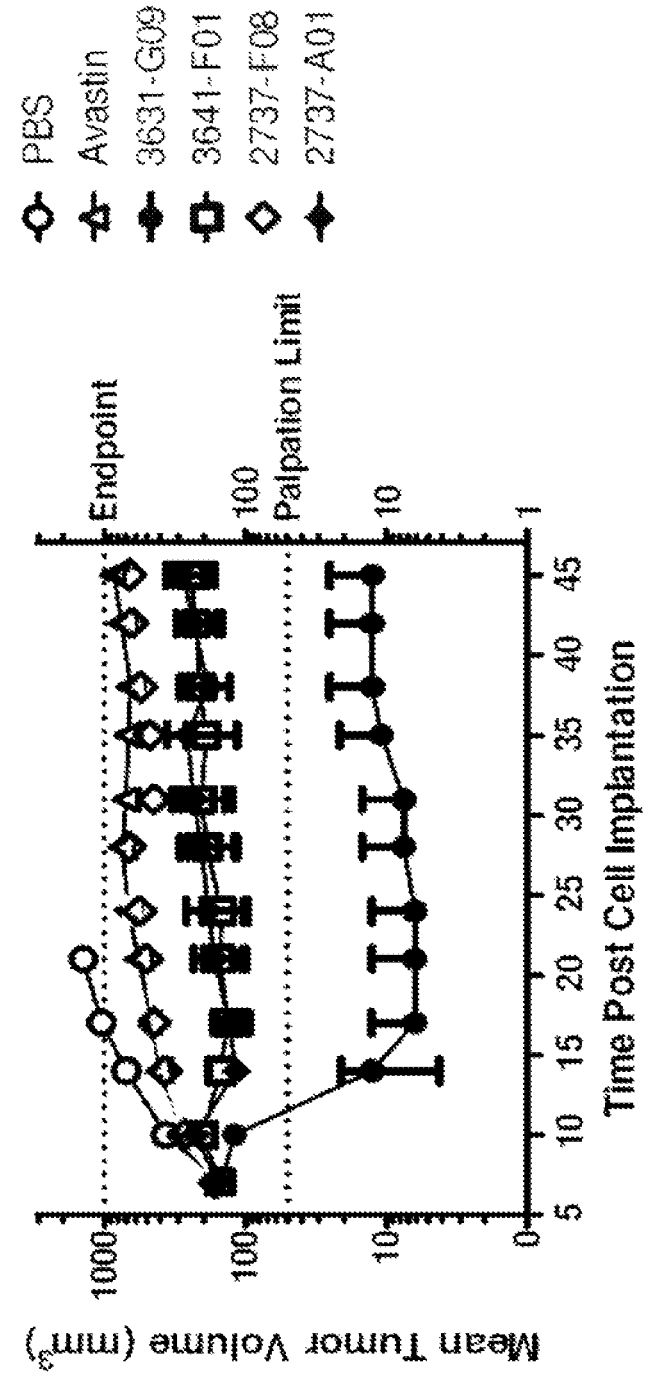
FIG. 14A illustrates the in vivo anti-tumor effects of Death Receptor agonist bivalent SBPs in a mouse xenograft tumor model.
Figure 14B:
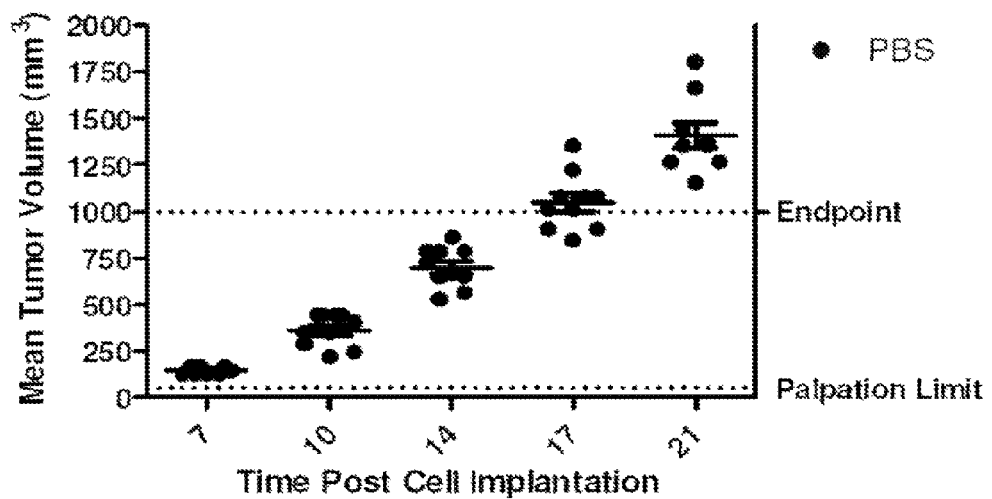
FIGS. 14B-14G illustrate individual in vivo tumor responses to Death Receptor agonist bivalent SBPs and controls.
Figure 14C:
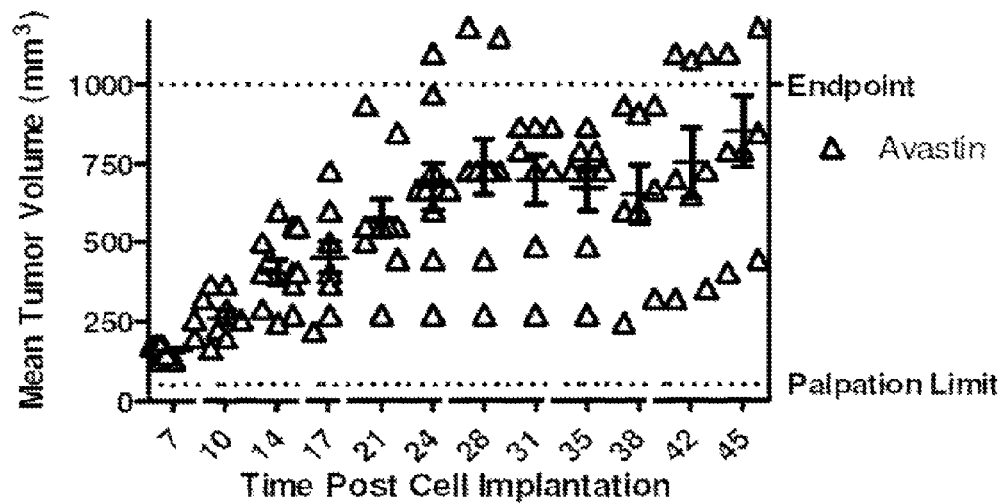
Figure 14D:
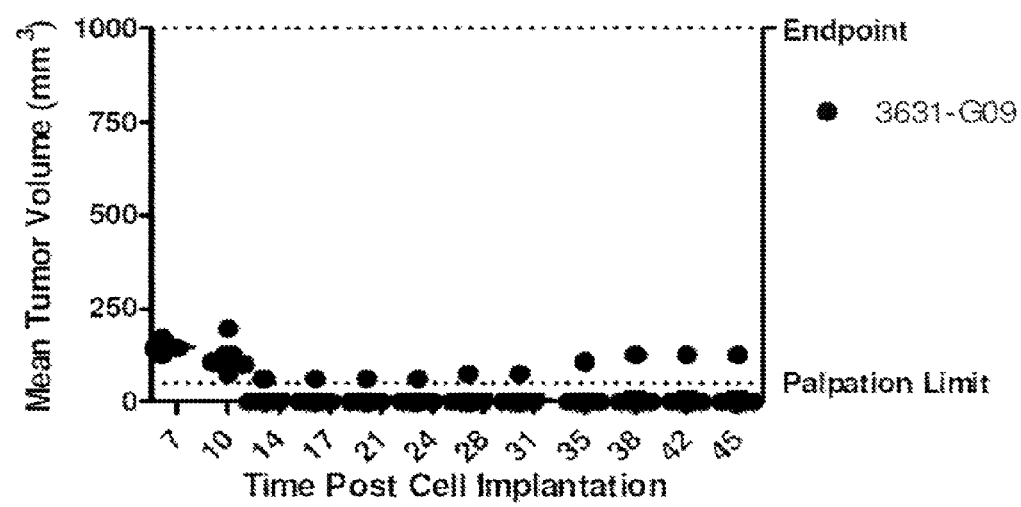
Figure 14E:
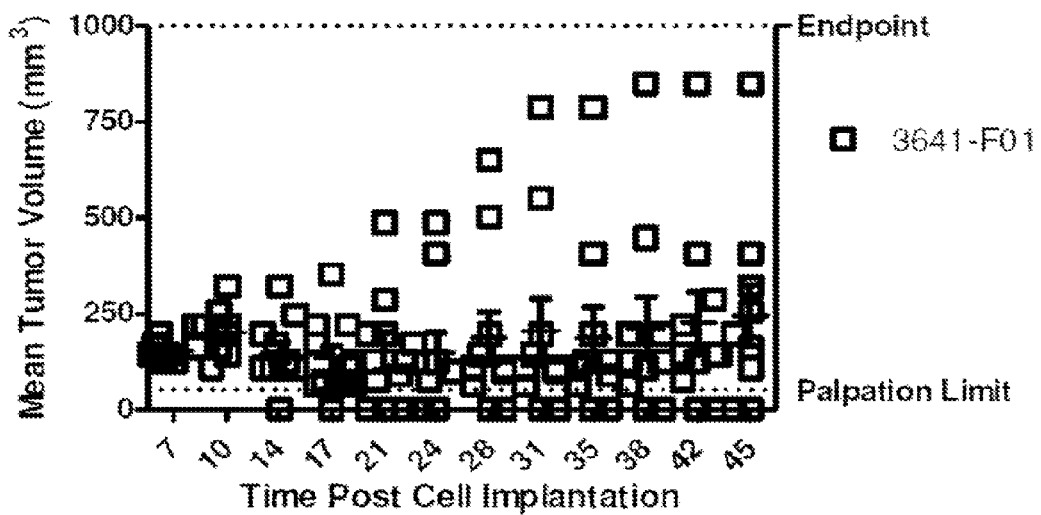
Figure 14F:
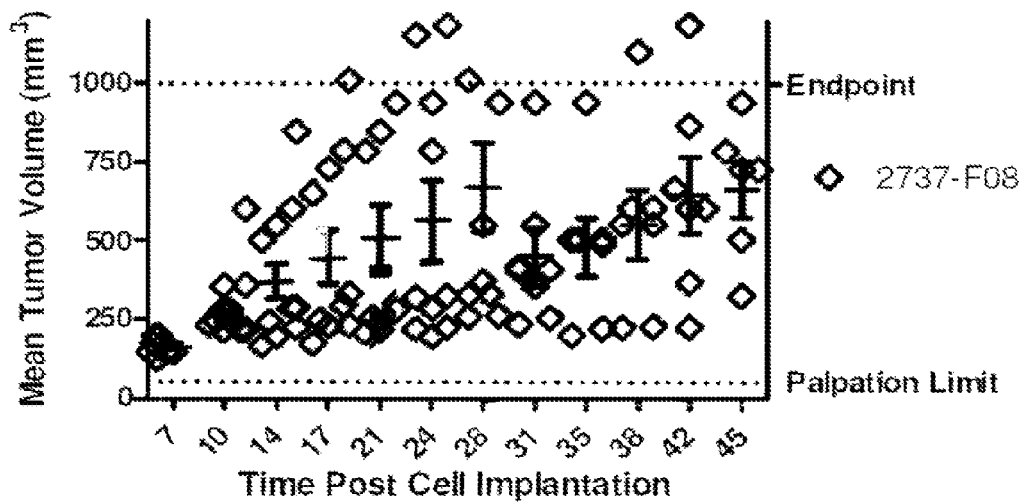
Figure 14G:
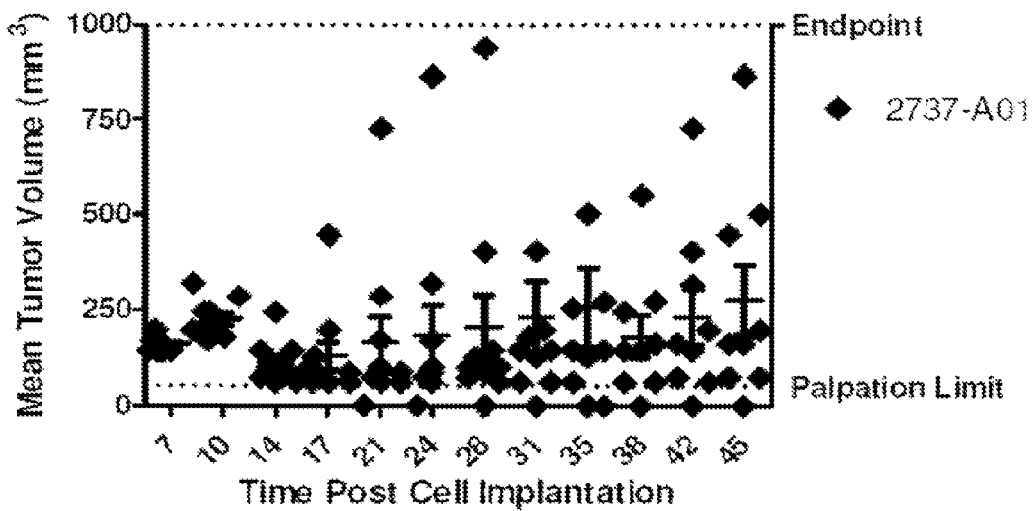
Figure 15A:
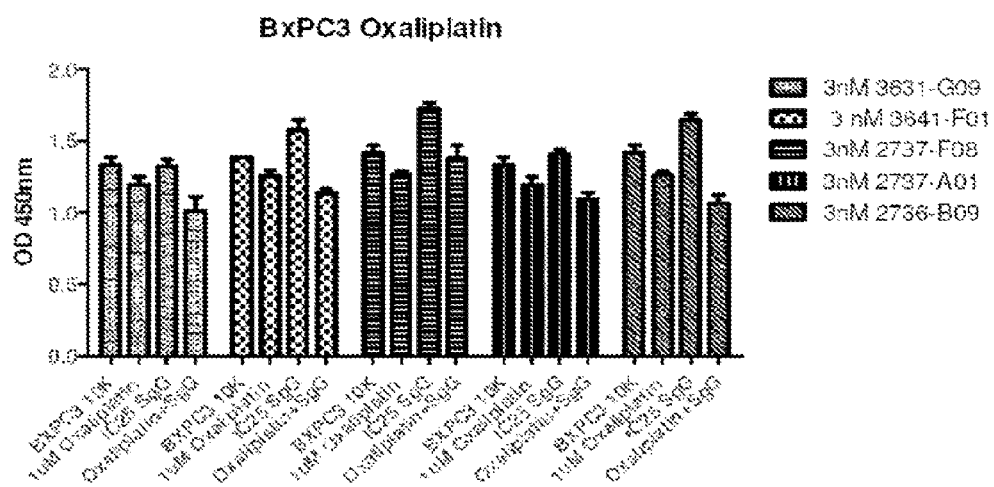
FIGS. 15A-15F illustrate the anti-proliferative effects of cross-linked bivalent SBPs in combination with chemotherapeutic treatment in the BxPC3 pancreatic cancer cell line.
Figure 15B:
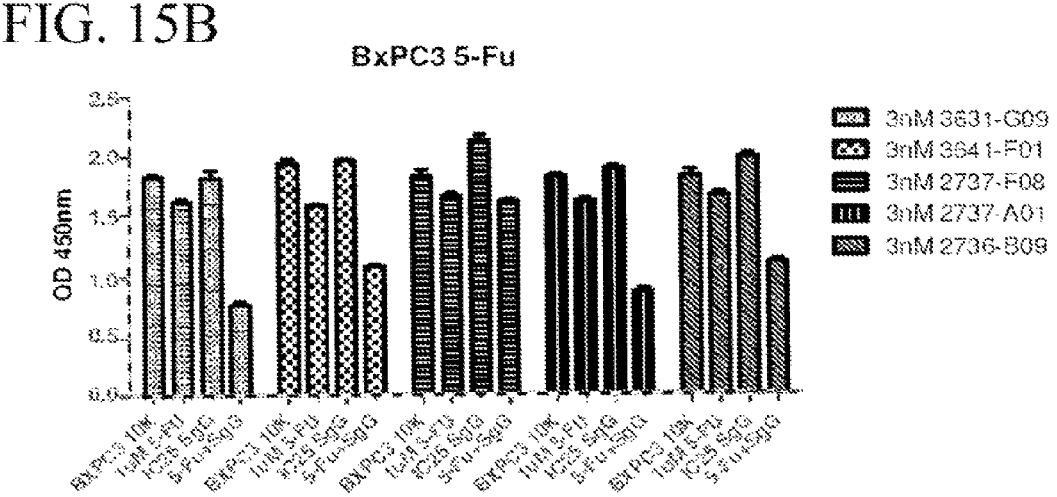
Figure 15C:
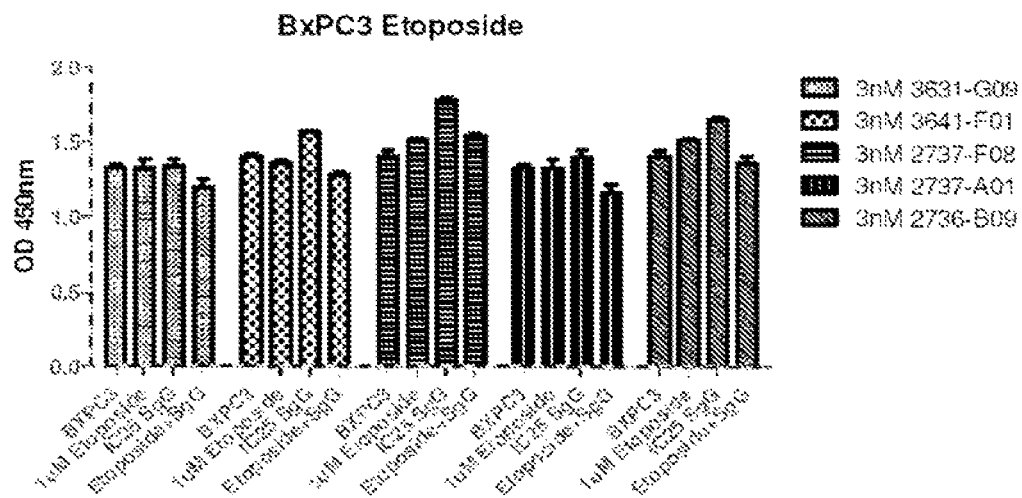
Figure 15D:
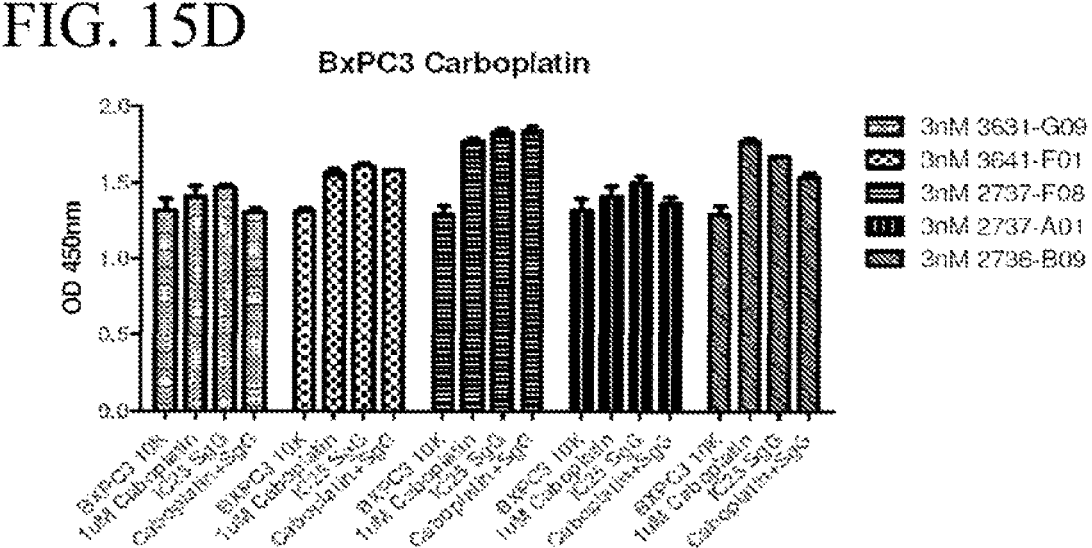
Figure 15E:
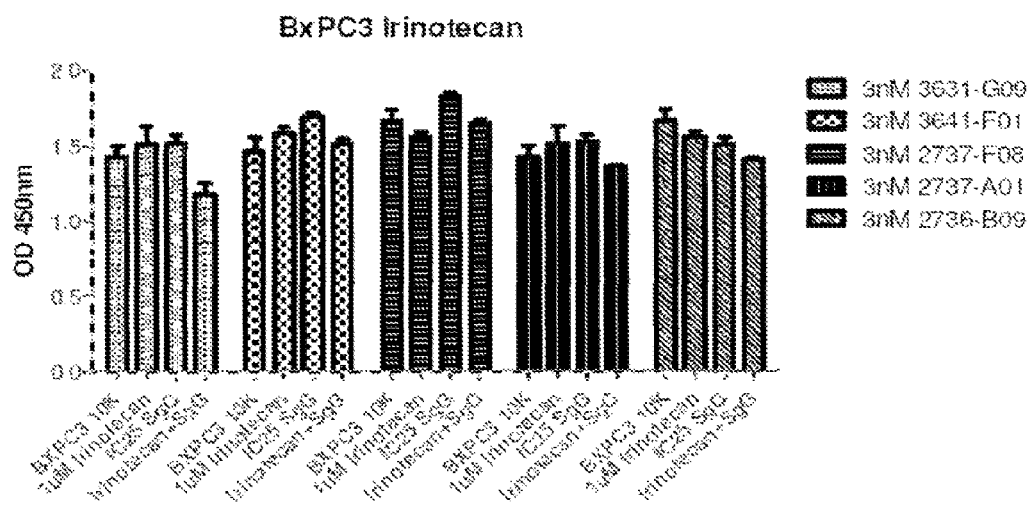
Figure 15F:
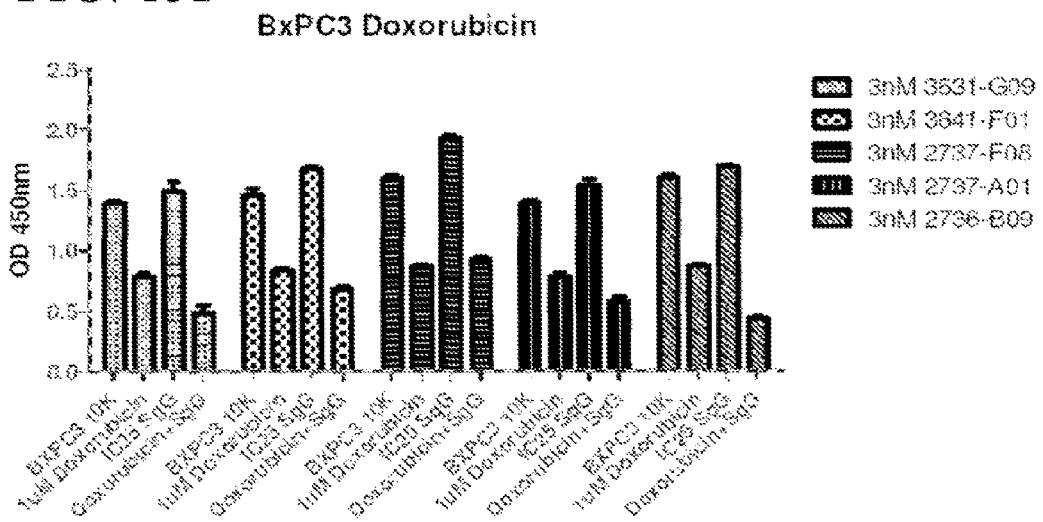
Figure 16A:
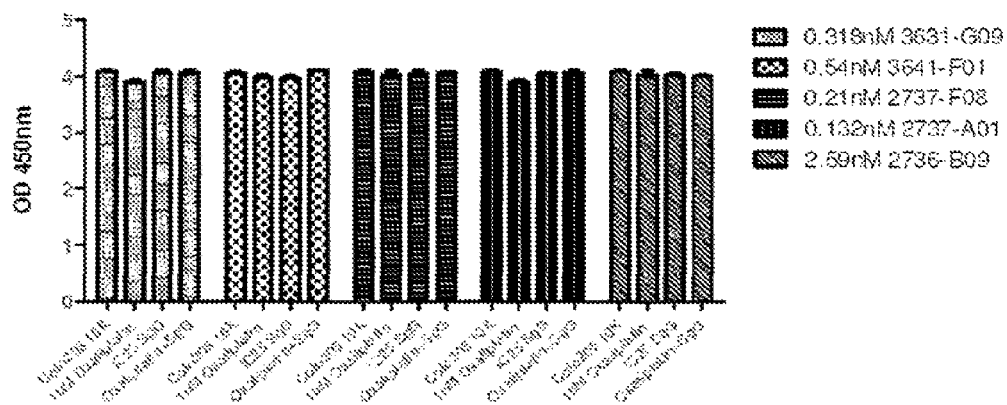
Figure 16B:
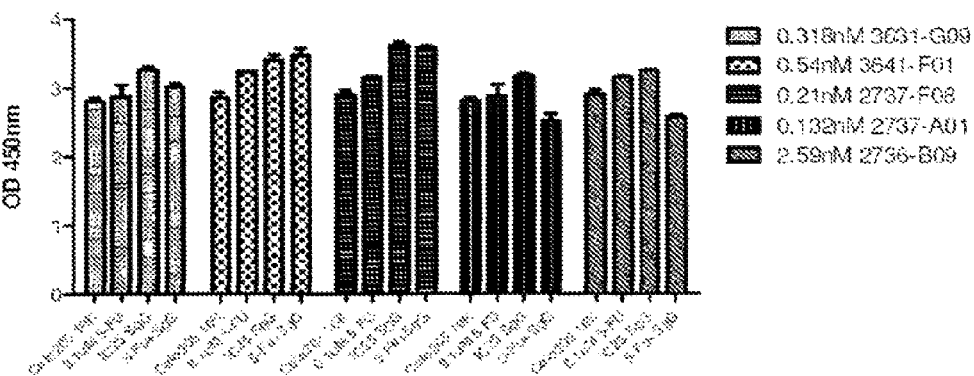
Figure 16C:
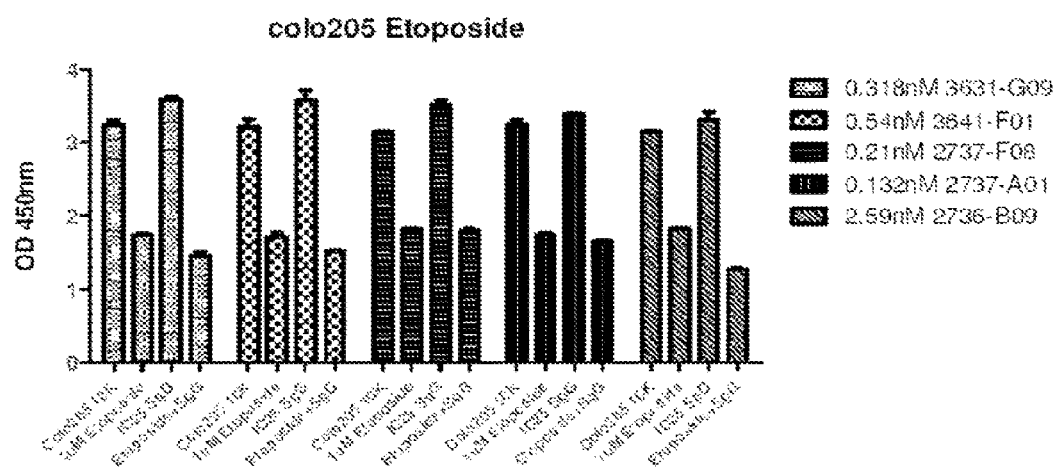
Figure 16D:
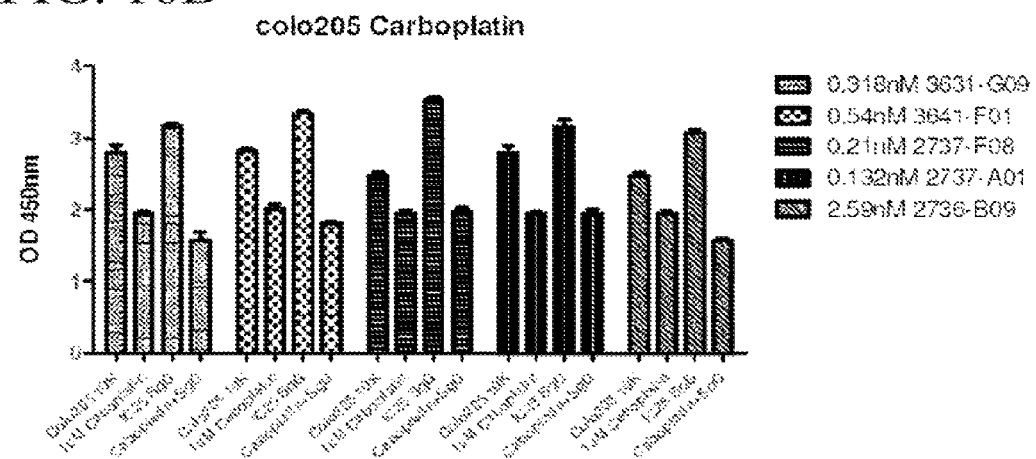
Figure 17A:
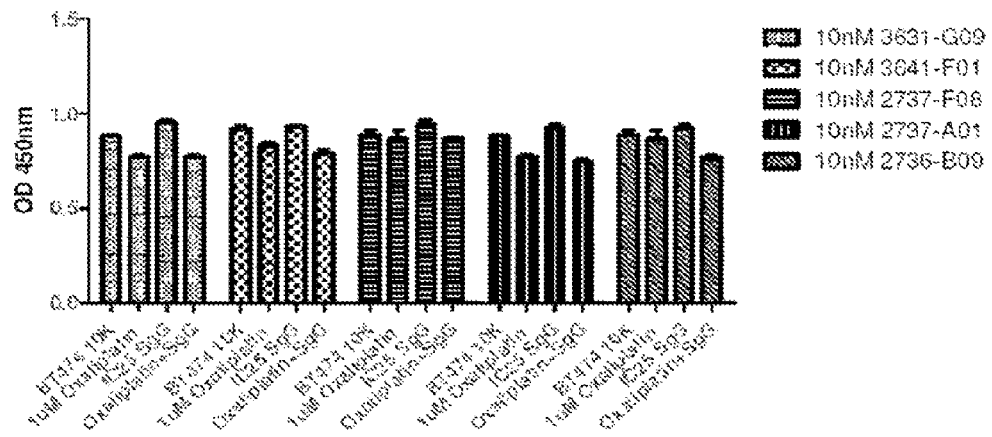
FIGS. 17A-17F illustrate the anti-proliferative effects of cross-linked, bivalent SBPs SBPs in combination with chemotherapeutic treatment in the BT-474 breast cancer cell line.
Figure 17B:
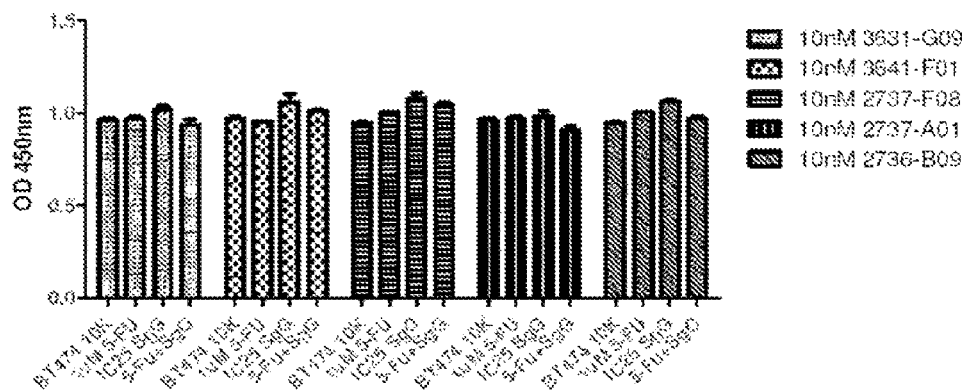
Figure 17C:
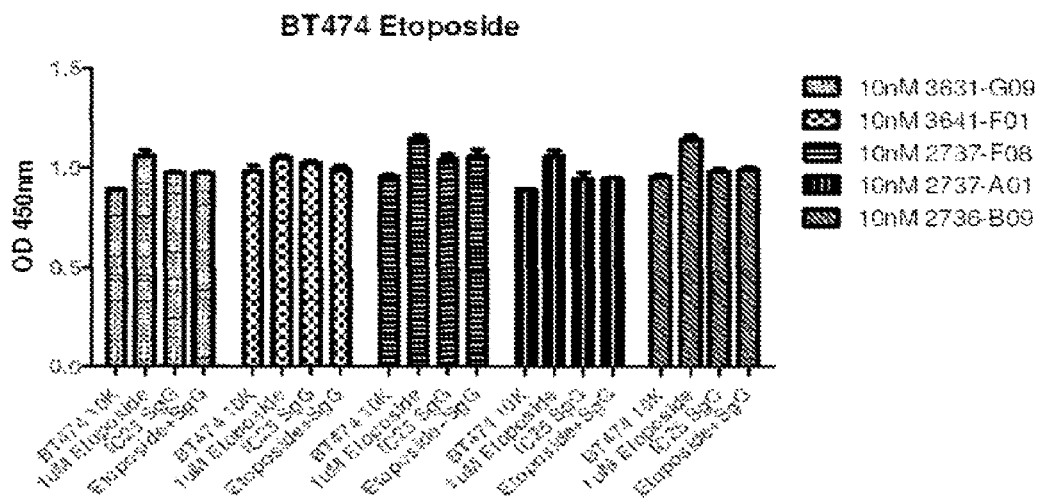
Figure 17D:
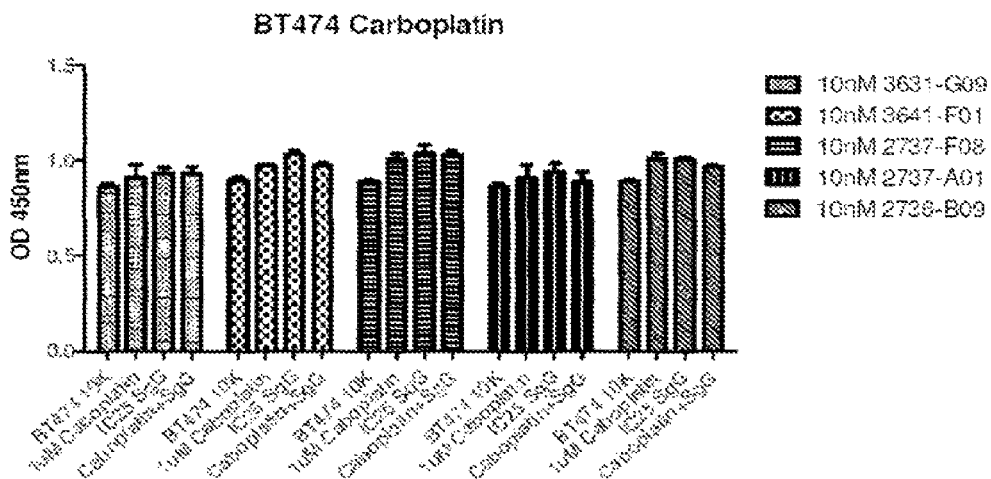
Figure 17E:
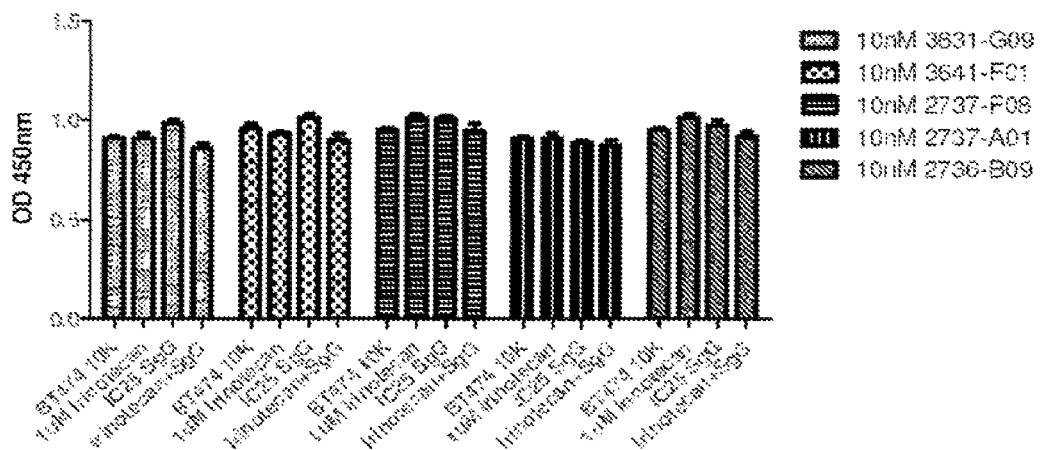
Figure 17F:
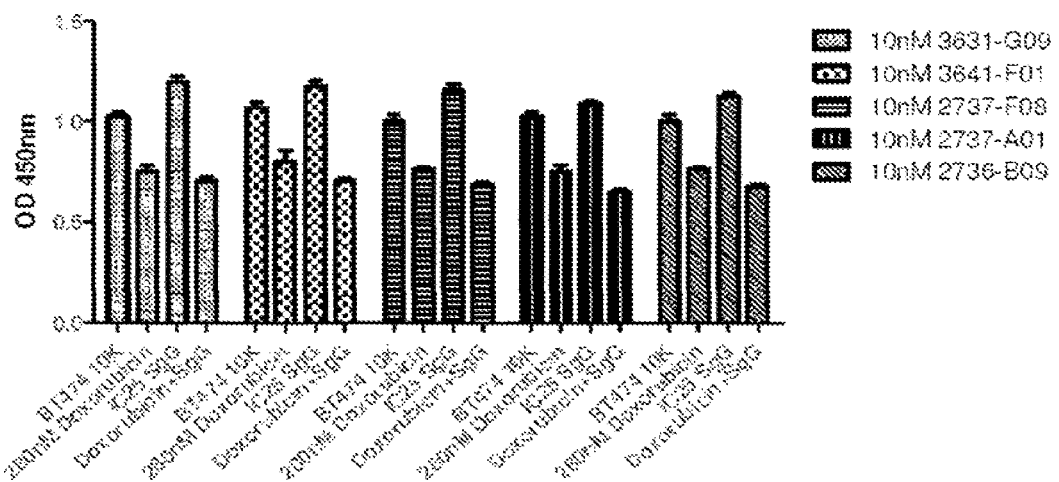

In Vivo Anti-Tumor Effects of Death Receptor Agonist Bivalent SBP in a Mouse Model A Colo205 xenograft study to determine the in vivo anti-tumor effects of death receptor agonist surroglobulins in a mouse model. $5 \times 10^6$ Colo205 cells in 50% Matrigel were injected subcutaneously in the right axilla of out bred nude mice. Tumors were allowed to develop until they reached a volume of ~150 mm$^3$, as determined by caliper measurement. Mice (10 per group) were then treated 2x/week with vehicle (1xPBS), control (Avastin, 5 mg/kg) or bivalent SBP (3631-G09, 3641-F01 2737-F08, and 2737-A01, all 3 mg/kg). Tumor volume and mouse weight were measured twice a week. Endpoint was 45 days or tumor volume reaching 1000 mm³. Dosing for all groups continued through day 45, except for the 3631-G09 bivalent SBP group in which dosing was halted at day 21 to allow tumor recurrence and PBS which reached endpoint. Mean tumor growth curves (FIG. 14A) and individual tumor responses (FIGS. 14B-G) were plotted.

Treatment with bivalent SBP severely impacted Colo205 xenograft tumor growth. 3631-G09 bivalent SBP generated tumor responses in all 10 mice, 9 complete regressions and 1 partial regression. After day 21 (treatment #5), no additional treatments were given to the 3631-G09 bivalent SBP group to evaluate tumor recurrence. All of the 3631-G09 bivalent SBP treated complete regression mice remained tumor free through the end of the study. In the 3641-F01 bivalent SBP group, all 10 mice survived and treatment generated 2 complete regressions and 2 partial regressions. 2737-F08 bivalent SBP treatment produced 6 surviving mice without any tumor regressions and 2737-A01 bivalent SBP had 9 surviving mice, with 1 complete regression and 3 partial regressions. Avastin treatment did not produce any tumor regressions, but did result in a tumor growth delay as expected for this model with a 50% survival rate.

Example 17

Combination Surroglobulin and Chemotherapeutic Treatment in a Pancreatic Cancer Cell Line Increased efficacy of combining chemotherapeutic treatment with death receptor agonist bivalent SBP at sub-maximal doses was observed for both agents in a pancreatic cancer cell line. BxPC3 cells alone, treated with 1 uM cytotoxic chemotherapeutics 3 nM bivalent SBP, or the combined chemotherapeutic/bivalent SBP treatments were evaluated for enhanced anti-proliferative effects of combined chemotherapy/death receptor agonism. FIGS. 15A-F. Chemotherapeutics were chosen based on standard of care and clinical validation and were added to cells 24 hours prior to addition of bivalent SBP, followed by 48 hours of incubation at 37 C and development using WST-1 reagent.

Increased anti-proliferative effects in BxPC3 cells were observed with most SBPs in combination with 5-FU or oxaliplatin. Weaker effects were detectable in bivalent SBP combinations with etoposide, irinotecan and possibly doxorubicin. Carboplatin was not observed to have any effect in combination with SBPs, nor was 2737-F08 bivalent SBP active in any combination, at this concentration.

In two similar studies increased efficacy or potency was observed following the combination of chemotherapeutic treatment with death receptor agonist bivalent SBP at sub-maximal doses for several agents in the PANC-1 and MiaPaCa pancreatic cancer cell line. Essentially the cells were treated with a fixed concentration of between 3 and 30 uM cytotoxic chemotherapeutics, and a dose range of SBP treatments and evaluated against SBP treatment alone. The assay was performed similar to previous, except that 10,000 cells per well were seeded and treatment lasted 72 hours prior to WST-1 assessment. Each cell line and treatment regimen was analyzed and plotted using Prism data analysis, as shown in FIGS. 44 and 45.

In the case of PANC-1 cells, all conditions showed increased activity or potency, while MiaPaCa cells only demonstrated increased activity or potency in some of the combination conditions, notably when combined with Vorinostat, Etoposide, or Obataclax.

Example 18

Combination Surroglobulin and Chemotherapeutic Treatment in a Colon Cancer Cell Line Increased efficacy of combining chemotherapeutic treatment with death receptor agonist surroglobulins at sub-maximal doses for both agents in a colon cancer cell line. Colo205 cells alone, treated with 0.1 uM or 1 uM cytotoxic chemotherapeutics, $IC_{25}$ of SBP, or the combined chemotherapeutic/bivalent SBP treatments were evaluated for enhanced anti-proliferative effects of combined chemotherapy/death receptor agonism. FIGS. 16A-16F. Chemotherapeutics were chosen based on standard of care and clinical validation and were added to cells 24 hours prior to addition of bivalent SBP, followed by 48 hours of incubation at 37 C and development using WST-1 reagent.

Increased anti-proliferative effects in Colo205 cells were observed with most bivalent SBP in combination with irinotecan. Weaker effects were detectable in bivalent SBP combinations with etoposide, carboplatin and possibly 5-FU and doxorubicin. Oxaliplatin was not observed to have any effect in bivalent SBP combination, nor was 2737-F08 bivalent SBP active in any combination, at this concentration.

Example 19

Combination Serroglobulin and Chemotherapeutic Treatment in a Breast Cancer Cell Line Increased efficacy of combining chemotherapeutic treatment with death receptor agonist surroglobulins at sub-maximal doses for both agents in a breast cancer cell line. BT-474 cells alone, treated with 0.28 uM or 1 uM cytotoxic chemotherapeutics, 10 nM SBP, or the combined chemotherapeutic/SEP treatments were evaluated for enhanced antiproliferative effects of combined chemotherapy/death receptor agonism. FIGS. 17A-F. Chemotherapeutics were chosen based on standard of care and clinical validation and were added to cells 24 hours prior to addition of bivalent SBP, followed by 48 hours of incubation at 37 C and development using WST-1 reagent.

Increased anti-proliferative effects in BT-474 cells were observed with most SBPs in combination with doxorubicin and possible weaker effects were seen in combination with oxaliplatin.

Example 20

3631-G09 Bivalent SBP Slows Ramos Xenograft Tumor Growth

Figure 18:
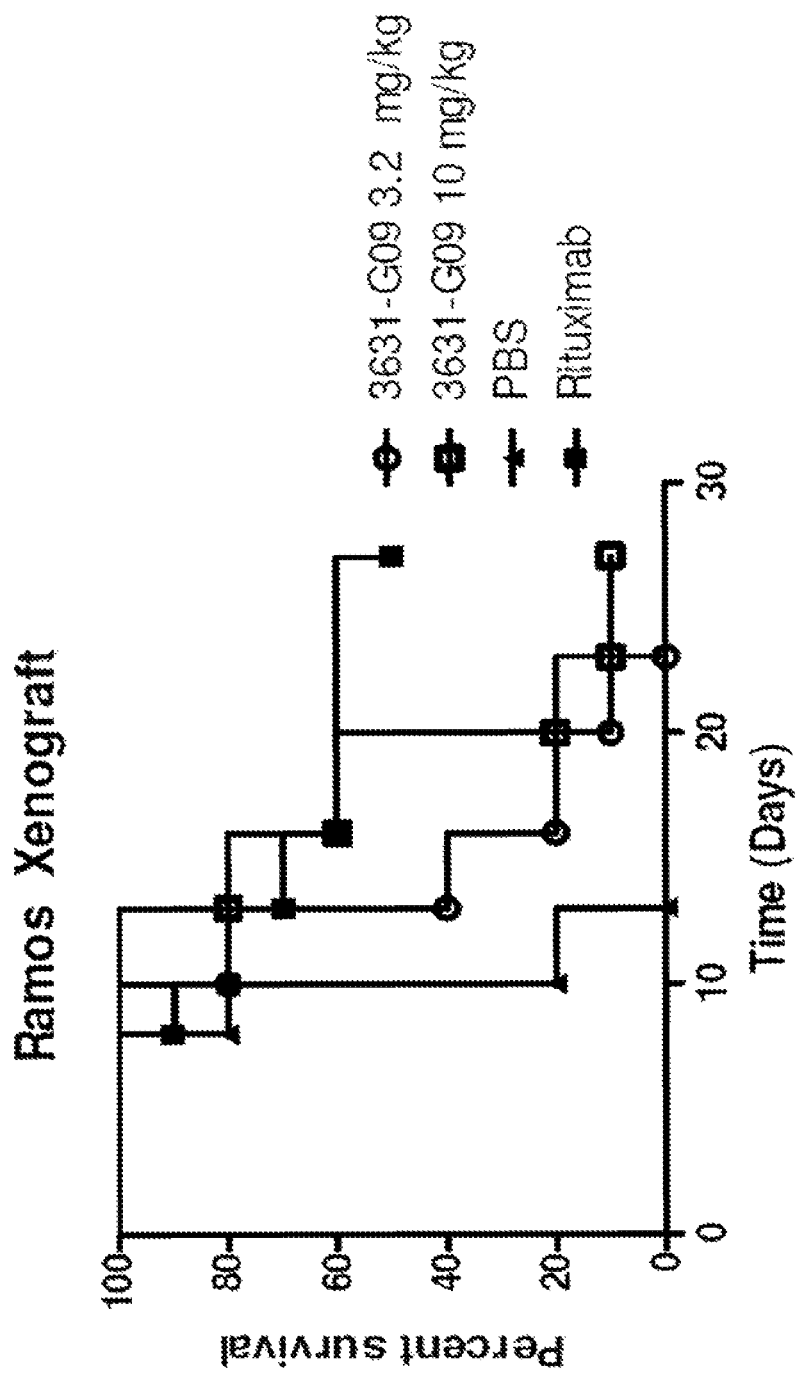
FIG. 18 illustrates the effect of 3631-G09 bivalent SBP treatment on Ramos xenograft tumor growth.
Figure 19A:
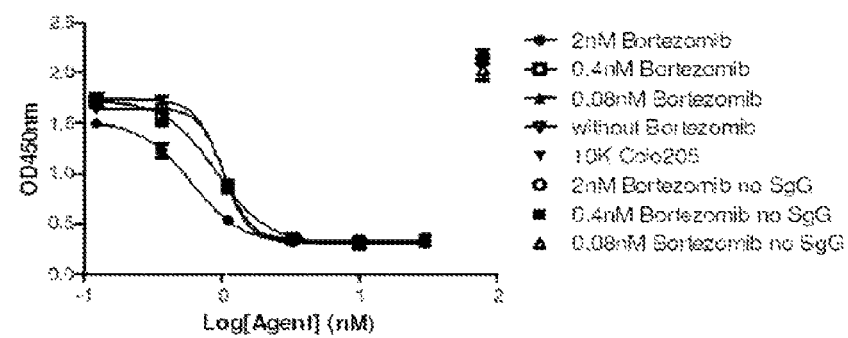
FIGS. 19A-19I illustrate the anti-proliferative effects of treatment with cross-linked 3631-G09 bivalent SBP and pathway-specific chemotherapeutic agents on Colo205 colon cancer cells.
Figure 19B:
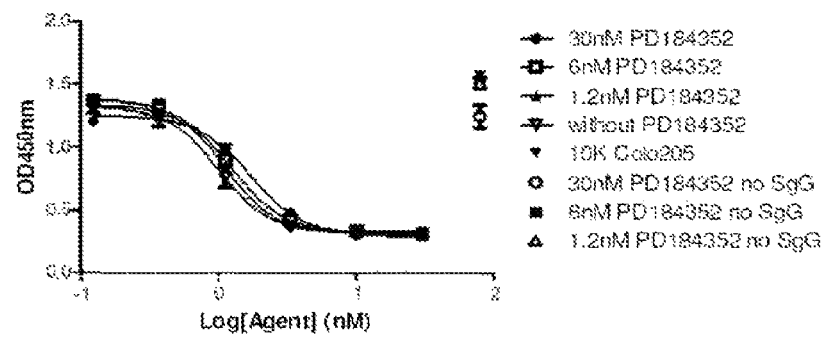
Figure 19C:
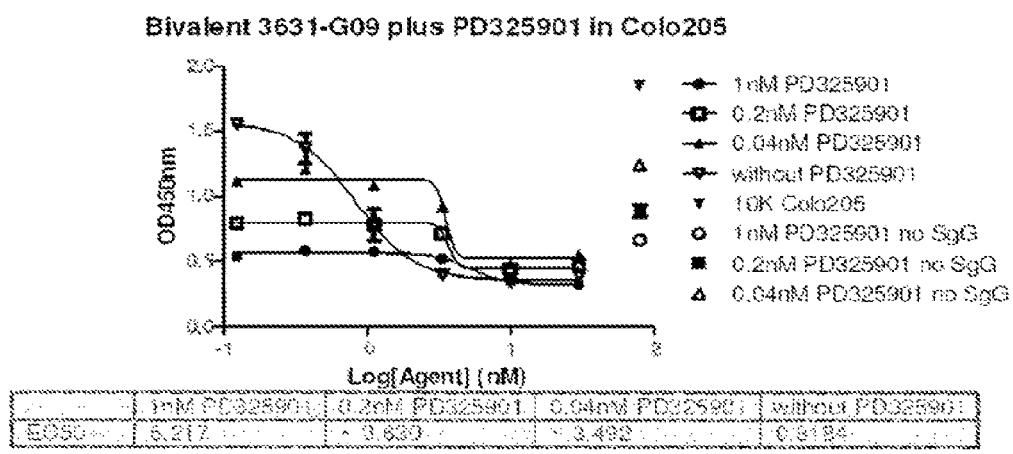
Figure 19D:
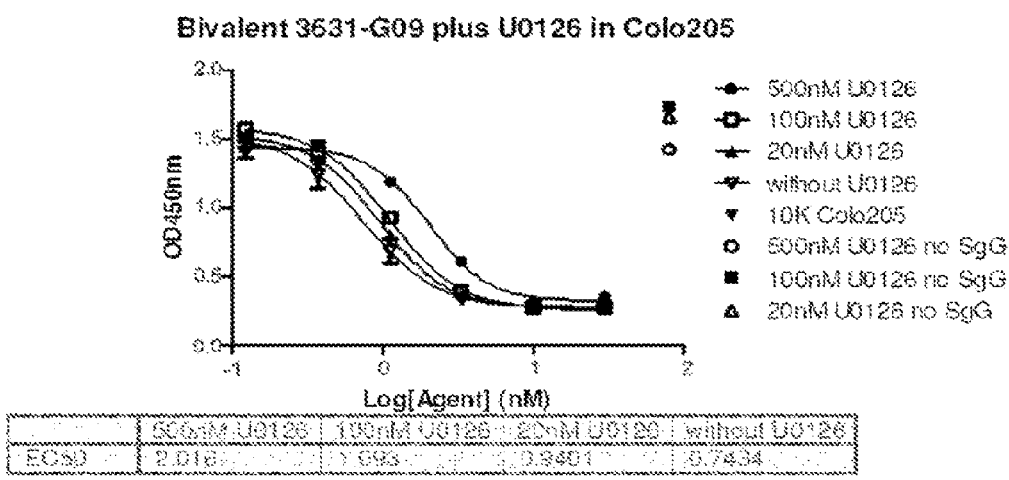
Figure 19E:
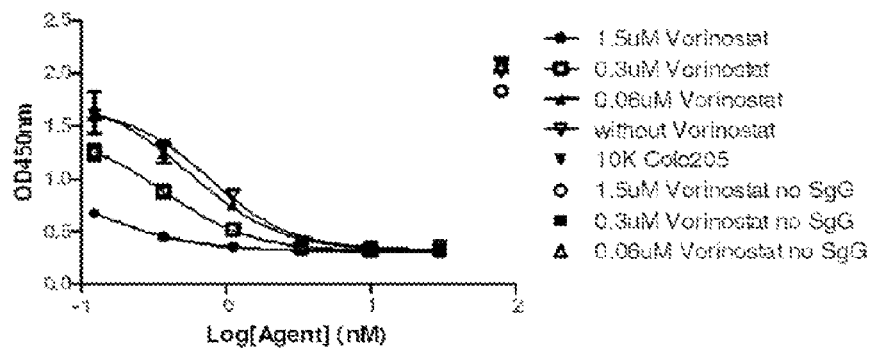
Figure 19F:
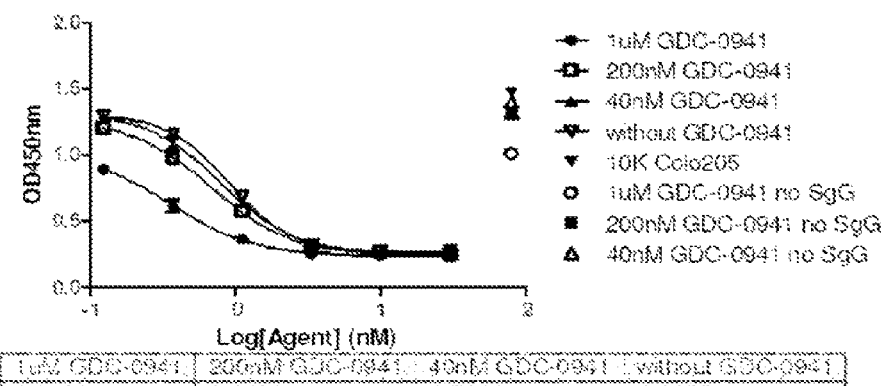
Figure 19G:
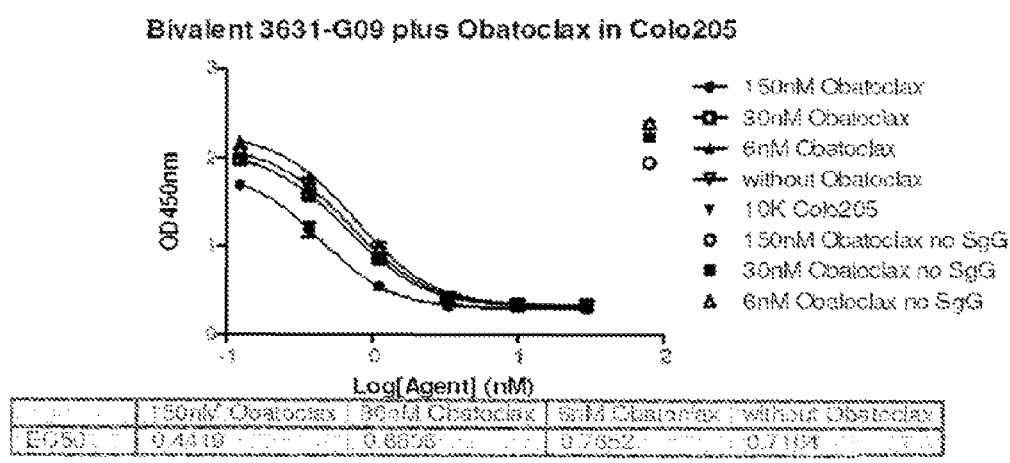
Figure 19H:
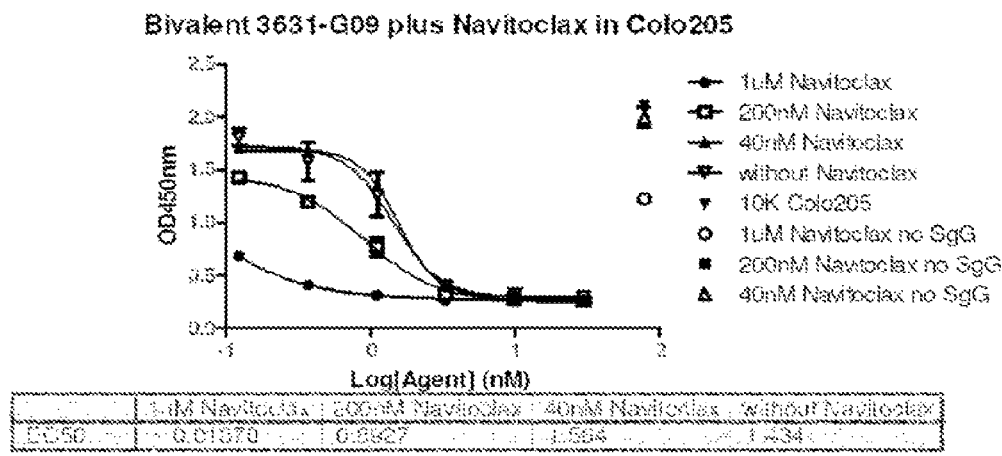
Figure 19I:
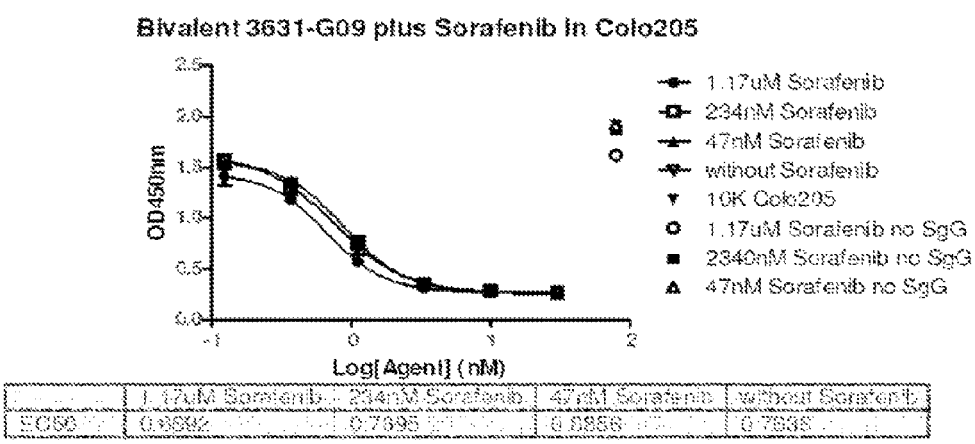
Figure 20A:
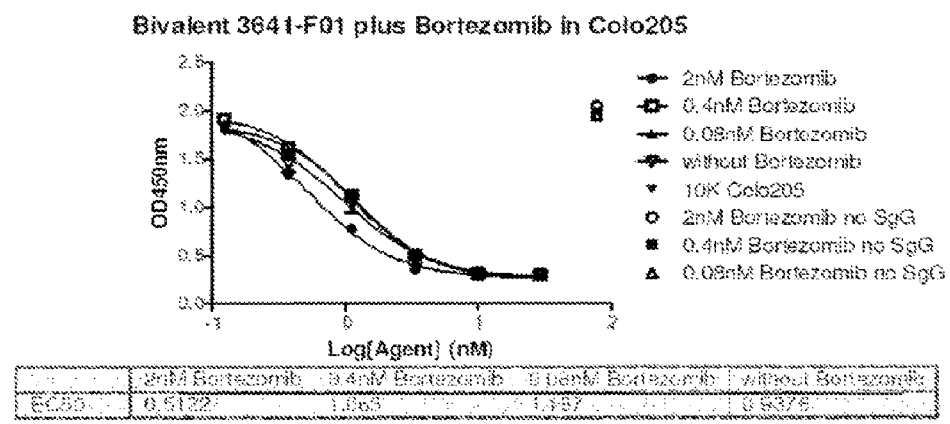
FIG. 20A-20I illustrate the anti-proliferative effects of treatment with cross-linked 3641-F01 bivalent SBP and pathway-specific chemotherapeutic agents on Colo205 colon cancer cells.
Figure 20B:
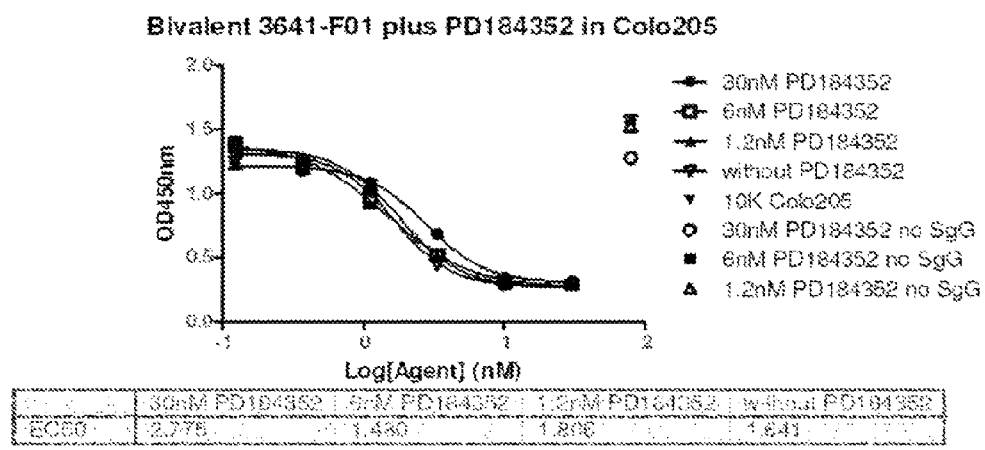
Figure 20C:
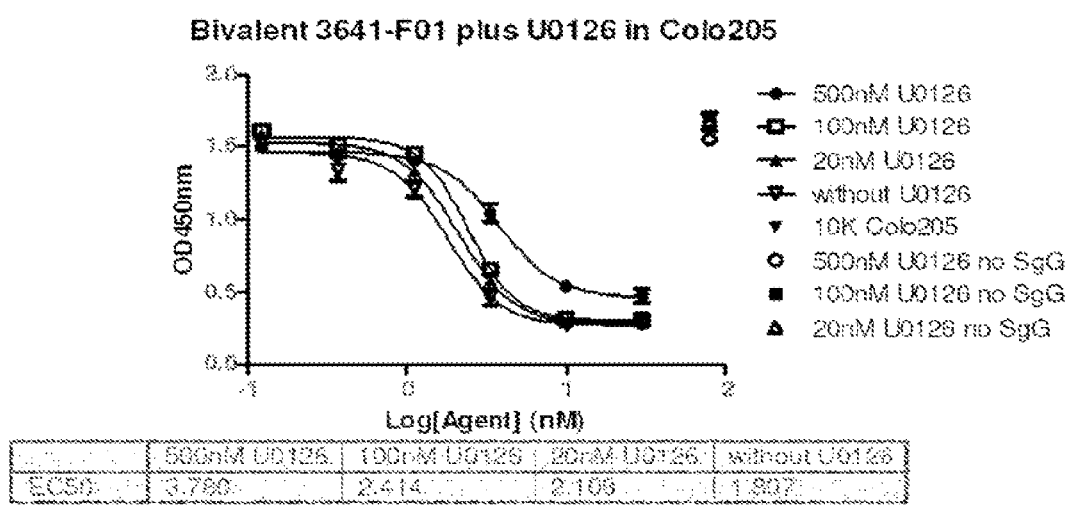
Figure 20D:
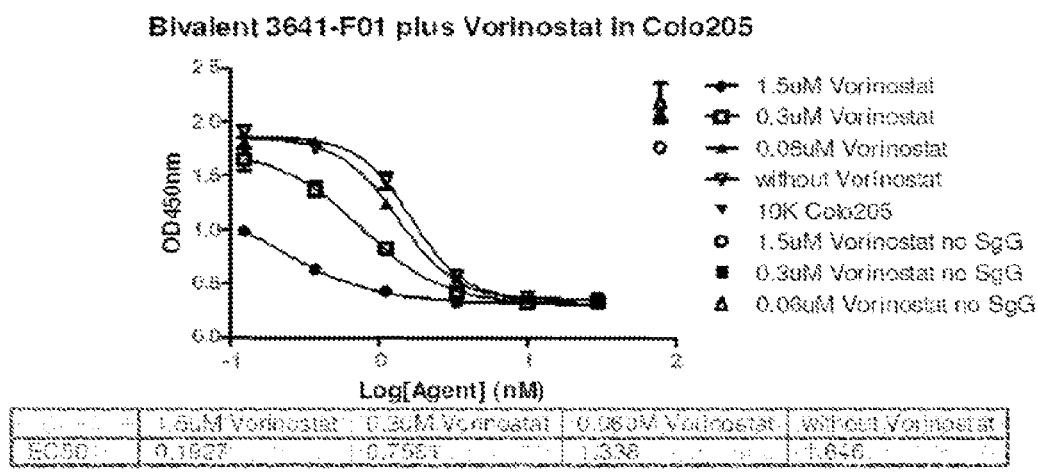
Figure 20E:
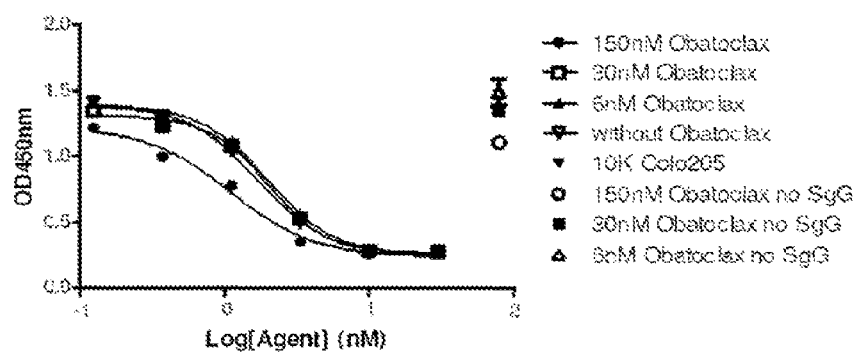
Figure 20F:
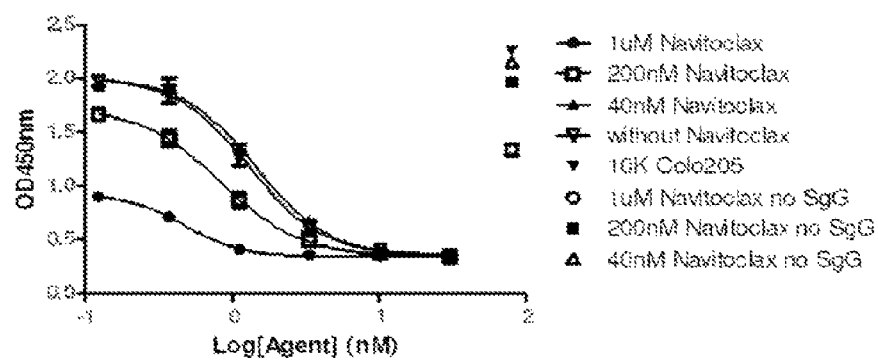
Figure 20G:
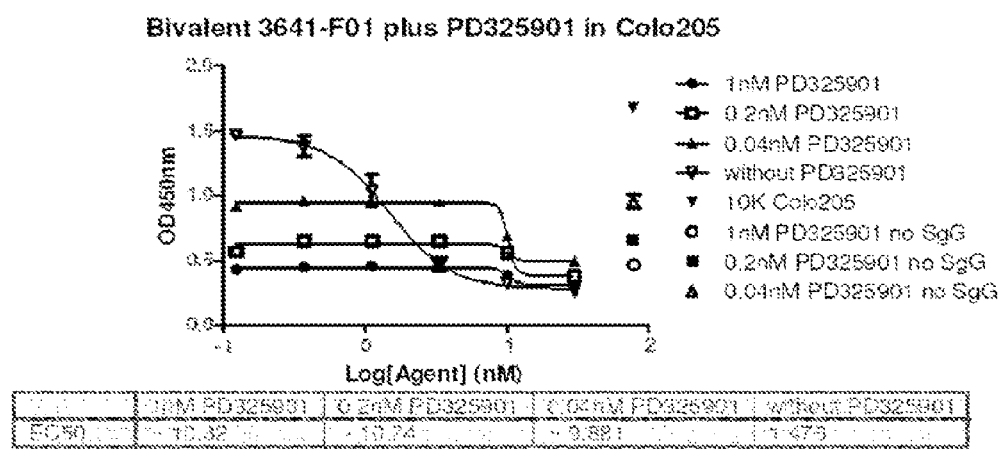
Figure 20H:
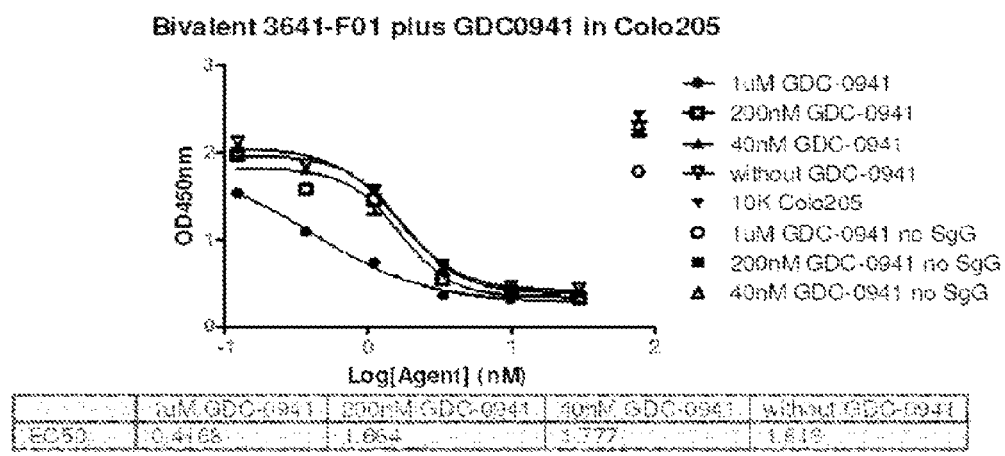
Figure 20I:
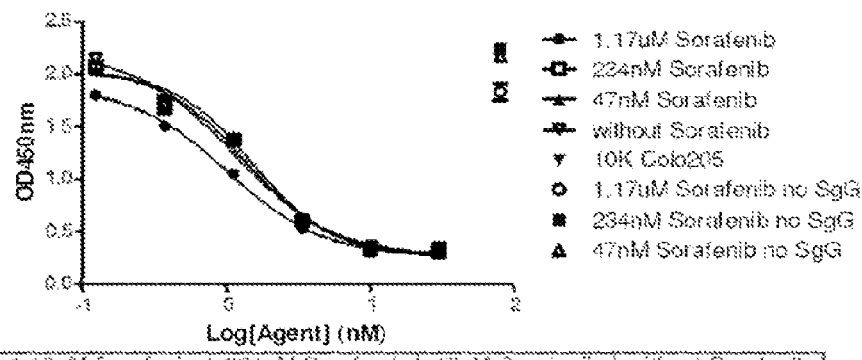
Figure 21A:
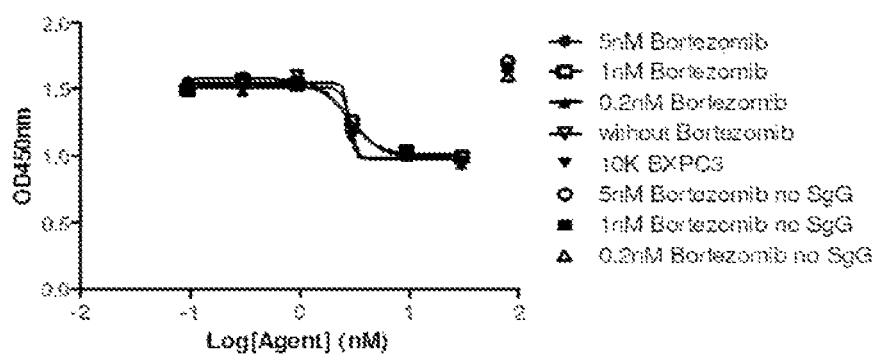
FIGS. 21A-21I illustrate the anti-proliferative effects of treatment with cross-linked 3631-G09 bivalent SBP and pathway-specific chemotherapeutic agents on BxPC3 pancreatic cancer cells.
Figure 21B:
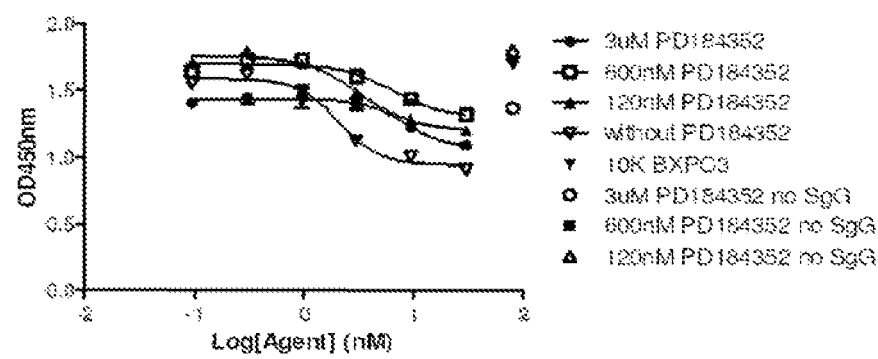
Figure 21C:
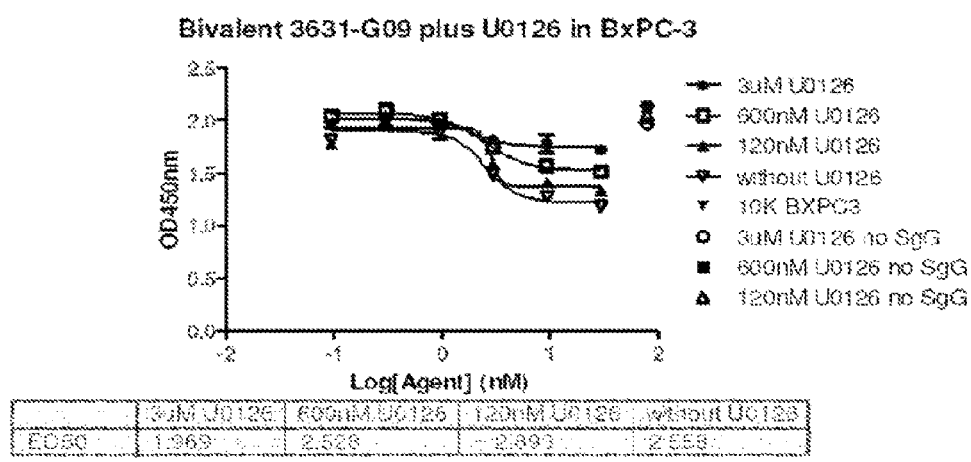
Figure 21D:
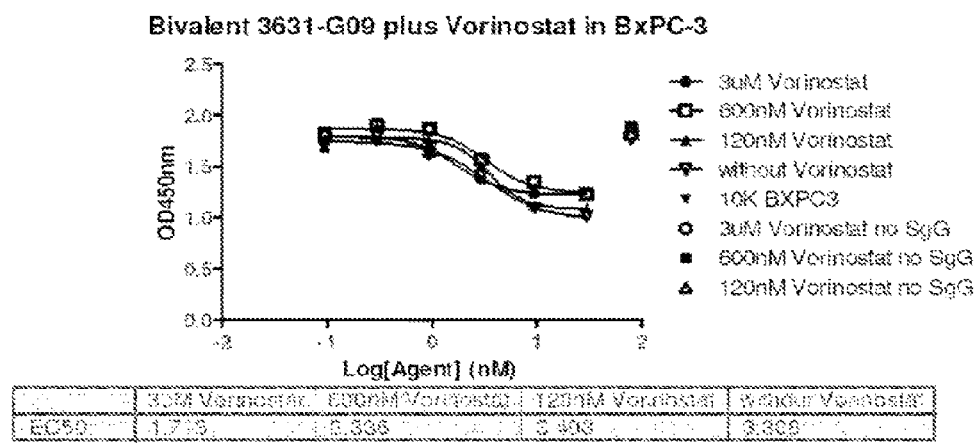
Figure 21E:
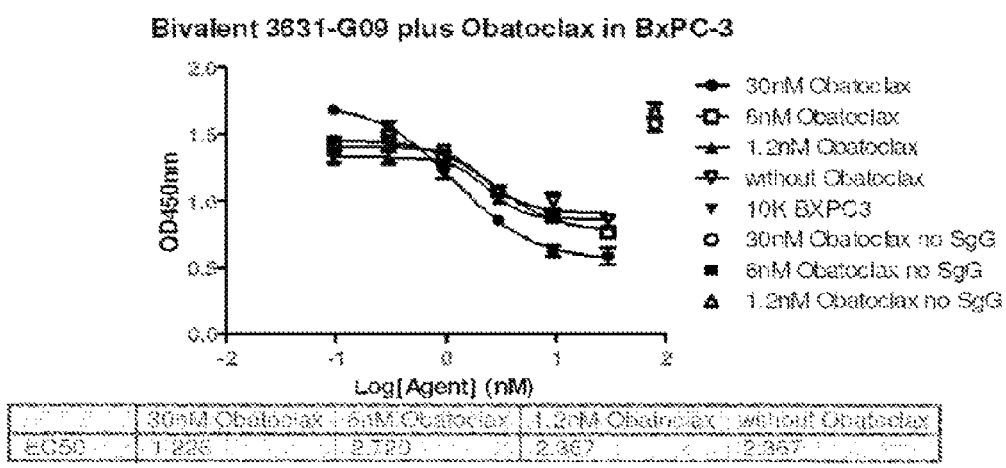
Figure 21F:
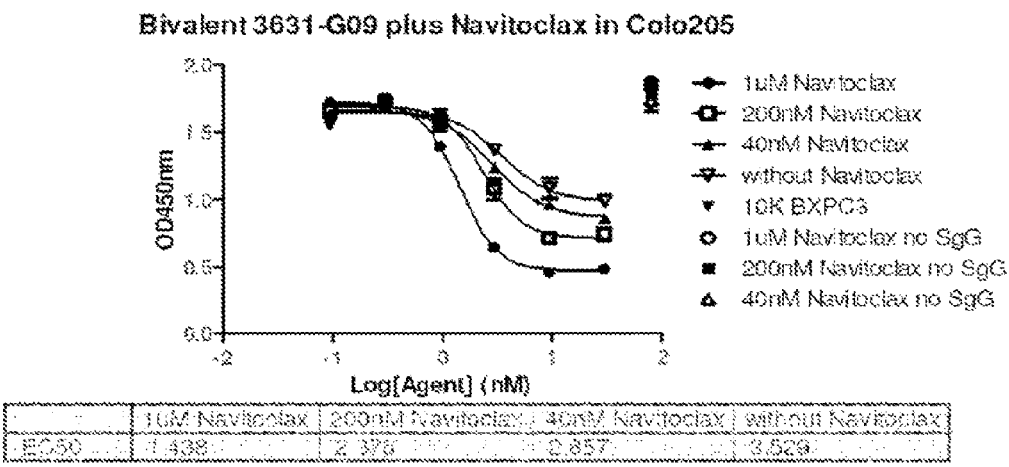
Figure 21G:
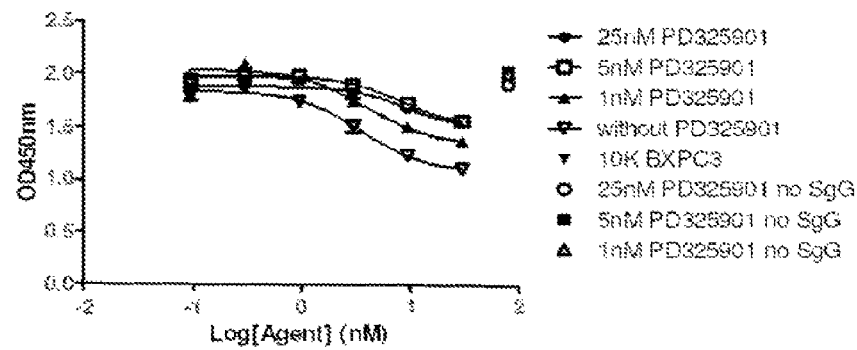
Figure 21H:
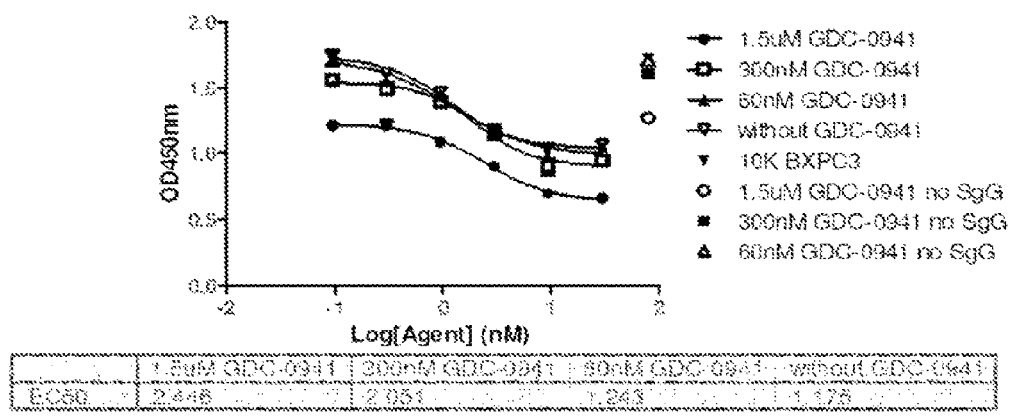
Figure 21:
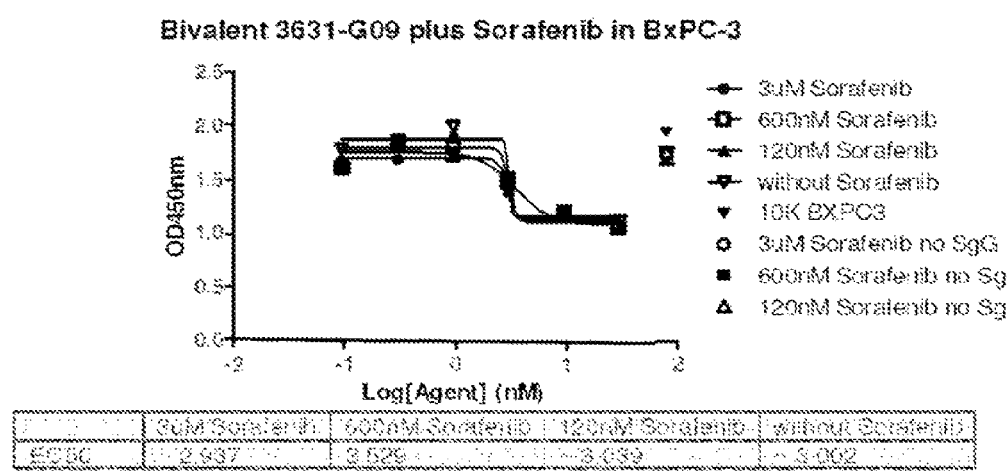
Figure 22A:
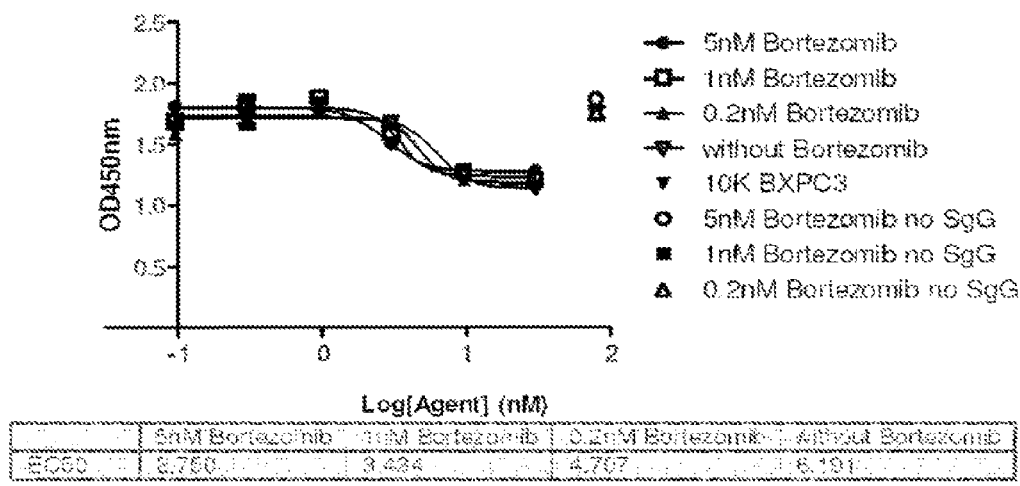
FIGS. 22A-22I illustrate the anti-proliferative effects of treatment with cross-linked 3641-F01 bivalent SBP and pathway-specific chemotherapeutic agents on BxPC3 pancreatic cancer cells.
Figure 22B:
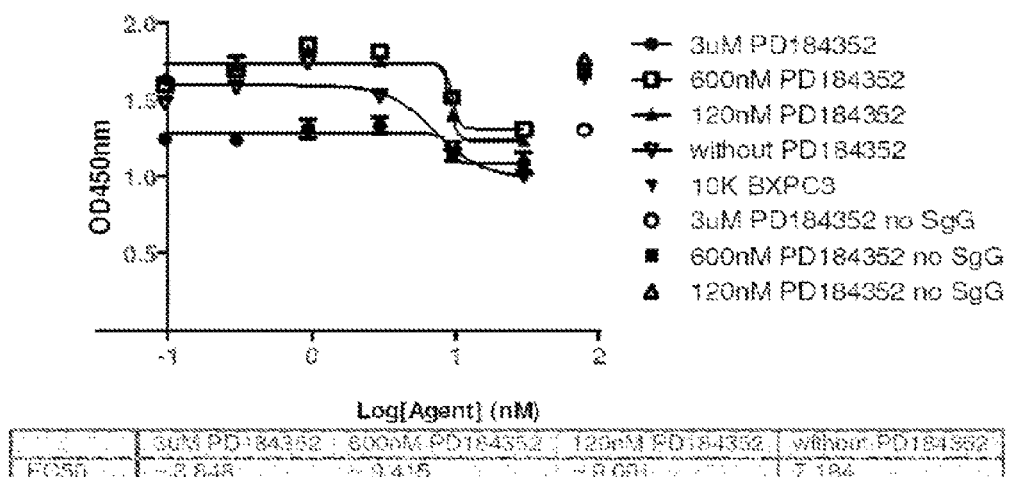
Figure 22C:
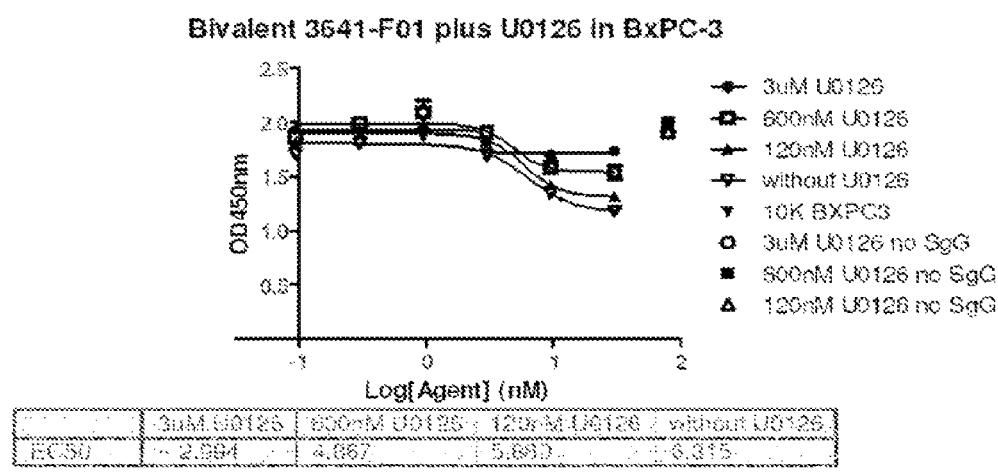
Figure 22D:
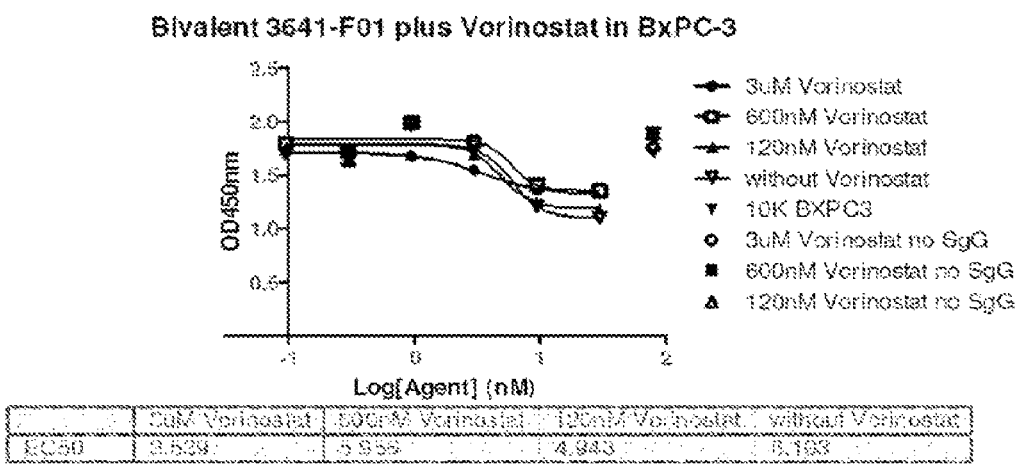
Figure 22E:
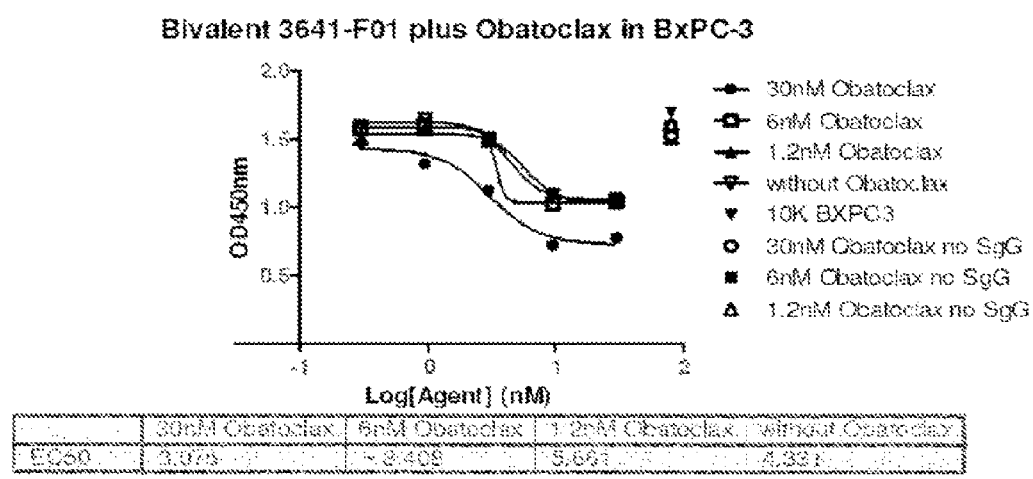
Figure 22F:
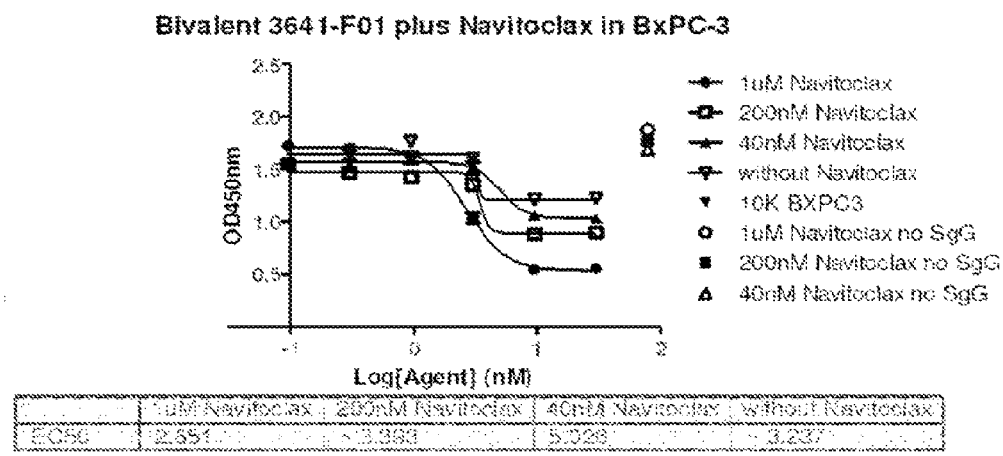
Figure 22G:
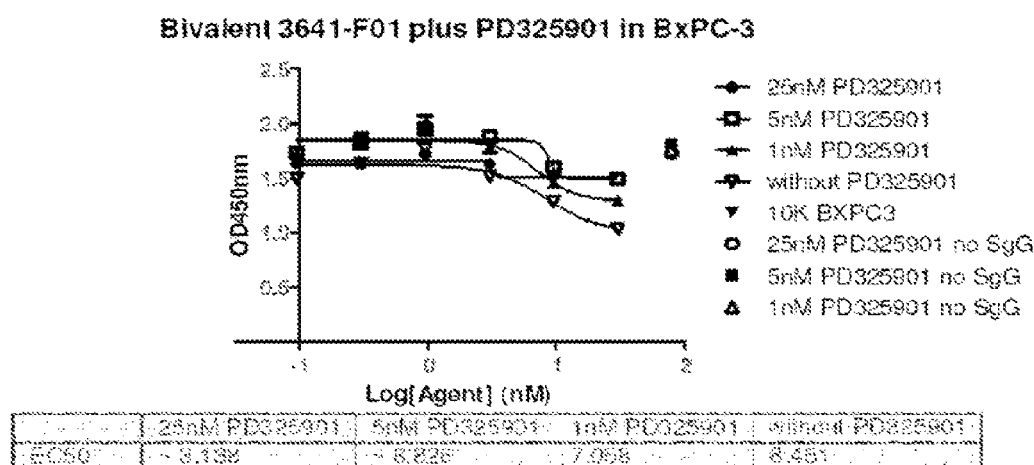
Figure 22H:
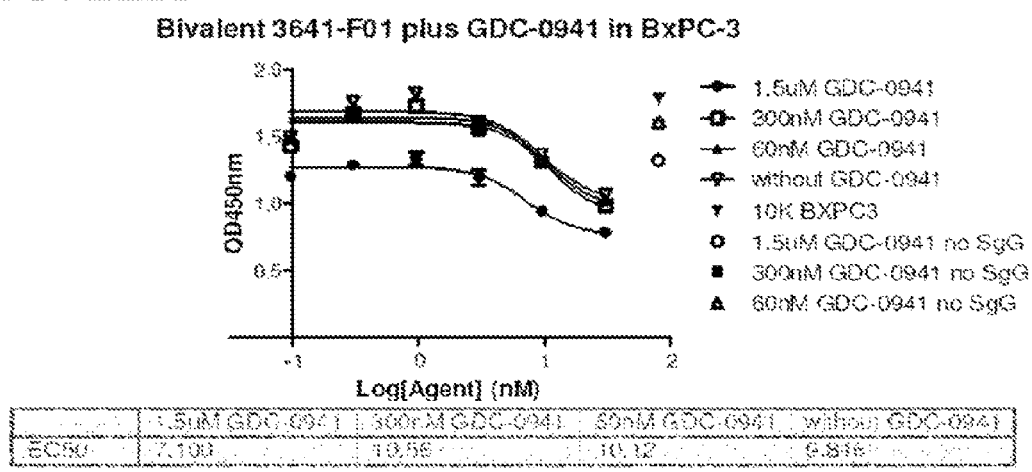
Figure 22I:
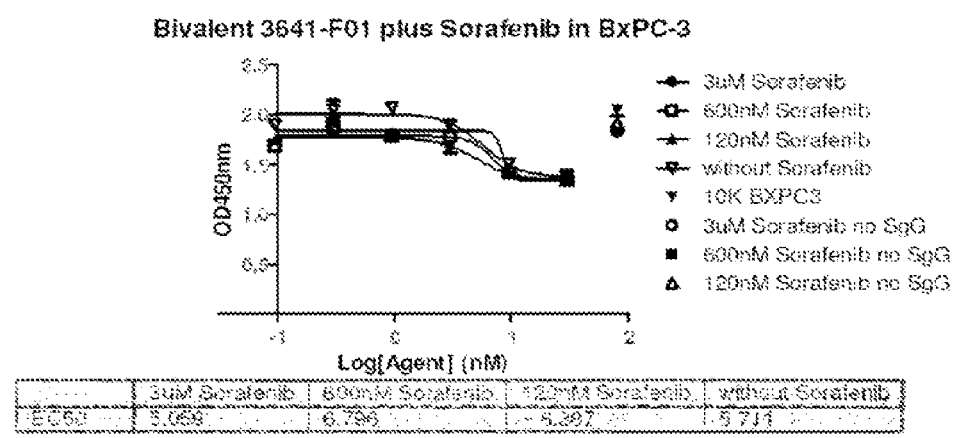
Figure 23A:
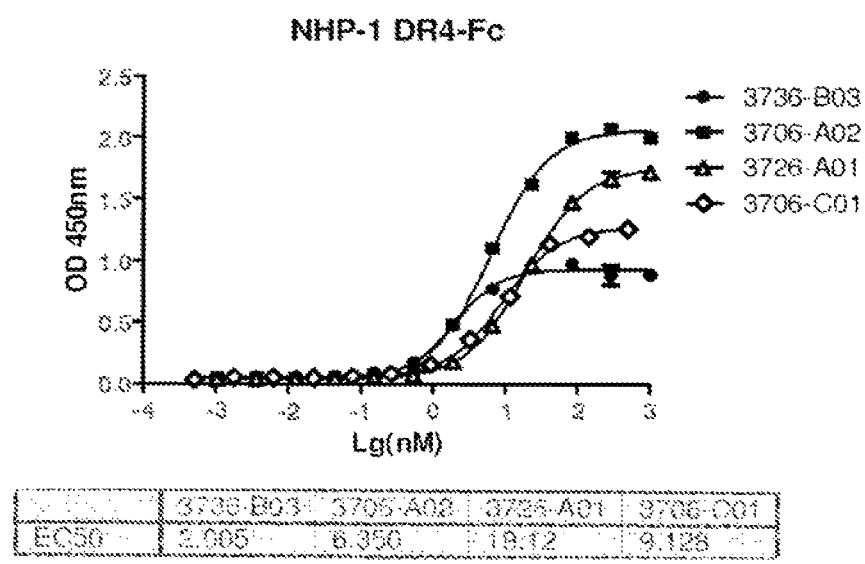
FIGS. 23A-23D show that the SgGs bind with high affinity to Cynomolgus and Rhesus DR4-Fc (FIGS. 23A and C) and Cynomolgus and Rhesus DR5-Fc (FIGS. 23B and D). Affinities are reported in FIG. 23A inset and FIG. 23B inset.
Figure 23B:
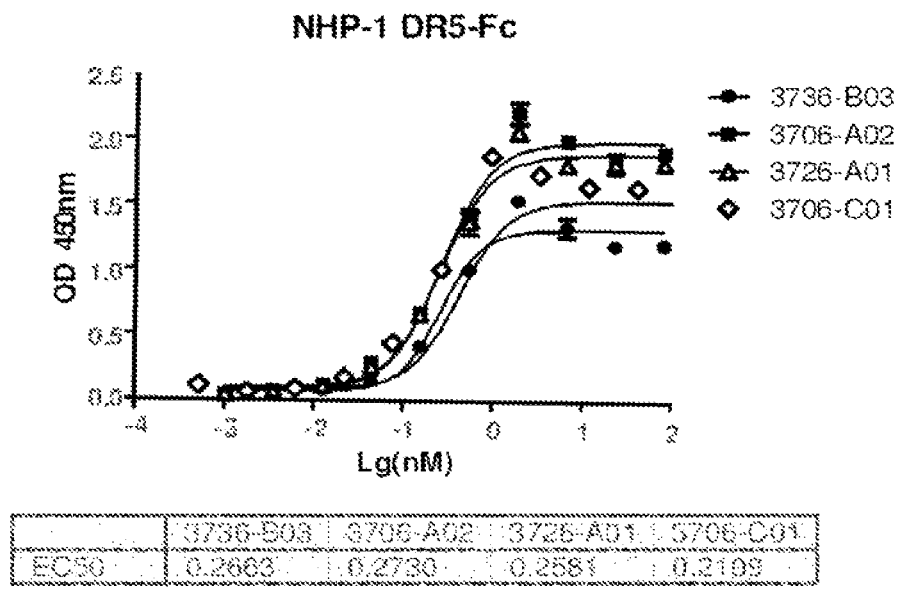
Figure 23C:
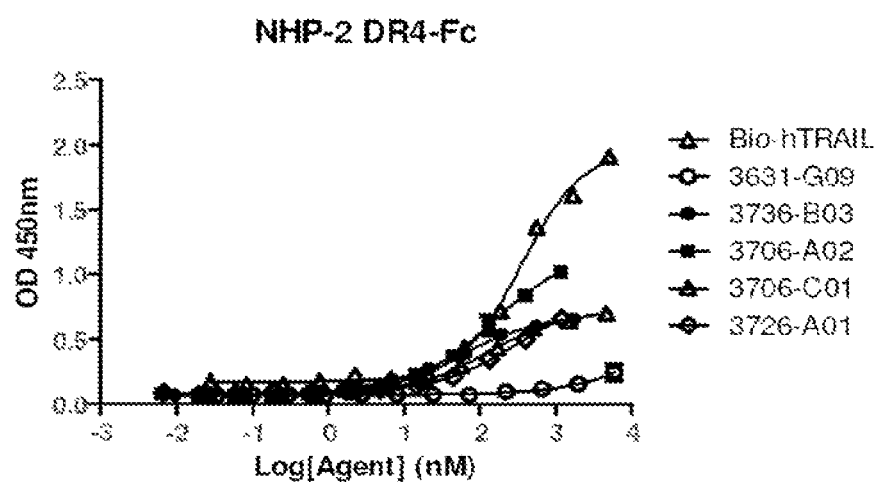
Figure 23D:
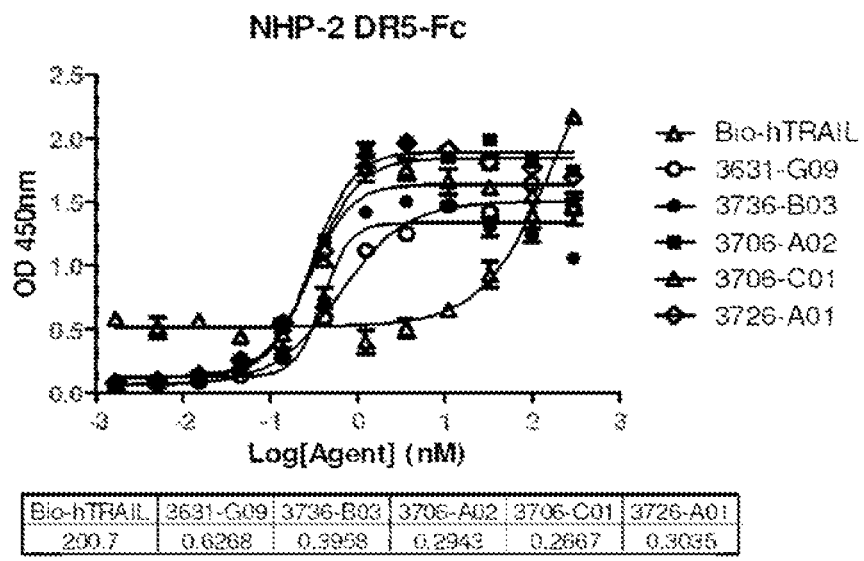
Figure 24A:
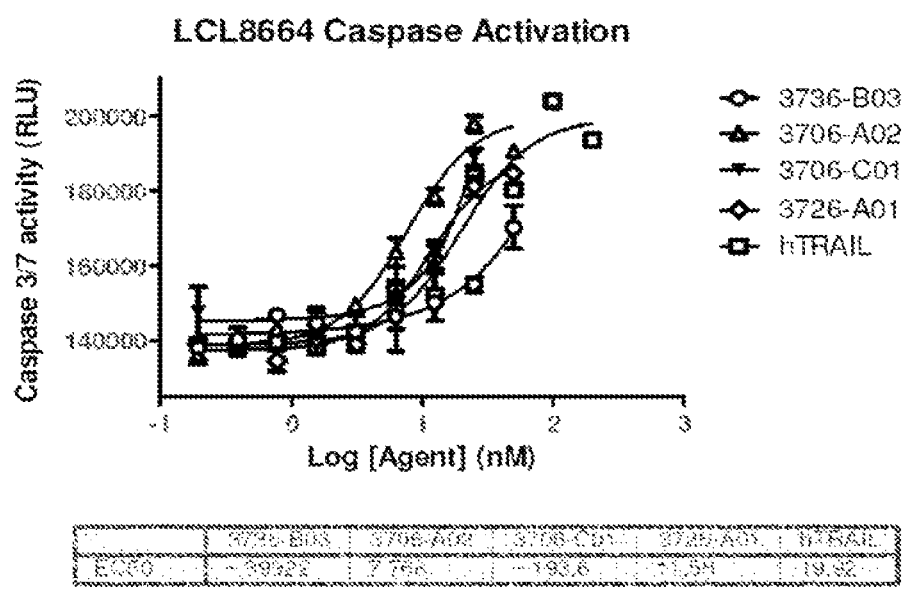
FIGS. 24A and 24B illustrate the activity of Death Receptor Sur-binding proteins on cell lines LCL8664 and CMMT, derived from the Rhesus monkey (*Macaca mulatta*).
Figure 24B:
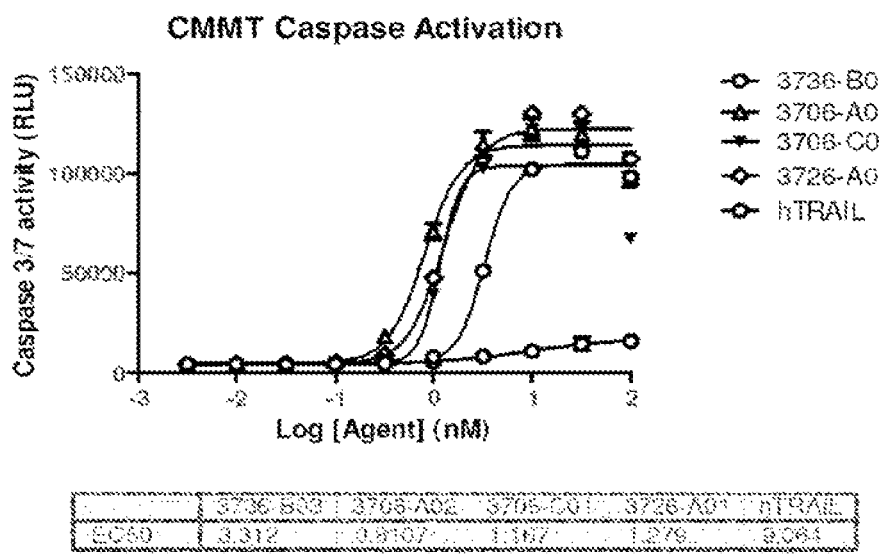

CB17 SCID (CRL) mice were injected with $1\times10^6$ Ramos cells in the right flank and the tumors were allowed to grow to a volume of 150 mm³. Mice were then sorted into groups of 10 for treatment 2×/week with 1×PBS, or 0.1, 0.3, 1, 3.2 or 10 mg/kg 3631-G09 bivalent SBP, or 5 mg/kg Rituximab (control for this xenograft model and clinical standard of care). Tumors were measured 2×/week and tumor volume tracked until the study endpoint (tumor volume≥2000 mm³ or 30 days). Mice with tumors reaching 2000 mm³ or found in moribund condition were removed from the study and humanely sacrificed. Mean and individual tumor volume was measured and Kaplan-Meier survival (FIG. 18) curves were plotted.

3631-G09 (SL231) bivalent SBP treatment at 3.2 and 10 mg/kg resulted in statistically significant survival benefit compared to PBS treatment and was not significantly different from Rituximab (5 mg/kg) treatment (top right panel). Additionally, mean tumor volume at day 8 post-treatment (the last data point where all animals were still in the study) was compared across the treatment groups by a one-way t-test. Rituximab and 10 mg/kg 3631-G09 bivalent SBP were statistically significant relative to PBS. In addition, no statistical difference was observed between Rituximab and the two dose levels of 3631-G09 (SL231) bivalent SBP.

Example 21

Combination Treatment of Colo205 Colon Cancer Cell Line with 3631-G09 Bivalent SBP Combination treatment of Colo205 colon cancer cell line with 3631-G09 (SL231) bivalent SBP and a number of different pathway-specific chemotherapeutics showed increased anti-proliferative effects. Colo205 cells were seeded at 10,000, cells/well in 96 well tissue culture plates. After incubation for 5 hours at 37 C+5% $CO_2$, the chemotherapeutics were added at the indicated concentrations and then incubated at 37 C+5% $CO_2$ overnight. The following day, a dilution series of 3631-G09 bivalent SBP was added to the appropriate wells followed by incubation for 24 hours at 37 C+5% $CO_2$. The assays were then developed using WST-1 reagent, incubated for 4 hours at 37 C+5% $CO_2$, read on a plate reader and plotted using GraphPad Prism v5.03 software.

Several pathway specific inhibitors showed increased potency when used in combination with the agonist death receptor SBPs. FIGS. 19A-I. Bortezomib, Vorinostat, Obatoclax, Navitoclax and GDC-0941 all showed additive or synergistic effects. The most pronounced effects were seen with Vorinostat, an HDAC inhibitor. Obatoclax and Navitoclax, Bcl-2 inhibitors, also showed increased potency with 3631-G09 bivalent SBP.

Example 22

Combination Treatment of Colo205 Colon Cancer Cell Line with 3641-F01 Bivalent SBP Combination treatment of Colo205 colon cancer cell line with 3641-F01 bivalent SBP and a number of different pathway-specific chemotherapeutics showed increased anti-proliferative effects. Colo205 cells were seeded at 10,000, cells/well in 96 well tissue culture plates. After incubation for 5 hours at 37 C+5% $CO_2$, the chemotherapeutics were added at the indicated concentrations and then incubated at 37 C+5% $CO_2$ overnight. The following day, a dilution series of 3641-F01 bivalent SBP was added to the appropriate wells followed by incubation for 24 hours at 37 C+5% $CO_2$. The assays were then developed using WST-1 reagent, incubated for 4 hours at 37 C+5% $CO_2$, read on a plate reader and plotted using GraphPad Prism v5.03 software.

Several pathway specific inhibitors showed increased potency when used in combination with the agonist death receptor SBPs. FIGS. 20A-I. Bortezomib, Vorinostat, Obatoclax, Navitoclax and GDC-0941 all showed additive or synergistic effects. The most pronounced effects were seen with Vorinostat, an HDAC inhibitor. Obatoclax and Navitoclax, Bcl-2 inhibitors, also showed increased potency with 3641-F01 bivalent SBP.

Example 23

Combination Treatment of BxPC3 Pancreatic Cancer Cell Line with 3631-G09 Bivalent SBP Combination treatment of the BxPC3 pancreatic cancer cell line with 3631-G09 bivalent SBP and a number of different pathway-specific chemotherapeutics showed increased anti-proliferative effects. BxPC3 cells were seeded at 10,000, cells/well in 96 well tissue culture plates. After incubation for 5 hours at 37 C+5% $CO_2$, the chemotherapeutics were added at the indicated concentrations and then incubated at 37 C+5% $CO_2$ overnight. The following day, a dilution series of 3631-G09 (SL-231) bivalent SBP was added to the appropriate wells followed by incubation for 24 hours at 37 C+5% $CO_2$. The assays were then developed using WST-1 reagent, incubated for 4 hours at 37 C+5% $CO_2$, read on a plate reader and plotted using GraphPad Prism v5. 03 software.

Several pathway specific inhibitors showed increased potency when used in combination with the agonist death receptor SBPs. FIGS. 21A-I. Obatoclax, Navitoclax and GDC-0941 all showed additive effects in combination with 3631-G09 (SL-231) bivalent SBP.

Example 24

Combination Treatment of BxPC3 Pancreatic Cancer Cell Line with 3641-F01 Bivalent SBP Combination treatment of the BxPC3 pancreatic cancer cell line with 3641-F01 bivalent SBP and a number of different pathway-specific chemotherapeutics showed increased anti-proliferative effects. BxPC3 cells were seeded at 10,000, cells/well in 96 well tissue culture plates. After incubation for 5 hours at 37 C+5% $CO_2$, the chemotherapeutics were added at the indicated concentrations and then incubated at 37 C+5% $CO_2$ overnight. The following day, a dilution series of 3641-F01 bivalent SBP was added to the appropriate wells followed by incubation for 24 hours at 37 C+5% $CO_2$. The assays were then developed using WST-1 reagent, incubated for 4 hours at 37 C+5% $CO_2$, read on a plate reader and plotted using GraphPad Prism v5. 03 software.

Several pathway specific inhibitors showed increased potency when used in combination with the agonist death receptor SBPs. FIGS. 22A-I. Obatoclax, Navitoclax and GDC-0941 all showed additive effects in combination with 3641-F01 bivalent SBP.

Example 25

Treatment of Cancer Using a Bivalent SBP to DR4 or DR5

This example outlines the treatment of a cancer using a bivalent SBP to DR4 and/or DR5.

A subject having a cancer in which tumor cells express or may be induced to express DR4 and/or DR5 is administered a dose of a DR4 and/or DR5 agonist surroglobulin, such as 3631-G09 (SL231) bivalent SBP, 3641-F01 bivalent SBP, 2737-F08 bivalent SBP or 2737-A01 bivalent SBP. The bivalent SBP is administered at an amount sufficient to inhibit tumor cell proliferation and/or reduce tumor size, thereby slowing, reducing, or eliminating the cancer.

Example 26

Treatment of Cancer Using a Bivalent SBP Combination Therapy

This example outlines the treatment of a cancer using a bivalent SBP to DR4 and/or DR5 in combination with a targeted compound that inhibits cancer growth. A subject having a cancer in which tumor cells express DR4 and/or DR5 is administered a dose of a DR4 and/or DR5 agonist surroglobulin, such as 3631-G09 bivalent SBP, 3641-F01 bivalent SBP, 2737-F08 bivalent SBP or 2737-A01 bivalent SBP (or other bivalent SBP) either prior to, subsequent to, or in combination with a compound that inhibits properly regulated cellular proliferation or survival. Inhibitors that can be used in this capacity include, without limitation, HDAC inhibitors, Bcl-2 inhibitors, PI3K inhibitors, Protein kinase C inhibitors, RAF inhibitors, MAPK inhibitors, MEK inhibitors, AKT inhibitors, mTOR inhibitors, BCR/ABL and Src family tyrosine kinase inhibitors, aurora kinase inhibitors, and HSP90 inhibitors. Examples of such inhibitors can include, but are not limited to BAY43-9006, PLX4032, SB590885, PLX4720, XL281, RAF265, XL518, CI-1040, PD035901, AZD6244, GSK1120212, Sorafenib, Dasatinib, nilotinib, and imatinib. In some embodiments, a DR4 and/or DR5 agonist bivalent SBP is administered in combination with one or more of Bortezomib, Vorinostat, Obatoclax, Navitoclax or GDC-0941.

The bivalent SBP is administered in an amount sufficient to induce apoptosis in tumor cells and/or decrease proliferation, thereby slowing or reducing the cancer. The result of the combined therapy is an improved inhibition of tumor growth that is at least greater than the use of the bivalent SBP and/or the compound alone at an equivalent dose.

Example 27

Treatment of Cancer Using a Bivalent SBP Combination Therapy with a Cytotoxic Chemotherapeutic Agent This example outlines the treatment of a cancer using a bivalent SBP to DR4 and/or DR5 and a chemotherapeutic agent that inhibits cancer growth. A subject having a cancer in which tumor cells express DR4 and/or DR5 is administered a dose of a DR4 and/or DR5 agonist surroglobulin, such as 3706-A02 (SL466), 3631-G09 (SL231) bivalent SBP, 3641-F01 bivalent SBP, 2737-F08 bivalent SBP or 2737-A01 bivalent SBP (or other bivalent SBP) either prior to, subsequent to, or in combination with one or more chemotherapeutic compounds. Compounds that can be used in this capacity, include, without limitation, topoisomerase inhibitors, alkylating agents, nucleoside analogs, microtubule inhibitors, DNA crosslinking agents and DNA intercalating agents. Examples of such inhibitors can include, but are not limited Cisplatin, Etoposide, Carboplatin, Oxaliplatin, Etoposide, Trinotecan, Paclitaxel, Docetaxel, Vinorelbine tartrate, Doxorubicin, Vincristine sulfate, Ifosfamide, Gemcitabine hydrochloride, and/or 5-FU. The bivalent SBP is administered in an amount sufficient to induce apoptosis in some of the tumor cells and/or reduce tumor cell proliferation, thereby slowing or reducing the cancer. The result of the combined therapy is an improved inhibition of tumor growth that is at least greater than the use of the bivalent SBP and/or the compound alone at an equivalent dose.

In some embodiments, agonist surroglobulins to DR4 and/or DR5 are administered in combination with a chemotherapeutic agent selected from 5-FU, oxaliplatin, etoposide, irinotecan and doxorubicin. In some embodiments, an agonist DR4 and/or DR5 surroglobulin is provided in combination with 5-FU and/or oxaliplatin.

Example 28

Treatment of Cancer Using a Bivalent SBP Combination Therapy with a Targeted Inhibitor of Angiogenesis This example outlines the treatment of a cancer using a bivalent SBP to DR4 and/or DR5 and a targeted inhibitor of angiogenesis that inhibits cancer growth. A subject having a cancer in which tumor cells express DR4 and/or DR5 is administered a dose of a DR4 and/or DR5 agonist surroglobulin, such as 3631-G09 (SL231) bivalent SBP, 3641-F01 bivalent SBP, 2737-F08 bivalent SBP, 2706-A02 (SL466) bivalent SBP or 2737-A01 bivalent SBP (or other bivalent SBP) either prior to, subsequent to, or in combination an inhibitor of angiogenesis. Compounds that can be used in this capacity include antibodies or surroglobulins to VEGF, PLGF, Angiopoietin, DLL-4 or receptors to any of these factors. Additional compounds that can be used in this capacity are decoy receptors, such as Aflibercept and inhibitors of signaling elicited by binding of proangiogenic compounds to the receptors including, but not limited to Axitinib, Cediranib, Regorafenib, Sunitinib, Vandetanib, Vatalanib. The bivalent SBP is administered in an amount sufficient to induce apoptosis in some tumor cells and/or to reduce tumor cell proliferation, thereby slowing or reducing the cancer. The result of the combined therapy is an improved inhibition of tumor growth that is at least greater than the use of the bivalent SBP and/or the compound alone at an equivalent dose.

Example 29

Uses of a Bispecific DR4 and/or DR5 SBP

This example outlines potential bispecific treatments of a cancer using a combination of a DR4 and/or DR5 sur-binding protein and another distinctly targeted specific sur-binding protein or antibody. As mentioned previously, coadministration of complimentary agents can have significant benefits compared to the use of single agents alone. However, bispecific entities, containing two or more specificities of these types of combinations, within a single molecular entity can yield even greater benefit compared either agent alone, as well as that of coadministered combinations.

A bispecific bivalent SBP is constructed so that it comprises a variable domain that recognizes DR4 and/or DR5 as well as one or more additional distinct variable domains. The variable domain of additional specificity may be derived by panning a monovalent SBP phage displayed library as outlined in Example 1. The variable domains can be joined by numerous methods. An example of such bispecific joining has been disclosed in (Xu, et. al, JMB 2010) Further strategies to generate bispecifics can adapt novel technologies or adapt techniques previously described for bispecific assembly.

Example 30

Antagonist Uses of DR4 and/or DR5 Sur-Binding Proteins

This examples outlines the treatment of inflammatory diseases such as lupus glomerlular nephritis, systemic lupus erythmatosis (SLE), in which DR4 and DR5 are overexpressed and transmits a proliferative signal rather than an apoptotic signaling with a Sur-binding protein that binds, but is not able to induce DR4 or DR5 receptor complexes to initiate signaling. This may be accomplished using a Sur-binding protein that contains a single Death Receptor binding domain, cannot be cross-linked in vivo, or that has differing specificities for each binding domain that precludes higher order receptor complex clustering. Such Sur-binding proteins may be manifest in different formats, including monovalent SBP, s(ab2'), bivalent SBP, bispecific SBP.

Example 31

Diagnostic Uses of DR4 and/or DR5 Sur-Binding Proteins

This section outlines the use of Death Receptor specific Sur-binding proteins for diagnostic use to assess the potential sensitivity of malignancies to Death Receptor agonists. Death Receptor Sur-binding proteins may be labeled with a radioactive tracer such as $^{125}I$, $^{111}In$, and fluorescent agents for in vivo use. Additionally, Sur-binding proteins may be covalently linked to enzymes such as horseradish peroxidase and alkaline phosphatase for immunohistochemical analysis of death receptor expression in biopsy samples. Kits for detection of death receptor expression in biopsies are also included in this description.

Example 32

Treatment of Viral Infections with Antagonist Death Receptor Surroglobulins

Figure 25A:
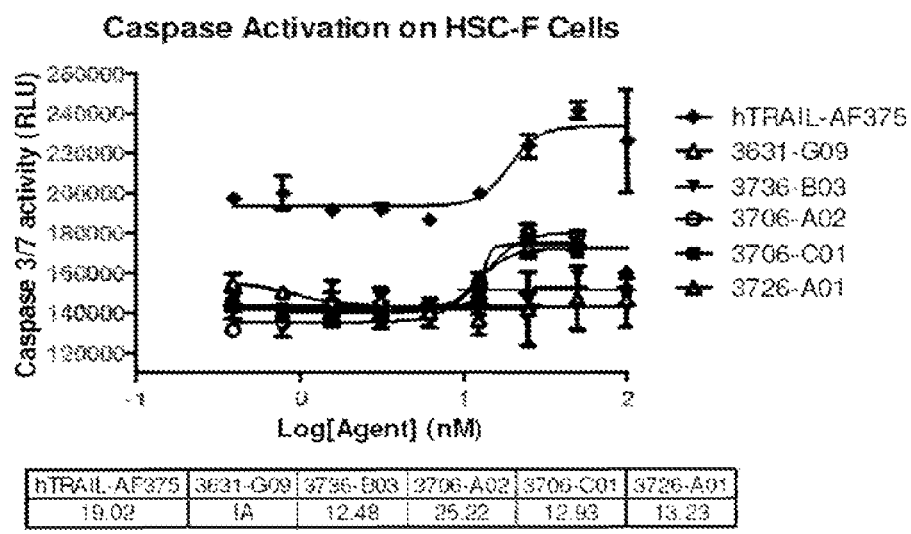
FIGS. 25A and 25B illustrate the activity of Death Receptor Sur-binding proteins on cell lines HSC-F and AG21329, derived from the Cynomolgus monkey (*Macaca fascicularis*).
Figure 25B:
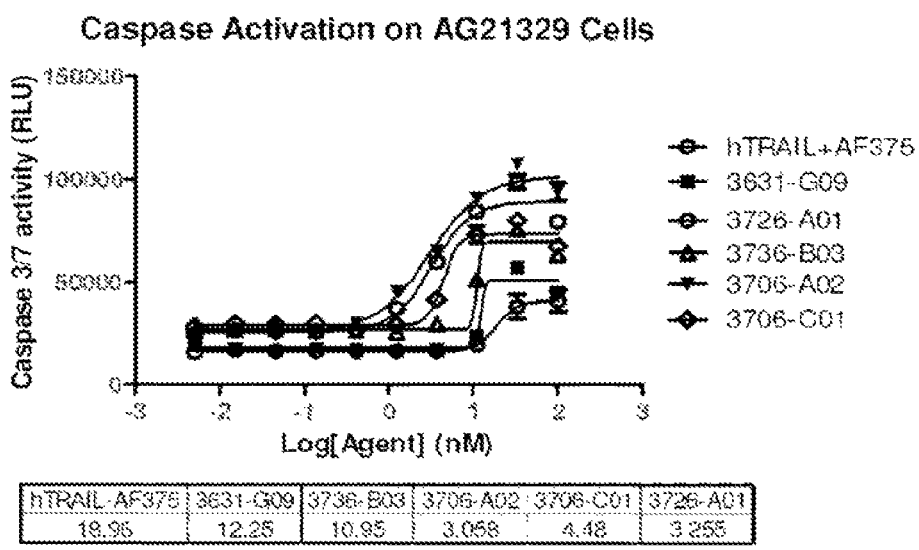

The potential beneficial use of Death Receptor antagonists fall into two broad areas; the first area of opportunity involves the preservation of desirable immune cell populations from inappropriate Death Receptor-specific elimination and the second area of opportunity is to reduce damage possible to uninfected cells via Death Receptor-specific activation.

Immune cells increase expression of Death Receptors and TRAIL in response to viral infection making them sensitive to the activity of TRAIL-producing cytotoxic T-cells. Some free viral proteins, liberated from infected cells (e.g. HIV TAT) induce the same response, producing a "bystander effect" in non-infected cells where upregulated Death Receptors and TRAIL on the cell surface leads to their elimination. The use of a Death Receptor antagonist SgG protects uninfected bystanders from cytotoxic T-cells. Additionally, deleteriously strong T-cell responses, such as those found following Hepatitis C infection, may be slowed and managed with Death Receptor antagonist SgGs to reduce injury to uninfected tissue. Further, as apoptosis via Death Receptor activation drives down the T-cell response through their elimination, antagonist Death Receptor SgGs may prolong T-cell activity and prevent T-cell exhaustion in chronic infections. In another scenario, virally infected antigen presenting cells having upregulated cell surface TRAIL would have deleterious effects on both cytotoxic and helper T-cell populations. To protect the T-cells and allow a robust adaptive immune response to the viral infection, antagonist SgGs can be used to block the T-cell Death Receptors from activation by these infected antigen presenting cells.

Example 33

Bivalent SBPs Binding to Nonhuman Primate Death Receptors

Death Receptor SBPs have strong binding to Cynomolgus and Rhesus DR4 and DR5. ELISA binding analysis was performed similarly to the method described in Example 2. Human Fc-fusion protein antigens Cynomolgus (NHP-1) DR4-Fc, Rhesus (NHP-2) DR4-Fc Cynomolgus (NHP-1) DR5-Fc, and Rhesus (NHP-2) DR5-Fc were used to coat the microtiter wells at 1 microgram/ml concentration and 100 ul used per well. Serial half-log dilutions of biotinylated TRAIL, 3631-G09 (SL231), 3736-B03 (SL465), 3706-A02 (SL466), 3706-001 (SL467), and 3726-A01 (SL468) were then added to the antigen coated wells to determine maximal and half-maximal binding concentrations. Streptavidin-HRP or a monoclonal anti-VpreB-HRP conjugated antibody was used for detection and the assay developed with a TMB solution. The SgGs bind with high affinity to Cynomolgus and Rhesus DR4-Fc (FIGS. 23A and C) and Cynomolgus and Rhesus DR5-Fc (FIGS. 23B and D). The data was analyzed with Prism GraphPad affinities reported (FIG. 23A-D, inset)

Example 34

Bivalent SBPs Activation of the Apoptosis-Inducing Caspases in Nonhuman Primate Rhesus Tumor Cell Lines This example describes the activity of Death Receptor Sur-binding proteins on cell lines derived from the Rhesus monkey (*Macaca mulatta*). LCL8664 and CMMT (ATCC) are virus-transformed cell lines of lymphoblast and mammary origin. 10,000 LCL8664 cells were treated with 1 microgram/ml cyclohexarnide and serial half-log dilutions of a 100 nM+50 nM protein G mixture in RPMI 1640+10% FBS. The cells were incubated overnight in a humidified 37 C incubator with 5% CO2. After 18 hours, the assay was developed by the addition of 100 ul of Caspase 3/7 glo (Promega) and read on a luminometer (FIG. 24A). For the CMMT cells, a similar approach was used in DMEM+10% FBS medium (FIG. 24B). LCL8664 cells activate apoptosis in response to DR4 stimulation, while the CMMT cells respond to DR5-specific stimulation. Both cell lines activate the apoptotic caspases cascade in response to agonist Sur-binding proteins and TRAIL. The data was analyzed with Prism GraphPad software and quantitative EC values are shown (FIG. 24A inset and FIG. 24B inset)

Example 35

Bivalent SBPs Activation of the Apoptosis-Inducing Caspases in Nonhuman Primate Cynomolgus Tumor Cell Lines This example describes the activity of Death Receptor Sur-binding proteins on cell lines derived from the Cynomolgus monkey (*Macaca fascicularis*). HSC-F (*Herpes samirii* transformed lymphoblast, NHPRR) and AG21329 (primary fibroblast, Coriell Institute) are used to assess Death Receptor signaling activity. 30,000 HSC-F cells were treated with 1 microgram/ml cyclohexamide and serial half-log dilutions of a 100 nM+50 nM protein G mixture in RPMI 1640+10% FBS. The cells were incubated overnight in a humidified 37 C incubator with 5% CO2. After 18 hours, the assay was developed by the addition of 100 ul of Caspase 3/7 glo (Promega) and read on a luminometer (FIG. 25A). For the AG21329 cells (10,000/well with 250 ng/ml Actinomycin D), a similar approach is used to induce caspase activity (FIG. 25B). Apoptotic signaling via caspase activation in response to agonist Sur-binding proteins and TRAIL is observed. The data was analyzed with Prism GraphPad software and quantitative EC values are shown (FIG. 25 inset)

Example 36

Surroglobulin Activation of the Apoptosis-Inducing Caspases in Death Receptor Stable Expressing Cell Lines This example outlines the use of Death Receptor Sur-binding proteins in cell lines that express recombinant death receptors. Death Receptors are expressed as either native full length proteins or as cross-species chimeras with, minimally, the intracellular domain of the host cell death receptor. Host cells, such as the mouse cell line NIH3T3, which are unresponsive to the Sur-binding proteins described here and provide a null background, are transfected with a stable integration plasmid (such as pCDNA3.1 with either hygromycin or zeomycin selectable markers) carrying a subcloned death receptor. Selection after recovery from transfection yields a cell population expressing the recombinant death receptor and can then be used to directly test death receptor signaling via caspase activation or inhibition of cell proliferation.

Example 37

Enhanced Dual Agonist Sur-Binding Protein Potency of the Apoptosis-Inducing Caspase Activation in Cells with Moderate Response to Monospecific Receptor Agonists and their Combination This example demonstrates the increased apoptotic activity of the dual Death Receptor agonist Sur-binding proteins relative to TRAIL, and known receptor specific antibodies individually and in combination. Receptor specific DR4 and DR5 antibodies (SL-240 and SL-297, respectively) were created using recombinant DNA methods. The proteins were expressed and purified as described in Example 6, with the exception that the antibody light chains were used in place of the surrogate light chain.

Figure 39A:
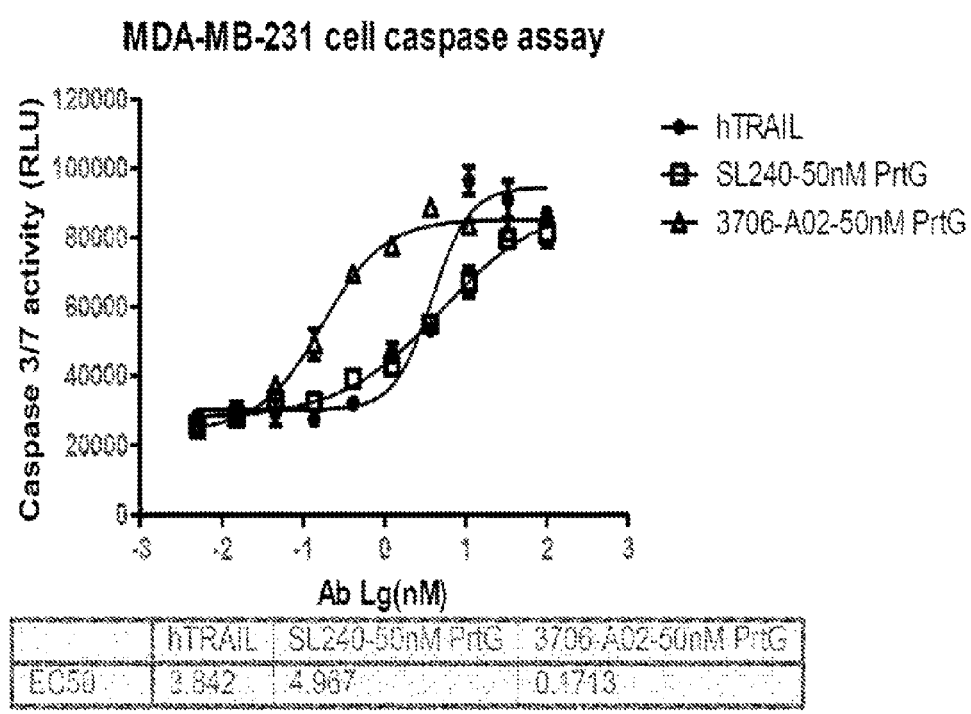
FIGS. 39A-39D show the induction of caspase activity in MDA-MB-231 cells by dual DR4 and DR5 Death Receptor agonist SBPs. The dual agonist SBPs activate caspase activity and induce apoptosis more potently than the monospecific receptor agonists or their combination.
Figure 39B:
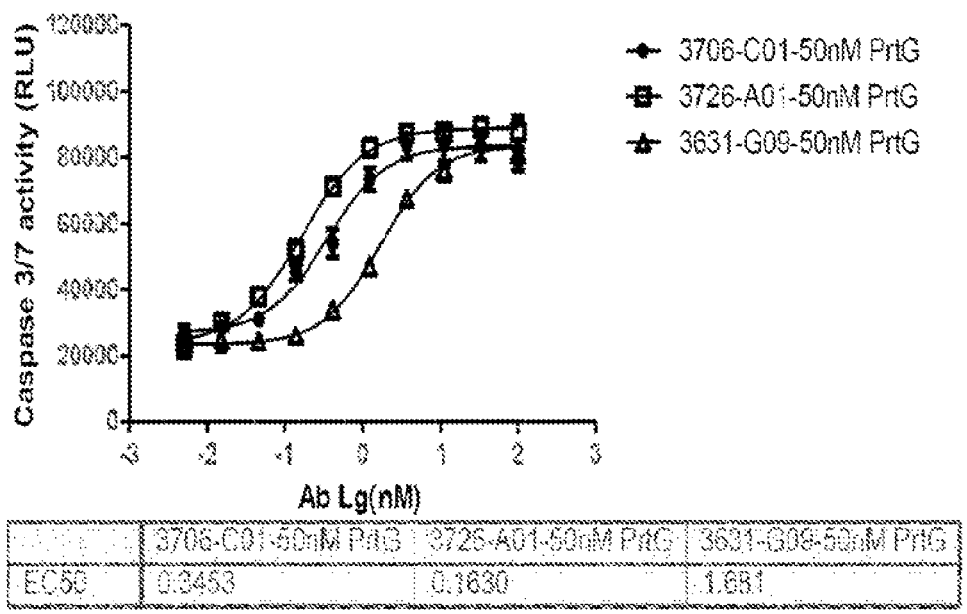
Figure 39C:
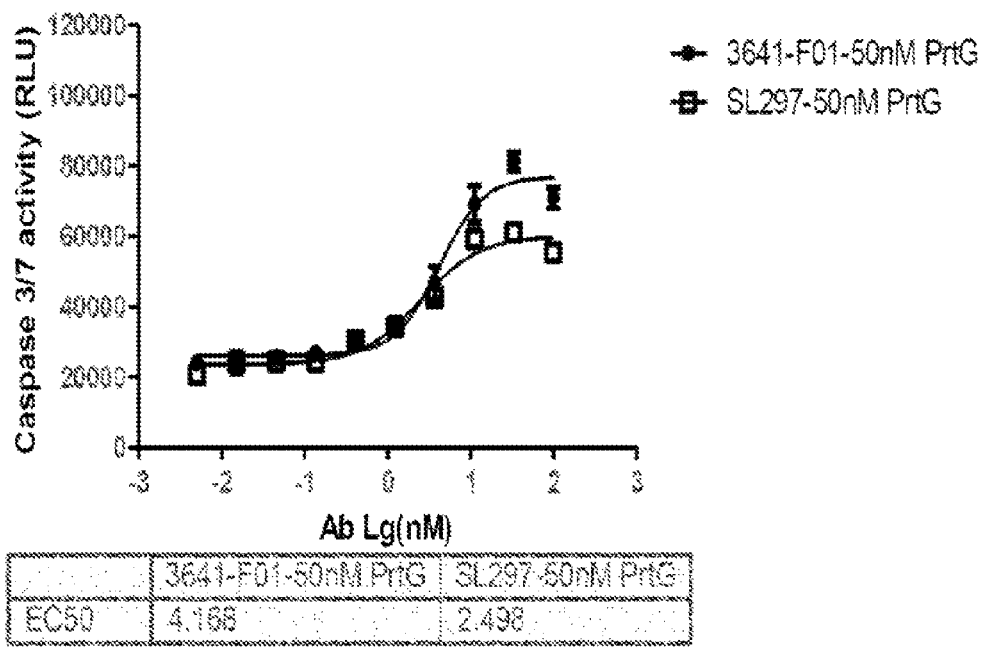
Figure 39D:
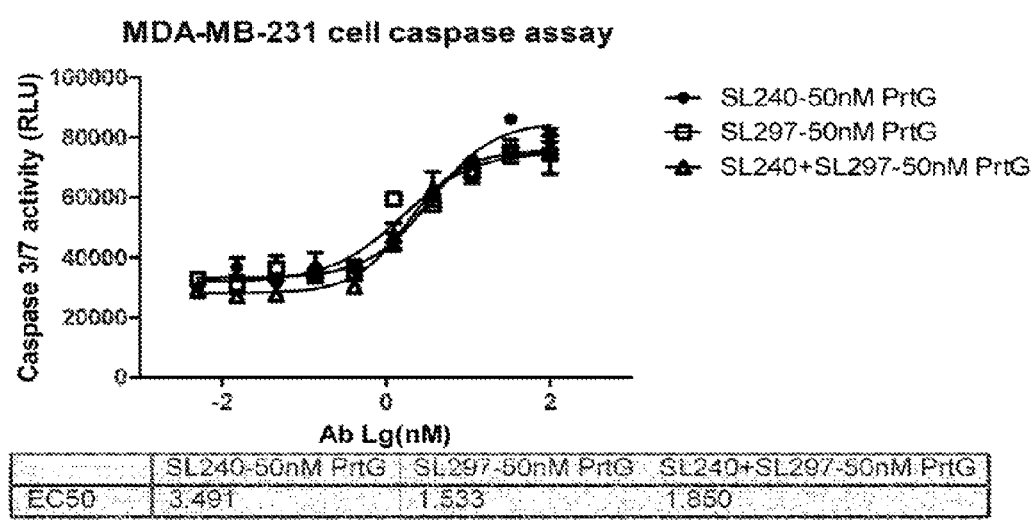

In the cell assay illustrated in FIG. 39, MDA-MB-231 breast cancer cells were seeded at 30,000 cells/well and then treated with dual Death Receptor agonist Sur-binding proteins; a DR5 specific antibody, SL-240; a DR4 specific antibody, SL-297; or an equimolar combination of receptor specific antibodies, resulting in a 100 nM total antibody concentration (FIG. 39B). The Sur-binding proteins and antibodies were treated as in Example 15. Induction of Caspase 3/7 and inhibition of cell proliferation data were obtained using Caspase 3/7 Glo (Promega) and WST-1 (Roche) reagents, respectively after 24-48 hours, or by western blot analysis using specific antibodies against PARP, Caspase-8, and active Caspase-3 (Cell Signaling Technology, MA).

The dual Death Receptor agonist Sur-binding proteins activate caspase activity and induce apoptosis more potently than the monospecific receptor agonists (FIGS. 39A-39C), their combination (FIG. 39D) and TRAIL These results demonstrate that the potent activation of caspase 3/7 and induction of apoptosis in this cell line is uniquely driven by the dual Death Receptor agonist Sur-binding protein. The dual Death Receptor agonist Sur-binding proteins more potently activate caspases because they can activate both DR4 and DR5 without Decoy Receptor complication and do so in a way that would bring both DR4 and DR5 complexes together.

Figure 42:
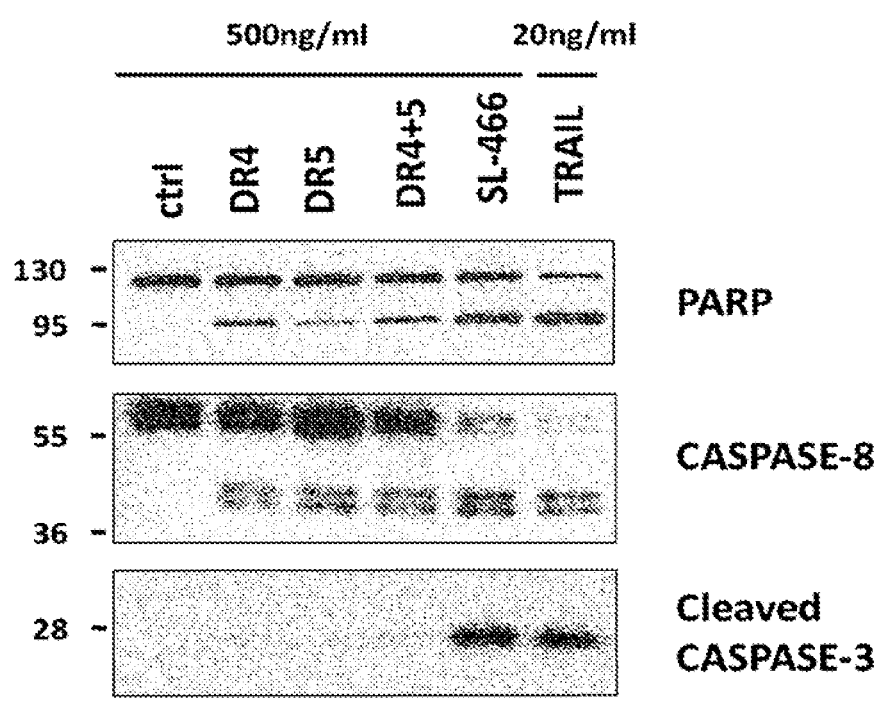
FIG. 42 provides a western blot showing caspase activation by a dual DR4 and DR5 agonist SBP (SL-466) relative to antibodies targeting DR4 and DR5 individually, as well as a combination of such antibodies.

In a second similar cell assay, MDA-MB-231 breast cancer cells were treated with dual Death Receptor agonist Sur-binding proteins; TRAIL, a DR5 specific antibody, SL-240; a DR4 specific antibody, SL-297; or an equimolar combination of the receptor specific antibodies (FIG. 42). The Sur-binding proteins and antibodies were treated as in Example 15. Activation of PARP and Caspase-8 were analyzed by western blot analysis using specific antibodies (Cell Signaling Technologies) and reflected by the generation of lower molecular weight bands. Caspase 3 activation was analyzed by western blot analysis using specific anti-active antibodies (Cell Signaling Technologies) and reflected by the generation of reactive bands. Again, the dual agonist DR4 and DR5 SBP was able to activate caspases more efficiently than single receptor agonists or their combination, and were comparable to TRAIL.

The dual Death Receptor agonist Sur-binding proteins were able to initiate a Type I apoptotic response, whereas the receptor monospecific antibodies function through a Type II response. In Type I responses, sufficient receptor expression and activation leads to high caspase activity that is able to directly activate effector caspase 3/7. In the Type II response, a lower level of receptor expression and activation requires caspase signal amplification through the intrinsic apoptotic pathway and caspase 9 activation. The ability to activate both DR4 and DR5 will maintain Type I apoptotic signaling activity in situations where receptor specific expression decreases, and permit Type II signaling as receptor levels drop below the threshold to activate Type I responses. The functional result is that the dual Death Receptor agonist Sur-binding proteins are efficacious over a wider range of cellular Death Receptor expression levels than monospecific agents.

Example 38

Targeting Activity of Drug-Conjugated Dual Agonist Sur-Binding Proteins on Cell Expressing Death Receptors This example describes the use of dual agonist Death Receptor Sur-binding proteins to target cells or tumors that express Death Receptors. Monomethyl Auristatin E was conjugated to two versions of a dual agonist Death Receptor Sur-binding protein (SL466; 3706-A02) modified to contain an introduced acceptor site: SL466T21C and SL466V213C. Both conjugated (SL466T21Cconj and SL466V213Cconj) and unconjugated sur-binding proteins were tested along with the parental sur-binding proteins (SL466T21C, SL466V213C and SL466) and a sur-binding protein recognizing a soluble ligand as a control (SL779V213Cconj).

Figure 40:
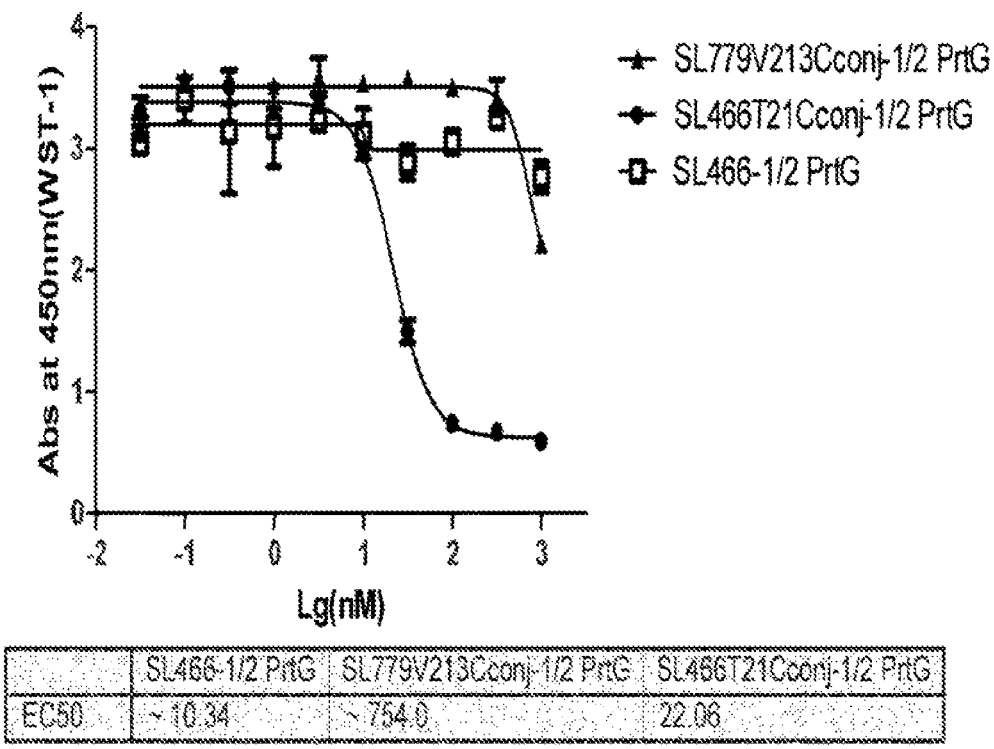
FIG. 40 shows inhibition of proliferation of 786-0 renal cell carcinoma cells that express DR4 and DR5 by a dual DR4 and DR5 agonist SBP conjugated to a toxin.
Figure 41:
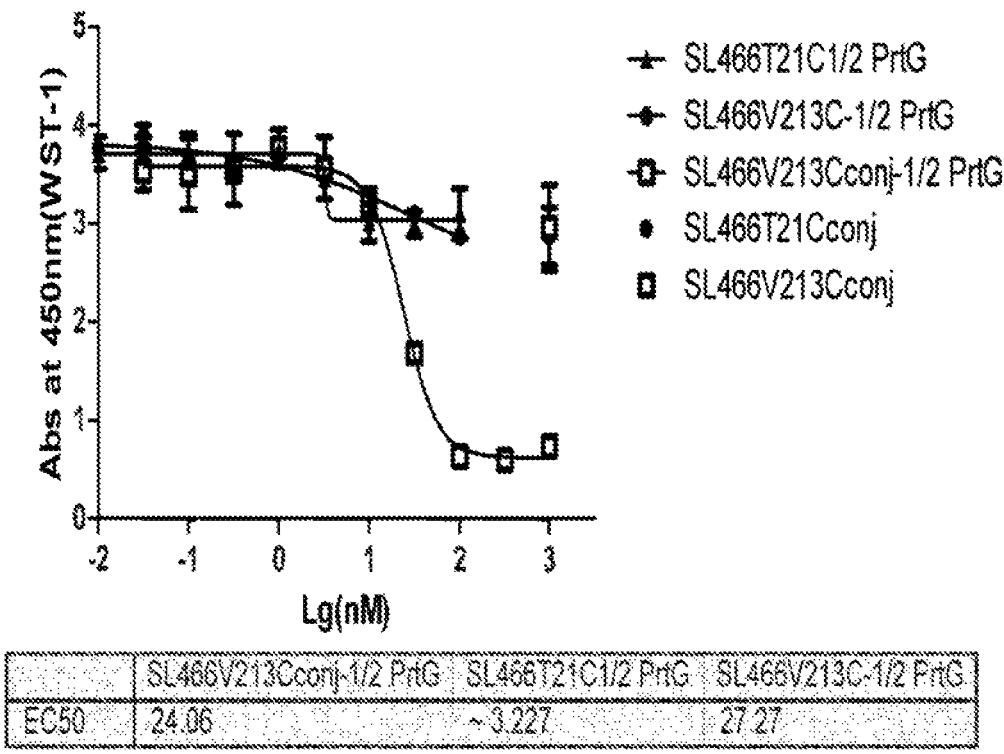
FIG. 41 shows inhibition of proliferation of 786-0 renal cell carcinoma cells that express DR4 and DR5 by a dual DR4 and DR5 agonist SBP conjugated to a toxin.

To evaluate the targeting ability of the dual agonist sur-binding protein, 786-0 renal cell carcinoma cells that express DR4 and DR5 but do not show any sensitivity to any Death Receptor agonist molecules were used. The assay was performed as described for Example 15. Only the Death Receptor dual agonist sur-binding proteins conjugated to the toxin were able to inhibit cell proliferation in a dose dependent manner. See FIG. 40 and FIG. 41. Cross-linking is still required for internalization and release of the toxin. Importantly, none of the other molecules with or without toxin inhibited cell proliferation on this cell line.

Other cell lines and tumors exhibiting a similar Death Receptor expression profile or those that express DR4 or DR5 will also provide the targeting necessary for the activity of these drug conjugates.

Example 39

Figure 43:
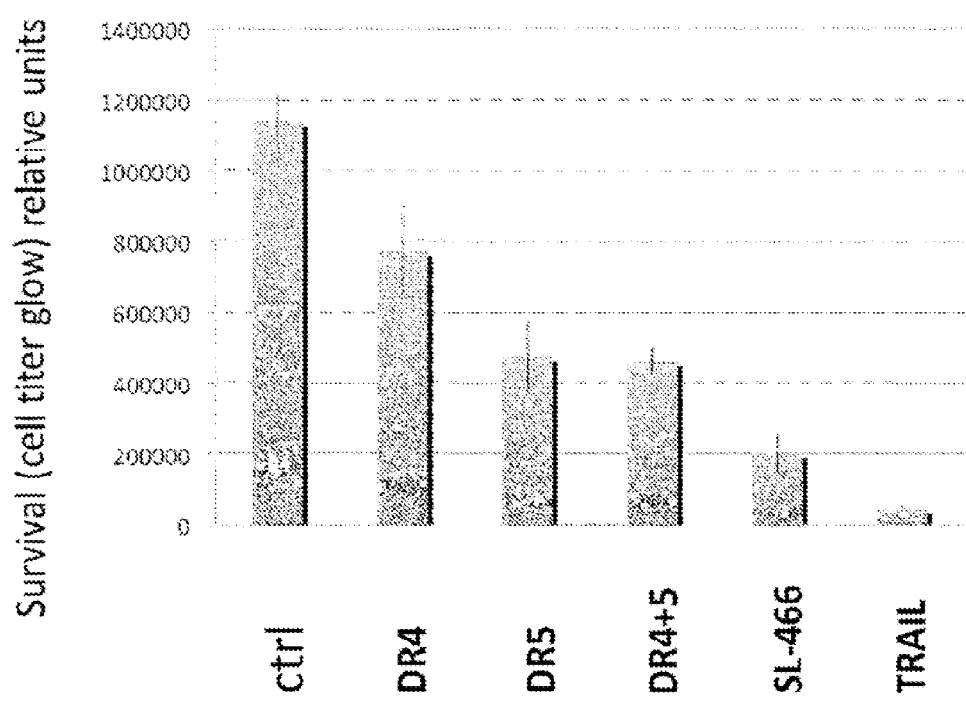
FIG. 43 shows the induction of spheroid apoptosis in MDA-MB-231 cells by a dual DR4 and DR5 agonist SBP (SL-466) relative to TRAIL, antibodies targeting DR4 and DR5 individually, and a combination of such antibodies.

Apoptotic Activity of Dual Agonist Sur-Binding Proteins on Non-Monolayer Cell Cultured Spheroid Masses To determine apoptotic potential in a cellular mass the apoptotic potential was tested against cultured cellular spheroids. To generate spheroids MDA-MB-231 cells were seeded at 3,000 per V-bottomed well of a 96-well plate and grown for 8 days at 37 degrees with 5% CO2 in growth media. The resulting spheroids were treated with TRAIL ligand (1 nM) or cross-linked antibodies (6 nM), individually and in combination, or cross-linked SBP SL466 (6 nM), prepared as previously described. After 48 hours of treatment cell viability was determined as described above using Cell Titer Glo (Promega) and analyzed by Excel as seen in FIG. 43. As can be seen the dual agonist SBP induces spheroid apoptosis better than individual receptor antibodies and the combination of individual receptor antibodies.

All references cited throughout the specification, and the references cited therein, are hereby expressly incorporated by reference in their entirety.

What is claimed is:

1. A sur-binding protein (SBP) comprising:
   (i) a surrogate light chain (SLC) sequence comprising, from N-terminus to C-terminus, a VpreB sequence conjugated to a λ5 sequence,
      wherein the VpreB sequence comprises an amino acid sequence that is at least 90% identical to a native VpreB sequence of SEQ ID NOs: 1-4, or fragments thereof which lack the C-terminal peptide extension of the native VpreB sequence,
      wherein the λ5 sequence comprises an amino acid sequence that is at least 90% identical to a native λ5 sequence of SEQ ID NOs: 5 or 6, or fragments thereof which lack the N-terminal peptide extension of the native λ5 sequence; and
   (ii) a heavy chain variable region amino acid sequence that is paired with the SLC to form an SBP, wherein the heavy chain variable region amino acid sequence comprises
      (a) a heavy chain complementarity determining region (CDR) 1 sequence comprising SEQ ID NO: 39, a heavy chain CDR2 sequence comprising SEQ ID NO: 40, and a heavy chain CDR3 sequence comprising SEQ ID NO: 41; or
      (b) a heavy chain CDR1 sequence comprising SEQ ID NO: 459, a heavy chain CDR2 sequence comprising SEQ ID NO: 460, and a heavy chain CDR3 sequence comprising SEQ ID NO: 461,
wherein said SBP binds to DR4, DR5, or DR4 and DR5.

2. The SBP of claim 1, wherein the SBP binds to DR5 and displaces TRAIL.

3. The SBP of claim 1, wherein the SBP binds to DR4 and DR5.

4. The SBP of claim 1, wherein the SBP selectively binds to DR5 when DR5 is expressed with DR4.

5. The SBP of claim 1, wherein the C-terminus of the VpreB sequence is conjugated to the N terminus of the λ5 sequence by direct fusion.

6. The SBP of claim 5, wherein the C-terminus of the VpreB sequence is directly fused to N terminus of the λ5 sequence at or around a LR3 region of the VpreB sequence.

7. The SBP of claim 5, wherein at least one of the VpreB sequence or λ5 sequence is other than a full-length native VpreB sequence or λ5 sequence, respectively.

8. The SBP of claim 5, wherein the N-terminus of the VpreB sequence is non-covalently conjugated to the heavy chain variable region amino acid sequence to form a dimeric complex.

9. The SBP of claim 1, wherein the VpreB sequence is conjugated to the λ5 sequence by a non-covalent association, and wherein at least one of the VpreB sequence or λ5 sequence is other than a full-length native VpreB sequence or λ5 sequence, respectively.

10. The SBP of claim 9, wherein the N-terminus of the VpreB sequence is covalently conjugated to the heavy chain variable region amino acid sequence to form a dimeric complex.

11. A bispecific sur-binding protein (SBP) comprising:
   (a) a first dimeric complex comprising
      (i) a first surrogate light chain (SLC) sequence comprising, from N-terminus to C-terminus a first VpreB sequence conjugated to a first λ5 sequence; and
      (ii) a first heavy chain variable region amino acid sequence that is paired with the first SLC sequence to form a first SBP binding site, wherein the first SBP binding site binds to a first target that is a DR4 and/or DR5 receptor; and
   (b) a second dimeric complex comprising
      (i) a second SLC sequence comprising, from N-terminus to C-terminus, a second VpreB sequence conjugated to a second λ5 sequence; and
      (ii) a second heavy chain variable region amino acid sequence that is paired with the second SLC sequence to form a second SBP site, wherein said second SBP site binds to a second target,
   wherein the first heavy chain variable region amino acid sequence comprises
      a heavy chain CDR1 sequence comprising SEQ ID NO: 39, a heavy chain CDR2 sequence comprising SEQ ID NO: 40, and a heavy chain CDR3 sequence comprising SEQ ID NO: 41, or
      a heavy chain CDR1 sequence comprising SEQ ID NO: 459, a heavy chain CDR2 sequence comprising SEQ ID NO: 460, and a heavy chain CDR3 sequence comprising SEQ ID NO: 461, and
   wherein the first and second VpreB sequences comprise an amino acid sequence that is at least 90% identical to a native VpreB sequence of SEQ ID NOs: 1-4, or fragments thereof which lack the C-terminal peptide extension of the native VpreB sequence, and the first and second λ5 sequences comprise an amino acid sequence that is at least 90% identical to a native λ5 sequence of SEQ ID NO: 5 or 6, or fragments thereof which lack the N-terminal peptide extension of the native λ5 sequence.

12. The bi-specific SBP of claim 11, wherein
   (a) the C-terminus of the first VpreB sequence is conjugated to the N-terminus of the first λ5 sequence by direct fusion at or around a LR3 region of the first VpreB sequence, and;
   (b) the C-terminus of the second VpreB sequence is conjugated to the N-terminus of the second λ5 sequence by direct fusion at or around a LR3 region of the second VpreB sequence,
   wherein at least one of the first VpreB or first λ5 sequence and at least one of the second VpreB or second λ5 sequence is a sequence other than a full-length native VpreB or λ5 sequence, respectively.

13. The bi-specific SBP of claim 12, wherein
   (a) the N-terminus of the first VpreB sequence is non-covalently conjugated to the first heavy chain variable region amino acid sequence to form the first dimeric complex, and;
   (b) the N-terminus of the second VpreB sequence is non-covalently conjugated to the second heavy chain variable region amino acid sequence to form the second dimeric complex.

14. The bi-specific SBP of claim 11, wherein
   (a) the C-terminus of the first VpreB sequence is non-covalently conjugated to the N-terminus of the first λ5 sequence, and;
   (b) the C-terminus of the second VpreB sequence is non-covalently conjugated to the N-terminus of the second λ5 sequence,
   wherein at least one of the first VpreB or first λ5 sequence and at least one of the second VpreB or second λ5 sequence is a sequence other than a full-length native VpreB or λ5 sequence, respectively.

15. The bi-specific SBP of claim 14 wherein
   (a) the N-terminus of the first VpreB sequence is covalently conjugated to the first heavy chain variable region amino acid sequence to form the first dimeric complex, and;
   (b) the N-terminus of the second VpreB sequence is covalently conjugated to the second heavy chain variable region amino acid sequence to form the second dimeric complex.

* * * * *

```
                          SEQUENCE LISTING

<160> NUMBER OF SEQ ID NOS: 501

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145

<210> SEQ ID NO 2
<211> LENGTH: 142
<212> TYPE: PRT
<213> ORGANISM: Mus musculus

<400> SEQUENCE: 2

Met Ala Trp Thr Ser Val Leu Leu Met Leu Leu Ala His Leu Thr Gly
1               5                   10                  15

Cys Gly Pro Gln Pro Met Val His Gln Pro Pro Ser Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
```

-continued

```
                50                  55                  60
Pro Arg Phe Leu Leu Arg Tyr Phe Ser His Ser Asp Lys His Gln Gly
 65                  70                  75                  80
Pro Asp Ile Pro Pro Arg Phe Ser Gly Ser Lys Asp Thr Ala Arg Asn
                 85                  90                  95
Leu Gly Tyr Leu Ser Ile Ser Glu Leu Gln Pro Glu Asp Glu Ala Val
            100                 105                 110
Tyr Tyr Cys Ala Val Gly Leu Arg Ser His Glu Lys Lys Arg Met Glu
        115                 120                 125
Arg Glu Trp Glu Gly Glu Lys Ser Tyr Thr Asp Leu Gly Ser
    130                 135                 140

<210> SEQ ID NO 3
<211> LENGTH: 171
<212> TYPE: PRT
<213> ORGANISM: Mus musculus

<400> SEQUENCE: 3

Met Ala Trp Thr Ser Val Leu Leu Met Leu Leu Ala His Leu Thr Gly
  1               5                  10                  15
Lys Gly Thr Leu Gly Val Gln Gly Phe Leu Ala Pro Pro Val Ala Leu
                 20                  25                  30
Leu Cys Pro Ser Asp Gly His Ala Ser Ile Phe Ser Gly Cys Gly Pro
             35                  40                  45
Gln Pro Met Val His Gln Pro Pro Ser Ala Ser Ser Ser Leu Gly Ala
         50                  55                  60
Thr Ile Arg Leu Ser Cys Thr Leu Ser Asn Asp His Asn Ile Gly Ile
 65                  70                  75                  80
Tyr Ser Ile Tyr Trp Tyr Gln Gln Arg Pro Gly His Pro Pro Arg Phe
                 85                  90                  95
Leu Leu Arg Tyr Phe Ser His Ser Asp Lys His Gln Gly Pro Asp Ile
            100                 105                 110
Pro Pro Arg Phe Ser Gly Ser Lys Asp Thr Ala Arg Asn Leu Gly Tyr
        115                 120                 125
Leu Ser Ile Ser Glu Leu Gln Pro Glu Asp Glu Ala Val Tyr Tyr Cys
    130                 135                 140
Ala Val Gly Leu Arg Ser His Glu Lys Lys Arg Met Glu Arg Glu Trp
145                 150                 155                 160
Glu Gly Glu Lys Ser Tyr Thr Asp Leu Gly Ser
                165                 170

<210> SEQ ID NO 4
<211> LENGTH: 123
<212> TYPE: PRT
<213> ORGANISM: Homo sapiens

<400> SEQUENCE: 4

Met Ala Cys Arg Cys Leu Ser Phe Leu Leu Met Gly Thr Phe Leu Ser
  1               5                  10                  15
Val Ser Gln Thr Val Leu Ala Gln Leu Asp Ala Leu Leu Val Phe Pro
                 20                  25                  30
Gly Gln Val Ala Gln Leu Ser Cys Thr Leu Ser Pro Gln His Val Thr
             35                  40                  45
Ile Arg Asp Tyr Gly Val Ser Trp Tyr Gln Gln Arg Ala Gly Ser Ala
         50                  55                  60
Pro Arg Tyr Leu Leu Tyr Tyr Arg Ser Glu Glu Asp His His Arg Pro
```

```
                        65                  70                  75                  80
Ala Asp Ile Pro Asp Arg Phe Ser Ala Ala Lys Asp Glu Ala His Asn
                    85                  90                  95

Ala Cys Val Leu Thr Ile Ser Pro Val Gln Pro Glu Asp Asp Ala Asp
                100                 105                 110

Tyr Tyr Cys Ser Val Gly Tyr Gly Phe Ser Pro
                115                 120

<210> SEQ ID NO 5
<211> LENGTH: 209
<212> TYPE: PRT
<213> ORGANISM: Mus musculus

<400> SEQUENCE: 5

Met Lys Leu Arg Val Gly Gln Thr Leu Gly Thr Ile Pro Arg Gln Cys
  1               5                  10                  15

Glu Val Leu Leu Leu Leu Leu Leu Gly Leu Val Asp Gly Val His
                 20                  25                  30

His Ile Leu Ser Pro Ser Ser Ala Glu Arg Ser Arg Ala Val Gly Pro
                 35                  40                  45

Gly Ala Ser Val Gly Ser Asn Arg Pro Ser Leu Trp Ala Leu Pro Gly
 50                  55                  60

Arg Leu Leu Phe Gln Ile Ile Pro Arg Gly Ala Gly Pro Arg Cys Ser
 65                  70                  75                  80

Pro His Arg Leu Pro Ser Lys Pro Gln Phe Trp Tyr Val Phe Gly Gly
                 85                  90                  95

Gly Thr Gln Leu Thr Ile Leu Gly Gln Pro Lys Ser Asp Pro Leu Val
                100                 105                 110

Thr Leu Phe Leu Pro Ser Leu Lys Asn Leu Gln Pro Thr Arg Pro His
                115                 120                 125

Val Val Cys Leu Val Ser Glu Phe Tyr Pro Gly Thr Leu Val Val Asp
                130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
                180                 185                 190

Thr His Glu Gly Asn Thr Val Glu Lys Ser Val Ser Pro Ala Glu Cys
                195                 200                 205

Ser

<210> SEQ ID NO 6
<211> LENGTH: 213
<212> TYPE: PRT
<213> ORGANISM: Homo sapiens

<400> SEQUENCE: 6

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Gly Leu Ala
                 20                  25                  30

Val Val Thr His Gly Leu Leu Arg Pro Thr Ala Ala Ser Gln Ser Arg
                 35                  40                  45

Ala Leu Gly Pro Gly Ala Pro Gly Gly Ser Ser Arg Ser Ser Leu Arg
 50                  55                  60
```

```
Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
             85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
            195                 200                 205

Pro Ala Glu Cys Ser
    210

<210> SEQ ID NO 7
<211> LENGTH: 158
<212> TYPE: PRT
<213> ORGANISM: Artificial Sequence
<220> FEATURE:
<223> OTHER INFORMATION: Synthetic Construct

<400> SEQUENCE: 7

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Gly Leu Ala
             20                  25                  30

Val Val Thr His Gly Ser Val Thr His Val Phe Gly Ser Gly Thr Gln
             35                  40                  45

Leu Thr Val Leu Ser Gln Pro Lys Ala Thr Pro Ser Val Thr Leu Phe
 50                  55                  60

Pro Pro Ser Ser Glu Glu Leu Gln Ala Asn Lys Ala Thr Leu Val Cys
 65                  70                  75                  80

Leu Met Asn Asp Phe Tyr Pro Gly Ile Leu Thr Val Thr Trp Lys Ala
                 85                  90                  95

Asp Gly Thr Pro Ile Thr Gln Gly Val Glu Met Thr Thr Pro Ser Lys
            100                 105                 110

Gln Ser Asn Asn Lys Tyr Ala Ala Ser Ser Tyr Leu Ser Leu Thr Pro
            115                 120                 125

Glu Gln Trp Arg Ser Arg Arg Ser Tyr Ser Cys Gln Val Met His Glu
130                 135                 140

Gly Ser Thr Val Glu Lys Thr Val Ala Pro Ala Glu Cys Ser
145                 150                 155

<210> SEQ ID NO 8

<400> SEQUENCE: 8

000
```

<210> SEQ ID NO 9

<400> SEQUENCE: 9

000

<210> SEQ ID NO 10
<211> LENGTH: 242
<212> TYPE: PRT
<213> ORGANISM: Artificial Sequence
<220> FEATURE:
<223> OTHER INFORMATION: Synthetic Construct

<400> SEQUENCE: 10

```
Met Ser Trp Ala Pro Val Leu Leu Met Leu Phe Val Tyr Cys Thr Gly
 1               5                  10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Val Thr His Val Phe Gly
        115                 120                 125

Ser Gly Thr Gln Leu Thr Val Leu Ser Gln Pro Lys Ala Thr Pro Ser
    130                 135                 140

Val Thr Leu Phe Pro Pro Ser Ser Glu Glu Leu Gln Ala Asn Lys Ala
145                 150                 155                 160

Thr Leu Val Cys Leu Met Asn Asp Phe Tyr Pro Gly Ile Leu Thr Val
                165                 170                 175

Thr Trp Lys Ala Asp Gly Thr Pro Ile Thr Gln Gly Val Glu Met Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Arg Ser Arg Ser Tyr Ser Cys Gln
    210                 215                 220

Val Met His Glu Gly Ser Thr Val Glu Lys Thr Val Ala Pro Ala Glu
225                 230                 235                 240

Cys Ser
```

<210> SEQ ID NO 11
<211> LENGTH: 243
<212> TYPE: PRT
<213> ORGANISM: Artificial Sequence
<220> FEATURE:
<223> OTHER INFORMATION: Synthetic Construct

<400> SEQUENCE: 11

```
Met Glu Thr Asp Thr Leu Leu Leu Trp Val Leu Leu Leu Trp Val Pro
 1               5                  10                  15

Gly Ser Thr Gly Gln Pro Val Leu His Gln Pro Pro Ala Met Ser Ser
            20                  25                  30
```

```
Ala Leu Gly Thr Thr Ile Arg Leu Thr Cys Thr Leu Arg Asn Asp His
         35                  40                  45

Asp Ile Gly Val Tyr Ser Val Tyr Trp Tyr Gln Gln Arg Pro Gly His
 50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                 85                  90                  95

Asn Arg Gly Tyr Leu Ser Ile Ser Glu Leu Gln Pro Glu Asp Glu Ala
             100                 105                 110

Met Tyr Tyr Cys Ala Met Gly Ala Arg Ser Ser Val Thr His Val Phe
         115                 120                 125

Gly Gly Gly Thr Lys Leu Thr Val Leu Ser Gln Pro Lys Ala Ala Pro
     130                 135                 140

Ser Val Thr Leu Phe Pro Pro Ser Ser Glu Glu Leu Gln Ala Asn Thr
145                 150                 155                 160

Ala Thr Leu Val Cys Leu Ile Ser Asp Phe Tyr Pro Gly Ala Val Thr
                 165                 170                 175

Val Ala Trp Lys Ala Asp Ser Ser Pro Val Lys Ala Gly Val Glu Thr
             180                 185                 190

Thr Thr Pro Ser Lys Gln Ser Asn Asn Lys Tyr Ala Ala Ser Ser Tyr
         195                 200                 205

Leu Ser Leu Thr Pro Glu Gln Trp Lys Ser His Arg Ser Tyr Ser Cys
     210                 215                 220

Gln Val Thr His Glu Gly Ser Thr Val Glu Lys Thr Val Ala Pro Thr
225                 230                 235                 240

Glu Cys Ser

<210> SEQ ID NO 12
<211> LENGTH: 256
<212> TYPE: PRT
<213> ORGANISM: Artificial Sequence
<220> FEATURE:
<223> OTHER INFORMATION: Synthetic Construct

<400> SEQUENCE: 12

Val Lys Lys Leu Leu Phe Ala Ile Pro Leu Val Val Pro Phe Tyr
 1               5                  10                  15

Ser His Ser Ala Gln Pro Val Leu His Gln Pro Ala Met Ser Ser
                 20                  25                  30

Ala Leu Gly Thr Thr Ile Arg Leu Thr Cys Thr Leu Arg Asn Asp His
         35                  40                  45

Asp Ile Gly Val Tyr Ser Val Tyr Trp Tyr Gln Gln Arg Pro Gly His
 50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                 85                  90                  95

Asn Arg Gly Tyr Leu Ser Ile Ser Glu Leu Gln Pro Glu Asp Glu Ala
             100                 105                 110

Met Tyr Tyr Cys Ala Met Gly Ala Arg Ser Ser Val Thr His Val Phe
         115                 120                 125

Gly Ser Gly Thr Gln Leu Thr Val Leu Ser Gln Pro Lys Ala Thr Pro
     130                 135                 140

Ser Val Thr Leu Phe Pro Pro Ser Ser Glu Glu Leu Gln Ala Asn Lys
```

```
                145                 150                 155                 160
Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
                180                 185                 190

Thr Thr Pro Ser Lys Gln Ser Asn Asn Lys Tyr Ala Ala Ser Ser Tyr
                195                 200                 205

Leu Ser Leu Thr Pro Glu Gln Trp Arg Ser Arg Ser Tyr Ser Cys
            210                 215                 220

Gln Val Met His Glu Gly Ser Thr Val Glu Lys Thr Val Ala Pro Ala
225                 230                 235                 240

Glu Cys Ser Gly Ala Pro Val Pro Tyr Pro Asp Pro Leu Glu Pro Arg
                245                 250                 255

<210> SEQ ID NO 13
<211> LENGTH: 135
<212> TYPE: PRT
<213> ORGANISM: Artificial Sequence
<220> FEATURE:
<223> OTHER INFORMATION: Synthetic Construct

<400> SEQUENCE: 13

Ala Gln Pro Val Leu His Gln Pro Pro Ala Met Ser Ser Ala Leu Gly
1               5                   10                  15

Thr Thr Ile Arg Leu Thr Cys Thr Leu Arg Asn Asp His Asp Ile Gly
            20                  25                  30

Val Tyr Ser Val Tyr Trp Tyr Gln Gln Arg Pro Gly His Pro Pro Arg
        35                  40                  45

Phe Leu Leu Arg Tyr Phe Ser Gln Ser Asp Lys Ser Gln Gly Pro Gln
    50                  55                  60

Val Pro Pro Arg Phe Ser Gly Ser Lys Asp Val Ala Arg Asn Arg Gly
65                  70                  75                  80

Tyr Leu Ser Ile Ser Glu Leu Gln Pro Glu Asp Glu Ala Met Tyr Tyr
                85                  90                  95

Cys Ala Met Gly Ala Arg Ser Ser Glu Lys Glu Arg Leu Pro Ser Lys
            100                 105                 110

Pro Gln Phe Trp Tyr Val Phe Gly Gly Gly Thr Gln Leu Thr Ile Leu
        115                 120                 125

Gly Gln Pro Lys Ser Asp Pro
    130                 135

<210> SEQ ID NO 14
<211> LENGTH: 104
<212> TYPE: PRT
<213> ORGANISM: Homo sapiens

<400> SEQUENCE: 14

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80
```

```
Leu Leu Ile Ser Gly Leu Gln Ser Glu Asp Glu Ala Asp Tyr Tyr Cys
                85                  90                  95

Met Ile Trp His Ser Ser Ala Ser
            100
```

<210> SEQ ID NO 15
<211> LENGTH: 105
<212> TYPE: PRT
<213> ORGANISM: Homo sapiens

<400> SEQUENCE: 15

```
Gln Pro Val Leu Thr Gln Pro Ser Ser His Ser Ala Ser Ser Gly Ala
  1               5                  10                  15

Ser Val Arg Leu Thr Cys Met Leu Ser Ser Gly Phe Ser Val Gly Asp
                20                  25                  30

Phe Trp Ile Arg Trp Tyr Gln Gln Lys Pro Gly Asn Pro Pro Arg Tyr
            35                  40                  45

Leu Leu Tyr Tyr His Ser Asp Ser Asn Lys Gly Gln Gly Ser Gly Val
        50                  55                  60

Pro Ser Arg Phe Ser Gly Ser Asn Asp Ala Ser Ala Asn Ala Gly Ile
 65                 70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
                100                 105
```

<210> SEQ ID NO 16
<211> LENGTH: 104
<212> TYPE: PRT
<213> ORGANISM: Homo sapiens

<400> SEQUENCE: 16

```
Gln Pro Val Leu Thr Gln Pro Pro Ser Ser Ala Ser Pro Gly Glu
  1               5                  10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Ala Ser Ala Asn Thr Gly Ile
 65                 70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100
```

<210> SEQ ID NO 17
<211> LENGTH: 113
<212> TYPE: PRT
<213> ORGANISM: Homo sapiens

<400> SEQUENCE: 17

```
Gly Thr Lys Leu Thr Val Leu Arg Gln Pro Lys Ala Ala Pro Ser Val
  1               5                  10                  15

Thr Leu Phe Pro Pro Ser Ser Glu Glu Leu Gln Ala Asn Lys Ala Thr
                20                  25                  30
```

```
Leu Val Cys Leu Ile Ser Asp Phe Tyr Pro Gly Ala Val Thr Val Ala
             35                  40                  45

Trp Lys Ala Asp Gly Ser Pro Val Lys Ala Gly Val Glu Thr Thr Thr
 50                  55                  60

Pro Ser Lys Gln Ser Asn Asn Lys Tyr Ala Ala Ser Ser Tyr Leu Ser
 65                  70                  75                  80

Leu Thr Pro Glu Gln Trp Lys Ser His Lys Ser Tyr Ser Cys Gln Val
             85                  90                  95

Thr His Glu Gly Ser Thr Val Glu Lys Thr Val Ala Pro Thr Glu Cys
            100                 105                 110

Ser

<210> SEQ ID NO 18
<211> LENGTH: 213
<212> TYPE: PRT
<213> ORGANISM: Homo sapiens

<400> SEQUENCE: 18

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Gly Leu Ala
             20                  25                  30

Val Val Thr His Gly Leu Leu Arg Pro Thr Ala Ala Ser Gln Ser Arg
             35                  40                  45

Ala Leu Gly Pro Gly Ala Pro Gly Gly Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
             85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
            130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
            195                 200                 205

Pro Ala Glu Cys Ser
    210

<210> SEQ ID NO 19
<211> LENGTH: 213
<212> TYPE: PRT
<213> ORGANISM: Homo sapiens

<400> SEQUENCE: 19

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Leu Gly Leu Ala
```

```
            20                  25                  30
Val Val Thr His Gly Leu Leu Arg Pro Thr Ala Ala Ser Gln Ser Arg
         35                  40                  45

Ala Leu Gly Pro Gly Ala Pro Gly Gly Ser Ser Arg Ser Ser Leu Arg
     50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                 85                  90                  95

Val Phe Gly Ser Gly Thr Gln Leu Thr Val Leu Ser Gln Pro Lys Ala
             100                 105                 110

Thr Pro Ser Val Thr Leu Phe Pro Pro Ser Ser Glu Glu Leu Gln Ala
         115                 120                 125

Asn Lys Ala Thr Leu Val Cys Leu Met Asn Asp Phe Tyr Pro Gly Ile
     130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                 165                 170                 175

Ser Tyr Leu Ser Leu Thr Pro Glu Gln Trp Arg Ser Arg Ser Ser Tyr
             180                 185                 190

Ser Cys Gln Val Met His Glu Gly Ser Thr Val Glu Lys Thr Val Ala
         195                 200                 205

Pro Ala Glu Cys Ser
     210

<210> SEQ ID NO 20
<211> LENGTH: 107
<212> TYPE: PRT
<213> ORGANISM: Homo sapiens

<400> SEQUENCE: 20

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 21
<211> LENGTH: 159
<212> TYPE: PRT
<213> ORGANISM: Homo sapiens

<400> SEQUENCE: 21

Met Ala Arg Ile Pro Lys Thr Leu Lys Phe Val Val Val Ile Val Ala
 1               5                  10                  15

Val Leu Leu Pro Val Leu Ala Tyr Ser Ala Thr Thr Ala Arg Gln Glu
```

```
            20                  25                  30
Glu Val Pro Gln Gln Thr Val Ala Pro Gln Gln Arg His Ser Phe
            35                  40                  45

Lys Gly Glu Glu Cys Pro Ala Gly Ser His Arg Ser Glu His Thr Gly
 50                  55                  60

Ala Cys Asn Pro Cys Thr Glu Gly Val Asp Tyr Thr Asn Ala Ser Asn
 65                  70                  75                  80

Asn Glu Pro Ser Cys Phe Pro Cys Thr Val Cys Lys Ser Asp Gln Lys
                 85                  90                  95

His Lys Ser Ser Cys Thr Met Thr Arg Asp Thr Val Cys Gln Cys Lys
                100                 105                 110

Glu Gly Thr Phe Arg Asn Glu Asn Ser Pro Glu Met Cys Arg Lys Cys
                115                 120                 125

Ser Arg Cys Pro Ser Gly Glu Val Gln Val Ser Asn Cys Thr Ser Trp
                130                 135                 140

Asp Asp Ile Gln Cys Val Glu Glu Phe Gly Ala Asn Ala Thr Val
145                 150                 155
```

<210> SEQ ID NO 22
<211> LENGTH: 238
<212> TYPE: PRT
<213> ORGANISM: Homo sapiens

<400> SEQUENCE: 22

```
Ala Pro Pro Pro Ala Arg Val His Leu Gly Ala Phe Leu Ala Val Thr
 1               5                  10                  15

Pro Asn Pro Gly Ser Ala Ala Ser Gly Thr Glu Ala Ala Ala Ala Thr
                 20                  25                  30

Pro Ser Lys Val Trp Gly Ser Ser Ala Gly Arg Ile Glu Pro Arg Gly
             35                  40                  45

Gly Gly Arg Gly Ala Leu Pro Thr Ser Met Gly Gln His Gly Pro Ser
 50                  55                  60

Ala Arg Ala Arg Ala Gly Arg Ala Pro Gly Pro Arg Pro Ala Arg Glu
 65                  70                  75                  80

Ala Ser Pro Arg Leu Arg Val His Lys Thr Phe Lys Phe Val Val Val
                 85                  90                  95

Gly Val Leu Leu Gln Val Val Pro Ser Ser Ala Ala Thr Ile Lys Leu
                100                 105                 110

His Asp Gln Ser Ile Gly Thr Gln Gln Trp Glu His Ser Pro Leu Gly
                115                 120                 125

Glu Leu Cys Pro Pro Gly Ser His Arg Ser Glu His Pro Gly Ala Cys
            130                 135                 140

Asn Arg Cys Thr Glu Gly Val Gly Tyr Thr Asn Ala Ser Asn Asn Leu
145                 150                 155                 160

Phe Ala Cys Leu Pro Cys Thr Ala Cys Lys Ser Asp Glu Glu Glu Arg
                165                 170                 175

Ser Pro Cys Thr Thr Thr Arg Asn Thr Ala Cys Gln Cys Lys Pro Gly
                180                 185                 190

Thr Phe Arg Asn Asp Asn Ser Ala Glu Met Cys Arg Lys Cys Ser Arg
            195                 200                 205

Gly Cys Pro Arg Gly Met Val Lys Val Lys Asp Cys Thr Pro Trp Ser
210                 215                 220

Asp Ile Glu Cys Val His Lys Glu Ser Gly Asn Gly His Asn
225                 230                 235
```

<210> SEQ ID NO 23
<211> LENGTH: 189
<212> TYPE: PRT
<213> ORGANISM: Homo sapiens

<400> SEQUENCE: 23

Met Gly Leu Trp Gly Gln Ser Val Pro Thr Ala Ser Ala Arg Ala
1               5                   10                  15

Gly Arg Tyr Pro Gly Ala Arg Thr Ala Ser Gly Thr Arg Pro Trp Leu
            20                  25                  30

Leu Asp Pro Lys Ile Leu Lys Phe Val Val Phe Ile Val Ala Val Leu
            35                  40                  45

Leu Pro Val Arg Val Asp Ser Ala Thr Ile Pro Arg Gln Asp Glu Val
50                  55                  60

Pro Gln Gln Thr Val Ala Pro Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
            115                 120                 125

Ser Ser Cys Thr Thr Thr Arg Asp Thr Val Cys Gln Cys Glu Lys Gly
130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr
            180                 185

<210> SEQ ID NO 24
<211> LENGTH: 188
<212> TYPE: PRT
<213> ORGANISM: Homo sapiens

<400> SEQUENCE: 24

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

```
Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser
            180                 185

<210> SEQ ID NO 25
<211> LENGTH: 132
<212> TYPE: PRT
<213> ORGANISM: Homo sapiens

<400> SEQUENCE: 25

Ala Ala Thr Ile Lys Leu His Asp Gln Ser Ile Gly Thr Gln Gln Trp
1               5                   10                  15

Glu His Ser Pro Leu Gly Glu Leu Cys Pro Pro Gly Ser His Arg Ser
                20                  25                  30

Glu His Pro Gly Ala Cys Asn Arg Cys Thr Glu Gly Val Gly Tyr Thr
            35                  40                  45

Asn Ala Ser Asn Asn Leu Phe Ala Cys Leu Pro Cys Thr Ala Cys Lys
    50                  55                  60

Ser Asp Glu Glu Glu Arg Ser Pro Cys Thr Thr Thr Arg Asn Thr Ala
65                  70                  75                  80

Cys Gln Cys Lys Pro Gly Thr Phe Arg Asn Asp Asn Ser Ala Glu Met
                85                  90                  95

Cys Arg Lys Cys Ser Arg Gly Cys Pro Arg Gly Met Val Lys Val Lys
            100                 105                 110

Asp Cys Thr Pro Trp Ser Asp Ile Glu Cys Val His Lys Glu Ser Gly
        115                 120                 125

Asn Gly His Asn
    130

<210> SEQ ID NO 26
<211> LENGTH: 135
<212> TYPE: PRT
<213> ORGANISM: Homo sapiens

<400> SEQUENCE: 26

Ala Leu Ile Thr Gln Gln Asp Leu Ala Pro Gln Gln Arg Val Ala Pro
1               5                   10                  15

Gln Gln Lys Arg Ser Ser Pro Ser Glu Gly Leu Cys Pro Pro Gly His
                20                  25                  30

His Ile Ser Glu Asp Gly Arg Asp Cys Ile Ser Cys Lys Tyr Gly Gln
            35                  40                  45

Asp Tyr Ser Thr His Trp Asn Asp Leu Leu Phe Cys Leu Arg Cys Thr
    50                  55                  60

Arg Cys Asp Ser Gly Glu Val Glu Leu Ser Pro Cys Thr Thr Thr Arg
65                  70                  75                  80

Asn Thr Val Cys Gln Cys Glu Glu Gly Thr Phe Arg Glu Glu Asp Ser
                85                  90                  95

Pro Glu Met Cys Arg Lys Cys Arg Thr Gly Cys Pro Arg Gly Met Val
            100                 105                 110

Lys Val Gly Asp Cys Thr Pro Trp Ser Asp Ile Glu Cys Val His Lys
        115                 120                 125

Glu Ser Gly Thr Lys His Ser
    130                 135
```

```
<210> SEQ ID NO 27
<211> LENGTH: 133
<212> TYPE: PRT
<213> ORGANISM: Mus musculus

<400> SEQUENCE: 27

Phe Val Pro Val Thr Ala Asn Pro Ala His Asn Arg Pro Ala Gly Leu
  1               5                  10                  15

Gln Arg Pro Glu Glu Ser Pro Ser Arg Gly Pro Cys Leu Ala Gly Gln
             20                  25                  30

Tyr Leu Ser Glu Gly Asn Cys Lys Pro Cys Arg Glu Gly Ile Asp Tyr
         35                  40                  45

Thr Ser His Ser Asn His Ser Leu Asp Ser Cys Ile Leu Cys Thr Val
     50                  55                  60

Cys Lys Glu Asp Lys Val Val Glu Thr Arg Cys Asn Ile Thr Thr Asn
 65                  70                  75                  80

Thr Val Cys Arg Cys Lys Pro Gly Thr Phe Glu Asp Lys Asp Ser Pro
                 85                  90                  95

Glu Ile Cys Gln Ser Cys Ser Asn Cys Thr Asp Gly Glu Glu Glu Leu
            100                 105                 110

Thr Ser Cys Thr Pro Arg Glu Asn Arg Lys Cys Val Ser Lys Thr Ala
        115                 120                 125

Trp Ala Ser Trp His
    130

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34
```

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38
<211> LENGTH: 121
<212> TYPE: PRT
<213> ORGANISM: Homo sapiens

<400> SEQUENCE: 38

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Thr Trp Leu Ser Arg His Leu Ser Tyr Trp Gly
            100                 105                 110

Gln Gly Thr Leu Val Thr Val Ser Ser
        115                 120
```

<210> SEQ ID NO 39
<211> LENGTH: 6
<212> TYPE: PRT
<213> ORGANISM: Homo sapiens

<400> SEQUENCE: 39

```
Ser Thr Tyr Gly Met His
 1               5
```

<210> SEQ ID NO 40
<211> LENGTH: 13
<212> TYPE: PRT
<213> ORGANISM: Homo sapiens

<400> SEQUENCE: 40

```
Trp Val Ala Gly Ile Asn Tyr Ser Gly Asn Asn Lys Tyr
 1               5                  10
```

<210> SEQ ID NO 41
<211> LENGTH: 13
<212> TYPE: PRT
<213> ORGANISM: Homo sapiens

<400> SEQUENCE: 41

Ala Arg Asp His Ser Thr Trp Leu Ser Arg His Leu Asp
1               5                   10

<210> SEQ ID NO 42
<211> LENGTH: 117
<212> TYPE: PRT
<213> ORGANISM: Homo sapiens

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Phe Gly Gly Pro Tyr Val Tyr Trp Gly Gln Gly Thr Leu
            100                 105                 110

Val Thr Val Ser Ser
        115

<210> SEQ ID NO 43
<211> LENGTH: 6
<212> TYPE: PRT
<213> ORGANISM: Homo sapiens

<400> SEQUENCE: 43

Ser Ser Tyr Ala Met Ser
1               5

<210> SEQ ID NO 44
<211> LENGTH: 13
<212> TYPE: PRT
<213> ORGANISM: Homo sapiens

<400> SEQUENCE: 44

Trp Val Ser Ser Ile Ser Ser Ser Ser Tyr Ile Tyr
1               5                   10

<210> SEQ ID NO 45
<211> LENGTH: 9
<212> TYPE: PRT
<213> ORGANISM: Homo sapiens

<400> SEQUENCE: 45

Ala Arg Ser Phe Gly Gly Pro Tyr Val
1               5

<210> SEQ ID NO 46

<211> LENGTH: 117
<212> TYPE: PRT
<213> ORGANISM: Homo sapiens

<400> SEQUENCE: 46

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Ser Tyr
            20                  25                  30
Ala Met Asn Trp Val Arg Gln Ala Pro Gly Lys Gly Leu Glu Trp Val
        35                  40                  45
Ala Leu Ile Ser Tyr Asp Ser Ser Tyr Ile Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Leu Leu Arg Gly Gly Phe Asp Tyr Trp Gly Gln Gly Thr Leu
                100                 105                 110
Val Thr Val Ser Ser
            115
```

<210> SEQ ID NO 47
<211> LENGTH: 6
<212> TYPE: PRT
<213> ORGANISM: Homo sapiens

<400> SEQUENCE: 47

```
Arg Ser Tyr Ala Met Asn
 1               5
```

<210> SEQ ID NO 48
<211> LENGTH: 13
<212> TYPE: PRT
<213> ORGANISM: Homo sapiens

<400> SEQUENCE: 48

```
Trp Val Ala Leu Ile Ser Tyr Asp Ser Ser Tyr Ile Tyr
 1               5                  10
```

<210> SEQ ID NO 49
<211> LENGTH: 9
<212> TYPE: PRT
<213> ORGANISM: Homo sapiens

<400> SEQUENCE: 49

```
Ala Arg Leu Leu Arg Gly Gly Phe Asp
 1               5
```

<210> SEQ ID NO 50
<211> LENGTH: 117
<212> TYPE: PRT
<213> ORGANISM: Homo sapiens

<400> SEQUENCE: 50

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Ser Phe
            20                  25                  30
Ala Met Ser Trp Val Arg Gln Ala Pro Gly Lys Gly Leu Glu Trp Val
        35                  40                  45
```

```
Ala Thr Ile Ser Ala Gly Gly Gly Tyr Ile Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gln Ser Trp Val Leu Asp Tyr Trp Gly Gln Gly Thr Leu
            100                 105                 110

Val Thr Val Ser Ser
            115

<210> SEQ ID NO 51
<211> LENGTH: 6
<212> TYPE: PRT
<213> ORGANISM: Homo sapiens

<400> SEQUENCE: 51

Arg Ser Phe Ala Met Ser
 1               5

<210> SEQ ID NO 52
<211> LENGTH: 13
<212> TYPE: PRT
<213> ORGANISM: Homo sapiens

<400> SEQUENCE: 52

Trp Val Ala Thr Ile Ser Ala Gly Gly Gly Tyr Ile Asn
 1               5                  10

<210> SEQ ID NO 53
<211> LENGTH: 9
<212> TYPE: PRT
<213> ORGANISM: Homo sapiens

<400> SEQUENCE: 53

Ala Arg Val Gln Ser Trp Val Leu Asp
 1               5

<210> SEQ ID NO 54
<211> LENGTH: 117
<212> TYPE: PRT
<213> ORGANISM: Homo sapiens

<400> SEQUENCE: 54

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Gly Tyr Asp Gly Ser Tyr Lys Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Ser Arg Gly Tyr Val Tyr Trp Gly Gln Gly Thr Leu
            100                 105                 110

Val Thr Val Ser Ser
```

<210> SEQ ID NO 55
<211> LENGTH: 6
<212> TYPE: PRT
<213> ORGANISM: Homo sapiens

<400> SEQUENCE: 55

Ser Ser Tyr Ala Met Ser
1               5

<210> SEQ ID NO 56
<211> LENGTH: 13
<212> TYPE: PRT
<213> ORGANISM: Homo sapiens

<400> SEQUENCE: 56

Trp Val Ala Ser Ile Gly Tyr Asp Gly Ser Tyr Lys Tyr
1               5                   10

<210> SEQ ID NO 57
<211> LENGTH: 9
<212> TYPE: PRT
<213> ORGANISM: Homo sapiens

<400> SEQUENCE: 57

Ala Arg Gly Val Ser Arg Gly Tyr Val
1               5

<210> SEQ ID NO 58
<211> LENGTH: 117
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Ala Met Ser Trp Val Arg Gln Ala Pro Gly Gln Gly Leu Glu Trp Met
        35                  40                  45

Gly Trp Ile Thr Pro Asn Ser Gly Thr Ala Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Ser Gly Tyr Tyr Asp Tyr Trp Gly Gln Gly Thr Leu
            100                 105                 110

Val Thr Val Ser Ser
        115

<210> SEQ ID NO 59
<211> LENGTH: 6
<212> TYPE: PRT
<213> ORGANISM: Homo sapiens

<400> SEQUENCE: 59

Ser Asn Tyr Ala Met Ser
1               5

```
<210> SEQ ID NO 60
<211> LENGTH: 13
<212> TYPE: PRT
<213> ORGANISM: Homo sapiens

<400> SEQUENCE: 60

Trp Met Gly Trp Ile Thr Pro Asn Ser Gly Thr Ala Lys
1               5                   10

<210> SEQ ID NO 61
<211> LENGTH: 9
<212> TYPE: PRT
<213> ORGANISM: Homo sapiens

<400> SEQUENCE: 61

Ala Arg Gly Val Ser Gly Tyr Tyr Asp
1               5

<210> SEQ ID NO 62
<211> LENGTH: 117
<212> TYPE: PRT
<213> ORGANISM: Homo sapiens

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
                20                  25                  30

Pro Ile Ser Trp Val Arg Gln Ala Pro Gly Gln Gly Leu Glu Trp Met
            35                  40                  45

Gly Trp Ile Ser Pro Gly Ser Gly Asn Thr Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Gly Gly Tyr Phe Asp Tyr Trp Gly Gln Gly Thr Leu
            100                 105                 110

Val Thr Val Ser Ser
        115

<210> SEQ ID NO 63
<211> LENGTH: 6
<212> TYPE: PRT
<213> ORGANISM: Homo sapiens

<400> SEQUENCE: 63

Ser Ala Tyr Pro Ile Ser
1               5

<210> SEQ ID NO 64
<211> LENGTH: 13
<212> TYPE: PRT
<213> ORGANISM: Homo sapiens

<400> SEQUENCE: 64

Trp Met Gly Trp Ile Ser Pro Gly Ser Gly Asn Thr Asn
1               5                   10

<210> SEQ ID NO 65
<211> LENGTH: 9
<212> TYPE: PRT
```

<213> ORGANISM: Homo sapiens

<400> SEQUENCE: 65

Ala Arg Gly Val Gly Gly Tyr Phe Asp
1               5

<210> SEQ ID NO 66
<211> LENGTH: 117
<212> TYPE: PRT
<213> ORGANISM: Homo sapiens

<400> SEQUENCE: 66

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Ala Ile Ala Asn Asp Ser Ala Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ser Ser Arg Leu Val Tyr Trp Gly Gln Gly Thr Leu
            100                 105                 110

Val Thr Val Ser Ser
        115

<210> SEQ ID NO 67
<211> LENGTH: 6
<212> TYPE: PRT
<213> ORGANISM: Homo sapiens

<400> SEQUENCE: 67

Ser Ser Tyr Ser Met Asn
1               5

<210> SEQ ID NO 68
<211> LENGTH: 13
<212> TYPE: PRT
<213> ORGANISM: Homo sapiens

<400> SEQUENCE: 68

Trp Val Ala Ala Ile Ala Asn Asp Ser Ala Tyr Thr Tyr
1               5                   10

<210> SEQ ID NO 69
<211> LENGTH: 9
<212> TYPE: PRT
<213> ORGANISM: Homo sapiens

<400> SEQUENCE: 69

Ala Arg Gly Pro Ser Ser Arg Leu Val
1               5

<210> SEQ ID NO 70
<211> LENGTH: 117
<212> TYPE: PRT
<213> ORGANISM: Homo sapiens

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Ala Ile Ala Asn Asp Ser Ala Tyr Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Pro Ser Thr Arg Leu Val Tyr Trp Gly Gln Gly Thr Leu
            100                 105                 110

Val Thr Val Ser Ser
            115

<210> SEQ ID NO 71
<211> LENGTH: 6
<212> TYPE: PRT
<213> ORGANISM: Homo sapiens

<400> SEQUENCE: 71

Ser Ser Tyr Ser Met Asn
1               5

<210> SEQ ID NO 72
<211> LENGTH: 13
<212> TYPE: PRT
<213> ORGANISM: Homo sapiens

<400> SEQUENCE: 72

Trp Val Ala Ala Ile Ala Asn Asp Ser Ala Tyr Thr Tyr
1               5                   10

<210> SEQ ID NO 73
<211> LENGTH: 9
<212> TYPE: PRT
<213> ORGANISM: Homo sapiens

<400> SEQUENCE: 73

Ala Arg Gly Pro Ser Thr Arg Leu Val
1               5

<210> SEQ ID NO 74
<211> LENGTH: 117
<212> TYPE: PRT
<213> ORGANISM: Homo sapiens

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ala Gly Ile Asn Tyr Ser Gly Thr Tyr Thr Tyr Tyr Ala Asp Ser Val
50                  55                  60

Lys Gly Arg Phe Thr Ile Ser Arg Asp Asn Ala Lys Asn Ser Leu Tyr

```
            65                  70                  75                  80
Leu Gln Met Asn Ser Leu Arg Ala Glu Asp Thr Ala Val Tyr Tyr Cys
                    85                  90                  95

Ala Arg Gly Phe Gly Arg Gly Phe Val Tyr Trp Gly Gln Gly Thr Leu
                100                 105                 110

Val Thr Val Ser Ser
            115

<210> SEQ ID NO 75
<211> LENGTH: 6
<212> TYPE: PRT
<213> ORGANISM: Homo sapiens

<400> SEQUENCE: 75

Arg Asn Tyr Ala Met Ser
1               5

<210> SEQ ID NO 76
<211> LENGTH: 13
<212> TYPE: PRT
<213> ORGANISM: Homo sapiens

<400> SEQUENCE: 76

Trp Val Ala Gly Ile Asn Tyr Ser Gly Thr Tyr Thr Tyr
1               5                   10

<210> SEQ ID NO 77
<211> LENGTH: 9
<212> TYPE: PRT
<213> ORGANISM: Homo sapiens

<400> SEQUENCE: 77

Ala Arg Gly Phe Gly Arg Gly Phe Val
1               5

<210> SEQ ID NO 78
<211> LENGTH: 117
<212> TYPE: PRT
<213> ORGANISM: Homo sapiens

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Gly Phe Gly Arg Gly Tyr Val Tyr Trp Gly Gln Gly Thr Leu
                100                 105                 110

Val Thr Val Ser Ser
            115

<210> SEQ ID NO 79
<211> LENGTH: 6
```

```
<212> TYPE: PRT
<213> ORGANISM: Homo sapiens

<400> SEQUENCE: 79

Ser Asn Tyr Gly Met Ser
1               5

<210> SEQ ID NO 80
<211> LENGTH: 13
<212> TYPE: PRT
<213> ORGANISM: Homo sapiens

<400> SEQUENCE: 80

Trp Val Ser Ser Ile Ser Ser Ser Ser Tyr Ile Tyr
1               5                   10

<210> SEQ ID NO 81
<211> LENGTH: 9
<212> TYPE: PRT
<213> ORGANISM: Homo sapiens

<400> SEQUENCE: 81

Ala Arg Gly Phe Gly Arg Gly Tyr Val
1               5

<210> SEQ ID NO 82
<211> LENGTH: 118
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ala Gly Ile Gly Trp Gly Gly Thr Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Arg Ala Tyr Ile Asp Tyr Trp Gly Gln Gly Thr
            100                 105                 110

Leu Val Thr Val Ser Ser
        115

<210> SEQ ID NO 83
<211> LENGTH: 6
<212> TYPE: PRT
<213> ORGANISM: Homo sapiens

<400> SEQUENCE: 83

Ser Ser Tyr Ser Met Ser
1               5

<210> SEQ ID NO 84
<211> LENGTH: 13
<212> TYPE: PRT
<213> ORGANISM: Homo sapiens
```

<400> SEQUENCE: 84

Trp Val Ala Gly Ile Gly Trp Gly Gly Thr Thr Lys Tyr
1               5                   10

<210> SEQ ID NO 85
<211> LENGTH: 10
<212> TYPE: PRT
<213> ORGANISM: Homo sapiens

<400> SEQUENCE: 85

Ala Arg Gly Gly Tyr Arg Ala Tyr Ile Asp
1               5                   10

<210> SEQ ID NO 86
<211> LENGTH: 118
<212> TYPE: PRT
<213> ORGANISM: Homo sapiens

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Val Val Arg Tyr Gly Phe Asp Tyr Trp Gly Gln Gly Thr
            100                 105                 110

Leu Val Thr Val Ser Ser
        115

<210> SEQ ID NO 87
<211> LENGTH: 6
<212> TYPE: PRT
<213> ORGANISM: Homo sapiens

<400> SEQUENCE: 87

Thr Asn Tyr Tyr Met His
1               5

<210> SEQ ID NO 88
<211> LENGTH: 13
<212> TYPE: PRT
<213> ORGANISM: Homo sapiens

<400> SEQUENCE: 88

Trp Met Gly Trp Ile Asn Pro Asn Ser Gly Asn Thr Asn
1               5                   10

<210> SEQ ID NO 89
<211> LENGTH: 10
<212> TYPE: PRT
<213> ORGANISM: Homo sapiens

<400> SEQUENCE: 89

Ala Arg Glu Val Val Arg Tyr Gly Phe Asp

<210> SEQ ID NO 90
<211> LENGTH: 119
<212> TYPE: PRT
<213> ORGANISM: Homo sapiens

<400> SEQUENCE: 90

Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Arg Asn Tyr
            20                  25                  30
Gly Met Asn Trp Val Arg Gln Ala Pro Gly Lys Gly Leu Glu Trp Val
        35                  40                  45
Ala Gly Ile Lys Asn Asp Gly Asp Thr Lys Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Arg Val Arg Tyr Gly His Ala Met Asp Tyr Trp Gly Gln Gly
            100                 105                 110
Thr Leu Val Thr Val Ser Ser
        115

<210> SEQ ID NO 91
<211> LENGTH: 6
<212> TYPE: PRT
<213> ORGANISM: Homo sapiens

<400> SEQUENCE: 91

Arg Asn Tyr Gly Met Asn
 1               5

<210> SEQ ID NO 92
<211> LENGTH: 13
<212> TYPE: PRT
<213> ORGANISM: Homo sapiens

<400> SEQUENCE: 92

Trp Val Ala Gly Ile Lys Asn Asp Gly Asp Thr Lys Tyr
 1               5                  10

<210> SEQ ID NO 93
<211> LENGTH: 11
<212> TYPE: PRT
<213> ORGANISM: Homo sapiens

<400> SEQUENCE: 93

Ala Lys Arg Val Arg Tyr Gly His Ala Met Asp
 1               5                  10

<210> SEQ ID NO 94
<211> LENGTH: 119
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Asn Phe

```
                 20                  25                  30

Ala Met Asn Trp Val Arg Gln Ala Pro Gly Lys Gly Leu Glu Trp Val
             35                  40                  45

Ala Gly Ile Lys Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Arg Trp Ala Gly His Gly Phe Asp Tyr Trp Gly Gln Gly
            100                 105                 110

Thr Leu Val Thr Val Ser Ser
            115

<210> SEQ ID NO 95
<211> LENGTH: 6
<212> TYPE: PRT
<213> ORGANISM: Homo sapiens

<400> SEQUENCE: 95

Arg Asn Phe Ala Met Asn
 1               5

<210> SEQ ID NO 96
<211> LENGTH: 13
<212> TYPE: PRT
<213> ORGANISM: Homo sapiens

<400> SEQUENCE: 96

Trp Val Ala Gly Ile Lys Tyr Asp Gly Ser Asn Lys Tyr
 1               5                  10

<210> SEQ ID NO 97
<211> LENGTH: 11
<212> TYPE: PRT
<213> ORGANISM: Homo sapiens

<400> SEQUENCE: 97

Ala Arg Arg Arg Trp Ala Gly His Gly Phe Asp
 1               5                  10

<210> SEQ ID NO 98
<211> LENGTH: 119
<212> TYPE: PRT
<213> ORGANISM: Homo sapiens

<400> SEQUENCE: 98

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Asn Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Arg Arg Trp Ala Gly His Gly Phe Asp Tyr Trp Gly Gln Gly
            100                 105                 110

Thr Leu Val Thr Val Ser Ser
        115

<210> SEQ ID NO 99
<211> LENGTH: 6
<212> TYPE: PRT
<213> ORGANISM: Homo sapiens

<400> SEQUENCE: 99

Ser Asn Tyr Ala Met Asn
1               5

<210> SEQ ID NO 100
<211> LENGTH: 13
<212> TYPE: PRT
<213> ORGANISM: Homo sapiens

<400> SEQUENCE: 100

Trp Val Ser Ala Ile Ser Gly Ser Gly Gly Ser Thr Tyr
1               5                   10

<210> SEQ ID NO 101
<211> LENGTH: 11
<212> TYPE: PRT
<213> ORGANISM: Homo sapiens

<400> SEQUENCE: 101

Ala Arg Arg Arg Trp Ala Gly His Gly Phe Asp
1               5                   10

<210> SEQ ID NO 102
<211> LENGTH: 119
<212> TYPE: PRT
<213> ORGANISM: Homo sapiens

<400> SEQUENCE: 102

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Ala Ile Ser Tyr Asn Gly Ala Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Lys Val Gly Tyr Pro Ser Ala Phe Asp Tyr Trp Gly Gln Gly
            100                 105                 110

Thr Leu Val Thr Val Ser Ser
        115

<210> SEQ ID NO 103
<211> LENGTH: 6
<212> TYPE: PRT
<213> ORGANISM: Homo sapiens

<400> SEQUENCE: 103
```

-continued

```
Ser Ser Tyr Ser Met Asn
 1               5

<210> SEQ ID NO 104
<211> LENGTH: 13
<212> TYPE: PRT
<213> ORGANISM: Homo sapiens

<400> SEQUENCE: 104

Trp Val Ala Ala Ile Ser Tyr Asn Gly Ala Asn Lys Tyr
 1               5                  10

<210> SEQ ID NO 105
<211> LENGTH: 11
<212> TYPE: PRT
<213> ORGANISM: Homo sapiens

<400> SEQUENCE: 105

Ala Arg Lys Val Gly Tyr Pro Ser Ala Phe Asp
 1               5                  10

<210> SEQ ID NO 106
<211> LENGTH: 119
<212> TYPE: PRT
<213> ORGANISM: Homo sapiens

<400> SEQUENCE: 106

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ala Ala Ile Ser Tyr Gly Ser Asp Tyr Ile Asn Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Tyr Ala Trp Gly Ala Gly Met Asp Tyr Trp Gly Gln Gly
            100                 105                 110

Thr Leu Val Thr Val Ser Ser
        115

<210> SEQ ID NO 107
<211> LENGTH: 6
<212> TYPE: PRT
<213> ORGANISM: Homo sapiens

<400> SEQUENCE: 107

Ser Ser Tyr Ala Met Ser
 1               5

<210> SEQ ID NO 108
<211> LENGTH: 13
<212> TYPE: PRT
<213> ORGANISM: Homo sapiens

<400> SEQUENCE: 108

Trp Val Ala Ala Ile Ser Tyr Gly Ser Asp Tyr Ile Asn
 1               5                  10
```

<210> SEQ ID NO 109
<211> LENGTH: 11
<212> TYPE: PRT
<213> ORGANISM: Homo sapiens

<400> SEQUENCE: 109

Ala Arg Arg Tyr Ala Trp Gly Ala Gly Met Asp
1               5                   10

<210> SEQ ID NO 110
<211> LENGTH: 119
<212> TYPE: PRT
<213> ORGANISM: Homo sapiens

<400> SEQUENCE: 110

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ala Ser Ile Ser Tyr Gly Ser Gly Tyr Lys Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Ala Gly Gly Tyr Gly Phe Asp Tyr Trp Gly Gln Gly
            100                 105                 110

Thr Leu Val Thr Val Ser Ser
        115

<210> SEQ ID NO 111
<211> LENGTH: 6
<212> TYPE: PRT
<213> ORGANISM: Homo sapiens

<400> SEQUENCE: 111

Ser Ser Tyr Ser Met Ser
1               5

<210> SEQ ID NO 112
<211> LENGTH: 13
<212> TYPE: PRT
<213> ORGANISM: Homo sapiens

<400> SEQUENCE: 112

Trp Val Ala Ser Ile Ser Tyr Gly Ser Gly Tyr Lys Asn
1               5                   10

<210> SEQ ID NO 113
<211> LENGTH: 11
<212> TYPE: PRT
<213> ORGANISM: Homo sapiens

<400> SEQUENCE: 113

Ala Arg Arg Tyr Ala Gly Gly Tyr Gly Phe Asp
1               5                   10

<210> SEQ ID NO 114
<211> LENGTH: 119

```
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ala Ile Ser Tyr Asn Ser Ala Asn Ile Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Leu Gly Trp Gly Asn Gly Phe Asp Tyr Trp Gly Gln Gly
            100                 105                 110

Thr Leu Val Thr Val Ser Ser
        115

<210> SEQ ID NO 115
<211> LENGTH: 6
<212> TYPE: PRT
<213> ORGANISM: Homo sapiens

<400> SEQUENCE: 115

Ser Ser Tyr Ser Met Ser
 1               5

<210> SEQ ID NO 116
<211> LENGTH: 13
<212> TYPE: PRT
<213> ORGANISM: Homo sapiens

<400> SEQUENCE: 116

Trp Val Ser Ala Ile Ser Tyr Asn Ser Ala Asn Ile Tyr
 1               5                  10

<210> SEQ ID NO 117
<211> LENGTH: 11
<212> TYPE: PRT
<213> ORGANISM: Homo sapiens

<400> SEQUENCE: 117

Ala Arg Arg Leu Gly Trp Gly Asn Gly Phe Asp
 1               5                  10

<210> SEQ ID NO 118
<211> LENGTH: 119
<212> TYPE: PRT
<213> ORGANISM: Homo sapiens

<400> SEQUENCE: 118

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45
```

```
Ser Ala Ile Ser Tyr Asn Ser Ala Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Gly Trp Gly Asn Gly Phe Asp Tyr Trp Gly Gln Gly
            100                 105                 110

Thr Leu Val Thr Val Ser Ser
            115
```

```
<210> SEQ ID NO 119
<211> LENGTH: 6
<212> TYPE: PRT
<213> ORGANISM: Homo sapiens

<400> SEQUENCE: 119

Ser Ser Tyr Ser Met Ser
1               5
```

```
<210> SEQ ID NO 120
<211> LENGTH: 13
<212> TYPE: PRT
<213> ORGANISM: Homo sapiens

<400> SEQUENCE: 120

Trp Val Ser Ala Ile Ser Tyr Asn Ser Ala Asn Ile Tyr
1               5                   10
```

```
<210> SEQ ID NO 121
<211> LENGTH: 11
<212> TYPE: PRT
<213> ORGANISM: Homo sapiens

<400> SEQUENCE: 121

Ala Arg Arg Leu Gly Trp Gly Asn Gly Phe Asp
1               5                   10
```

```
<210> SEQ ID NO 122
<211> LENGTH: 119
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Tyr Ser Gly Ala Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Val Gly Trp Gly His Gly Met Asp Tyr Trp Gly Gln Gly
            100                 105                 110

Thr Leu Val Thr Val Ser Ser
            115
```

<210> SEQ ID NO 123
<211> LENGTH: 6
<212> TYPE: PRT
<213> ORGANISM: Homo sapiens

<400> SEQUENCE: 123

Ser Ser Tyr Ala Met Ser
1               5

<210> SEQ ID NO 124
<211> LENGTH: 13
<212> TYPE: PRT
<213> ORGANISM: Homo sapiens

<400> SEQUENCE: 124

Trp Val Ser Val Ile Ser Tyr Ser Gly Ala Tyr Ile Tyr
1               5                   10

<210> SEQ ID NO 125
<211> LENGTH: 11
<212> TYPE: PRT
<213> ORGANISM: Homo sapiens

<400> SEQUENCE: 125

Ala Arg Lys Val Gly Trp Gly His Gly Met Asp
1               5                   10

<210> SEQ ID NO 126
<211> LENGTH: 119
<212> TYPE: PRT
<213> ORGANISM: Homo sapiens

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Asn Gly Gly Thr Ile Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ala Ser Ser Arg Gly Phe Asp Tyr Trp Gly Gln Gly
            100                 105                 110

Thr Leu Val Thr Val Ser Ser
        115

<210> SEQ ID NO 127
<211> LENGTH: 6
<212> TYPE: PRT
<213> ORGANISM: Homo sapiens

<400> SEQUENCE: 127

Ser Ser Tyr Ala Met Ser
1               5

<210> SEQ ID NO 128

```
<211> LENGTH: 13
<212> TYPE: PRT
<213> ORGANISM: Homo sapiens

<400> SEQUENCE: 128

Trp Val Ala Ser Ile Ser Asn Gly Gly Thr Ile Thr Asn
1               5                   10

<210> SEQ ID NO 129
<211> LENGTH: 11
<212> TYPE: PRT
<213> ORGANISM: Homo sapiens

<400> SEQUENCE: 129

Ala Arg Gly Tyr Ala Ser Ser Arg Gly Phe Asp
1               5                   10

<210> SEQ ID NO 130
<211> LENGTH: 120
<212> TYPE: PRT
<213> ORGANISM: Homo sapiens

<400> SEQUENCE: 130

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Arg Ile Ser Asn Asn Gly Ala Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Gly Tyr Tyr Ala Phe Asp Tyr Trp Gly Gln
            100                 105                 110

Gly Thr Leu Val Thr Val Ser Ser
        115                 120

<210> SEQ ID NO 131
<211> LENGTH: 6
<212> TYPE: PRT
<213> ORGANISM: Homo sapiens

<400> SEQUENCE: 131

Ser Asp Tyr Gly Met His
1               5

<210> SEQ ID NO 132
<211> LENGTH: 13
<212> TYPE: PRT
<213> ORGANISM: Homo sapiens

<400> SEQUENCE: 132

Trp Val Ala Arg Ile Ser Asn Asn Gly Ala Ile Ile Tyr
1               5                   10

<210> SEQ ID NO 133
<211> LENGTH: 12
<212> TYPE: PRT
<213> ORGANISM: Homo sapiens
```

-continued

```
<400> SEQUENCE: 133

Ala Arg Gly Gly Tyr Gly Gly Tyr Tyr Ala Phe Asp
1               5                   10

<210> SEQ ID NO 134
<211> LENGTH: 120
<212> TYPE: PRT
<213> ORGANISM: Homo sapiens

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
                20                  25                  30

Tyr Met His Trp Val Arg Gln Ala Pro Gly Gln Gly Leu Glu Trp Met
            35                  40                  45

Gly Gly Ile Asn Pro Ile Asn Gly Thr Ala Lys Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Tyr Gly Gly Tyr Tyr Thr Phe Asp Tyr Trp Gly Gln
                100                 105                 110

Gly Thr Leu Val Thr Val Ser Ser
        115                 120

<210> SEQ ID NO 135
<211> LENGTH: 6
<212> TYPE: PRT
<213> ORGANISM: Homo sapiens

<400> SEQUENCE: 135

Ser Asn Tyr Tyr Met His
1               5

<210> SEQ ID NO 136
<211> LENGTH: 13
<212> TYPE: PRT
<213> ORGANISM: Homo sapiens

<400> SEQUENCE: 136

Trp Met Gly Gly Ile Asn Pro Ile Asn Gly Thr Ala Lys
1               5                   10

<210> SEQ ID NO 137
<211> LENGTH: 12
<212> TYPE: PRT
<213> ORGANISM: Homo sapiens

<400> SEQUENCE: 137

Ala Arg Arg Gly Tyr Gly Gly Tyr Tyr Thr Phe Asp
1               5                   10

<210> SEQ ID NO 138
<211> LENGTH: 120
<212> TYPE: PRT
<213> ORGANISM: Homo sapiens

<400> SEQUENCE: 138
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ser Met Ser Trp Val Arg Gln Ala Pro Gly Lys Gly Leu Glu Trp Val
        35                  40                  45

Ala Gly Ile Gly Trp Asp Ser Ala Ile Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Ser Gly Gly Arg Asp Ala Phe Asp Tyr Trp Gly Gln
            100                 105                 110

Gly Thr Leu Val Thr Val Ser Ser
            115                 120

<210> SEQ ID NO 139
<211> LENGTH: 6
<212> TYPE: PRT
<213> ORGANISM: Homo sapiens

<400> SEQUENCE: 139

Arg Asn Tyr Ser Met Ser
1               5

<210> SEQ ID NO 140
<211> LENGTH: 13
<212> TYPE: PRT
<213> ORGANISM: Homo sapiens

<400> SEQUENCE: 140

Trp Val Ala Gly Ile Gly Trp Asp Ser Ala Ile Lys Tyr
1               5                   10

<210> SEQ ID NO 141
<211> LENGTH: 12
<212> TYPE: PRT
<213> ORGANISM: Homo sapiens

<400> SEQUENCE: 141

Ala Arg Gly Thr Ser Gly Gly Arg Asp Ala Phe Asp
1               5                   10

<210> SEQ ID NO 142
<211> LENGTH: 120
<212> TYPE: PRT
<213> ORGANISM: Homo sapiens

<400> SEQUENCE: 142

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Arg Ile Ser Asn Asn Gly Ala Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

-continued

Leu Gln Met Asn Ser Leu Arg Ala Glu Asp Thr Ala Val Tyr Tyr Cys
                85                  90                  95

Ala Arg Gly Gly Thr Ser Gly Tyr Tyr Ala Phe Asp Tyr Trp Gly Gln
            100                 105                 110

Gly Thr Leu Val Thr Val Ser Ser
        115                 120

<210> SEQ ID NO 143
<211> LENGTH: 6
<212> TYPE: PRT
<213> ORGANISM: Homo sapiens

<400> SEQUENCE: 143

Ser Asp Tyr Gly Met His
1               5

<210> SEQ ID NO 144
<211> LENGTH: 13
<212> TYPE: PRT
<213> ORGANISM: Homo sapiens

<400> SEQUENCE: 144

Trp Val Ala Arg Ile Ser Asn Asn Gly Ala Ile Ile Tyr
1               5                   10

<210> SEQ ID NO 145
<211> LENGTH: 12
<212> TYPE: PRT
<213> ORGANISM: Homo sapiens

<400> SEQUENCE: 145

Ala Arg Gly Gly Thr Ser Gly Tyr Tyr Ala Phe Asp
1               5                   10

<210> SEQ ID NO 146
<211> LENGTH: 120
<212> TYPE: PRT
<213> ORGANISM: Homo sapiens

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Tyr Asn Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Arg Ala Pro Phe Asp Tyr Trp Gly Gln
            100                 105                 110

Gly Thr Leu Val Thr Val Ser Ser
        115                 120

<210> SEQ ID NO 147
<211> LENGTH: 6
<212> TYPE: PRT

```
<213> ORGANISM: Homo sapiens

<400> SEQUENCE: 147

Ser Ser Tyr Ala Met Ser
1               5

<210> SEQ ID NO 148
<211> LENGTH: 13
<212> TYPE: PRT
<213> ORGANISM: Homo sapiens

<400> SEQUENCE: 148

Trp Val Ser Ser Ile Ser Tyr Asn Gly Gly Asn Lys Tyr
1               5                   10

<210> SEQ ID NO 149
<211> LENGTH: 12
<212> TYPE: PRT
<213> ORGANISM: Homo sapiens

<400> SEQUENCE: 149

Ala Arg Gly Gln Trp Gly Tyr Arg Ala Pro Phe Asp
1               5                   10

<210> SEQ ID NO 150
<211> LENGTH: 120
<212> TYPE: PRT
<213> ORGANISM: Homo sapiens

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ser Met Ser Trp Val Arg Gln Ala Pro Gly Lys Gly Leu Glu Trp Val
        35                  40                  45

Ala Ser Ile Ser Ala Gly Ser Ala Tyr Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Ser Ala Gly Tyr Ala Phe Asp Tyr Gly Gly Gln
            100                 105                 110

Gly Thr Leu Val Thr Val Ser Ser
        115                 120

<210> SEQ ID NO 151
<211> LENGTH: 6
<212> TYPE: PRT
<213> ORGANISM: Homo sapiens

<400> SEQUENCE: 151

Arg Asn Tyr Ser Met Ser
1               5

<210> SEQ ID NO 152
<211> LENGTH: 13
<212> TYPE: PRT
<213> ORGANISM: Homo sapiens

<400> SEQUENCE: 152
```

```
Trp Val Ala Ser Ile Ser Ala Gly Ser Ala Tyr Lys Asn
1               5                   10
```

```
<210> SEQ ID NO 153
<211> LENGTH: 12
<212> TYPE: PRT
<213> ORGANISM: Homo sapiens

<400> SEQUENCE: 153

Ala Arg Gly Leu Trp Ser Ala Gly Tyr Ala Phe Asp
1               5                   10
```

```
<210> SEQ ID NO 154
<211> LENGTH: 120
<212> TYPE: PRT
<213> ORGANISM: Homo sapiens

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Ser Met Ser Trp Val Arg Gln Ala Pro Gly Lys Gly Leu Glu Trp Val
        35                  40                  45

Ala Ala Ile Ser Tyr Asn Ser Ala Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ala Trp Ser Arg Ser Pro Phe Asp Tyr Trp Gly Gln
            100                 105                 110

Gly Thr Leu Val Thr Val Ser Ser
        115                 120
```

```
<210> SEQ ID NO 155
<211> LENGTH: 6
<212> TYPE: PRT
<213> ORGANISM: Homo sapiens

<400> SEQUENCE: 155

Arg Ser Phe Ser Met Ser
1               5
```

```
<210> SEQ ID NO 156
<211> LENGTH: 13
<212> TYPE: PRT
<213> ORGANISM: Homo sapiens

<400> SEQUENCE: 156

Trp Val Ala Ala Ile Ser Tyr Asn Ser Ala Asn Thr Tyr
1               5                   10
```

```
<210> SEQ ID NO 157
<211> LENGTH: 12
<212> TYPE: PRT
<213> ORGANISM: Homo sapiens

<400> SEQUENCE: 157

Ala Arg Arg Ala Ala Trp Ser Arg Ser Pro Phe Asp
1               5                   10
```

<210> SEQ ID NO 158
<211> LENGTH: 120
<212> TYPE: PRT
<213> ORGANISM: Homo sapiens

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ser Ile Asn Pro Phe Asn Gly Ser Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Trp Trp Thr Ser Ser Ala Phe Asp Tyr Trp Gly Gln
            100                 105                 110

Gly Thr Leu Val Thr Val Ser Ser
        115                 120

<210> SEQ ID NO 159
<211> LENGTH: 6
<212> TYPE: PRT
<213> ORGANISM: Homo sapiens

<400> SEQUENCE: 159

Thr Gly Tyr Tyr Met His
1               5

<210> SEQ ID NO 160
<211> LENGTH: 13
<212> TYPE: PRT
<213> ORGANISM: Homo sapiens

<400> SEQUENCE: 160

Trp Met Gly Ser Ile Asn Pro Phe Asn Gly Ser Thr Asn
1               5                   10

<210> SEQ ID NO 161
<211> LENGTH: 12
<212> TYPE: PRT
<213> ORGANISM: Homo sapiens

<400> SEQUENCE: 161

Ala Arg Arg Gly Trp Trp Thr Ser Ser Ala Phe Asp
1               5                   10

<210> SEQ ID NO 162
<211> LENGTH: 120
<212> TYPE: PRT
<213> ORGANISM: Homo sapiens

<400> SEQUENCE: 162

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

```
Ala Met Ser Trp Val Arg Gln Ala Pro Gly Lys Gly Leu Glu Trp Val
        35                  40                  45

Ala Ser Ile Asn Ser Asn Gly Ala Tyr Thr Asn Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Gly Ala Tyr Asp Arg Gly Phe Asp Tyr Trp Gly Gln
            100                 105                 110

Gly Thr Leu Val Thr Val Ser Ser
            115                 120

<210> SEQ ID NO 163
<211> LENGTH: 6
<212> TYPE: PRT
<213> ORGANISM: Homo sapiens

<400> SEQUENCE: 163

Arg Ser Tyr Ala Met Ser
 1               5

<210> SEQ ID NO 164
<211> LENGTH: 13
<212> TYPE: PRT
<213> ORGANISM: Homo sapiens

<400> SEQUENCE: 164

Trp Val Ala Ser Ile Asn Ser Asn Gly Ala Tyr Thr Asn
 1               5                  10

<210> SEQ ID NO 165
<211> LENGTH: 12
<212> TYPE: PRT
<213> ORGANISM: Homo sapiens

<400> SEQUENCE: 165

Ala Arg Gly Arg Gly Ala Tyr Asp Arg Gly Phe Asp
 1               5                  10

<210> SEQ ID NO 166
<211> LENGTH: 120
<212> TYPE: PRT
<213> ORGANISM: Homo sapiens

<400> SEQUENCE: 166

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                 20                  25                  30

Ala Met His Trp Val Arg Gln Ala Pro Gly Lys Gly Leu Glu Trp Val
            35                  40                  45

Ala Gly Ile Ser Gly Gly Gly Thr Tyr Lys Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Arg Ser Val Ala Tyr Ala Asn Phe Asp Tyr Trp Gly Gln
```

```
                    100                 105                 110
Gly Thr Leu Val Thr Val Ser Ser
            115                 120

<210> SEQ ID NO 167
<211> LENGTH: 6
<212> TYPE: PRT
<213> ORGANISM: Homo sapiens

<400> SEQUENCE: 167

Ser Thr Tyr Ala Met His
1               5

<210> SEQ ID NO 168
<211> LENGTH: 13
<212> TYPE: PRT
<213> ORGANISM: Homo sapiens

<400> SEQUENCE: 168

Trp Val Ala Gly Ile Ser Gly Gly Gly Thr Tyr Lys Tyr
1               5                   10

<210> SEQ ID NO 169
<211> LENGTH: 12
<212> TYPE: PRT
<213> ORGANISM: Homo sapiens

<400> SEQUENCE: 169

Ala Arg Pro Arg Ser Val Ala Tyr Ala Asn Phe Asp
1               5                   10

<210> SEQ ID NO 170
<211> LENGTH: 120
<212> TYPE: PRT
<213> ORGANISM: Homo sapiens

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met His Trp Val Arg Gln Ala Pro Gly Lys Gly Leu Glu Trp Val
        35                  40                  45

Ala Gly Ile Trp Gly Asp Ser Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Leu Ala Ala Asp Gly Phe Asp Tyr Trp Gly Gln
            100                 105                 110

Gly Thr Leu Val Thr Val Ser Ser
            115                 120

<210> SEQ ID NO 171
<211> LENGTH: 6
<212> TYPE: PRT
<213> ORGANISM: Homo sapiens

<400> SEQUENCE: 171

Ser Asn Tyr Ser Met His
```

```
                1               5

<210> SEQ ID NO 172
<211> LENGTH: 13
<212> TYPE: PRT
<213> ORGANISM: Homo sapiens

<400> SEQUENCE: 172

Trp Val Ala Gly Ile Trp Gly Asp Ser Gly Tyr Ile Tyr
1               5                   10

<210> SEQ ID NO 173
<211> LENGTH: 12
<212> TYPE: PRT
<213> ORGANISM: Homo sapiens

<400> SEQUENCE: 173

Ala Arg Ala Arg Val Leu Ala Ala Asp Gly Phe Asp
1               5                   10

<210> SEQ ID NO 174
<211> LENGTH: 121
<212> TYPE: PRT
<213> ORGANISM: Homo sapiens

<400> SEQUENCE: 174

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Gly Met Asn Trp Val Arg Gln Ala Pro Gly Lys Gly Leu Glu Trp Val
        35                  40                  45

Ala Gly Ile Lys Asn Asp Gly Asp Thr Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Tyr Lys Gly Tyr Val Gly Pro Leu Asp Tyr Trp Gly
            100                 105                 110

Gln Gly Thr Leu Val Thr Val Ser Ser
        115                 120

<210> SEQ ID NO 175
<211> LENGTH: 6
<212> TYPE: PRT
<213> ORGANISM: Homo sapiens

<400> SEQUENCE: 175

Arg Asn Tyr Gly Met Asn
1               5

<210> SEQ ID NO 176
<211> LENGTH: 13
<212> TYPE: PRT
<213> ORGANISM: Homo sapiens

<400> SEQUENCE: 176

Trp Val Ala Gly Ile Lys Asn Asp Gly Asp Thr Lys Tyr
1               5                   10
```

```
<210> SEQ ID NO 177
<211> LENGTH: 13
<212> TYPE: PRT
<213> ORGANISM: Homo sapiens

<400> SEQUENCE: 177

Ala Lys Gly Arg Tyr Lys Gly Tyr Val Gly Pro Leu Asp
1               5                   10

<210> SEQ ID NO 178
<211> LENGTH: 121
<212> TYPE: PRT
<213> ORGANISM: Homo sapiens

<400> SEQUENCE: 178

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Gly Met Ser Trp Val Arg Gln Ala Pro Gly Lys Gly Leu Glu Trp Val
        35                  40                  45

Ala Gly Ile Trp Ser Asn Ser Gly Ile Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Tyr Ala Ser Tyr Trp Ser Ala Phe Asp Tyr Trp Gly
            100                 105                 110

Gln Gly Thr Leu Val Thr Val Ser Ser
        115                 120

<210> SEQ ID NO 179
<211> LENGTH: 6
<212> TYPE: PRT
<213> ORGANISM: Homo sapiens

<400> SEQUENCE: 179

Arg Asn Tyr Gly Met Ser
1               5

<210> SEQ ID NO 180
<211> LENGTH: 13
<212> TYPE: PRT
<213> ORGANISM: Homo sapiens

<400> SEQUENCE: 180

Trp Val Ala Gly Ile Trp Ser Asn Ser Gly Ile Ile Asn
1               5                   10

<210> SEQ ID NO 181
<211> LENGTH: 13
<212> TYPE: PRT
<213> ORGANISM: Homo sapiens

<400> SEQUENCE: 181

Ala Lys Ser Ser Tyr Ala Ser Tyr Trp Ser Ala Phe Asp
1               5                   10

<210> SEQ ID NO 182
<211> LENGTH: 121
<212> TYPE: PRT
```

<213> ORGANISM: Homo sapiens

<400> SEQUENCE: 182

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ile Asn Tyr
            20                  25                  30

Ala Met Ser Trp Val Arg Gln Ala Pro Gly Lys Gly Leu Glu Trp Val
        35                  40                  45

Ala Ser Ile Gly Asn Asp Ser Thr Asn Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asn Thr Ala Val Tyr Tyr Cys
                85                  90                  95

Ala Lys Ser Arg Tyr Ile Ala Leu Ser Arg Pro Leu Asp Tyr Trp Gly
            100                 105                 110

Gln Gly Thr Leu Val Thr Val Ser Ser
        115                 120

<210> SEQ ID NO 183
<211> LENGTH: 6
<212> TYPE: PRT
<213> ORGANISM: Homo sapiens

<400> SEQUENCE: 183

Ile Asn Tyr Ala Met Ser
1               5

<210> SEQ ID NO 184
<211> LENGTH: 13
<212> TYPE: PRT
<213> ORGANISM: Homo sapiens

<400> SEQUENCE: 184

Trp Val Ala Ser Ile Gly Asn Asp Ser Thr Asn Thr Tyr
1               5                   10

<210> SEQ ID NO 185
<211> LENGTH: 13
<212> TYPE: PRT
<213> ORGANISM: Homo sapiens

<400> SEQUENCE: 185

Ala Lys Ser Arg Tyr Ile Ala Leu Ser Arg Pro Leu Asp
1               5                   10

<210> SEQ ID NO 186
<211> LENGTH: 122
<212> TYPE: PRT
<213> ORGANISM: Homo sapiens

<400> SEQUENCE: 186

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Gly Pro Arg Pro Ser Tyr Tyr Ala Gly Trp Phe Asp Tyr Trp
                100                 105                 110

Gly Gln Gly Thr Leu Val Thr Val Ser Ser
            115                 120
```

<210> SEQ ID NO 187
<211> LENGTH: 6
<212> TYPE: PRT
<213> ORGANISM: Homo sapiens

<400> SEQUENCE: 187

```
Ser Ser Tyr Ser Met Asn
 1               5
```

<210> SEQ ID NO 188
<211> LENGTH: 13
<212> TYPE: PRT
<213> ORGANISM: Homo sapiens

<400> SEQUENCE: 188

```
Trp Val Ser Ser Ile Ser Ser Ser Ser Tyr Ile Tyr
 1               5                  10
```

<210> SEQ ID NO 189
<211> LENGTH: 14
<212> TYPE: PRT
<213> ORGANISM: Homo sapiens

<400> SEQUENCE: 189

```
Ala Arg Gly Pro Arg Pro Ser Tyr Tyr Ala Gly Trp Phe Asp
 1               5                  10
```

<210> SEQ ID NO 190
<211> LENGTH: 122
<212> TYPE: PRT
<213> ORGANISM: Homo sapiens

<400> SEQUENCE: 190

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
                20                  25                  30

Ser Met Ser Trp Val Arg Gln Ala Pro Gly Lys Gly Leu Glu Trp Val
            35                  40                  45

Ser Gly Ile Ser Gly Gly Gly Ala Tyr Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Ser Arg Ser Pro Arg Tyr Tyr His Phe Asp Tyr Trp
                100                 105                 110

Gly Gln Gly Thr Leu Val Thr Val Ser Ser
            115                 120
```

<210> SEQ ID NO 191
<211> LENGTH: 6
<212> TYPE: PRT
<213> ORGANISM: Homo sapiens

<400> SEQUENCE: 191

Ser Asn Tyr Ser Met Ser
 1               5

<210> SEQ ID NO 192
<211> LENGTH: 13
<212> TYPE: PRT
<213> ORGANISM: Homo sapiens

<400> SEQUENCE: 192

Trp Val Ser Gly Ile Ser Gly Gly Gly Ala Tyr Lys Tyr
 1               5                  10

<210> SEQ ID NO 193
<211> LENGTH: 14
<212> TYPE: PRT
<213> ORGANISM: Homo sapiens

<400> SEQUENCE: 193

Ala Arg Ala Gly Ser Arg Ser Pro Arg Tyr Tyr His Phe Asp
 1               5                  10

<210> SEQ ID NO 194
<211> LENGTH: 121
<212> TYPE: PRT
<213> ORGANISM: Homo sapiens

<400> SEQUENCE: 194

Gln Val Gln Leu Leu Glu Ser Gly Gly Asp Leu Val His Pro Gly Gly
 1               5                  10                  15

Ser Leu Arg Arg Ser Gly Ala His Arg Gly Phe Thr Phe Met Ser Asn
            20                  25                  30

Ala Trp Ser Gly Val Leu Gln Ala Pro Gly Lys Gly Arg Lys Gly Gly
        35                  40                  45

Val Gly Phe Ser Arg Gly Pro Gly Asn Ile Thr Tyr Pro Asn Ser Ser
    50                  55                  60

Lys Gly Pro Phe Pro Phe Pro Arg Asp Asn Ser Asn Pro Leu Asn Trp
65                  70                  75                  80

Lys Met Asn Ser Leu Arg Ala Glu Asn Thr Ala Phe Tyr Tyr Cys Ala
                85                  90                  95

Arg Val Ala Arg Thr Tyr Glu Met His Tyr Gly Phe Asp Tyr Gly Gly
            100                 105                 110

Gln Gly Thr Leu Val Thr Val Ser Ser
        115                 120

<210> SEQ ID NO 195
<211> LENGTH: 6
<212> TYPE: PRT
<213> ORGANISM: Homo sapiens

<400> SEQUENCE: 195

Met Ser Asn Ala Trp Ser
 1               5

<210> SEQ ID NO 196
<211> LENGTH: 15

<212> TYPE: PRT
<213> ORGANISM: Homo sapiens

<400> SEQUENCE: 196

Gly Gly Val Gly Phe Ser Arg Gly Pro Gly Asn Ile Thr Arg Val
1               5                   10                  15

<210> SEQ ID NO 197
<211> LENGTH: 12
<212> TYPE: PRT
<213> ORGANISM: Homo sapiens

<400> SEQUENCE: 197

Ala Arg Thr Tyr Glu Met His Tyr Gly Phe Asp Tyr
1               5                   10

<210> SEQ ID NO 198
<211> LENGTH: 122
<212> TYPE: PRT
<213> ORGANISM: Homo sapiens

<400> SEQUENCE: 198

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Gly Ile Ser Gly Ser Gly Asn Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Arg Ser Tyr Glu Arg Asp Tyr Gly Phe Asp Tyr Trp
            100                 105                 110

Gly Gln Gly Thr Leu Val Thr Val Ser Ser
        115                 120

<210> SEQ ID NO 199
<211> LENGTH: 6
<212> TYPE: PRT
<213> ORGANISM: Homo sapiens

<400> SEQUENCE: 199

Ser Ser Tyr Ala Met Ser
1               5

<210> SEQ ID NO 200
<211> LENGTH: 16
<212> TYPE: PRT
<213> ORGANISM: Homo sapiens

<400> SEQUENCE: 200

Trp Val Ala Gly Ile Ser Gly Gly Ser Gly Asn Ile Ser Ala Arg Val
1               5                   10                  15

<210> SEQ ID NO 201
<211> LENGTH: 11
<212> TYPE: PRT
<213> ORGANISM: Homo sapiens

<400> SEQUENCE: 201

Ala Arg Ser Tyr Glu Arg Asp Tyr Gly Phe Asp
1               5                   10

<210> SEQ ID NO 202
<211> LENGTH: 122
<212> TYPE: PRT
<213> ORGANISM: Homo sapiens

<400> SEQUENCE: 202

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Arg Ile Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ser Leu Gly Gly Asn Tyr Tyr Phe Asp Tyr Trp
            100                 105                 110

Gly Gln Gly Thr Leu Val Thr Val Ser Ser
        115                 120

<210> SEQ ID NO 203
<211> LENGTH: 6
<212> TYPE: PRT
<213> ORGANISM: Homo sapiens

<400> SEQUENCE: 203

Ser Asn Tyr Gly Met His
1               5

<210> SEQ ID NO 204
<211> LENGTH: 13
<212> TYPE: PRT
<213> ORGANISM: Homo sapiens

<400> SEQUENCE: 204

Trp Val Ala Arg Ile Ser Gly Gly Gly Tyr Thr Tyr
1               5                   10

<210> SEQ ID NO 205
<211> LENGTH: 14
<212> TYPE: PRT
<213> ORGANISM: Homo sapiens

<400> SEQUENCE: 205

Ala Arg Glu Asp Ser Leu Gly Gly Asn Tyr Tyr Phe Asp
1               5                   10

<210> SEQ ID NO 206
<211> LENGTH: 123
<212> TYPE: PRT
<213> ORGANISM: Homo sapiens

<400> SEQUENCE: 206

Glu Val Gln Leu Val Glu Ser Gly Gly Gly Leu Val Lys Pro Gly Gly

```
                1               5                   10                  15
            Ser Leu Arg Leu Ser Cys Ala Ala Ser Gly Phe Thr Phe Ser Ser Tyr
                            20                  25                  30

Gly Met Ser Trp Val Arg Gln Ala Pro Gly Lys Gly Leu Glu Trp Val
                            35                  40                  45

Ala Gly Ile Asn Ser Ser Gly Arg Asn Lys Tyr Tyr Ala Asp Ser Val
                            50                  55                  60

Lys Gly Arg Phe Thr Ile Ser Arg Asp Asn Ala Lys Asn Ser Leu Tyr
            65                  70                  75                  80

Leu Gln Met Asn Ser Leu Arg Ala Glu Asp Thr Ala Val Tyr Tyr Cys
                            85                  90                  95

Ala Arg Gly Phe Tyr Ala Val Arg Ser Asp Val Gly Ala Met Asp Tyr
                            100                 105                 110

Trp Gly Gln Gly Thr Leu Val Thr Val Ser Ser
                            115                 120

<210> SEQ ID NO 207
<211> LENGTH: 6
<212> TYPE: PRT
<213> ORGANISM: Homo sapiens

<400> SEQUENCE: 207

Ser Ser Tyr Gly Met Ser
1               5

<210> SEQ ID NO 208
<211> LENGTH: 13
<212> TYPE: PRT
<213> ORGANISM: Homo sapiens

<400> SEQUENCE: 208

Trp Val Ala Gly Ile Asn Ser Ser Gly Arg Asn Lys Tyr
1               5                   10

<210> SEQ ID NO 209
<211> LENGTH: 15
<212> TYPE: PRT
<213> ORGANISM: Homo sapiens

<400> SEQUENCE: 209

Ala Arg Gly Phe Tyr Ala Val Arg Ser Asp Val Gly Ala Met Asp
1               5                   10                  15

<210> SEQ ID NO 210
<211> LENGTH: 123
<212> TYPE: PRT
<213> ORGANISM: Homo sapiens

<400> SEQUENCE: 210

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
                35                  40                  45

Ser Ser Ile Ser Ser Ser Ser Ser Tyr Ile Tyr Tyr Ala Asp Ser Val
                50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Ala Phe Asn Ala Trp Arg Gly Asn Glu Ser Asn Gly Asp Tyr
            100                 105                 110

Trp Gly Gln Gly Thr Leu Val Thr Val Ser Ser
        115                 120

<210> SEQ ID NO 211
<211> LENGTH: 6
<212> TYPE: PRT
<213> ORGANISM: Homo sapiens

<400> SEQUENCE: 211

Ser Asn Tyr Gly Met His
1               5

<210> SEQ ID NO 212
<211> LENGTH: 13
<212> TYPE: PRT
<213> ORGANISM: Homo sapiens

<400> SEQUENCE: 212

Trp Val Ser Ser Ile Ser Ser Ser Ser Tyr Ile Tyr
1               5                   10

<210> SEQ ID NO 213
<211> LENGTH: 15
<212> TYPE: PRT
<213> ORGANISM: Homo sapiens

<400> SEQUENCE: 213

Ala Arg Ala Phe Asn Ala Trp Arg Gly Asn Glu Ser Asn Gly Asp
1               5                   10                  15

<210> SEQ ID NO 214
<211> LENGTH: 121
<212> TYPE: PRT
<213> ORGANISM: Homo sapiens

<400> SEQUENCE: 214

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 215
<211> LENGTH: 6
<212> TYPE: PRT
<213> ORGANISM: Homo sapiens

<400> SEQUENCE: 215

Arg Thr Tyr Gly Met His
1               5

<210> SEQ ID NO 216
<211> LENGTH: 13
<212> TYPE: PRT
<213> ORGANISM: Homo sapiens

<400> SEQUENCE: 216

Trp Val Ala Gly Ile Asn Tyr Ser Gly Asn Asn Lys Tyr
1               5                   10

<210> SEQ ID NO 217
<211> LENGTH: 13
<212> TYPE: PRT
<213> ORGANISM: Homo sapiens

<400> SEQUENCE: 217

Ala Arg Asp Ser Ser Thr Thr Arg Thr Arg Ala Leu Asp
1               5                   10

<210> SEQ ID NO 218
<211> LENGTH: 121
<212> TYPE: PRT
<213> ORGANISM: Homo sapiens

<400> SEQUENCE: 218

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 219
<211> LENGTH: 6
<212> TYPE: PRT
<213> ORGANISM: Homo sapiens

<400> SEQUENCE: 219

Arg Ser Tyr Gly Met His
1               5

<210> SEQ ID NO 220
<211> LENGTH: 13
<212> TYPE: PRT
<213> ORGANISM: Homo sapiens

<400> SEQUENCE: 220

```
Trp Val Ala Gly Ile Asn Tyr Ser Gly Asn Asn Lys Tyr
  1               5                  10
```

<210> SEQ ID NO 221
<211> LENGTH: 13
<212> TYPE: PRT
<213> ORGANISM: Homo sapiens

<400> SEQUENCE: 221

```
Ala Arg Asp Ser Ser Thr Thr Arg Thr Arg Ala Leu Asp
  1               5                  10
```

<210> SEQ ID NO 222
<211> LENGTH: 121
<212> TYPE: PRT
<213> ORGANISM: Homo sapiens

<400> SEQUENCE: 222

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
             35                  40                  45

Ala Gly Ile Asn Tyr Ser Gly Asn Asn Lys Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
            115                 120
```

<210> SEQ ID NO 223
<211> LENGTH: 6
<212> TYPE: PRT
<213> ORGANISM: Homo sapiens

<400> SEQUENCE: 223

```
Ser Ser Phe Gly Met His
  1               5
```

<210> SEQ ID NO 224
<211> LENGTH: 13
<212> TYPE: PRT
<213> ORGANISM: Homo sapiens

<400> SEQUENCE: 224

```
Trp Val Ala Gly Ile Asn Tyr Ser Gly Asn Asn Lys Tyr
  1               5                  10
```

<210> SEQ ID NO 225
<211> LENGTH: 13
<212> TYPE: PRT
<213> ORGANISM: Homo sapiens

<400> SEQUENCE: 225

```
Ala Arg Asp Ser Ser Thr Thr Arg Thr Arg Ala Leu Asp
  1               5                  10
```

<210> SEQ ID NO 226
<211> LENGTH: 121
<212> TYPE: PRT
<213> ORGANISM: Homo sapiens

<400> SEQUENCE: 226

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ser Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 227
<211> LENGTH: 6
<212> TYPE: PRT
<213> ORGANISM: Homo sapiens

<400> SEQUENCE: 227

Ser Thr Tyr Gly Met His
1               5

<210> SEQ ID NO 228
<211> LENGTH: 13
<212> TYPE: PRT
<213> ORGANISM: Homo sapiens

<400> SEQUENCE: 228

Trp Val Ser Gly Ile Asn Tyr Ser Gly Asn Asn Lys Tyr
1               5                   10

<210> SEQ ID NO 229
<211> LENGTH: 13
<212> TYPE: PRT
<213> ORGANISM: Homo sapiens

<400> SEQUENCE: 229

Ala Arg Asp Ser Ser Thr Thr Arg Thr Arg Ala Leu Asp
1               5                   10

<210> SEQ ID NO 230
<211> LENGTH: 121
<212> TYPE: PRT
<213> ORGANISM: Homo sapiens

<400> SEQUENCE: 230

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
                100                 105                 110

Gln Gly Thr Leu Val Thr Val Ser Ser
        115                 120

<210> SEQ ID NO 231
<211> LENGTH: 6
<212> TYPE: PRT
<213> ORGANISM: Homo sapiens

<400> SEQUENCE: 231

Ser Asn Tyr Gly Met His
1               5

<210> SEQ ID NO 232
<211> LENGTH: 13
<212> TYPE: PRT
<213> ORGANISM: Homo sapiens

<400> SEQUENCE: 232

Trp Val Ala Gly Ile Asn Tyr Ser Gly Asn Asn Lys Tyr
1               5                   10

<210> SEQ ID NO 233
<211> LENGTH: 13
<212> TYPE: PRT
<213> ORGANISM: Homo sapiens

<400> SEQUENCE: 233

Ala Arg Asp Ser Ser Thr Thr Arg Thr Arg Ala Leu Asp
1               5                   10

<210> SEQ ID NO 234
<211> LENGTH: 121
<212> TYPE: PRT
<213> ORGANISM: Homo sapiens

<400> SEQUENCE: 234

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
                100                 105                 110

Gln Gly Thr Leu Val Thr Val Ser Ser
        115                 120

<210> SEQ ID NO 235
<211> LENGTH: 6
<212> TYPE: PRT
<213> ORGANISM: Homo sapiens

<400> SEQUENCE: 235

Ser Ser Tyr Gly Met His
1               5

<210> SEQ ID NO 236
<211> LENGTH: 13
<212> TYPE: PRT
<213> ORGANISM: Homo sapiens

<400> SEQUENCE: 236

Trp Val Ala Gly Ile Asn Tyr Ser Gly Asn Asn Lys Tyr
1               5                   10

<210> SEQ ID NO 237
<211> LENGTH: 13
<212> TYPE: PRT
<213> ORGANISM: Homo sapiens

<400> SEQUENCE: 237

Ala Arg Asp Ser Ser Thr Thr Arg Thr Arg Ala Leu Asp
1               5                   10

<210> SEQ ID NO 238
<211> LENGTH: 121
<212> TYPE: PRT
<213> ORGANISM: Homo sapiens

<400> SEQUENCE: 238

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Phe
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 239
<211> LENGTH: 6
<212> TYPE: PRT
<213> ORGANISM: Homo sapiens

<400> SEQUENCE: 239

Arg Ser Phe Gly Met His
1               5

<210> SEQ ID NO 240
<211> LENGTH: 13
<212> TYPE: PRT
<213> ORGANISM: Homo sapiens

<400> SEQUENCE: 240

Trp Val Ala Gly Ile Asn Tyr Ser Gly Asn Asn Lys Tyr
1               5                   10

<210> SEQ ID NO 241
<211> LENGTH: 13
<212> TYPE: PRT
<213> ORGANISM: Homo sapiens

<400> SEQUENCE: 241

Ala Arg Asp Ser Ser Thr Thr Arg Thr Arg Ala Leu Asp
1               5                   10

<210> SEQ ID NO 242
<211> LENGTH: 121
<212> TYPE: PRT
<213> ORGANISM: Homo sapiens

<400> SEQUENCE: 242

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Gly Ile Asn Phe Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 243
<211> LENGTH: 6
<212> TYPE: PRT
<213> ORGANISM: Homo sapiens

<400> SEQUENCE: 243

Ser Ser Tyr Gly Met His
1               5

<210> SEQ ID NO 244
<211> LENGTH: 13
<212> TYPE: PRT
<213> ORGANISM: Homo sapiens

<400> SEQUENCE: 244

Trp Val Ala Gly Ile Asn Phe Ser Gly Asn Asn Lys Tyr
1               5                   10

<210> SEQ ID NO 245

```
<211> LENGTH: 13
<212> TYPE: PRT
<213> ORGANISM: Homo sapiens

<400> SEQUENCE: 245

Ala Arg Asp Ser Ser Thr Thr Arg Thr Arg Ala Leu Asp
 1               5                  10

<210> SEQ ID NO 246
<211> LENGTH: 121
<212> TYPE: PRT
<213> ORGANISM: Homo sapiens

<400> SEQUENCE: 246

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Thr Gly Ile Asn Tyr Ser Gly Asn Asn Arg Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 247
<211> LENGTH: 6
<212> TYPE: PRT
<213> ORGANISM: Homo sapiens

<400> SEQUENCE: 247

Ser Ser Tyr Gly Met His
 1               5

<210> SEQ ID NO 248
<211> LENGTH: 13
<212> TYPE: PRT
<213> ORGANISM: Homo sapiens

<400> SEQUENCE: 248

Trp Val Thr Gly Ile Asn Tyr Ser Gly Asn Asn Arg Tyr
 1               5                  10

<210> SEQ ID NO 249
<211> LENGTH: 13
<212> TYPE: PRT
<213> ORGANISM: Homo sapiens

<400> SEQUENCE: 249

Ala Arg Asp Ser Ser Thr Thr Arg Thr Arg Ala Leu Asp
 1               5                  10

<210> SEQ ID NO 250
<211> LENGTH: 121
<212> TYPE: PRT
<213> ORGANISM: Homo sapiens
```

-continued

<400> SEQUENCE: 250

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Gly Asn Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120

<210> SEQ ID NO 251
<211> LENGTH: 6
<212> TYPE: PRT
<213> ORGANISM: Homo sapiens

<400> SEQUENCE: 251

Ser Asp Tyr Gly Met His
1               5

<210> SEQ ID NO 252
<211> LENGTH: 13
<212> TYPE: PRT
<213> ORGANISM: Homo sapiens

<400> SEQUENCE: 252

Trp Val Ala Gly Asn Asn Tyr Ser Gly Asn Asn Lys Tyr
1               5                   10

<210> SEQ ID NO 253
<211> LENGTH: 13
<212> TYPE: PRT
<213> ORGANISM: Homo sapiens

<400> SEQUENCE: 253

Ala Arg Asp Ser Ser Thr Thr Arg Thr Arg Ala Leu Asp
1               5                   10

<210> SEQ ID NO 254
<211> LENGTH: 121
<212> TYPE: PRT
<213> ORGANISM: Homo sapiens

<400> SEQUENCE: 254

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Arg Tyr Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Thr Arg Thr Arg Ala Leu Asp Tyr Trp Gly
            100                 105                 110

Gln Gly Thr Leu Val Thr Val Ser Ser
        115                 120
```

<210> SEQ ID NO 255
<211> LENGTH: 6
<212> TYPE: PRT
<213> ORGANISM: Homo sapiens

<400> SEQUENCE: 255

```
Ser Asp Tyr Gly Met His
 1               5
```

<210> SEQ ID NO 256
<211> LENGTH: 13
<212> TYPE: PRT
<213> ORGANISM: Homo sapiens

<400> SEQUENCE: 256

```
Trp Val Ala Gly Ile Asn Tyr Ser Gly Asn Asn Lys Tyr
 1               5                  10
```

<210> SEQ ID NO 257
<211> LENGTH: 13
<212> TYPE: PRT
<213> ORGANISM: Homo sapiens

<400> SEQUENCE: 257

```
Ala Arg Asp Ser Ser Thr Thr Arg Thr Arg Ala Leu Asp
 1               5                  10
```

<210> SEQ ID NO 258
<211> LENGTH: 121
<212> TYPE: PRT
<213> ORGANISM: Homo sapiens

<400> SEQUENCE: 258

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Arg Ser Phe
             20                  25                  30

Gly Met His Trp Val Arg Gln Ala Pro Gly Lys Gly Leu Glu Trp Val
         35                  40                  45

Ala Gly Ile Asn Tyr Ser Gly Asn Asn Arg Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Val Arg Thr Arg Ala Leu Asp Tyr Trp Gly
            100                 105                 110

Gln Gly Thr Leu Val Thr Val Ser Ser
        115                 120
```

```
<210> SEQ ID NO 259
<211> LENGTH: 6
<212> TYPE: PRT
<213> ORGANISM: Homo sapiens

<400> SEQUENCE: 259

Arg Ser Phe Gly Met His
1               5

<210> SEQ ID NO 260
<211> LENGTH: 13
<212> TYPE: PRT
<213> ORGANISM: Homo sapiens

<400> SEQUENCE: 260

Trp Val Ala Gly Ile Asn Tyr Ser Gly Asn Asn Lys Tyr
1               5                   10

<210> SEQ ID NO 261
<211> LENGTH: 13
<212> TYPE: PRT
<213> ORGANISM: Homo sapiens

<400> SEQUENCE: 261

Ala Arg Asp Ser Ser Thr Val Arg Thr Arg Ala Leu Asp
1               5                   10

<210> SEQ ID NO 262
<211> LENGTH: 121
<212> TYPE: PRT
<213> ORGANISM: Homo sapiens

<400> SEQUENCE: 262

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Arg Ser Phe
                20                  25                  30

Gly Met His Trp Val Arg Gln Ala Pro Gly Lys Gly Leu Glu Trp Val
            35                  40                  45

Ala Gly Ile Asn Tyr Ser Gly Asn Asn Arg Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ser Leu Asp Tyr Trp Gly
            100                 105                 110

Gln Gly Thr Leu Val Thr Val Ser Ser
        115                 120

<210> SEQ ID NO 263
<211> LENGTH: 6
<212> TYPE: PRT
<213> ORGANISM: Homo sapiens

<400> SEQUENCE: 263

Arg Ser Phe Gly Met His
1               5

<210> SEQ ID NO 264
<211> LENGTH: 13
<212> TYPE: PRT
```

<213> ORGANISM: Homo sapiens

<400> SEQUENCE: 264

Trp Val Ala Gly Ile Asn Tyr Ser Gly Asn Asn Lys Tyr
1               5                   10

<210> SEQ ID NO 265
<211> LENGTH: 13
<212> TYPE: PRT
<213> ORGANISM: Homo sapiens

<400> SEQUENCE: 265

Ala Arg Asp Ser Ser Thr Val Arg Thr Arg Ser Leu Asp
1               5                   10

<210> SEQ ID NO 266
<211> LENGTH: 121
<212> TYPE: PRT
<213> ORGANISM: Homo sapiens

<400> SEQUENCE: 266

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Phe
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Arg Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Ile Arg Thr Arg Ser Leu Asp Tyr Trp Gly
            100                 105                 110

Gln Gly Thr Leu Val Thr Val Ser Ser
        115                 120

<210> SEQ ID NO 267
<211> LENGTH: 6
<212> TYPE: PRT
<213> ORGANISM: Homo sapiens

<400> SEQUENCE: 267

Arg Ser Phe Gly Met His
1               5

<210> SEQ ID NO 268
<211> LENGTH: 13
<212> TYPE: PRT
<213> ORGANISM: Homo sapiens

<400> SEQUENCE: 268

Trp Val Ala Gly Ile Asn Tyr Ser Gly Asn Asn Lys Tyr
1               5                   10

<210> SEQ ID NO 269
<211> LENGTH: 13
<212> TYPE: PRT
<213> ORGANISM: Homo sapiens

<400> SEQUENCE: 269

Ala Arg Asp Ser Ser Thr Ile Arg Thr Arg Ser Leu Asp
 1               5                  10

<210> SEQ ID NO 270
<211> LENGTH: 121
<212> TYPE: PRT
<213> ORGANISM: Homo sapiens

<400> SEQUENCE: 270

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ser Gly Ile Asn Tyr Ser Gly Asn Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ser Leu Asp Tyr Trp Gly
            100                 105                 110

Gln Gly Thr Leu Val Thr Val Ser Ser
        115                 120

<210> SEQ ID NO 271
<211> LENGTH: 6
<212> TYPE: PRT
<213> ORGANISM: Homo sapiens

<400> SEQUENCE: 271

Ser Thr Tyr Gly Met His
 1               5

<210> SEQ ID NO 272
<211> LENGTH: 13
<212> TYPE: PRT
<213> ORGANISM: Homo sapiens

<400> SEQUENCE: 272

Trp Val Ser Gly Ile Asn Tyr Ser Gly Asn Asn Ile Tyr
 1               5                  10

<210> SEQ ID NO 273
<211> LENGTH: 13
<212> TYPE: PRT
<213> ORGANISM: Homo sapiens

<400> SEQUENCE: 273

Ala Arg Asp Ser Ser Thr Thr Arg Thr Arg Ser Leu Asp
 1               5                  10

<210> SEQ ID NO 274
<211> LENGTH: 121
<212> TYPE: PRT
<213> ORGANISM: Homo sapiens

<400> SEQUENCE: 274

Glu Val Gln Leu Val Glu Ser Gly Gly Gly Leu Val Lys Pro Gly Gly
 1               5                  10                  15

```
Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ser Leu Asp Tyr Trp Gly
            100                 105                 110

Gln Gly Thr Leu Val Thr Val Ser Ser
        115                 120
```

<210> SEQ ID NO 275
<211> LENGTH: 6
<212> TYPE: PRT
<213> ORGANISM: Homo sapiens

<400> SEQUENCE: 275

```
Ser Thr Tyr Gly Met His
1               5
```

<210> SEQ ID NO 276
<211> LENGTH: 13
<212> TYPE: PRT
<213> ORGANISM: Homo sapiens

<400> SEQUENCE: 276

```
Trp Val Ala Gly Ile Asn Tyr Ser Gly Asn Asn Ile Tyr
1               5                   10
```

<210> SEQ ID NO 277
<211> LENGTH: 13
<212> TYPE: PRT
<213> ORGANISM: Homo sapiens

<400> SEQUENCE: 277

```
Ala Arg Asp Ser Ser Thr Thr Arg Thr Arg Ser Leu Asp
1               5                   10
```

<210> SEQ ID NO 278
<211> LENGTH: 121
<212> TYPE: PRT
<213> ORGANISM: Homo sapiens

<400> SEQUENCE: 278

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Gly Val Asn Tyr Ser Gly Asn Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95

Ala Arg Asp Ser Ser Thr Thr Arg Thr Arg Ser Leu Asp Tyr Trp Gly
            100                 105                 110

Gln Gly Thr Leu Val Thr Val Ser Ser
            115                 120

<210> SEQ ID NO 279
<211> LENGTH: 6
<212> TYPE: PRT
<213> ORGANISM: Homo sapiens

<400> SEQUENCE: 279

Ser Asp Tyr Gly Met His
1               5

<210> SEQ ID NO 280
<211> LENGTH: 13
<212> TYPE: PRT
<213> ORGANISM: Homo sapiens

<400> SEQUENCE: 280

Trp Val Ala Gly Val Asn Tyr Ser Gly Asn Asn Ile Tyr
1               5                   10

<210> SEQ ID NO 281
<211> LENGTH: 13
<212> TYPE: PRT
<213> ORGANISM: Homo sapiens

<400> SEQUENCE: 281

Ala Arg Asp Ser Ser Thr Thr Arg Thr Arg Ser Leu Asp
1               5                   10

<210> SEQ ID NO 282
<211> LENGTH: 121
<212> TYPE: PRT
<213> ORGANISM: Homo sapiens

<400> SEQUENCE: 282

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Phe
            20                  25                  30

Gly Met His Trp Val Arg Gln Ala Pro Gly Lys Gly Leu Glu Trp Val
        35                  40                  45

Ala Gly Val Asn Tyr Ser Gly Asn Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Gly Arg Ser Leu Asp Tyr Trp Gly
            100                 105                 110

Gln Gly Thr Leu Val Thr Val Ser Ser
            115                 120

<210> SEQ ID NO 283
<211> LENGTH: 6
<212> TYPE: PRT
<213> ORGANISM: Homo sapiens
```

<400> SEQUENCE: 283

Arg Ser Phe Gly Met His
1               5

<210> SEQ ID NO 284
<211> LENGTH: 13
<212> TYPE: PRT
<213> ORGANISM: Homo sapiens

<400> SEQUENCE: 284

Trp Val Ala Gly Val Asn Tyr Ser Gly Asn Asn Ile Tyr
1               5                   10

<210> SEQ ID NO 285
<211> LENGTH: 13
<212> TYPE: PRT
<213> ORGANISM: Homo sapiens

<400> SEQUENCE: 285

Ala Arg Asp Ser Ser Thr Asn Arg Gly Arg Ser Leu Asp
1               5                   10

<210> SEQ ID NO 286
<211> LENGTH: 121
<212> TYPE: PRT
<213> ORGANISM: Homo sapiens

<400> SEQUENCE: 286

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Arg Ser Phe
                20                  25                  30

Gly Met His Trp Val Arg Gln Ala Pro Gly Lys Gly Leu Glu Trp Val
            35                  40                  45

Ala Gly Val Asn Tyr Ser Gly Asn Asn Ile Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ser Ile Arg Gly Arg Pro Leu Asp Tyr Trp Gly
            100                 105                 110

Gln Gly Thr Leu Val Thr Val Ser Ser
        115                 120

<210> SEQ ID NO 287
<211> LENGTH: 6
<212> TYPE: PRT
<213> ORGANISM: Homo sapiens

<400> SEQUENCE: 287

Arg Ser Phe Gly Met His
1               5

<210> SEQ ID NO 288
<211> LENGTH: 13
<212> TYPE: PRT
<213> ORGANISM: Homo sapiens

<400> SEQUENCE: 288

Trp Val Ala Gly Val Asn Tyr Ser Gly Asn Asn Ile Tyr

```
                1               5                    10
```

<210> SEQ ID NO 289
<211> LENGTH: 13
<212> TYPE: PRT
<213> ORGANISM: Homo sapiens

<400> SEQUENCE: 289

```
Ala Arg Asp Arg Ser Ser Ile Arg Gly Arg Pro Leu Asp
1               5                   10
```

<210> SEQ ID NO 290
<211> LENGTH: 121
<212> TYPE: PRT
<213> ORGANISM: Homo sapiens

<400> SEQUENCE: 290

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Ser Tyr Ser Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Ala Val Arg Gly Arg Pro Leu Asp Tyr Trp Gly
            100                 105                 110

Gln Gly Thr Leu Val Thr Val Ser Ser
        115                 120
```

<210> SEQ ID NO 291
<211> LENGTH: 6
<212> TYPE: PRT
<213> ORGANISM: Homo sapiens

<400> SEQUENCE: 291

```
Ser Asn Phe Gly Met His
1               5
```

<210> SEQ ID NO 292
<211> LENGTH: 13
<212> TYPE: PRT
<213> ORGANISM: Homo sapiens

<400> SEQUENCE: 292

```
Trp Val Ala Ala Ile Ser Tyr Ser Gly Ser Tyr Thr Tyr
1               5                   10
```

<210> SEQ ID NO 293
<211> LENGTH: 13
<212> TYPE: PRT
<213> ORGANISM: Homo sapiens

<400> SEQUENCE: 293

```
Ala Arg Asp Ser Ser Ala Val Arg Gly Arg Pro Leu Asp
1               5                   10
```

```
<210> SEQ ID NO 294
<211> LENGTH: 121
<212> TYPE: PRT
<213> ORGANISM: Homo sapiens

<400> SEQUENCE: 294

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Thr Arg Ala Leu Asp Tyr Trp Gly
            100                 105                 110

Gln Gly Thr Leu Val Thr Val Ser Ser
        115                 120

<210> SEQ ID NO 295
<211> LENGTH: 6
<212> TYPE: PRT
<213> ORGANISM: Homo sapiens

<400> SEQUENCE: 295

Ser Thr Tyr Gly Met His
 1               5

<210> SEQ ID NO 296
<211> LENGTH: 13
<212> TYPE: PRT
<213> ORGANISM: Homo sapiens

<400> SEQUENCE: 296

Trp Val Ala Gly Ile Asn Tyr Ser Gly Asn Asn Lys Tyr
 1               5                  10

<210> SEQ ID NO 297
<211> LENGTH: 13
<212> TYPE: PRT
<213> ORGANISM: Homo sapiens

<400> SEQUENCE: 297

Ala Arg Asp Ser Ser Thr Asn Arg Thr Arg Ala Leu Asp
 1               5                  10

<210> SEQ ID NO 298
<211> LENGTH: 121
<212> TYPE: PRT
<213> ORGANISM: Homo sapiens

<400> SEQUENCE: 298

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
```

```
                35                  40                  45
Ala Gly Ile Asn Tyr Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Leu Thr Arg Ser Leu Asp Tyr Trp Gly
            100                 105                 110

Gln Gly Thr Leu Val Thr Val Ser Ser
            115                 120

<210> SEQ ID NO 299
<211> LENGTH: 6
<212> TYPE: PRT
<213> ORGANISM: Homo sapiens

<400> SEQUENCE: 299

Ser Thr Tyr Gly Met His
 1               5

<210> SEQ ID NO 300
<211> LENGTH: 13
<212> TYPE: PRT
<213> ORGANISM: Homo sapiens

<400> SEQUENCE: 300

Trp Val Ala Gly Ile Asn Tyr Ser Gly Asn Asn Lys Tyr
 1               5                  10

<210> SEQ ID NO 301
<211> LENGTH: 13
<212> TYPE: PRT
<213> ORGANISM: Homo sapiens

<400> SEQUENCE: 301

Ala Arg Asp Ser Ser Thr Asn Leu Thr Arg Ser Leu Asp
 1               5                  10

<210> SEQ ID NO 302
<211> LENGTH: 121
<212> TYPE: PRT
<213> ORGANISM: Homo sapiens

<400> SEQUENCE: 302

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Leu Thr Arg Ser Leu Asp Tyr Trp Gly
            100                 105                 110
```

Gln Gly Thr Leu Val Thr Val Ser Ser
        115                 120

<210> SEQ ID NO 303
<211> LENGTH: 6
<212> TYPE: PRT
<213> ORGANISM: Homo sapiens

<400> SEQUENCE: 303

Ser Thr Tyr Gly Met His
1               5

<210> SEQ ID NO 304
<211> LENGTH: 13
<212> TYPE: PRT
<213> ORGANISM: Homo sapiens

<400> SEQUENCE: 304

Trp Val Ala Gly Ile Asn Tyr Ser Gly Asn Asn Lys Tyr
1               5                   10

<210> SEQ ID NO 305
<211> LENGTH: 13
<212> TYPE: PRT
<213> ORGANISM: Homo sapiens

<400> SEQUENCE: 305

Ala Arg Asp Ser Ser Thr Asn Leu Thr Arg Thr Leu Asp
1               5                   10

<210> SEQ ID NO 306
<211> LENGTH: 121
<212> TYPE: PRT
<213> ORGANISM: Homo sapiens

<400> SEQUENCE: 306

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Leu Thr Arg Ala Leu Asp Tyr Trp Gly
            100                 105                 110

Gln Gly Thr Leu Val Thr Val Ser Ser
        115                 120

<210> SEQ ID NO 307
<211> LENGTH: 6
<212> TYPE: PRT
<213> ORGANISM: Homo sapiens

<400> SEQUENCE: 307

Ser Thr Tyr Gly Met His
1               5

```
<210> SEQ ID NO 308
<211> LENGTH: 13
<212> TYPE: PRT
<213> ORGANISM: Homo sapiens

<400> SEQUENCE: 308

Trp Val Ala Gly Ile Asn Tyr Ser Gly Asn Asn Lys Tyr
 1               5                  10

<210> SEQ ID NO 309
<211> LENGTH: 13
<212> TYPE: PRT
<213> ORGANISM: Homo sapiens

<400> SEQUENCE: 309

Ala Arg Asp Ser Ser Thr Asn Leu Thr Arg Ala Leu Asp
 1               5                  10

<210> SEQ ID NO 310
<211> LENGTH: 121
<212> TYPE: PRT
<213> ORGANISM: Homo sapiens

<400> SEQUENCE: 310

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
             20                  25                  30

Gly Met His Trp Val Arg Gln Ala Pro Gly Lys Gly Leu Glu Trp Val
         35                  40                  45

Ala Gly Ile Asn Tyr Ser Gly Asn Asn Lys Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Asn Arg Thr Arg Ala Leu Asp Tyr Trp Gly
            100                 105                 110

Gln Gly Thr Leu Val Thr Val Ser Ser
        115                 120

<210> SEQ ID NO 311
<211> LENGTH: 6
<212> TYPE: PRT
<213> ORGANISM: Homo sapiens

<400> SEQUENCE: 311

Ser Thr Tyr Gly Met His
 1               5

<210> SEQ ID NO 312
<211> LENGTH: 13
<212> TYPE: PRT
<213> ORGANISM: Homo sapiens

<400> SEQUENCE: 312

Trp Val Ala Gly Ile Asn Tyr Ser Gly Asn Asn Lys Tyr
 1               5                  10

<210> SEQ ID NO 313
<211> LENGTH: 13
```

<212> TYPE: PRT
<213> ORGANISM: Homo sapiens

<400> SEQUENCE: 313

Ala Arg Asp Ser Ser Thr Asn Arg Thr Arg Ala Leu Asp
1               5                   10

<210> SEQ ID NO 314
<211> LENGTH: 121
<212> TYPE: PRT
<213> ORGANISM: Homo sapiens

<400> SEQUENCE: 314

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Trp Thr Arg Ala Leu Asp Tyr Trp Gly
            100                 105                 110

Gln Gly Thr Leu Val Thr Val Ser Ser
        115                 120

<210> SEQ ID NO 315
<211> LENGTH: 6
<212> TYPE: PRT
<213> ORGANISM: Homo sapiens

<400> SEQUENCE: 315

Ser Thr Tyr Gly Met His
1               5

<210> SEQ ID NO 316
<211> LENGTH: 13
<212> TYPE: PRT
<213> ORGANISM: Homo sapiens

<400> SEQUENCE: 316

Trp Val Ala Gly Ile Asn Tyr Ser Gly Asn Asn Lys Tyr
1               5                   10

<210> SEQ ID NO 317
<211> LENGTH: 13
<212> TYPE: PRT
<213> ORGANISM: Homo sapiens

<400> SEQUENCE: 317

Ala Arg Asp Ser Ser Thr Asn Trp Thr Arg Ala Leu Asp
1               5                   10

<210> SEQ ID NO 318
<211> LENGTH: 121
<212> TYPE: PRT
<213> ORGANISM: Homo sapiens

```
<400> SEQUENCE: 318

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Tyr Thr Arg Ala Leu Asp Tyr Trp Gly
            100                 105                 110

Gln Gly Thr Leu Val Thr Val Ser Ser
        115                 120

<210> SEQ ID NO 319
<211> LENGTH: 6
<212> TYPE: PRT
<213> ORGANISM: Homo sapiens

<400> SEQUENCE: 319

Ser Thr Tyr Gly Met His
 1               5

<210> SEQ ID NO 320
<211> LENGTH: 13
<212> TYPE: PRT
<213> ORGANISM: Homo sapiens

<400> SEQUENCE: 320

Trp Val Ala Gly Ile Asn Tyr Ser Gly Asn Asn Lys Tyr
 1               5                  10

<210> SEQ ID NO 321
<211> LENGTH: 13
<212> TYPE: PRT
<213> ORGANISM: Homo sapiens

<400> SEQUENCE: 321

Ala Arg Asp Ser Ser Thr Asn Tyr Thr Arg Ala Leu Asp
 1               5                  10

<210> SEQ ID NO 322
<211> LENGTH: 121
<212> TYPE: PRT
<213> ORGANISM: Homo sapiens

<400> SEQUENCE: 322

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Ser Ser Asn Arg Ser Arg Ser Leu Asp Tyr Trp Gly
            100                 105                 110

Gln Gly Thr Leu Val Thr Val Ser Ser
        115                 120

<210> SEQ ID NO 323
<211> LENGTH: 6
<212> TYPE: PRT
<213> ORGANISM: Homo sapiens

<400> SEQUENCE: 323

Ser Thr Tyr Gly Met His
 1               5

<210> SEQ ID NO 324
<211> LENGTH: 13
<212> TYPE: PRT
<213> ORGANISM: Homo sapiens

<400> SEQUENCE: 324

Trp Val Ala Gly Ile Asn Tyr Ser Gly Asn Asn Lys Tyr
 1               5                  10

<210> SEQ ID NO 325
<211> LENGTH: 13
<212> TYPE: PRT
<213> ORGANISM: Homo sapiens

<400> SEQUENCE: 325

Ala Arg Asp His Ser Ser Asn Arg Ser Arg Ser Leu Asp
 1               5                  10

<210> SEQ ID NO 326
<211> LENGTH: 121
<212> TYPE: PRT
<213> ORGANISM: Homo sapiens

<400> SEQUENCE: 326

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Gly Ile Asn Tyr Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Ser Ser Asn Val Ser Arg Ser Leu Asp Tyr Trp Gly
            100                 105                 110

Gln Gly Thr Leu Val Thr Val Ser Ser
        115                 120

<210> SEQ ID NO 327
```

```
<211> LENGTH: 6
<212> TYPE: PRT
<213> ORGANISM: Homo sapiens

<400> SEQUENCE: 327

Ser Thr Tyr Gly Met His
1               5

<210> SEQ ID NO 328
<211> LENGTH: 13
<212> TYPE: PRT
<213> ORGANISM: Homo sapiens

<400> SEQUENCE: 328

Trp Val Ala Gly Ile Asn Tyr Ser Gly Asn Asn Lys Tyr
1               5                   10

<210> SEQ ID NO 329
<211> LENGTH: 13
<212> TYPE: PRT
<213> ORGANISM: Homo sapiens

<400> SEQUENCE: 329

Ala Arg Asp His Ser Ser Asn Val Ser Arg Ser Leu Asp
1               5                   10

<210> SEQ ID NO 330
<211> LENGTH: 121
<212> TYPE: PRT
<213> ORGANISM: Homo sapiens

<400> SEQUENCE: 330

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Gly Ile Asn Tyr Ser Gly Asn Asn Lys Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Asn Arg Ser Arg Asp Leu Asp Tyr Trp Gly
            100                 105                 110

Gln Gly Thr Leu Val Thr Val Ser Ser
        115                 120

<210> SEQ ID NO 331
<211> LENGTH: 6
<212> TYPE: PRT
<213> ORGANISM: Homo sapiens

<400> SEQUENCE: 331

Ser Thr Tyr Gly Met His
1               5

<210> SEQ ID NO 332
<211> LENGTH: 13
<212> TYPE: PRT
<213> ORGANISM: Homo sapiens
```

<400> SEQUENCE: 332

Trp Val Ala Gly Ile Asn Tyr Ser Gly Asn Asn Lys Tyr
1               5                   10

<210> SEQ ID NO 333
<211> LENGTH: 13
<212> TYPE: PRT
<213> ORGANISM: Homo sapiens

<400> SEQUENCE: 333

Ala Arg Asp His Ser Ser Asn Arg Ser Arg Asp Leu Asp
1               5                   10

<210> SEQ ID NO 334
<211> LENGTH: 121
<212> TYPE: PRT
<213> ORGANISM: Homo sapiens

<400> SEQUENCE: 334

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Asn Phe Ser Arg His Leu Asp Tyr Trp Gly
            100                 105                 110

Gln Gly Thr Leu Val Thr Val Ser Ser
        115                 120

<210> SEQ ID NO 335
<211> LENGTH: 6
<212> TYPE: PRT
<213> ORGANISM: Homo sapiens

<400> SEQUENCE: 335

Ser Thr Tyr Gly Met His
1               5

<210> SEQ ID NO 336
<211> LENGTH: 13
<212> TYPE: PRT
<213> ORGANISM: Homo sapiens

<400> SEQUENCE: 336

Trp Val Ala Gly Ile Asn Tyr Ser Gly Asn Asn Lys Tyr
1               5                   10

<210> SEQ ID NO 337
<211> LENGTH: 13
<212> TYPE: PRT
<213> ORGANISM: Homo sapiens

<400> SEQUENCE: 337

-continued

Ala Arg Asp His Ser Ser Asn Phe Ser Arg His Leu Asp
1               5                   10

<210> SEQ ID NO 338
<211> LENGTH: 121
<212> TYPE: PRT
<213> ORGANISM: Homo sapiens

<400> SEQUENCE: 338

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Thr Arg Gly Arg Ser Leu Asp Tyr Trp Gly
            100                 105                 110

Gln Gly Thr Leu Val Thr Val Ser Ser
        115                 120

<210> SEQ ID NO 339
<211> LENGTH: 6
<212> TYPE: PRT
<213> ORGANISM: Homo sapiens

<400> SEQUENCE: 339

Ser Thr Tyr Gly Met His
1               5

<210> SEQ ID NO 340
<211> LENGTH: 13
<212> TYPE: PRT
<213> ORGANISM: Homo sapiens

<400> SEQUENCE: 340

Trp Val Ala Gly Ile Asn Tyr Ser Gly Asn Asn Lys Tyr
1               5                   10

<210> SEQ ID NO 341
<211> LENGTH: 13
<212> TYPE: PRT
<213> ORGANISM: Homo sapiens

<400> SEQUENCE: 341

Ala Arg Asp His Ser Ser Thr Arg Gly Arg Ser Leu Asp
1               5                   10

<210> SEQ ID NO 342
<211> LENGTH: 121
<212> TYPE: PRT
<213> ORGANISM: Homo sapiens

<400> SEQUENCE: 342

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Thr Arg Ser Arg Ser Leu Asp Tyr Trp Gly
            100                 105                 110

Gln Gly Thr Leu Val Thr Val Ser Ser
        115                 120

<210> SEQ ID NO 343
<211> LENGTH: 6
<212> TYPE: PRT
<213> ORGANISM: Homo sapiens

<400> SEQUENCE: 343

Ser Thr Tyr Gly Met His
1               5

<210> SEQ ID NO 344
<211> LENGTH: 13
<212> TYPE: PRT
<213> ORGANISM: Homo sapiens

<400> SEQUENCE: 344

Trp Val Ala Gly Ile Asn Tyr Ser Gly Asn Asn Lys Tyr
1               5                   10

<210> SEQ ID NO 345
<211> LENGTH: 13
<212> TYPE: PRT
<213> ORGANISM: Homo sapiens

<400> SEQUENCE: 345

Ala Arg Asp His Ser Ser Thr Arg Ser Arg Ser Leu Asp
1               5                   10

<210> SEQ ID NO 346
<211> LENGTH: 121
<212> TYPE: PRT
<213> ORGANISM: Homo sapiens

<400> SEQUENCE: 346

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Asp His Ser Ser Thr Trp Ser Arg Ser Leu Asp Tyr Trp Gly
            100                 105                 110

Gln Gly Thr Leu Val Thr Val Ser Ser
        115                 120

<210> SEQ ID NO 347
<211> LENGTH: 6
<212> TYPE: PRT
<213> ORGANISM: Homo sapiens

<400> SEQUENCE: 347

Ser Thr Tyr Gly Met His
1               5

<210> SEQ ID NO 348
<211> LENGTH: 13
<212> TYPE: PRT
<213> ORGANISM: Homo sapiens

<400> SEQUENCE: 348

Trp Val Ala Gly Ile Asn Tyr Ser Gly Asn Asn Lys Tyr
1               5                   10

<210> SEQ ID NO 349
<211> LENGTH: 13
<212> TYPE: PRT
<213> ORGANISM: Homo sapiens

<400> SEQUENCE: 349

Ala Arg Asp His Ser Ser Thr Trp Ser Arg Ser Leu Asp
1               5                   10

<210> SEQ ID NO 350
<211> LENGTH: 121
<212> TYPE: PRT
<213> ORGANISM: Homo sapiens

<400> SEQUENCE: 350

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Asn Arg Gly Arg Ser Leu Asp Tyr Trp Gly
            100                 105                 110

Gln Gly Thr Leu Val Thr Val Ser Ser
        115                 120

<210> SEQ ID NO 351
<211> LENGTH: 6
<212> TYPE: PRT
<213> ORGANISM: Homo sapiens

<400> SEQUENCE: 351

Ser Thr Tyr Gly Met His
1               5

<210> SEQ ID NO 352
<211> LENGTH: 13
<212> TYPE: PRT
<213> ORGANISM: Homo sapiens

<400> SEQUENCE: 352

Trp Val Ala Gly Ile Asn Tyr Ser Gly Asn Asn Lys Tyr
1               5                   10

<210> SEQ ID NO 353
<211> LENGTH: 13
<212> TYPE: PRT
<213> ORGANISM: Homo sapiens

<400> SEQUENCE: 353

Ala Arg Asp His Ser Ser Asn Arg Gly Arg Ser Leu Asp
1               5                   10

<210> SEQ ID NO 354
<211> LENGTH: 121
<212> TYPE: PRT
<213> ORGANISM: Homo sapiens

<400> SEQUENCE: 354

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Thr Leu Tyr Arg Ala Leu Asp Tyr Trp Gly
            100                 105                 110

Gln Gly Thr Leu Val Thr Val Ser Ser
        115                 120

<210> SEQ ID NO 355
<211> LENGTH: 6
<212> TYPE: PRT
<213> ORGANISM: Homo sapiens

<400> SEQUENCE: 355

Ser Thr Tyr Gly Met His
1               5

<210> SEQ ID NO 356
<211> LENGTH: 13
<212> TYPE: PRT
<213> ORGANISM: Homo sapiens

<400> SEQUENCE: 356

Trp Val Ala Gly Ile Asn Tyr Ser Gly Asn Asn Lys Tyr
1               5                   10

<210> SEQ ID NO 357
<211> LENGTH: 13
<212> TYPE: PRT
<213> ORGANISM: Homo sapiens

<400> SEQUENCE: 357

Ala Arg Asp His Ser Ser Thr Leu Tyr Arg Ala Leu Asp
1               5                   10

<210> SEQ ID NO 358
<211> LENGTH: 121
<212> TYPE: PRT
<213> ORGANISM: Homo sapiens

<400> SEQUENCE: 358

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Thr Leu His Arg Ala Leu Asp Tyr Trp Gly
            100                 105                 110

Gln Gly Thr Leu Val Thr Val Ser Ser
        115                 120

<210> SEQ ID NO 359
<211> LENGTH: 6
<212> TYPE: PRT
<213> ORGANISM: Homo sapiens

<400> SEQUENCE: 359

Ser Thr Tyr Gly Met His
1               5

<210> SEQ ID NO 360
<211> LENGTH: 13
<212> TYPE: PRT
<213> ORGANISM: Homo sapiens

<400> SEQUENCE: 360

Trp Val Ala Gly Ile Asn Tyr Ser Gly Asn Asn Lys Tyr
1               5                   10

<210> SEQ ID NO 361
<211> LENGTH: 13
<212> TYPE: PRT
<213> ORGANISM: Homo sapiens

<400> SEQUENCE: 361

Ala Arg Asp His Ser Ser Thr Leu His Arg Ala Leu Asp
1               5                   10

<210> SEQ ID NO 362

```
<211> LENGTH: 121
<212> TYPE: PRT
<213> ORGANISM: Homo sapiens

<400> SEQUENCE: 362

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Ser Asn Leu Tyr Arg Ala Leu Asp Tyr Trp Gly
            100                 105                 110

Gln Gly Thr Leu Val Thr Val Ser Ser
        115                 120

<210> SEQ ID NO 363
<211> LENGTH: 6
<212> TYPE: PRT
<213> ORGANISM: Homo sapiens

<400> SEQUENCE: 363

Ser Thr Tyr Gly Met His
 1               5

<210> SEQ ID NO 364
<211> LENGTH: 13
<212> TYPE: PRT
<213> ORGANISM: Homo sapiens

<400> SEQUENCE: 364

Trp Val Ala Gly Ile Asn Tyr Ser Gly Asn Asn Lys Tyr
 1               5                  10

<210> SEQ ID NO 365
<211> LENGTH: 13
<212> TYPE: PRT
<213> ORGANISM: Homo sapiens

<400> SEQUENCE: 365

Ala Arg Asp His Ser Ser Asn Leu Tyr Arg Ala Leu Asp
 1               5                  10

<210> SEQ ID NO 366
<211> LENGTH: 121
<212> TYPE: PRT
<213> ORGANISM: Homo sapiens

<400> SEQUENCE: 366

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45
```

```
Ala Gly Ile Asn Tyr Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Ser Gly Tyr Trp Thr Arg Ser Leu Asp Tyr Trp Gly
            100                 105                 110

Gln Gly Thr Leu Val Thr Val Ser Ser
            115                 120
```

<210> SEQ ID NO 367
<211> LENGTH: 6
<212> TYPE: PRT
<213> ORGANISM: Homo sapiens

<400> SEQUENCE: 367

```
Ser Thr Tyr Gly Met His
 1               5
```

<210> SEQ ID NO 368
<211> LENGTH: 13
<212> TYPE: PRT
<213> ORGANISM: Homo sapiens

<400> SEQUENCE: 368

```
Trp Val Ala Gly Ile Asn Tyr Ser Gly Asn Asn Lys Tyr
 1               5                  10
```

<210> SEQ ID NO 369
<211> LENGTH: 13
<212> TYPE: PRT
<213> ORGANISM: Homo sapiens

<400> SEQUENCE: 369

```
Ala Arg Asp His Ser Gly Tyr Trp Thr Arg Ser Leu Asp
 1               5                  10
```

<210> SEQ ID NO 370
<211> LENGTH: 121
<212> TYPE: PRT
<213> ORGANISM: Homo sapiens

<400> SEQUENCE: 370

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
             35                  40                  45

Ala Gly Ile Asn Tyr Ser Gly Asn Asn Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ser Asn Ile Val Gly Arg Pro Leu Asp Tyr Trp Gly
            100                 105                 110

Gln Gly Thr Leu Val Thr Val Ser Ser
            115                 120
```

115                 120

<210> SEQ ID NO 371
<211> LENGTH: 6
<212> TYPE: PRT
<213> ORGANISM: Homo sapiens

<400> SEQUENCE: 371

Ser Thr Tyr Gly Met His
1               5

<210> SEQ ID NO 372
<211> LENGTH: 13
<212> TYPE: PRT
<213> ORGANISM: Homo sapiens

<400> SEQUENCE: 372

Trp Val Ala Gly Ile Asn Tyr Ser Gly Asn Asn Lys Tyr
1               5                   10

<210> SEQ ID NO 373
<211> LENGTH: 13
<212> TYPE: PRT
<213> ORGANISM: Homo sapiens

<400> SEQUENCE: 373

Ala Arg Asp Arg Ser Asn Ile Val Gly Arg Pro Leu Asp
1               5                   10

<210> SEQ ID NO 374
<211> LENGTH: 121
<212> TYPE: PRT
<213> ORGANISM: Homo sapiens

<400> SEQUENCE: 374

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ser Ile Arg Gly Arg Pro Leu Asp Tyr Trp Gly
            100                 105                 110

Gln Gly Thr Leu Val Thr Val Ser Ser
        115                 120

<210> SEQ ID NO 375
<211> LENGTH: 6
<212> TYPE: PRT
<213> ORGANISM: Homo sapiens

<400> SEQUENCE: 375

Ser Thr Tyr Gly Met His
1               5

```
<210> SEQ ID NO 376
<211> LENGTH: 13
<212> TYPE: PRT
<213> ORGANISM: Homo sapiens

<400> SEQUENCE: 376

Trp Val Ala Gly Ile Asn Tyr Ser Gly Asn Asn Lys Tyr
1               5                   10

<210> SEQ ID NO 377
<211> LENGTH: 13
<212> TYPE: PRT
<213> ORGANISM: Homo sapiens

<400> SEQUENCE: 377

Ala Arg Asp Arg Ser Ser Ile Arg Gly Arg Pro Leu Asp
1               5                   10

<210> SEQ ID NO 378
<211> LENGTH: 121
<212> TYPE: PRT
<213> ORGANISM: Homo sapiens

<400> SEQUENCE: 378

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Thr Thr Tyr Ser Arg Ala Leu Asp Tyr Trp Gly
            100                 105                 110

Gln Gly Thr Leu Val Thr Val Ser Ser
        115                 120

<210> SEQ ID NO 379
<211> LENGTH: 6
<212> TYPE: PRT
<213> ORGANISM: Homo sapiens

<400> SEQUENCE: 379

Ser Thr Tyr Gly Met His
1               5

<210> SEQ ID NO 380
<211> LENGTH: 13
<212> TYPE: PRT
<213> ORGANISM: Homo sapiens

<400> SEQUENCE: 380

Trp Val Ala Gly Ile Asn Tyr Ser Gly Asn Asn Lys Tyr
1               5                   10

<210> SEQ ID NO 381
<211> LENGTH: 13
<212> TYPE: PRT
```

<213> ORGANISM: Homo sapiens

<400> SEQUENCE: 381

Ala Arg Asp Arg Ser Thr Thr Tyr Ser Arg Ala Leu Asp
1               5                   10

<210> SEQ ID NO 382
<211> LENGTH: 121
<212> TYPE: PRT
<213> ORGANISM: Homo sapiens

<400> SEQUENCE: 382

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Thr Thr Leu Asn Arg Ala Leu Asp Tyr Trp Gly
            100                 105                 110

Gln Gly Thr Leu Val Thr Val Ser Ser
        115                 120

<210> SEQ ID NO 383
<211> LENGTH: 6
<212> TYPE: PRT
<213> ORGANISM: Homo sapiens

<400> SEQUENCE: 383

Ser Thr Tyr Gly Met His
1               5

<210> SEQ ID NO 384
<211> LENGTH: 13
<212> TYPE: PRT
<213> ORGANISM: Homo sapiens

<400> SEQUENCE: 384

Trp Val Ala Gly Ile Asn Tyr Ser Gly Asn Asn Lys Tyr
1               5                   10

<210> SEQ ID NO 385
<211> LENGTH: 13
<212> TYPE: PRT
<213> ORGANISM: Homo sapiens

<400> SEQUENCE: 385

Ala Arg Asp Arg Ser Thr Thr Leu Asn Arg Ala Leu Asp
1               5                   10

<210> SEQ ID NO 386
<211> LENGTH: 121
<212> TYPE: PRT
<213> ORGANISM: Homo sapiens

<400> SEQUENCE: 386

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp His Ser Thr Asn Arg Gly Arg Ser Leu Asp Tyr Trp Gly
        100                 105                 110

Gln Gly Thr Leu Val Thr Val Ser Ser
            115                 120

<210> SEQ ID NO 387
<211> LENGTH: 6
<212> TYPE: PRT
<213> ORGANISM: Homo sapiens

<400> SEQUENCE: 387

Ser Thr Tyr Gly Met His
1               5

<210> SEQ ID NO 388
<211> LENGTH: 13
<212> TYPE: PRT
<213> ORGANISM: Homo sapiens

<400> SEQUENCE: 388

Trp Val Ala Gly Ile Asn Tyr Ser Gly Asn Asn Lys Tyr
1               5                   10

<210> SEQ ID NO 389
<211> LENGTH: 13
<212> TYPE: PRT
<213> ORGANISM: Homo sapiens

<400> SEQUENCE: 389

Ala Arg Asp His Ser Thr Asn Arg Gly Arg Ser Leu Asp
1               5                   10

<210> SEQ ID NO 390
<211> LENGTH: 121
<212> TYPE: PRT
<213> ORGANISM: Homo sapiens

<400> SEQUENCE: 390

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Val Tyr Tyr Cys
                        85                  90                  95

Ala Arg Asp His Ser Thr Asn Leu Gly Arg Ser Leu Asp Tyr Trp Gly
                    100                 105                 110

Gln Gly Thr Leu Val Thr Val Ser Ser
            115                 120

<210> SEQ ID NO 391
<211> LENGTH: 6
<212> TYPE: PRT
<213> ORGANISM: Homo sapiens

<400> SEQUENCE: 391

Ser Thr Tyr Gly Met His
1               5

<210> SEQ ID NO 392
<211> LENGTH: 13
<212> TYPE: PRT
<213> ORGANISM: Homo sapiens

<400> SEQUENCE: 392

Trp Val Ala Gly Ile Asn Tyr Ser Gly Asn Asn Lys Tyr
1               5                   10

<210> SEQ ID NO 393
<211> LENGTH: 13
<212> TYPE: PRT
<213> ORGANISM: Homo sapiens

<400> SEQUENCE: 393

Ala Arg Asp His Ser Thr Asn Leu Gly Arg Ser Leu Asp
1               5                   10

<210> SEQ ID NO 394
<211> LENGTH: 121
<212> TYPE: PRT
<213> ORGANISM: Homo sapiens
<220> FEATURE:
<221> NAME/KEY: VARIANT
<222> LOCATION: 107
<223> OTHER INFORMATION: Xaa=any amino

<400> SEQUENCE: 394

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Thr Asn Arg Arg Arg Xaa Leu Asp Tyr Trp Gly
                    100                 105                 110

Gln Gly Thr Leu Val Thr Val Ser Ser
            115                 120
```

<210> SEQ ID NO 395
<211> LENGTH: 6
<212> TYPE: PRT
<213> ORGANISM: Homo sapiens

<400> SEQUENCE: 395

Ser Thr Tyr Gly Met His
1               5

<210> SEQ ID NO 396
<211> LENGTH: 13
<212> TYPE: PRT
<213> ORGANISM: Homo sapiens

<400> SEQUENCE: 396

Trp Val Ala Gly Ile Asn Tyr Ser Gly Asn Asn Lys Tyr
1               5                   10

<210> SEQ ID NO 397
<211> LENGTH: 13
<212> TYPE: PRT
<213> ORGANISM: Homo sapiens
<220> FEATURE:
<221> NAME/KEY: VARIANT
<222> LOCATION: 11
<223> OTHER INFORMATION: Xaa=any amino

<400> SEQUENCE: 397

Ala Arg Asp His Ser Thr Asn Arg Arg Xaa Leu Asp
1               5                   10

<210> SEQ ID NO 398
<211> LENGTH: 121
<212> TYPE: PRT
<213> ORGANISM: Homo sapiens

<400> SEQUENCE: 398

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Ser Arg Ser Leu Asp Tyr Trp Gly
            100                 105                 110

Gln Gly Thr Leu Val Thr Val Ser Ser
        115                 120

<210> SEQ ID NO 399
<211> LENGTH: 6
<212> TYPE: PRT
<213> ORGANISM: Homo sapiens

<400> SEQUENCE: 399

Ser Thr Tyr Gly Met His

<210> SEQ ID NO 400
<211> LENGTH: 13
<212> TYPE: PRT
<213> ORGANISM: Homo sapiens

<400> SEQUENCE: 400

Trp Val Ala Gly Ile Asn Tyr Ser Gly Asn Asn Lys Tyr
1               5                   10

<210> SEQ ID NO 401
<211> LENGTH: 13
<212> TYPE: PRT
<213> ORGANISM: Homo sapiens

<400> SEQUENCE: 401

Ala Arg Asp Ser Ser Thr Asn Arg Ser Arg Ser Leu Asp
1               5                   10

<210> SEQ ID NO 402
<211> LENGTH: 121
<212> TYPE: PRT
<213> ORGANISM: Homo sapiens

<400> SEQUENCE: 402

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Ser Arg Thr Leu Asp Tyr Trp Gly
            100                 105                 110

Gln Gly Thr Leu Val Thr Val Ser Ser
        115                 120

<210> SEQ ID NO 403
<211> LENGTH: 6
<212> TYPE: PRT
<213> ORGANISM: Homo sapiens

<400> SEQUENCE: 403

Ser Thr Tyr Gly Met His
1               5

<210> SEQ ID NO 404
<211> LENGTH: 13
<212> TYPE: PRT
<213> ORGANISM: Homo sapiens

<400> SEQUENCE: 404

Trp Val Ala Gly Ile Asn Tyr Ser Gly Asn Asn Lys Tyr
1               5                   10

```
<210> SEQ ID NO 405
<211> LENGTH: 13
<212> TYPE: PRT
<213> ORGANISM: Homo sapiens

<400> SEQUENCE: 405

Ala Arg Asp Ser Ser Thr Thr Arg Ser Arg Thr Leu Asp
1               5                   10

<210> SEQ ID NO 406
<211> LENGTH: 121
<212> TYPE: PRT
<213> ORGANISM: Homo sapiens

<400> SEQUENCE: 406

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Ser Arg Ser Leu Asp Tyr Trp Gly
            100                 105                 110

Gln Gly Thr Leu Val Thr Val Ser Ser
        115                 120

<210> SEQ ID NO 407
<211> LENGTH: 6
<212> TYPE: PRT
<213> ORGANISM: Homo sapiens

<400> SEQUENCE: 407

Ser Thr Tyr Gly Met His
1               5

<210> SEQ ID NO 408
<211> LENGTH: 13
<212> TYPE: PRT
<213> ORGANISM: Homo sapiens

<400> SEQUENCE: 408

Trp Val Ala Gly Ile Asn Tyr Ser Gly Asn Asn Lys Tyr
1               5                   10

<210> SEQ ID NO 409
<211> LENGTH: 13
<212> TYPE: PRT
<213> ORGANISM: Homo sapiens

<400> SEQUENCE: 409

Ala Arg Asp Ser Ser Thr Thr Arg Ser Arg Ser Leu Asp
1               5                   10

<210> SEQ ID NO 410
<211> LENGTH: 121
<212> TYPE: PRT
```

<213> ORGANISM: Homo sapiens

<400> SEQUENCE: 410

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Ser Arg Ala Leu Asp Tyr Trp Gly
            100                 105                 110

Gln Gly Thr Leu Val Thr Val Ser Ser
        115                 120

<210> SEQ ID NO 411
<211> LENGTH: 6
<212> TYPE: PRT
<213> ORGANISM: Homo sapiens

<400> SEQUENCE: 411

Ser Thr Tyr Gly Met His
1               5

<210> SEQ ID NO 412
<211> LENGTH: 13
<212> TYPE: PRT
<213> ORGANISM: Homo sapiens

<400> SEQUENCE: 412

Trp Val Ala Gly Ile Asn Tyr Ser Gly Asn Asn Lys Tyr
1               5                   10

<210> SEQ ID NO 413
<211> LENGTH: 13
<212> TYPE: PRT
<213> ORGANISM: Homo sapiens

<400> SEQUENCE: 413

Ala Arg Asp Ser Ser Thr Asn Arg Ser Arg Ala Leu Asp
1               5                   10

<210> SEQ ID NO 414
<211> LENGTH: 121
<212> TYPE: PRT
<213> ORGANISM: Homo sapiens

<400> SEQUENCE: 414

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val

```
                      50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Asp Ser Ser Thr Asn Arg Gly Arg Ala Leu Asp Tyr Trp Gly
                100                 105                 110

Gln Gly Thr Leu Val Thr Val Ser Ser
            115                 120

<210> SEQ ID NO 415
<211> LENGTH: 6
<212> TYPE: PRT
<213> ORGANISM: Homo sapiens

<400> SEQUENCE: 415

Ser Thr Tyr Gly Met His
 1               5

<210> SEQ ID NO 416
<211> LENGTH: 13
<212> TYPE: PRT
<213> ORGANISM: Homo sapiens

<400> SEQUENCE: 416

Trp Val Ala Gly Ile Asn Tyr Ser Gly Asn Asn Lys Tyr
 1               5                  10

<210> SEQ ID NO 417
<211> LENGTH: 13
<212> TYPE: PRT
<213> ORGANISM: Homo sapiens

<400> SEQUENCE: 417

Ala Arg Asp Ser Ser Thr Asn Arg Gly Arg Ala Leu Asp
 1               5                  10

<210> SEQ ID NO 418
<211> LENGTH: 121
<212> TYPE: PRT
<213> ORGANISM: Homo sapiens

<400> SEQUENCE: 418

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
             35                  40                  45

Ala Gly Ile Asn Tyr Ser Gly Asn Asn Lys Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Asp Ser Ser Thr Val Arg Gly Arg Ala Leu Asp Tyr Trp Gly
                100                 105                 110

Gln Gly Thr Leu Val Thr Val Ser Ser
            115                 120
```

```
<210> SEQ ID NO 419
<211> LENGTH: 6
<212> TYPE: PRT
<213> ORGANISM: Homo sapiens

<400> SEQUENCE: 419

Ser Thr Tyr Gly Met His
 1               5

<210> SEQ ID NO 420
<211> LENGTH: 13
<212> TYPE: PRT
<213> ORGANISM: Homo sapiens

<400> SEQUENCE: 420

Trp Val Ala Gly Ile Asn Tyr Ser Gly Asn Asn Lys Tyr
 1               5                  10

<210> SEQ ID NO 421
<211> LENGTH: 13
<212> TYPE: PRT
<213> ORGANISM: Homo sapiens

<400> SEQUENCE: 421

Ala Arg Asp Ser Ser Thr Val Arg Gly Arg Ala Leu Asp
 1               5                  10

<210> SEQ ID NO 422
<211> LENGTH: 121
<212> TYPE: PRT
<213> ORGANISM: Homo sapiens

<400> SEQUENCE: 422

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Thr Arg Ser Leu Asp Tyr Trp Gly
            100                 105                 110

Gln Gly Thr Leu Val Thr Val Ser Ser
        115                 120

<210> SEQ ID NO 423
<211> LENGTH: 6
<212> TYPE: PRT
<213> ORGANISM: Homo sapiens

<400> SEQUENCE: 423

Ser Thr Tyr Gly Met His
 1               5

<210> SEQ ID NO 424
<211> LENGTH: 13
```

```
<212> TYPE: PRT
<213> ORGANISM: Homo sapiens

<400> SEQUENCE: 424

Trp Val Ala Gly Ile Asn Tyr Ser Gly Asn Asn Lys Tyr
  1               5                  10

<210> SEQ ID NO 425
<211> LENGTH: 13
<212> TYPE: PRT
<213> ORGANISM: Homo sapiens

<400> SEQUENCE: 425

Ala Arg Asp Ser Ser Thr Asn Arg Thr Arg Ser Leu Asp
  1               5                  10

<210> SEQ ID NO 426
<211> LENGTH: 121
<212> TYPE: PRT
<213> ORGANISM: Homo sapiens

<400> SEQUENCE: 426

Glu Val Gln Leu Val Glu Ser Gly Gly Leu Val Lys Pro Gly Gly
  1               5                  10                  15

Ser Leu Arg Leu Ser Cys Ala Ala Ser Gly Phe Thr Phe Ser Thr Tyr
                 20                  25                  30

Gly Met His Trp Val Arg Gln Ala Pro Gly Lys Gly Leu Glu Trp Val
             35                  40                  45

Ala Gly Ile Asn Tyr Ser Gly Asn Asn Lys Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Asn Arg Thr Arg Ser Leu Asp Tyr Trp Gly
            100                 105                 110

Arg Gly Thr Leu Val Thr Val Ser Ser
        115                 120

<210> SEQ ID NO 427
<211> LENGTH: 6
<212> TYPE: PRT
<213> ORGANISM: Homo sapiens

<400> SEQUENCE: 427

Ser Thr Tyr Gly Met His
  1               5

<210> SEQ ID NO 428
<211> LENGTH: 13
<212> TYPE: PRT
<213> ORGANISM: Homo sapiens

<400> SEQUENCE: 428

Trp Val Ala Gly Ile Asn Tyr Ser Gly Asn Asn Lys Tyr
  1               5                  10

<210> SEQ ID NO 429
<211> LENGTH: 13
<212> TYPE: PRT
<213> ORGANISM: Homo sapiens
```

```
<400> SEQUENCE: 429

Ala Arg Asp Ser Ser Thr Asn Arg Thr Arg Ser Leu Asp
1               5                   10

<210> SEQ ID NO 430
<211> LENGTH: 121
<212> TYPE: PRT
<213> ORGANISM: Homo sapiens

<400> SEQUENCE: 430

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Val Arg Thr Arg Ser Leu Asp Tyr Trp Gly
            100                 105                 110

Gln Gly Thr Leu Val Thr Val Ser Ser
        115                 120

<210> SEQ ID NO 431
<211> LENGTH: 6
<212> TYPE: PRT
<213> ORGANISM: Homo sapiens

<400> SEQUENCE: 431

Ser Thr Tyr Gly Met His
1               5

<210> SEQ ID NO 432
<211> LENGTH: 13
<212> TYPE: PRT
<213> ORGANISM: Homo sapiens

<400> SEQUENCE: 432

Trp Val Ala Gly Ile Asn Tyr Ser Gly Asn Asn Lys Tyr
1               5                   10

<210> SEQ ID NO 433
<211> LENGTH: 13
<212> TYPE: PRT
<213> ORGANISM: Homo sapiens

<400> SEQUENCE: 433

Ala Arg Asp Ser Ser Thr Val Arg Thr Arg Ser Leu Asp
1               5                   10

<210> SEQ ID NO 434
<211> LENGTH: 121
<212> TYPE: PRT
<213> ORGANISM: Homo sapiens

<400> SEQUENCE: 434

Glu Val Gln Leu Val Glu Ser Gly Gly Gly Leu Val Lys Pro Gly Gly
```

```
                1               5                   10                  15
Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
                35                  40                  45

Ala Gly Ile Asn Tyr Ser Gly Asn Asn Lys Tyr Tyr Ala Asp Ser Val
                50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Ser Leu Asp Tyr Trp Gly
                100                 105                 110

Gln Gly Thr Leu Val Thr Val Ser Ser
                115                 120
```

<210> SEQ ID NO 435
<211> LENGTH: 6
<212> TYPE: PRT
<213> ORGANISM: Homo sapiens

<400> SEQUENCE: 435

```
Ser Thr Tyr Gly Met His
 1               5
```

<210> SEQ ID NO 436
<211> LENGTH: 13
<212> TYPE: PRT
<213> ORGANISM: Homo sapiens

<400> SEQUENCE: 436

```
Trp Val Ala Gly Ile Asn Tyr Ser Gly Asn Asn Lys Tyr
 1               5                   10
```

<210> SEQ ID NO 437
<211> LENGTH: 13
<212> TYPE: PRT
<213> ORGANISM: Homo sapiens

<400> SEQUENCE: 437

```
Ala Arg Asp Ser Ser Thr Thr Arg Thr Arg Ser Leu Asp
 1               5                   10
```

<210> SEQ ID NO 438
<211> LENGTH: 121
<212> TYPE: PRT
<213> ORGANISM: Homo sapiens

<400> SEQUENCE: 438

```
Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
                35                  40                  45

Ala Gly Ile Asn Tyr Ser Gly Asn Asn Lys Tyr Tyr Ala Asp Ser Val
                50                  55                  60

Lys Gly Arg Phe Thr Ile Ser Arg Asp Asn Ala Lys Asn Ser Leu Tyr
 65                 70                  75                  80
```

Leu Gln Met Asn Ser Leu Arg Ala Glu Asp Thr Ala Val Tyr Tyr Cys
                85                  90                  95

Ala Arg Asp Thr Ser Thr Asn Arg Thr Arg Gly Leu Asp Tyr Trp Gly
            100                 105                 110

Gln Gly Thr Leu Val Thr Val Ser Ser
        115                 120

<210> SEQ ID NO 439
<211> LENGTH: 6
<212> TYPE: PRT
<213> ORGANISM: Homo sapiens

<400> SEQUENCE: 439

Ser Thr Tyr Gly Met His
1               5

<210> SEQ ID NO 440
<211> LENGTH: 13
<212> TYPE: PRT
<213> ORGANISM: Homo sapiens

<400> SEQUENCE: 440

Trp Val Ala Gly Ile Asn Tyr Ser Gly Asn Asn Lys Tyr
1               5                   10

<210> SEQ ID NO 441
<211> LENGTH: 13
<212> TYPE: PRT
<213> ORGANISM: Homo sapiens

<400> SEQUENCE: 441

Ala Arg Asp Thr Ser Thr Asn Arg Thr Arg Gly Leu Asp
1               5                   10

<210> SEQ ID NO 442
<211> LENGTH: 121
<212> TYPE: PRT
<213> ORGANISM: Homo sapiens

<400> SEQUENCE: 442

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Thr Arg Gly Leu Asp Tyr Trp Gly
            100                 105                 110

Gln Gly Thr Leu Val Thr Val Ser Ser
        115                 120

<210> SEQ ID NO 443
<211> LENGTH: 6
<212> TYPE: PRT
<213> ORGANISM: Homo sapiens

<400> SEQUENCE: 443

Ser Thr Tyr Gly Met His
1               5

<210> SEQ ID NO 444
<211> LENGTH: 13
<212> TYPE: PRT
<213> ORGANISM: Homo sapiens

<400> SEQUENCE: 444

Trp Val Ala Gly Ile Asn Tyr Ser Gly Asn Asn Lys Tyr
1               5                   10

<210> SEQ ID NO 445
<211> LENGTH: 13
<212> TYPE: PRT
<213> ORGANISM: Homo sapiens

<400> SEQUENCE: 445

Ala Arg Asp Ser Ser Thr Asn Arg Thr Arg Gly Leu Asp
1               5                   10

<210> SEQ ID NO 446
<211> LENGTH: 121
<212> TYPE: PRT
<213> ORGANISM: Homo sapiens

<400> SEQUENCE: 446

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Ile Arg Thr Arg Gly Leu Asp Tyr Trp Gly
            100                 105                 110

Gln Gly Thr Leu Val Thr Val Ser Ser
        115                 120

<210> SEQ ID NO 447
<211> LENGTH: 6
<212> TYPE: PRT
<213> ORGANISM: Homo sapiens

<400> SEQUENCE: 447

Ser Thr Tyr Gly Met His
1               5

<210> SEQ ID NO 448
<211> LENGTH: 13
<212> TYPE: PRT
<213> ORGANISM: Homo sapiens

<400> SEQUENCE: 448

Trp Val Ala Gly Ile Asn Tyr Ser Gly Asn Asn Lys Tyr
1               5                   10

<210> SEQ ID NO 449
<211> LENGTH: 13
<212> TYPE: PRT
<213> ORGANISM: Homo sapiens

<400> SEQUENCE: 449

Ala Arg Asp Ser Ser Thr Ile Arg Thr Arg Gly Leu Asp
1               5                   10

<210> SEQ ID NO 450
<211> LENGTH: 121
<212> TYPE: PRT
<213> ORGANISM: Homo sapiens

<400> SEQUENCE: 450

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Thr Arg Thr Arg Gly Leu Asp Tyr Trp Gly
            100                 105                 110

Gln Gly Thr Leu Val Thr Val Ser Ser
        115                 120

<210> SEQ ID NO 451
<211> LENGTH: 6
<212> TYPE: PRT
<213> ORGANISM: Homo sapiens

<400> SEQUENCE: 451

Ser Thr Tyr Gly Met His
1               5

<210> SEQ ID NO 452
<211> LENGTH: 13
<212> TYPE: PRT
<213> ORGANISM: Homo sapiens

<400> SEQUENCE: 452

Trp Val Ala Gly Ile Asn Tyr Ser Gly Asn Asn Lys Tyr
1               5                   10

<210> SEQ ID NO 453
<211> LENGTH: 13
<212> TYPE: PRT
<213> ORGANISM: Homo sapiens

<400> SEQUENCE: 453

Ala Arg Asp Ser Ser Thr Thr Arg Thr Arg Gly Leu Asp
1               5                   10

<210> SEQ ID NO 454
<211> LENGTH: 121
<212> TYPE: PRT
<213> ORGANISM: Homo sapiens

<400> SEQUENCE: 454

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Asn Arg Thr Arg Thr Leu Asp Tyr Trp Gly
            100                 105                 110

Gln Gly Thr Leu Val Thr Val Ser Ser
        115                 120

<210> SEQ ID NO 455
<211> LENGTH: 6
<212> TYPE: PRT
<213> ORGANISM: Homo sapiens

<400> SEQUENCE: 455

Ser Thr Tyr Gly Met His
1               5

<210> SEQ ID NO 456
<211> LENGTH: 13
<212> TYPE: PRT
<213> ORGANISM: Homo sapiens

<400> SEQUENCE: 456

Trp Val Ala Gly Ile Asn Tyr Ser Gly Asn Asn Lys Tyr
1               5                   10

<210> SEQ ID NO 457
<211> LENGTH: 13
<212> TYPE: PRT
<213> ORGANISM: Homo sapiens

<400> SEQUENCE: 457

Ala Arg Asp Ser Ser Thr Asn Arg Thr Arg Thr Leu Asp
1               5                   10

<210> SEQ ID NO 458
<211> LENGTH: 121
<212> TYPE: PRT
<213> ORGANISM: Homo sapiens

<400> SEQUENCE: 458

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

-continued

```
Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Thr Arg Thr Arg Ala Leu Asp Tyr Trp Gly
                100                 105                 110

Gln Gly Thr Leu Val Thr Val Ser Ser
        115                 120

<210> SEQ ID NO 459
<211> LENGTH: 6
<212> TYPE: PRT
<213> ORGANISM: Homo sapiens

<400> SEQUENCE: 459

Ser Thr Tyr Gly Met His
 1               5

<210> SEQ ID NO 460
<211> LENGTH: 13
<212> TYPE: PRT
<213> ORGANISM: Homo sapiens

<400> SEQUENCE: 460

Trp Val Ala Gly Ile Asn Tyr Ser Gly Asn Asn Lys Tyr
 1               5                  10

<210> SEQ ID NO 461
<211> LENGTH: 13
<212> TYPE: PRT
<213> ORGANISM: Homo sapiens

<400> SEQUENCE: 461

Ala Arg Asp Ser Ser Thr Thr Arg Thr Arg Ala Leu Asp
 1               5                  10

<210> SEQ ID NO 462
<211> LENGTH: 121
<212> TYPE: PRT
<213> ORGANISM: Homo sapiens

<400> SEQUENCE: 462

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ser Thr Val Arg Thr Arg Ala Leu Asp Tyr Trp Gly
                100                 105                 110
```

Gln Gly Thr Leu Val Thr Val Ser Ser
        115                 120

<210> SEQ ID NO 463
<211> LENGTH: 6
<212> TYPE: PRT
<213> ORGANISM: Homo sapiens

<400> SEQUENCE: 463

Ser Thr Tyr Gly Met His
1               5

<210> SEQ ID NO 464
<211> LENGTH: 13
<212> TYPE: PRT
<213> ORGANISM: Homo sapiens

<400> SEQUENCE: 464

Trp Val Ala Gly Ile Asn Tyr Ser Gly Asn Asn Lys Tyr
1               5                   10

<210> SEQ ID NO 465
<211> LENGTH: 13
<212> TYPE: PRT
<213> ORGANISM: Homo sapiens

<400> SEQUENCE: 465

Ala Arg Asp Ser Ser Thr Val Arg Thr Arg Ala Leu Asp
1               5                   10

<210> SEQ ID NO 466
<211> LENGTH: 121
<212> TYPE: PRT
<213> ORGANISM: Homo sapiens

<400> SEQUENCE: 466

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Ile Ser Thr Arg Ala Leu Asp Tyr Trp Gly
            100                 105                 110

Gln Gly Thr Leu Val Thr Val Ser Ser
        115                 120

<210> SEQ ID NO 467
<211> LENGTH: 6
<212> TYPE: PRT
<213> ORGANISM: Homo sapiens

<400> SEQUENCE: 467

Ser Thr Tyr Gly Met His
1               5

<210> SEQ ID NO 468
<211> LENGTH: 13
<212> TYPE: PRT
<213> ORGANISM: Homo sapiens

<400> SEQUENCE: 468

Trp Val Ala Gly Ile Asn Tyr Ser Gly Asn Asn Lys Tyr
1               5                   10

<210> SEQ ID NO 469
<211> LENGTH: 13
<212> TYPE: PRT
<213> ORGANISM: Homo sapiens

<400> SEQUENCE: 469

Ala Arg Asp Ser Ser Thr Ile Ser Thr Arg Ala Leu Asp
1               5                   10

<210> SEQ ID NO 470
<211> LENGTH: 121
<212> TYPE: PRT
<213> ORGANISM: Homo sapiens

<400> SEQUENCE: 470

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Gly Ile Asn Tyr Ser Gly Asn Asn Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Thr Ile Arg Thr Arg Ala Leu Asp Tyr Trp Gly
            100                 105                 110

Gln Gly Thr Leu Val Thr Val Ser Ser
        115                 120

<210> SEQ ID NO 471
<211> LENGTH: 6
<212> TYPE: PRT
<213> ORGANISM: Homo sapiens

<400> SEQUENCE: 471

Ser Thr Tyr Gly Met His
1               5

<210> SEQ ID NO 472
<211> LENGTH: 13
<212> TYPE: PRT
<213> ORGANISM: Homo sapiens

<400> SEQUENCE: 472

Trp Val Ala Gly Ile Asn Tyr Ser Gly Asn Asn Lys Tyr
1               5                   10

<210> SEQ ID NO 473

```
<211> LENGTH: 13
<212> TYPE: PRT
<213> ORGANISM: Homo sapiens

<400> SEQUENCE: 473

Ala Arg Asp Ser Ser Thr Ile Arg Thr Arg Ala Leu Asp
 1               5                  10

<210> SEQ ID NO 474
<211> LENGTH: 467
<212> TYPE: PRT
<213> ORGANISM: Homo sapiens

<400> SEQUENCE: 474

Ala Pro Pro Pro Ala Arg Val His Leu Gly Ala Phe Leu Ala Val Thr
 1               5                  10                  15

Pro Asn Pro Gly Ser Ala Ala Ser Gly Thr Glu Ala Ala Ala Ala Thr
             20                  25                  30

Pro Ser Lys Val Trp Gly Ser Ser Ala Gly Arg Ile Glu Pro Arg Gly
         35                  40                  45

Gly Gly Arg Gly Ala Leu Pro Thr Ser Met Gly Gln His Gly Pro Ser
     50                  55                  60

Ala Arg Ala Arg Ala Gly Arg Ala Pro Gly Pro Arg Pro Ala Arg Glu
65                  70                  75                  80

Ala Ser Pro Arg Leu Arg Val His Lys Thr Phe Lys Phe Val Val Val
                 85                  90                  95

Gly Val Leu Leu Gln Val Val Pro Ser Ser Ala Ala Thr Ile Lys Leu
            100                 105                 110

His Asp Gln Ser Ile Gly Thr Gln Gln Trp Glu His Ser Pro Leu Gly
        115                 120                 125

Glu Leu Cys Pro Pro Gly Ser His Arg Ser Glu His Pro Gly Ala Cys
    130                 135                 140

Asn Arg Cys Thr Glu Gly Val Gly Tyr Thr Asn Ala Ser Asn Asn Leu
145                 150                 155                 160

Phe Ala Cys Leu Pro Cys Thr Ala Cys Lys Ser Asp Glu Glu Glu Arg
                165                 170                 175

Ser Pro Cys Thr Thr Thr Arg Asn Thr Ala Cys Gln Cys Lys Pro Gly
            180                 185                 190

Thr Phe Arg Asn Asp Asn Ser Ala Glu Met Cys Arg Lys Cys Ser Arg
        195                 200                 205

Gly Cys Pro Arg Gly Met Val Lys Val Lys Asp Cys Thr Pro Trp Ser
    210                 215                 220

Asp Ile Glu Cys Val His Lys Glu Ser Gly Asn Gly His Asn Ile Trp
225                 230                 235                 240

Val Ile Leu Val Val Thr Leu Val Val Pro Leu Leu Leu Val Ala Val
                245                 250                 255

Leu Ile Val Cys Cys Cys Ile Gly Ser Gly Cys Gly Gly Asp Pro Lys
            260                 265                 270

Cys Met Asp Arg Val Cys Phe Trp Arg Leu Gly Leu Leu Arg Gly Pro
        275                 280                 285

Gly Ala Glu Asp Asn Ala His Asn Glu Ile Leu Ser Asn Ala Asp Ser
    290                 295                 300

Leu Ser Thr Phe Val Ser Glu Gln Gln Met Glu Ser Gln Glu Pro Ala
305                 310                 315                 320

Asp Leu Thr Gly Val Thr Val Gln Ser Pro Gly Glu Ala Gln Cys Leu
                325                 330                 335
```

-continued

Leu Gly Pro Ala Glu Ala Glu Gly Ser Gln Arg Arg Leu Leu Val
                340                 345                 350

Pro Ala Asn Gly Ala Asp Pro Thr Glu Thr Leu Met Leu Phe Phe Asp
                355                 360                 365

Lys Phe Ala Asn Ile Val Pro Phe Asp Ser Trp Asp Gln Leu Met Arg
        370                 375                 380

Gln Leu Asp Leu Thr Lys Asn Glu Ile Asp Val Val Arg Ala Gly Thr
385                 390                 395                 400

Ala Gly Pro Gly Asp Ala Leu Tyr Ala Met Leu Met Lys Trp Val Asn
                405                 410                 415

Lys Thr Gly Arg Asn Ala Ser Ile His Thr Leu Leu Asp Ala Leu Glu
        420                 425                 430

Arg Met Glu Glu Arg His Ala Lys Glu Lys Ile Gln Asp Leu Leu Val
        435                 440                 445

Asp Ser Gly Lys Phe Ile Tyr Leu Glu Asp Gly Thr Gly Ser Ala Val
        450                 455                 460

Ser Leu Glu
465

<210> SEQ ID NO 475
<211> LENGTH: 468
<212> TYPE: PRT
<213> ORGANISM: Homo sapiens

<400> SEQUENCE: 475

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
                20                  25                  30

Thr Pro Ser Lys Val Trp Gly Ser Ala Gly Arg Ile Glu Pro Arg
        35                  40                  45

Gly Gly Gly Arg Gly Ala Leu Pro Thr Ser Met Gly Gln His Gly Pro
    50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
            100                 105                 110

Leu His Asp Gln Ser Ile Gly Thr Gln Gln Trp Glu His Ser Pro Leu
        115                 120                 125

Gly Glu Leu Cys Pro Pro Gly Ser His Arg Ser Glu His Pro Gly Ala
    130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Thr Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile

```
                225                 230                 235                 240
Trp Val Ile Leu Val Val Thr Leu Val Val Pro Leu Leu Val Ala
                    245                 250                 255

Val Leu Ile Val Cys Cys Cys Ile Gly Ser Gly Cys Gly Gly Asp Pro
                    260                 265                 270

Lys Cys Met Asp Arg Val Cys Phe Trp Arg Leu Gly Leu Leu Arg Gly
                275                 280                 285

Pro Gly Ala Glu Asp Asn Ala His Asn Glu Ile Leu Ser Asn Ala Asp
            290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                    325                 330                 335

Leu Leu Gly Pro Ala Glu Ala Glu Gly Ser Gln Arg Arg Arg Leu Leu
                340                 345                 350

Val Pro Ala Asn Gly Ala Asp Pro Thr Glu Thr Leu Met Leu Phe Phe
                355                 360                 365

Asp Lys Phe Ala Asn Ile Val Pro Phe Asp Ser Trp Asp Gln Leu Met
            370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                    405                 410                 415

Asn Lys Thr Gly Arg Asn Ala Ser Ile His Thr Leu Leu Asp Ala Leu
                420                 425                 430

Glu Arg Met Glu Glu Arg His Ala Lys Glu Lys Ile Gln Asp Leu Leu
                435                 440                 445

Val Asp Ser Gly Lys Phe Ile Tyr Leu Glu Asp Gly Thr Gly Ser Ala
            450                 455                 460

Val Ser Leu Glu
465

<210> SEQ ID NO 476
<211> LENGTH: 468
<212> TYPE: PRT
<213> ORGANISM: Homo sapiens

<400> SEQUENCE: 476

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
                20                  25                  30

Thr Pro Ser Lys Val Trp Gly Ser Ser Ala Gly Arg Ile Glu Pro Arg
            35                  40                  45

Gly Gly Gly Arg Gly Ala Leu Pro Thr Ser Met Gly Gln His Gly Pro
        50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                    85                  90                  95

Val Gly Val Leu Leu Gln Val Val Pro Ser Ala Ala Thr Ile Lys
                100                 105                 110

Leu His Asp Gln Ser Ile Gly Thr Gln Gln Trp Glu His Ser Pro Leu
            115                 120                 125
```

Gly Glu Leu Cys Pro Pro Gly Ser His Arg Ser Glu Arg Pro Gly Ala
            130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Thr Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
        435                 440                 445

Val Asp Ser Gly Lys Phe Ile Tyr Leu Glu Asp Gly Thr Gly Ser Ala
    450                 455                 460

Val Ser Leu Glu
465

<210> SEQ ID NO 477
<211> LENGTH: 468
<212> TYPE: PRT
<213> ORGANISM: Homo sapiens

<400> SEQUENCE: 477

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
                20                  25                  30

```
Thr Pro Ser Lys Val Trp Gly Ser Ala Gly Arg Ile Glu Pro Arg
        35                  40                  45
Gly Gly Gly Arg Gly Ala Leu Pro Thr Ser Met Gly Gln His Gly Pro
    50                  55                  60
Ser Ala Arg Ala Arg Ala Gly Arg Ala Pro Gly Pro Arg Pro Ala Arg
65                  70                  75                  80
Glu Ala Ser Pro Arg Leu Arg Val His Lys Thr Phe Lys Phe Val Val
                85                  90                  95
Val Gly Val Leu Leu Gln Val Val Pro Ser Ala Ala Thr Ile Lys
            100                 105                 110
Leu His Asp Gln Ser Ile Gly Thr Gln Gln Trp Glu His Ser Pro Leu
            115                 120                 125
Gly Glu Leu Cys Pro Pro Gly Ser His Arg Ser Glu Arg Pro Gly Ala
        130                 135                 140
Cys Asn Arg Cys Thr Glu Gly Val Gly Tyr Thr Asn Ala Ser Asn Asn
145                 150                 155                 160
Leu Phe Ala Cys Leu Pro Cys Thr Ala Cys Lys Ser Asp Glu Glu Glu
                165                 170                 175
Arg Ser Pro Cys Thr Thr Thr Arg Asn Thr Ala Cys Gln Cys Lys Pro
            180                 185                 190
Gly Thr Phe Arg Asn Asp Asn Ser Ala Glu Met Cys Arg Lys Cys Ser
        195                 200                 205
Thr Gly Cys Pro Arg Gly Met Val Lys Val Lys Asp Cys Thr Pro Trp
    210                 215                 220
Ser Asp Ile Glu Cys Val His Lys Glu Ser Gly Asn Gly His Asn Ile
225                 230                 235                 240
Trp Val Ile Leu Val Val Thr Leu Val Val Pro Leu Leu Leu Val Ala
                245                 250                 255
Val Leu Ile Val Cys Cys Cys Ile Gly Ser Gly Cys Gly Gly Asp Pro
            260                 265                 270
Lys Cys Met Asp Arg Val Cys Phe Trp Arg Leu Gly Leu Leu Arg Gly
        275                 280                 285
Pro Gly Ala Glu Asp Asn Ala His Asn Glu Ile Leu Ser Asn Ala Asp
        290                 295                 300
Ser Leu Ser Thr Phe Val Ser Glu Gln Gln Met Glu Ser Gln Glu Pro
305                 310                 315                 320
Ala Asp Leu Thr Gly Val Thr Val Gln Ser Pro Gly Glu Ala Gln Cys
                325                 330                 335
Leu Leu Gly Pro Ala Glu Ala Glu Gly Ser Gln Arg Arg Leu Leu
            340                 345                 350
Val Pro Ala Asn Gly Ala Asp Pro Thr Glu Thr Leu Met Leu Phe Phe
        355                 360                 365
Asp Lys Phe Ala Asn Ile Val Pro Phe Asp Ser Trp Asp Gln Leu Met
        370                 375                 380
Arg Gln Leu Asp Leu Thr Lys Asn Glu Ile Asp Val Val Arg Ala Gly
385                 390                 395                 400
Thr Ala Gly Pro Gly Asp Ala Leu Tyr Ala Met Leu Met Lys Trp Val
                405                 410                 415
Asn Lys Thr Gly Arg Asn Ala Ser Ile His Thr Leu Leu Asp Ala Leu
            420                 425                 430
Glu Arg Met Glu Glu Arg His Ala Lys Glu Lys Ile Gln Asp Leu Leu
        435                 440                 445
```

```
Val Asp Ser Gly Lys Phe Ile Tyr Leu Glu Asp Gly Thr Gly Ser Ala
450                 455                 460

Val Ser Leu Glu
465

<210> SEQ ID NO 478
<211> LENGTH: 448
<212> TYPE: PRT
<213> ORGANISM: Homo sapiens

<400> SEQUENCE: 478

Met Glu Gln Arg Gly Gln Asn Ala Pro Ala Ser Gly Ala Arg Lys
  1               5                  10                  15

Arg His Gly Pro Gly Pro Arg Glu Ala Arg Gly Ala Arg Pro Gly Pro
                 20                  25                  30

Arg Val Pro Lys Thr Leu Val Leu Val Val Ala Ala Val Leu Leu Leu
             35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                     85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Asx Ile Val Ala Leu Glu Asn Thr
                245                 250                 255

Ser Asx Pro Gly Gly Asp Pro Glu Arg Val Asp Arg Ser Ser Gln Arg
            260                 265                 270

Pro Gly Ala Glu Asp Asn Val Leu Asn Glu Ile Val Ser Ile Leu Gln
        275                 280                 285

Pro Thr Gln Val Pro Glu Gln Glu Met Glu Val Gln Glu Pro Ala Glu
290                 295                 300

Pro Thr Gly Val Asn Met Leu Ser Pro Gly Glu Ser Glu His Leu Leu
305                 310                 315                 320

Glu Pro Ala Glu Ala Glu Arg Ser Gln Arg Arg Arg Leu Leu Val Pro
                325                 330                 335

Ala Asn Glu Gly Asp Pro Thr Glu Thr Leu Arg Gln Cys Phe Asp Asp
            340                 345                 350
```

```
Phe Ala Asp Leu Val Pro Phe Asp Ser Trp Glu Pro Leu Met Arg Lys
            355                 360                 365

Leu Gly Leu Met Asp Asn Glu Ile Lys Val Ala Lys Ala Glu Ala Ala
        370                 375                 380

Gly His Arg Asp Thr Leu Tyr Thr Met Leu Ile Lys Trp Val Asn Lys
385                 390                 395                 400

Thr Gly Arg Asp Ala Ser Val His Thr Leu Leu Asp Ala Leu Glu Thr
                405                 410                 415

Leu Gly Glu Arg Leu Ala Lys Gln Lys Ile Glu Asp His Leu Leu Ser
            420                 425                 430

Ser Gly Lys Phe Met Tyr Leu Gly Asn Ala Asp Ser Ala Met Ser
        435                 440                 445

<210> SEQ ID NO 479
<211> LENGTH: 448
<212> TYPE: PRT
<213> ORGANISM: Homo sapiens

<400> SEQUENCE: 479

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Asx Ile Val Ala Leu Glu Asn Thr
                245                 250                 255

Ser Asx Pro Gly Gly Asp Pro Glu Arg Val Asp Arg Ser Ser Gln Arg
            260                 265                 270

Pro Gly Ala Glu Asp Asn Val Leu Asn Glu Ile Val Ser Ile Leu Gln
```

```
            275                 280                 285
Pro Thr Gln Val Pro Glu Gln Glu Met Glu Val Gln Glu Pro Ala Glu
290                 295                 300
Pro Thr Gly Val Asn Met Leu Ser Pro Gly Glu Ser Glu His Leu Leu
305                 310                 315                 320
Glu Pro Ala Glu Ala Glu Arg Ser Gln Arg Arg Leu Leu Val Pro
                325                 330                 335
Ala Asn Glu Gly Asp Pro Thr Glu Thr Leu Arg Gln Cys Phe Asp Asp
                340                 345                 350
Phe Ala Asp Leu Val Pro Phe Asp Ser Trp Glu Pro Leu Met Arg Lys
                355                 360                 365
Leu Gly Leu Met Asp Asn Glu Ile Lys Val Ala Lys Ala Glu Ala Ala
            370                 375                 380
Gly His Arg Asp Thr Leu Tyr Thr Met Leu Ile Lys Trp Val Asn Lys
385                 390                 395                 400
Thr Gly Arg Asp Ala Ser Val His Thr Leu Leu Asp Ala Leu Glu Thr
                405                 410                 415
Leu Gly Glu Arg Leu Ala Lys Gln Lys Ile Glu Asp His Leu Leu Ser
                420                 425                 430
Ser Gly Lys Phe Met Tyr Leu Glu Gly Asn Ala Asp Ser Ala Met Ser
                435                 440                 445

<210> SEQ ID NO 480
<211> LENGTH: 448
<212> TYPE: PRT
<213> ORGANISM: Homo sapiens

<400> SEQUENCE: 480

Met Glu Gln Arg Gly Gln Asn Ala Pro Ala Ala Ser Gly Ala Arg Lys
1               5                   10                  15
Arg His Gly Pro Gly Pro Arg Glu Ala Arg Gly Ala Arg Pro Gly Leu
                20                  25                  30
Arg Val Pro Lys Thr Leu Val Leu Val Val Ala Ala Val Leu Leu Leu
            35                  40                  45
Val Ser Ala Glu Ser Ala Leu Ile Thr Gln Gln Asp Leu Ala Pro Gln
        50                  55                  60
Gln Arg Ala Ala Pro Gln Gln Lys Arg Ser Ser Pro Ser Glu Gly Leu
65                  70                  75                  80
Cys Pro Pro Gly His His Ile Ser Glu Asp Gly Arg Asp Cys Ile Ser
                85                  90                  95
Cys Lys Tyr Gly Gln Asp Tyr Ser Thr His Trp Asn Asp Leu Leu Phe
                100                 105                 110
Cys Leu Arg Cys Thr Arg Cys Asp Ser Gly Glu Val Glu Leu Ser Pro
            115                 120                 125
Cys Thr Thr Thr Arg Asn Thr Val Cys Gln Cys Glu Glu Gly Thr Phe
        130                 135                 140
Arg Glu Glu Asp Ser Pro Glu Met Cys Arg Lys Cys Arg Thr Gly Cys
145                 150                 155                 160
Pro Arg Gly Met Val Lys Val Gly Asp Cys Thr Pro Trp Ser Asp Ile
                165                 170                 175
Glu Cys Val His Lys Glu Ser Gly Thr Lys His Ser Gly Glu Ala Pro
                180                 185                 190
Ala Val Glu Glu Thr Val Thr Ser Ser Pro Gly Thr Pro Ala Ser Pro
            195                 200                 205
```

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Asx Ile Val Ala Leu Glu Asn Thr
                245                 250                 255

Ser Asx Pro Gly Gly Asp Pro Glu Arg Val Asp Arg Ser Ser Gln Arg
            260                 265                 270

Pro Gly Ala Glu Asp Asn Val Leu Asn Glu Ile Val Ser Ile Leu Gln
            275                 280                 285

Pro Thr Gln Val Pro Glu Gln Glu Met Glu Val Gln Glu Pro Ala Glu
290                 295                 300

Pro Thr Gly Val Asn Met Leu Ser Pro Gly Glu Ser Glu His Leu Leu
305                 310                 315                 320

Glu Pro Ala Glu Ala Glu Arg Ser Gln Arg Arg Arg Leu Leu Val Pro
                325                 330                 335

Ala Asn Glu Gly Asp Pro Thr Glu Thr Leu Arg Gln Cys Phe Asp Asp
            340                 345                 350

Phe Ala Asp Leu Val Pro Phe Asp Ser Trp Glu Pro Leu Met Arg Lys
355                 360                 365

Leu Gly Leu Met Asp Asn Glu Ile Lys Val Ala Lys Ala Glu Ala Ala
370                 375                 380

Gly His Arg Asp Thr Leu Tyr Thr Met Leu Ile Lys Trp Val Asn Lys
385                 390                 395                 400

Thr Gly Arg Asp Ala Ser Val His Thr Leu Leu Asp Ala Leu Glu Thr
                405                 410                 415

Leu Gly Glu Arg Leu Ala Lys Gln Lys Ile Glu Asp His Leu Leu Ser
            420                 425                 430

Ser Gly Lys Phe Met Tyr Leu Glu Gly Asn Ala Asp Ser Ala Met Ser
            435                 440                 445

<210> SEQ ID NO 481
<211> LENGTH: 448
<212> TYPE: PRT
<213> ORGANISM: Homo sapiens

<400> SEQUENCE: 481

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

```
Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
            195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Asx Ile Val Ala Leu Glu Asn Thr
                245                 250                 255

Ser Asx Pro Gly Gly Asp Pro Glu Arg Val Asp Arg Ser Ser Gln Arg
            260                 265                 270

Pro Gly Ala Glu Asp Asn Val Leu Asn Glu Ile Val Ser Ile Leu Gln
            275                 280                 285

Pro Thr Gln Val Pro Glu Gln Glu Met Glu Val Gln Glu Pro Ala Glu
290                 295                 300

Pro Thr Gly Val Asn Met Leu Ser Pro Gly Glu Ser Glu His Leu Leu
305                 310                 315                 320

Glu Pro Ala Glu Ala Glu Arg Ser Gln Arg Arg Arg Leu Leu Val Pro
                325                 330                 335

Ala Asn Glu Gly Asp Pro Thr Glu Thr Leu Arg Gln Cys Phe Asp Asp
            340                 345                 350

Phe Ala Asp Leu Val Pro Phe Asp Ser Trp Glu Pro Leu Met Arg Lys
            355                 360                 365

Leu Gly Leu Met Asp Asn Glu Ile Lys Val Ala Lys Ala Glu Ala Ala
370                 375                 380

Gly His Arg Asp Thr Leu Tyr Thr Met Leu Ile Lys Trp Val Asn Lys
385                 390                 395                 400

Thr Gly Arg Asp Ala Ser Val His Thr Leu Leu Asp Ala Leu Glu Thr
                405                 410                 415

Leu Gly Glu Arg Leu Ala Lys Gln Lys Ile Glu Asp His Leu Leu Ser
            420                 425                 430

Ser Gly Lys Phe Met Tyr Leu Glu Gly Asn Ala Asp Ser Ala Met Ser
            435                 440                 445
```

<210> SEQ ID NO 482
<211> LENGTH: 448
<212> TYPE: PRT
<213> ORGANISM: Homo sapiens

<400> SEQUENCE: 482

```
Met Glu Gln Arg Gly Gln Asn Ala Pro Ala Ala Ser Gly Ala Arg Lys
1               5                   10                  15

Arg His Gly Pro Gly Pro Arg Glu Ala Trp Gly Ala Arg Pro Gly Leu
            20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
```

```
            65                  70                  75                  80
Cys Pro Pro Gly His His Ile Ser Glu Asp Gly Arg Asp Cys Ile Ser
                    85                  90                  95
Cys Lys Tyr Gly Gln Asp Tyr Ser Thr His Trp Asn Asp Leu Leu Phe
                100                 105                 110
Cys Leu Arg Cys Thr Arg Cys Asp Ser Gly Glu Val Glu Leu Ser Pro
                115                 120                 125
Cys Thr Thr Thr Arg Asn Thr Val Cys Gln Cys Glu Glu Gly Thr Phe
                130                 135                 140
Arg Glu Glu Asp Ser Pro Glu Met Cys Arg Lys Cys Arg Thr Gly Cys
145                 150                 155                 160
Pro Arg Gly Met Val Lys Val Gly Asp Cys Thr Pro Trp Ser Asp Ile
                165                 170                 175
Glu Cys Val His Lys Glu Ser Gly Thr Lys His Ser Gly Glu Ala Pro
                180                 185                 190
Ala Val Glu Glu Thr Val Thr Ser Ser Pro Gly Thr Pro Ala Ser Pro
                195                 200                 205
Cys Ser Leu Ser Gly Ile Ile Ile Gly Val Thr Val Ala Ala Val Val
                210                 215                 220
Leu Ile Val Ala Val Phe Val Cys Lys Ser Leu Leu Trp Lys Lys Val
225                 230                 235                 240
Leu Pro Tyr Leu Lys Gly Ile Cys Asx Ile Val Ala Leu Glu Asn Thr
                245                 250                 255
Ser Asx Pro Gly Gly Asp Pro Glu Arg Val Asp Arg Ser Ser Gln Arg
                260                 265                 270
Pro Gly Ala Glu Asp Asn Val Leu Asn Glu Ile Val Ser Ile Leu Gln
                275                 280                 285
Pro Thr Gln Val Pro Glu Gln Glu Met Glu Val Gln Glu Pro Ala Glu
                290                 295                 300
Pro Thr Gly Val Asn Met Leu Ser Pro Gly Glu Ser Glu His Leu Leu
305                 310                 315                 320
Glu Pro Ala Glu Ala Glu Arg Ser Gln Arg Arg Arg Leu Leu Val Pro
                325                 330                 335
Ala Asn Glu Gly Asp Pro Thr Glu Thr Leu Arg Gln Cys Phe Asp Asp
                340                 345                 350
Phe Ala Asp Leu Val Pro Phe Asp Ser Trp Glu Pro Leu Met Arg Lys
                355                 360                 365
Leu Gly Leu Met Asp Asn Glu Ile Lys Val Ala Lys Ala Glu Ala Ala
                370                 375                 380
Gly His Arg Asp Thr Leu Tyr Thr Met Leu Ile Lys Trp Val Asn Lys
385                 390                 395                 400
Thr Gly Arg Asp Ala Ser Val His Thr Leu Leu Asp Ala Leu Glu Thr
                405                 410                 415
Leu Gly Glu Arg Leu Ala Lys Gln Lys Ile Glu Asp His Leu Leu Ser
                420                 425                 430
Ser Gly Lys Phe Met Tyr Leu Glu Gly Asn Ala Asp Ser Ala Met Ser
                435                 440                 445

<210> SEQ ID NO 483
<211> LENGTH: 223
<212> TYPE: PRT
<213> ORGANISM: Artificial Sequence
<220> FEATURE:
<223> OTHER INFORMATION: Synthetic Construct
```

<400> SEQUENCE: 483

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 484
<211> LENGTH: 10
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa = D or E
<220> FEATURE:
<221> NAME/KEY: VARIANT
<222> LOCATION: (2)...(2)
<223> OTHER INFORMATION: Xaa = I, V or L
<220> FEATURE:
<221> NAME/KEY: VARIANT
<222> LOCATION: (3)...(3)
<223> OTHER INFORMATION: Xaa = G or A
<220> FEATURE:
<221> NAME/KEY: VARIANT
<222> LOCATION: 4, 7
<223> OTHER INFORMATION: Xaa = V, I or L
<220> FEATURE:
<221> NAME/KEY: VARIANT
<222> LOCATION: 5, 8, 10
<223> OTHER INFORMATION: Xaa = Y or F
<220> FEATURE:
<221> NAME/KEY: VARIANT
<222> LOCATION: (6)...(6)
<223> OTHER INFORMATION: Xaa = S or T

<400> SEQUENCE: 484

Xaa Xaa Xaa Xaa Xaa Xaa Xaa Xaa Trp Xaa
1               5                   10

```
<210> SEQ ID NO 485
<211> LENGTH: 13
<212> TYPE: PRT
<213> ORGANISM: Homo sapiens
<220> FEATURE:
<221> NAME/KEY: VARIANT
<222> LOCATION: 1, 2
<223> OTHER INFORMATION: Xaa = L, I or V
<220> FEATURE:
<221> NAME/KEY: VARIANT
<222> LOCATION: (3)...(3)
<223> OTHER INFORMATION: Xaa = R or K
<220> FEATURE:
<221> NAME/KEY: VARIANT
<222> LOCATION: (4)...(4)
<223> OTHER INFORMATION: Xaa = Y or F
<220> FEATURE:
<221> NAME/KEY: VARIANT
<222> LOCATION: (5)...(5)
<223> OTHER INFORMATION: Xaa = F or Y
<220> FEATURE:
<221> NAME/KEY: VARIANT
<222> LOCATION: 6, 8, 11
<223> OTHER INFORMATION: Xaa = S or T
<220> FEATURE:
<221> NAME/KEY: VARIANT
<222> LOCATION: 7, 12
<223> OTHER INFORMATION: Xaa = Q or N
<220> FEATURE:
<221> NAME/KEY: VARIANT
<222> LOCATION: (9)...(9)
<223> OTHER INFORMATION: Xaa = D or E
<220> FEATURE:
<221> NAME/KEY: VARIANT
<222> LOCATION: (10)...(10)
<223> OTHER INFORMATION: Xaa = K or R
<220> FEATURE:
<221> NAME/KEY: VARIANT
<222> LOCATION: (13)...(13)
<223> OTHER INFORMATION: Xaa = G or A

<400> SEQUENCE: 485

Xaa Xaa Xaa Xaa Xaa Xaa Xaa Xaa Xaa Xaa Xaa Xaa Xaa
 1               5                  10

<210> SEQ ID NO 486
<211> LENGTH: 10
<212> TYPE: PRT
<213> ORGANISM: Homo sapiens
<220> FEATURE:
<221> NAME/KEY: VARIANT
<222> LOCATION: 1, 4
<223> OTHER INFORMATION: Xaa = A or G
<220> FEATURE:
<221> NAME/KEY: VARIANT
<222> LOCATION: (2)...(2)
<223> OTHER INFORMATION: Xaa = M or L
<220> FEATURE:
<221> NAME/KEY: VARIANT
<222> LOCATION: (3)...(3)
<223> OTHER INFORMATION: Xaa = G or A
<220> FEATURE:
<221> NAME/KEY: VARIANT
<222> LOCATION: (4)...(4)
<223> OTHER INFORMATION: Xaa = A or G
<220> FEATURE:
<221> NAME/KEY: VARIANT
<222> LOCATION: (5)...(5)
<223> OTHER INFORMATION: Xaa = R or K
<220> FEATURE:
<221> NAME/KEY: VARIANT
<222> LOCATION: 6, 7
<223> OTHER INFORMATION: Xaa = S or T
<220> FEATURE:
<221> NAME/KEY: VARIANT
<222> LOCATION: (8)...(8)
```

```
<223> OTHER INFORMATION: Xaa = V, I or L
<220> FEATURE:
<221> NAME/KEY: VARIANT
<222> LOCATION: (9)...(9)
<223> OTHER INFORMATION: Xaa = T or S

<400> SEQUENCE: 486

Xaa Xaa Xaa Xaa Xaa Xaa Xaa Xaa His
 1               5                   10

<210> SEQ ID NO 487
<211> LENGTH: 223
<212> TYPE: PRT
<213> ORGANISM: Artificial Sequence
<220> FEATURE:
<223> OTHER INFORMATION: Synthetic Construct

<400> SEQUENCE: 487

Gln Pro Val Leu His Gln Pro Ala Met Ser Ser Ala Leu Gly Cys
 1               5                   10                  15

Thr Ile Arg Leu Thr Cys Thr Leu Arg Asn Asp His Asp Ile Gly Val
                20                  25                  30

Tyr Ser Val Tyr Trp Tyr Gln Gln Arg Pro Gly His Pro Pro Arg Phe
             35                  40                  45

Leu Leu Arg Tyr Phe Ser Gln Ser Asp Lys Ser Gln Gly Pro Gln Val
     50                  55                  60

Pro Pro Arg Phe Ser Gly Ser Lys Asp Val Ala Arg Asn Arg Gly Tyr
 65                  70                  75                  80

Leu Ser Ile Ser Glu Leu Gln Pro Glu Asp Glu Ala Met Tyr Tyr Cys
                 85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 488
<211> LENGTH: 223
<212> TYPE: PRT
<213> ORGANISM: Artificial Sequence
<220> FEATURE:
<223> OTHER INFORMATION: Synthetic Construct

<400> SEQUENCE: 488

Gln Pro Val Leu His Gln Pro Ala Met Ser Ser Ala Leu Gly Thr
 1               5                   10                  15

Thr Ile Arg Leu Cys Cys Thr Leu Arg Asn Asp His Asp Ile Gly Val
                20                  25                  30
```

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
210                 215                 220

<210> SEQ ID NO 489
<211> LENGTH: 223
<212> TYPE: PRT
<213> ORGANISM: Artificial Sequence
<220> FEATURE:
<223> OTHER INFORMATION: Synthetic Construct

<400> SEQUENCE: 489

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Cys Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 490
<211> LENGTH: 223
<212> TYPE: PRT
<213> ORGANISM: Artificial Sequence
<220> FEATURE:
<223> OTHER INFORMATION: Synthetic Construct

<400> SEQUENCE: 490

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Cys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 491
<211> LENGTH: 223
<212> TYPE: PRT
<213> ORGANISM: Artificial Sequence
<220> FEATURE:
<223> OTHER INFORMATION: Synthetic Construct

<400> SEQUENCE: 491

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
        50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Cys Val Thr Leu
        115                 120                 125

Phe Pro Pro Ser Ser Glu Glu Leu Gln Ala Asn Lys Ala Thr Leu Val
130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
210                 215                 220

<210> SEQ ID NO 492
<211> LENGTH: 223
<212> TYPE: PRT
<213> ORGANISM: Artificial Sequence
<220> FEATURE:
<223> OTHER INFORMATION: Synthetic Construct

<400> SEQUENCE: 492

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Cys Thr Leu
        115                 120                 125

Phe Pro Pro Ser Ser Glu Glu Leu Gln Ala Asn Lys Ala Thr Leu Val
130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

```
Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 493
<211> LENGTH: 223
<212> TYPE: PRT
<213> ORGANISM: Artificial Sequence
<220> FEATURE:
<223> OTHER INFORMATION: Synthetic Construct

<400> SEQUENCE: 493

Gln Pro Val Leu His Gln Pro Ala Met Ser Ser Ala Leu Gly Thr
1               5                   10                  15

Thr Ile Arg Leu Thr Cys Thr Leu Arg Asn Asp His Asp Ile Gly Val
        20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Cys Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 494
<211> LENGTH: 223
<212> TYPE: PRT
<213> ORGANISM: Artificial Sequence
<220> FEATURE:
<223> OTHER INFORMATION: Synthetic Construct

<400> SEQUENCE: 494

Gln Pro Val Leu His Gln Pro Ala Met Ser Ser Ala Leu Gly Thr
1               5                   10                  15

Thr Ile Arg Leu Thr Cys Thr Leu Arg Asn Asp His Asp Ile Gly Val
        20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
```

```
                 50                  55                  60
Pro Pro Arg Phe Ser Gly Ser Lys Asp Val Ala Arg Asn Arg Gly Tyr
 65                  70                  75                  80

Leu Ser Ile Ser Glu Leu Gln Pro Glu Asp Glu Ala Met Tyr Tyr Cys
                     85                  90                  95

Ala Met Gly Ala Arg Ser Ser Val Thr His Val Phe Gly Ser Gly Thr
                    100                 105                 110

Gln Leu Thr Val Leu Ser Gln Pro Lys Ala Thr Pro Ser Val Thr Leu
                115                 120                 125

Phe Pro Pro Ser Ser Glu Glu Leu Gln Cys Asn Lys Ala Thr Leu Val
            130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                    165                 170                 175

Lys Gln Ser Asn Asn Lys Tyr Ala Ala Ser Ser Tyr Leu Ser Leu Thr
                180                 185                 190

Pro Glu Gln Trp Arg Ser Arg Arg Ser Tyr Ser Cys Gln Val Met His
            195                 200                 205

Glu Gly Ser Thr Val Glu Lys Thr Val Ala Pro Ala Glu Cys Ser
        210                 215                 220

<210> SEQ ID NO 495
<211> LENGTH: 223
<212> TYPE: PRT
<213> ORGANISM: Artificial Sequence
<220> FEATURE:
<223> OTHER INFORMATION: Synthetic Construct

<400> SEQUENCE: 495

Gln Pro Val Leu His Gln Pro Ala Met Ser Ser Ala Leu Gly Thr
  1               5                  10                  15

Thr Ile Arg Leu Thr Cys Thr Leu Arg Asn Asp His Asp Ile Gly Val
                 20                  25                  30

Tyr Ser Val Tyr Trp Tyr Gln Gln Arg Pro Gly His Pro Pro Arg Phe
             35                  40                  45

Leu Leu Arg Tyr Phe Ser Gln Ser Asp Lys Ser Gln Gly Pro Gln Val
 50                  55                  60

Pro Pro Arg Phe Ser Gly Ser Lys Asp Val Ala Arg Asn Arg Gly Tyr
 65                  70                  75                  80

Leu Ser Ile Ser Glu Leu Gln Pro Glu Asp Glu Ala Met Tyr Tyr Cys
                     85                  90                  95

Ala Met Gly Ala Arg Ser Ser Val Thr His Val Phe Gly Ser Gly Thr
                    100                 105                 110

Gln Leu Thr Val Leu Ser Gln Pro Lys Ala Thr Pro Ser Val Thr Leu
                115                 120                 125

Phe Pro Pro Ser Ser Glu Glu Leu Gln Ala Asn Lys Ala Thr Leu Val
            130                 135                 140

Cys Leu Met Asn Asp Phe Tyr Pro Gly Ile Leu Thr Cys Thr Trp Lys
145                 150                 155                 160

Ala Asp Gly Thr Pro Ile Thr Gln Gly Val Glu Met Thr Thr Pro Ser
                    165                 170                 175

Lys Gln Ser Asn Asn Lys Tyr Ala Ala Ser Ser Tyr Leu Ser Leu Thr
                180                 185                 190

Pro Glu Gln Trp Arg Ser Arg Arg Ser Tyr Ser Cys Gln Val Met His
```

```
            195                 200                 205
Glu Gly Ser Thr Val Glu Lys Thr Val Ala Pro Ala Glu Cys Ser
    210                 215                 220

<210> SEQ ID NO 496
<211> LENGTH: 223
<212> TYPE: PRT
<213> ORGANISM: Artificial Sequence
<220> FEATURE:
<223> OTHER INFORMATION: Synthetic Construct

<400> SEQUENCE: 496

Gln Pro Val Leu His Gln Pro Pro Ala Met Ser Ser Ala Leu Gly Thr
 1               5                  10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Cys Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220

<210> SEQ ID NO 497
<211> LENGTH: 223
<212> TYPE: PRT
<213> ORGANISM: Artificial Sequence
<220> FEATURE:
<223> OTHER INFORMATION: Synthetic Construct

<400> SEQUENCE: 497

Gln Pro Val Leu His Gln Pro Pro Ala Met Ser Ser Ala Leu Gly Thr
 1               5                  10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60
```

```
Pro Pro Arg Phe Ser Gly Ser Lys Asp Val Ala Arg Asn Arg Gly Tyr
 65                  70                  75                  80

Leu Ser Ile Ser Glu Leu Gln Pro Glu Asp Glu Ala Met Tyr Tyr Cys
                 85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Cys Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205

Glu Gly Ser Thr Val Glu Lys Thr Val Ala Pro Ala Glu Cys Ser
    210                 215                 220
```

<210> SEQ ID NO 498
<211> LENGTH: 223
<212> TYPE: PRT
<213> ORGANISM: Artificial Sequence
<220> FEATURE:
<223> OTHER INFORMATION: Synthetic Construct

<400> SEQUENCE: 498

```
Gln Pro Val Leu His Gln Pro Pro Ala Met Ser Ser Ala Leu Gly Thr
 1               5                  10                  15

Thr Ile Arg Leu Thr Cys Thr Leu Arg Asn Asp His Asp Ile Gly Val
                 20                  25                  30

Tyr Ser Val Tyr Trp Tyr Gln Gln Arg Pro Gly His Pro Pro Arg Phe
             35                  40                  45

Leu Leu Arg Tyr Phe Ser Gln Ser Asp Lys Ser Gln Gly Pro Gln Val
         50                  55                  60

Pro Pro Arg Phe Ser Gly Ser Lys Asp Val Ala Arg Asn Arg Gly Tyr
 65                  70                  75                  80

Leu Ser Ile Ser Glu Leu Gln Pro Glu Asp Glu Ala Met Tyr Tyr Cys
                 85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Cys Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
        195                 200                 205
```

```
Glu Gly Ser Thr Val Glu Lys Thr Val Ala Pro Ala Glu Cys Ser
    210                 215                 220
```

<210> SEQ ID NO 499
<211> LENGTH: 223
<212> TYPE: PRT
<213> ORGANISM: Artificial Sequence
<220> FEATURE:
<223> OTHER INFORMATION: Synthetic Construct

<400> SEQUENCE: 499

```
Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Ser Tyr Ser Cys Gln Val Met His
        195                 200                 205

Glu Gly Ser Thr Cys Glu Lys Thr Val Ala Pro Ala Glu Cys Ser
    210                 215                 220
```

<210> SEQ ID NO 500
<211> LENGTH: 223
<212> TYPE: PRT
<213> ORGANISM: Artificial Sequence
<220> FEATURE:
<223> OTHER INFORMATION: Synthetic Construct

<400> SEQUENCE: 500

```
Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80
```

```
Leu Ser Ile Ser Glu Leu Gln Pro Glu Asp Glu Ala Met Tyr Tyr Cys
            85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
            115                 120                 125

Phe Pro Pro Ser Ser Glu Glu Leu Gln Ala Asn Lys Ala Thr Leu Val
            130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Arg Ser Arg Arg Ser Tyr Ser Cys Gln Val Met His
            195                 200                 205

Glu Gly Ser Thr Val Glu Lys Thr Cys Ala Pro Ala Glu Cys Ser
            210                 215                 220

<210> SEQ ID NO 501
<211> LENGTH: 121
<212> TYPE: PRT
<213> ORGANISM: Artificial Sequence
<220> FEATURE:
<223> OTHER INFORMATION: Synthetic Construct

<400> SEQUENCE: 501

Gly Ser Gln Ser Val Leu Thr Gln Pro Pro Ser Val Ser Ala Ala Pro
1               5                   10                  15

Gly Gln Lys Val Thr Ile Ser Cys Ser Gly Ser Ser Ser Asn Ile Gly
            20                  25                  30

Asn Asn Tyr Val Ser Trp Tyr Gln Gln Leu Pro Gly Thr Ala Pro Lys
            35                  40                  45

Leu Leu Ile Tyr Asp Asn Asn Lys Arg Pro Ser Gly Ile Pro Asp Arg
50                  55                  60

Phe Ser Gly Ser Lys Ser Gly Thr Ser Ala Thr Leu Gly Ile Thr Gly
65                  70                  75                  80

Leu Gln Thr Gly Asp Glu Ala Asp Tyr Tyr Cys Gly Thr Trp Asp Ser
            85                  90                  95

Ser Leu Ser Ala Val Val Phe Gly Gly Gly Thr Lys Leu Thr Val Leu
            100                 105                 110

Arg Thr Ala Ser Gly Ala Ala Ala
            115                 120
```